US011673901B2

(12) United States Patent
Koltun et al.

(10) Patent No.: US 11,673,901 B2
(45) Date of Patent: Jun. 13, 2023

(54) POLYCYCLIC COMPOUNDS AS ALLOSTERIC SHP2 INHIBITORS

(71) Applicant: Revolution Medicines, Inc., Redwood City, CA (US)

(72) Inventors: Elena S. Koltun, Redwood City, CA (US); Naing N. Aay, Redwood City, CA (US); Andreas Buckl, Redwood City, CA (US); Kevin T. Mellem, Redwood City, CA (US); Brian R. Blank, Redwood City, CA (US); Jennifer Pitzen, Redwood City, CA (US); Gang Wang, Redwood City, CA (US); Ashutosh S. Jogalekar, Redwood City, CA (US); Walter S. Won, Redwood City, CA (US); Christos Tzitzilonis, Redwood City, CA (US); Jie Jack Li, Redwood City, CA (US); Adrian Liam Gill, Redwood City, CA (US); James Joseph Cregg, Redwood City, CA (US)

(73) Assignee: REVOLUTION MEDICINES, INC., Redwood City, CA (US)

( * ) Notice: Subject to any disclaimer, the term of this patent is extended or adjusted under 35 U.S.C. 154(b) by 37 days.

(21) Appl. No.: 16/899,446

(22) Filed: Jun. 11, 2020

(65) Prior Publication Data

US 2020/0407372 A1 Dec. 31, 2020

Related U.S. Application Data

(63) Continuation of application No. PCT/US2018/065817, filed on Dec. 14, 2018.

(60) Provisional application No. 62/599,583, filed on Dec. 15, 2017, provisional application No. 62/678,891, filed on May 31, 2018.

(51) Int. Cl.
*C07D 471/04* (2006.01)
*C07D 487/04* (2006.01)
*C07D 487/14* (2006.01)
*C07D 519/00* (2006.01)
*A61K 31/519* (2006.01)
*A61K 31/437* (2006.01)
*A61P 35/00* (2006.01)

(52) U.S. Cl.
CPC ......... *C07D 519/00* (2013.01); *C07D 471/04* (2013.01); *C07D 487/04* (2013.01)

(58) Field of Classification Search
CPC .. C07D 471/04; C07D 487/04; C07D 487/14; C07D 519/00; A61K 31/519; A61K 31/437; A61P 35/00
See application file for complete search history.

(56) References Cited

U.S. PATENT DOCUMENTS

| | | | |
|---|---|---|---|
| 2,572,728 A | 10/1951 | Hultquist | |
| 2,636,882 A | 4/1953 | Dunlop et al. | |
| 3,701,779 A | 10/1972 | Donninger et al. | |
| 4,687,848 A | 8/1987 | Brunnmueller et al. | |
| 5,262,564 A | 11/1993 | Kun et al. | |
| 6,921,762 B2 * | 7/2005 | Cai ......................... | A61P 31/16 514/249 |
| 7,863,288 B2 | 1/2011 | Ibrahim et al. | |
| 8,324,200 B2 | 12/2012 | Li et al. | |
| 8,703,770 B2 | 4/2014 | Coleman et al. | |
| 9,169,261 B2 | 10/2015 | Fan et al. | |
| 9,394,368 B2 | 7/2016 | Brogdon et al. | |
| 10,590,090 B2 | 3/2020 | Jogalekar et al. | |
| 2004/0213795 A1 | 10/2004 | Collins et al. | |
| 2004/0220189 A1 | 11/2004 | Sun et al. | |
| 2006/0189664 A1 | 8/2006 | Barth et al. | |
| 2008/0176309 A1 | 7/2008 | Wu et al. | |
| 2009/0325973 A1 | 12/2009 | Watterson et al. | |
| 2010/0190980 A1 | 7/2010 | Umemiya et al. | |
| 2011/0257184 A1 | 10/2011 | Qu et al. | |
| 2012/0034186 A1 | 2/2012 | Wu et al. | |
| 2012/0065205 A1 | 3/2012 | Mercer et al. | |
| 2012/0266264 A1 | 10/2012 | Lee | |
| 2012/0330012 A1 | 12/2012 | Frank et al. | |
| 2013/0005949 A1 | 1/2013 | Fertig et al. | |
| 2014/0154179 A1 | 6/2014 | Fan et al. | |
| 2016/0031976 A1 | 2/2016 | Seubert et al. | |
| 2017/0042881 A1 | 2/2017 | Fagin et al. | |
| 2018/0200381 A1 | 7/2018 | Kannan et al. | |
| 2019/0210977 A1 | 7/2019 | Jogalekar et al. | |
| 2019/0290649 A1 | 9/2019 | Xie et al. | |
| 2020/0017511 A1 | 1/2020 | Blank et al. | |
| 2020/0017517 A1 | 1/2020 | Gill et al. | |

(Continued)

FOREIGN PATENT DOCUMENTS

| | | | |
|---|---|---|---|
| CN | 102869666 A | 1/2013 | |
| CN | 103181918 A | 7/2013 | |

(Continued)

OTHER PUBLICATIONS

Anonymous: 3-Amino-6-phenyl-4-trifluoromethylpyridine, C12H9F3N2, PubChem CID 129781129, retrieved from https://pubchem.ncbi.nlm.nih.gov/compound/129781129 on Oct. 20, 2021. (8 pages).

(Continued)

*Primary Examiner* — Bruck Kifle

(74) *Attorney, Agent, or Firm* — Cooley LLP

(57) ABSTRACT

The present disclosure is directed to inhibitors of SHP2 and their use in the treatment of disease. Also disclosed are pharmaceutical compositions comprising the same.

19 Claims, No Drawings

(56) References Cited

U.S. PATENT DOCUMENTS

| | | |
|---|---|---|
| 2020/0108071 A1 | 4/2020 | Chin et al. |
| 2020/0339552 A1 | 10/2020 | Li et al. |
| 2020/0368238 A1 | 11/2020 | Nichols et al. |
| 2021/0053989 A1 | 2/2021 | Zou et al. |
| 2021/0101870 A1 | 4/2021 | Koltun et al. |
| 2021/0154190 A1 | 5/2021 | Wildes |
| 2022/0031695 A1 | 2/2022 | Nichols et al. |
| 2022/0073521 A1 | 3/2022 | Zou et al. |
| 2022/0127271 A1 | 4/2022 | Wan et al. |

FOREIGN PATENT DOCUMENTS

| | | |
|---|---|---|
| CN | 103554038 | 2/2014 |
| CN | 110156786 A | 8/2019 |
| EA | 201691442 A1 | 12/2016 |
| EP | 0 088 593 A2 | 9/1983 |
| EP | 0 579 835 A1 | 1/1994 |
| GB | 1459571 A | 12/1976 |
| JP | S5762269 A | 4/1982 |
| JP | H02-049775 A | 2/1990 |
| JP | H04-112877 A | 4/1992 |
| JP | H09510987 A | 11/1997 |
| JP | 2002-512628 | 4/2002 |
| JP | 2007-514638 | 6/2007 |
| JP | 2007277097 A | 10/2007 |
| JP | 2007530434 A | 11/2007 |
| JP | 2008-503591 A | 7/2008 |
| JP | 2013502424 A | 1/2013 |
| JP | 2013526526 A | 6/2013 |
| JP | 2013531025 A | 8/2013 |
| JP | 2017502993 A | 1/2017 |
| JP | 2017502994 A | 1/2017 |
| JP | 2017503000 A | 1/2017 |
| JP | 2017522346 A | 9/2019 |
| KR | 20090121309 A | 11/2009 |
| TW | 201609726 A | 3/2016 |
| WO | WO 93/09664 | 5/1993 |
| WO | WO 97/29109 A1 | 8/1997 |
| WO | WO 98/56376 | 12/1998 |
| WO | WO 01/16097 A1 | 3/2001 |
| WO | WO 2001060806 A2 | 8/2001 |
| WO | WO 2003045924 A1 | 6/2003 |
| WO | WO 03/082191 A2 | 10/2003 |
| WO | WO 2004/024719 A1 | 3/2004 |
| WO | WO 2004099201 A1 | 11/2004 |
| WO | WO 2004/111034 | 12/2004 |
| WO | WO 2005028480 A2 | 3/2005 |
| WO | WO-2005035532 A1 | 4/2005 |
| WO | WO 2005/040151 | 5/2005 |
| WO | WO 2005/000817 A2 | 6/2005 |
| WO | WO 2005/106286 | 11/2005 |
| WO | WO 2006/002284 | 1/2006 |
| WO | WO 2006/071759 A2 | 7/2006 |
| WO | WO 2006/113704 | 10/2006 |
| WO | WO 2007/048067 A2 | 4/2007 |
| WO | WO 2007106142 A2 | 9/2007 |
| WO | WO-2007127448 A2 | 11/2007 |
| WO | WO-2007131991 A1 | 11/2007 |
| WO | WO-2007145921 A1 | 12/2007 |
| WO | WO-2007138072 A3 | 2/2008 |
| WO | WO 2008/122615 | 10/2008 |
| WO | WO-2008138842 A1 | 11/2008 |
| WO | WO-2008138843 A1 | 11/2008 |
| WO | WO 2009/020642 A1 | 2/2009 |
| WO | WO-2009025823 A1 | 2/2009 |
| WO | WO 2010/011666 A2 | 1/2010 |
| WO | WO 2011/022440 A2 | 2/2011 |
| WO | WO 2011/154327 A1 | 12/2011 |
| WO | WO-2011154327 A1 | 12/2011 |
| WO | WO 2012/055942 | 5/2012 |
| WO | WO-2012116237 A2 | 8/2012 |
| WO | WO 2013/105063 | 7/2013 |
| WO | WO-2014023385 A1 | 2/2014 |
| WO | WO-2014072881 A1 | 5/2014 |
| WO | WO 2014/113584 | 7/2014 |
| WO | WO 2014/121885 | 8/2014 |
| WO | WO 2015/107493 A1 | 7/2015 |
| WO | WO 2015/107494 A1 | 7/2015 |
| WO | WO 2015/107495 A1 | 7/2015 |
| WO | WO 2016/007731 A1 | 1/2016 |
| WO | WO-2016007731 A1 | 1/2016 |
| WO | WO-2016081290 A1 | 5/2016 |
| WO | WO-2016100116 A1 | 6/2016 |
| WO | WO-2016103155 A1 | 6/2016 |
| WO | WO 2016/112295 A1 | 7/2016 |
| WO | WO-2016125169 A1 | 8/2016 |
| WO | WO 2016/161282 A1 | 10/2016 |
| WO | WO 2016/203404 A1 | 12/2016 |
| WO | WO 2016/203405 A1 | 12/2016 |
| WO | WO 2016/203406 A1 | 12/2016 |
| WO | WO-2017059207 A1 | 4/2017 |
| WO | WO 2017/156397 A1 | 9/2017 |
| WO | WO 2017/211303 A1 | 12/2017 |
| WO | WO 2017/216706 A1 | 12/2017 |
| WO | WO 2018/013597 A1 | 1/2018 |
| WO | WO 2018/057884 A1 | 3/2018 |
| WO | WO 2018/081091 A1 | 5/2018 |
| WO | WO 2018/130928 A1 | 7/2018 |
| WO | WO 2018/136264 A1 | 7/2018 |
| WO | WO 2018/136265 A1 | 7/2018 |
| WO | WO 2018/172984 A1 | 9/2018 |
| WO | WO 2018/187401 A1 | 10/2018 |
| WO | WO 2018/187423 A1 | 10/2018 |
| WO | WO 2018/218133 A1 | 11/2018 |
| WO | WO 2019/051084 A1 | 3/2019 |
| WO | WO 2019/075265 A1 | 4/2019 |
| WO | WO 2019/118909 A1 | 6/2019 |
| WO | WO 2019/158019 A1 | 8/2019 |
| WO | WO-2019158019 A1 | 8/2019 |
| WO | WO 2019/199792 A1 | 10/2019 |
| WO | WO 2019/212990 A1 | 11/2019 |
| WO | WO 2019/212991 A1 | 11/2019 |
| WO | WO 2020/055761 A1 | 3/2020 |
| WO | WO 2020/061101 A1 | 3/2020 |
| WO | WO 2020/106647 A2 | 5/2020 |
| WO | WO-2020094104 A1 | 5/2020 |
| WO | WO-2020/132597 A1 | 6/2020 |
| WO | WO-2020108590 A1 | 6/2020 |
| WO | WO 2021/091967 A | 5/2021 |

OTHER PUBLICATIONS

Anonymous: RMC-4630, Jul. 20, 2018, pp. 1-1, Retrieved from the Internet: URL:https://integrity.clarivate.com/integrity/xmlxsl/pk_prod_list.exec_form_pro_pr.

Banker et al., Modern Pharmaceutics, Third Edition, Revised and Expanded, 1976, pp. 451 and 596.

Belanger, David B. et al., Discovery of imidazo [1,2-a] pyrazine-based Aurora kinase inhibitors, Bioorganic & medicinal chemistry letters, 2010, pp. 5170-5174, vol. 20, No. 17.

Bhatia et al., A Review on Bioisosterism: A Rational Approach for Drug Design and Molecular Modification, Pharmacologyonline, 2011, pp. 272-299.

Belton, et al., A Novel N→S Oxygen Migration in 2,1,3-Benzoxadiazole Systems, Proceedings of the Royal Irish Academy. Section B: Biological, Geological, and Chemical Science, Royal Irish Academy, 1974, pp. 185-192, vol. 74. [Abstract Only].

Boamah, et al., Pyridazines. XXXV†‡ Novel triazanaphthalene derivatives via intramolecular cyclization reactions of vic-disubstituted pyridazines, Journal of Heterocyclic Chemistry, 1988, pp. 879-883, vol. 25, No. 3. [Abstract Only].

CAS Registry No. 777873-58-2, Entry date Nov. 10, 2004, 2,1,3-Benzoxadiazole, 4-(4-methyl-1-piperidinyl)-7-[(4-methyl-1-piperidinyl)sulfonyl]—(CA Index Name).

CAS Registry No. 777873-55-9, Entry date Nov. 10, 2004, 2,1,3-Benzoxadiazole, 4-(3-methyl-1-piperidinyl)-7-[(3-methyl-1-piperidinyl)sulfonyl]—(CA Index Name).

CAS Registry No. 1918848-03-9, Entry date May 26, 2016, 4-Piperidinamine, 1-[2-(1-methylethyl)pyrazolo[1,5-a]pyrazin-4-yl]—(CA Index Name).

(56) References Cited

OTHER PUBLICATIONS

CAS Registry No. 1918847-95-6, Entry date May 26, 2016, 4-Piperidinamine, 1-[2-(1,1-dimethylethyl)pyrazolo[1,5-a]pyrazin-4-yl]—(CA Index Name).
Database Registry, Compound with CAS Registry No. 1119718-06-7-1,4-Dioxa-8-azaspiro[4.5]decane, 8-[5-(6,7-dimethoxy-4-cinnolinyl)-3-methyl-2-pyridinyl], Mar. 12, 2009.
Database Registry, Compound with CAS Registry No. 1384576-77-5, 1,4-Dioxa-8-azaspiro[4.5]decane, 8-[6-(3-fluorophenyl)-4-methyl-3-pyridazinyl], Jul. 27, 2012.
Database Registry, RN 1629858-36-1, entered STN Oct. 23, 2014.
Database Registry, RN 1028262-30-7, entered STN Jun. 15, 2008.
Database Registry, RN 1027952-21-1, entered STN Jun. 13, 2008.
Database Registry, RN 1026418-24-5, entered STN Jun. 8, 2008.
Database Registry, RN 1026270-53-0, entered STN Jun. 8, 2008.
Database Registry, RN 1026250-49-6, entered STN Jun. 8, 2008.
Database Registry, RN 1334203-33-6, entered STN Sep. 30, 2011.
Database Registry, RN 900624-41-1, entered STN Aug. 11, 2006.
Database Registry, RN 893813-11-1, entered STN Jul. 17, 2006.
Database Registry, RN 590404-14-1, entered STN Sep. 22, 2003.
Database Registry, RN 1860803-32-2, entered STN Feb. 5, 2016.
European Patent Office, European Office Action for European Application No. 18701883.3, dated Sep. 15, 2021, 6 pages.
European Patent Office, International Preliminary Report on Patentability for pct International Application No. PCT/US2019/026543, dated Oct. 13, 2020, 15 pages.
European Paent Office, International Search Report mailed and Written Opinion dated Sep. 2, 2019, for International Application No. PCT/US2019/026543, 23 pages.
Fedele et al., SHP2 Inhibition Prevents Adaptive Resistance to MEK inhibitors in Multiple Cancer Models, Cancer Discov. Oct. 2018, pp. 1237-1249, vol. 8, No. 10.
Hydrates, Products of the addition of water (hydration) to molecules, atoms, or ions. M. b. gaseous, liquid, and solid; the last called, crystal hydrates. XUMUK, Wayback internet archive machine, Oct. 27, 2007. (machine translated from Russian) [retrieved Sep. 3, 2021] Retrieved from the Internet: <URL: https://xumuk.ru/encyklopedia/1022.html>.
Jiang, et al., Optimal therapeutic positioning of a seective bi-steric inhibitor of MTORC1 in geneticaly defined cancers, European Journal of Cancer, Oct. 1, 2020, 2 pages, vol. 138.
Larochelle et al. "Structural reorganization of SHP2 by oncogenic mutations and implications for oncoprotein resistance to allosteric inhibition", Nature Communications, Oct. 30, 2018, 10 pages, vol. 9, No. 1.
Larochelle et al., Structural and Functional Consequences of Three Cancer-Associated Mutations of the Oncogenic Phosphatase SHP2, Biochemistry, Apr. 11, 2016, pp. 2269-2277, vol. 55, No. 15.
Masuda H. et al., Synthesis of Alkoxy-, (Alkylthio)-, Phenoxy-, and (Phenylthio)pyrazines and their Olfactive Properties, J. Agric. Food Chem., 1986, pp. 377-381, vol. 34, No. 2.
Monson et al., The reactions of some ketones with hexamethylphosphoric triamide a novel synthesis of 3, 5-dialkyl-2, 6-diphenylpyridines, Tetrahedron, 1975, pp. 1145-1147, vol. 31.
Nichols et al., Efficacy of SHP2 phosphatase inhibition in cancers with nucleotide-cycling oncogenic RAS, RAS-GTP dependent oncogenic BRAF and NF1 loss, bioRxiv preprint first posted online Sep. 14, 2017, 16 pages.
Patani et al., Bioisosterism: A Rational Approach in Drug Design, Chemical Reviews, 1996, pp. 3147-3176, vol. 96.
Sayer, The Synthesis of Imidazo [1,2-a] pyrazines as Inhibitors of the VirB11 ATPase and their Incorporation into Bivalent Compounds, Diss. UCL (University College London), 2013, 396 pages.
Sun et al., Selective inhibition of leukemia-associated SHP2E69K mutant by the allosteric SHP2 inhibitor SHP099, Leukemia, Jan. 30, 2018, 4 pages, vol. 32, No. 5.
Vernier et al., Thioether benzenesulfonamide inhibitors of carbonic anhydrases II and IV: structure-based drug design, synthesis, and biological evaluation, Bioorganic & Medicinal Chemistry, May 1, 2010, pp. 3307-3319, vol. 18, Issue 9.

Xiao et al., Myeloid-restricted ablation of Shp2 restrains melanoma growth by amplifying the reciprocal promotion of CXCL9 and IFN-γ production in tumor microenvironment, Oncogene, pp. 5088-5100, vol. 37, No. 37.
Yamanishi, et al., Syntheses of trimethylpyrazines and their antibacterial properties, Yakugaku Zasshi, 1967, pp. 105-107, vol. 87, No. 1.
Zhao et al., SHP2 inhibition triggers anti-tumor immunity and synergizes with PD-1 blockade, Acta Pharmaceutica Sinica B 2019, pp. 304-315, vol. 9, No. 2.
CAS Registry No. 1349160-17-3; STN Entry Date Dec. 5, 2011; 5-(2-Chloro-4-methoxyphenyl)-3,6-diethyl-N-(1-ethylbutyl)-2-pyrazinamine.
CAS Registry No. 1349131-06-1; STN Entry Date Dec. 5, 2011; 3,6-Diethyl-N-(1-ethylpropyl)-5-[6-(1-methylethyl)-2-[(2-methylpropyl)amino]-3-pyridinyl]-2-pyrazinamine.
CAS Registry No. 1350134-68-7; STN Entry Date Dec. 7, 2011; N-[(3S,4S)-4-Butoxytetrahydro-3-furanyl]-5-(2-chloro-4-methoxyphenyl)-3,6-diethyl-2-pyrazinamine.
CAS Registry No. 1027540-93-7; STN Entry Date Jun. 12, 2008; 5-(2,4-Dichlorophenyl)-N-(4-ethoxy-1-methyl-3-pyrrolidinyl)-3,6-diethyl-2-pyrazinamine.
CAS Registry No. 1026750-06-0; STN Entry Date Jun. 9, 2008; 5-[2-(Cyclohexyloxy)-6-methyl-4-pyrimidinyl]-2,3-dihydro-2-[3-methyl-5-(4-methyl-1-piperazinyl)-2-pyrazinyl]-2-thiazolamine.
International Search Report and Written Opinion dated Dec. 20, 2017, for PCT/US2017/041577, 18 pages.
International Search Report and Written Opinion dated Sep. 21, 2018, for PCT/US2018/013018, 10 pages.
International Search Report and Written Opinion dated Apr. 5, 2018, for PCT/US2018/013023, 13 pages.
International Search Report and Written Opinion dated Jan. 24, 2019, for PCT/US2018/055502, 16 pages.
International Search Report and Written Opinion dated Dec. 12, 2018, for PCT/US2018/049744, 13 pages.
International Search Report and Written Opinion dated Feb. 20, 2019, for PCT/US2018/065817, 11 pages.
Chen et al., "Allosteric inhibition of SHP2 phosphatase inhibits cancers driven by receptor tyrosine kinases," Nature 2016, 535, 148-152.
Chen et al., "Identification of demethylincisterol A3 as a selective inhibitor of protein tyrosine phosphatase Shp2," Eur J Pharmacol. Jan. 15, 2017;795:124-133.
Ellsworth et al., "Discovery of pyrazine carboxamide CBI antagonists: The introduction of a hydroxyl group improves the pharmaceutical properties and in vivo efficacy of the series," Bioorganic & Medicinal Chemistry Letters, vol. 17, No. 14, Jul. 1, 2007, pp. 3978-3982.
Fortanet et al., "Allosteric Inhibition of SHP2: Identification of a Potent, Selective, and Orally Efficacious Phosphatase Inhibitor," J. Med. Chem. 2016, 59, 7773-7782.
Giori et al., "Synthesis of 6,7-Disubstituted Pteridine-2,4-Diones," Heterocycles, vol. 32, No. 1, 1991, 6 pages.
Jordan, "Tamoxifen: A Most Unlikely Pioneering Medicine," Nature Reviews: Drug Discovery, vol. 2, Mar. 2003, 205-213.
Larochelle et al., "Identification of an allosteric benzothiazolopyrimidone inhibitor of the oncogenic protein tyrosine phosphatase SHP2," Bioorg. Med. Chem. 2017, 17, 31394-31399.
Meurer et al., "Synthesis and SAR of 5,6-diarylpyridines as human CB1 inverse agonists," Bioorg Med Chem Lett. Feb. 1, 2005;15(3):645-51.
Mohi et al., "The role of Shp2 (PTPN11) in cancer," Curr Opin Genet Dev. Feb. 2007;17(1):23-30.
Nichols et al., "RAS nucleotide cycling underlies the SHP2 phosphatase dependence of mutant BRAF-, NF1- and RAS-driven cancers," Nat Cell Biol. Sep. 2018;20(9):1064-1073.
Ruess et al., "Mutant KRAS-driven cancers depend on PTPN11/SHP2 phosphatase," Nat Med. Jul. 2018;24(7):954-960.
Vippagunta et al., "Crystalline solids," Advanced Drug Delivery Reviews 48, 2001, 3-26.
Wolff, "Burger's Medicinal Chemistry and Drug Discovery," Fifth Edition, vol. 1: Principles and Practice, New York: John Wiley & Sons, 1994, 975-977.

(56) References Cited

OTHER PUBLICATIONS

Wustrow D.J. et al., "Aminopyrazine CB1 receptor inverse agonists," Bioorganic & Medicinal Chemistry Letters, vol. 18, No. 11, 2008, p. 3376-3381.
Xie et al., "Allosteric Inhibitors of SHP2 with Therapeutic Potential for Cancer Treatment," J. Med. Chem. 2017, 60, 10205-10219.
Database Registry [Online] Chemical Abstracts Service, Columbus, Ohio, US; Apr. 27, 2011 (Apr. 27, 2011), XP002787392, retrieved from STN Database accession No. 1286273-60-6 compound with CAS registry No. 1286273-60-6.
Database Registry [Online] Chemical Abstracts Service, Columbus, Ohio, US; Nov. 9, 2007 (Nov. 9, 2007), XP002787393, retrieved from stn Database accession No. 952723-55-6 compound with CAS registry No. 952723-55-6.
Database Registry [Online] Chemical Abstracts Service, Columbus, Ohio, US; Jan. 22, 2015 (Jan. 22, 2015), XP002787394, retrieved from stn Database accession No. 1643677-14-8 compound with CAS registry No. 1643677-14-8.
Database Registry [Online] Chemical Abstracts Service, Columbus, Ohio, US; Nov. 16, 1984 (Nov. 16, 1984), XP002787395, retrieved from stn Database accession No. 86663-20-9 compound with CAS registry No. 86663-20-9.
Database Registry [Online] Chemical Abstracts Service, Columbus, Ohio, US; Dec. 18, 1984 (Dec. 18, 1984), XP002787396, retrieved from stn Database accession No. 93034-72-1 compound with CAS registry No. 93034-72-1.
Database Registry [Online] Chemical Abstracts Service, Columbus, Ohio, US; Nov. 16, 1984 (Nov. 16, 1984), XP002787397, retrieved from stn Database accession No. 68559-45-5 compound with CAS registry No. 68559-45-5.
Database Registry [Online] Chemical Abstracts Service, Columbus, Ohio, US; Nov. 23, 2004 (Nov. 23, 2004), XP002787398, retrieved from stn Database accession No. 786652-86-6 compound with CAS registry No. 786652-86-6.
Database Registry [Online] Chemical Abstracts Service, Columbus, Ohio, US; Nov. 23, 2004 (Nov. 23, 2004), XP002787399, retrieved from stn Database accession No. 786652-83-3 compound with CAS registry No. 786652-83-3.
Database Registry [Online] Chemical Abstracts Service, Columbus, Ohio, US; Apr. 6, 1990 (Apr. 6, 1990), XP002787400, Database accession No. 126317-60-0 compound with CAS registry No. 126317-60-0.
Database Registry [Online] Chemical Abstracts Service, Columbus, Ohio, US; May 31, 2006 (May 31, 2006), XP002787401, retrieved from stn Database accession No. 886208-65-7 compound with CAS registry No. 886208-65-7.
Database Registry [Online] Chemical Abstracts Service, Columbus, Ohio, US; Aug. 27, 2010 (Aug. 27, 2010), XP002787406, retrieved from stn Database accession No. 1239320-06-9 compound with CAS registry No. 1239320-06-9.
Database Registry, Compound with CAS Registry No. 78246-19-2. 3-Methyl-5-(2-methylpropyl)-2-(phenylthio)pyrazine. Nov. 16, 1984 Citation is not enclosed due to copyright restrictions.
Database Registry, Compound with CAS Registry No. 15033-82-6. 4-[(3,5,6-Trimethyl-2-pyrazinyl)sulfonyl]benzenamine. Nov. 16, 1984 Citation is not enclosed due to copyright restrictions.
Belton, et al., A Novel N→S Oxygen Migration in 2,1,3-Benzoxadiazole Systems, Proceedings of the Royal Irish Academy. Section B: Biological, Geological, and Chemical Science, Royal Irish Academy, 1974, pp. 185-192, vol. 74.
Dardaei, et al., SHP2 inhibition restores sensitivity in ALK-rearranged non-small-cell lung cancer resistant to ALK inhibitors, Nature Medicine, Mar. 5, 2018, pp. 512-517, vol. 24, No. 4.
Dardaei, et al., Supplemental Material, SHP2 inhibition restores sensitivity in ALK-rearranged nonsmall-cell lung cancer resistant to ALK inhibitors, Nature Medicine, Mar. 5, 2018, pp. 1-58, vol. 24.
Database Registry, (STN)[online] online], [date of search Nov. 10, 2021], May 26, 2016, CAS Registry No. 1918768-32-7.
Davare, et al., Foretinib is a potent inhibitor of oncogenic ROS1 fusion proteins, PNAS, Nov. 11, 2013, pp. 19519-19524, vol. 110, No. 48.
Huang, Y., et al., "Discovery of First-in-Class, Potent, and Orally Bioavailable Embryonic Ectoderm Development (EED) Inhibitor with Robust Anticancer Efficacy," J. Med. Chem., Jan. 16, 2017, pp. 2215-2226, vol. 60, No. 6.
Intellectual Property of Singapore, Search Report for Application No. 11202004090Y, dated Dec. 6, 2021, 11 pages.
Leroy et al., Di-tert-butyl (methyl) phosphonium tetrafluoro borate, e-EROS Encyclopedia of Reagents for Organic Synthesis, Dec. 31, 2015, pp. 1-7.
Neel, et al., Differential Subcellular Localization Regulates Oncogenic Signaling by ROS1 Kinase Fusion Proteins, Cancer Res, Dec. 11, 2018, pp. 546-556, vol. 79, No. 3 . . . .
Ozawa, T et al., "The importance of CH/phydrogen bonds in rational drug design: An abinitio fragment molecular orbital study to leukocyte-specific protein tyrosine (LCK) kinase," Bioorganic & Medicinal Chemistry, Dec. 31, 2008, vol. 16, pp. 10311-10318.
Rauen, et al., The RASopathies, Annu Rev Genomics Hum Genet. 2013, pp. 355-369, vol. 14.
Voena, et al., The Tyrosine Phosphatase Shp2 Interacts with NPM-ALK and Regulates Anaplastic Lymphoma Cell Growth and Migration, Cancer Res, Apr. 24, 2007, pp. 4278-4286, vol. 67, No. 9.
Wang, J., et al., Palladium-Catalyzed Direct Heck Arylation of Dual rr-Deficient/rr-Excessive Heteroaromatics. Synthesis of C-5 Arylated Imidazo[1, 5-a]pyrazines, Organic Letters, Jun. 25, 2008, pp. 2215-2226, vol. 10, No. 14.
Yap, et al, The NF1 gene revisited—from bench to bedside, Oncotarget, Aug. 2014, pp. 5873-5892, vol. 5, No. 15.
Zou, et al., PF-06463922 is a potent and selective next-generation ROS1/ALK inhibitor capable of blocking crizotinib-resistant ROS1 mutations, PNAS, Mar. 2, 2015, pp. 3493-3498, vol. 112, No. 11.
Belikov, Pharmaceutical Chemistry, Chapter 2.6 Relationship between the chemical structure, properties of substances and their effect on the body-M .: MEDpress-inform, 2007, pp. 27-29. [Human Translation].
Fialkov, Solvent as a means of controlling a chemical process, Publishing house "Chemistry", 1990, p. 240.
Yatsyuk et al. General principles of xenobiotic metabolism as a basis for the development of methods for the synthesis of prodrugs, Elective course textbook, 2009, pp. 71-79.
Wayback Internet Archive Machine, Oct. 27, 2007, Retrieved from: https://xumuk.ru/encyklopedia/1022.html.
Adam et al., "Concise synthesis of 1H-pyrazin-2-ones and 2-aminopyrazines" Synlett (11): 2004 2031-2033 compounds 6a, 6c and 6d.
Akhapkina.V.I et al, "Fundamentals of modulatory concept and classification of modulatory drugs;" RMZh, N19, 2012, pp. 933-951.
Amato, C. et al., "Modulation of a proteolytic enzyme activity by means of photochromic inhibitor", Journal of Photochemistry and Photobiology B: Biology, 1995, vol. 28(1), p. 71-75.
CAS Registry No. 1119717-53-1, Entry date Mar. 12, 2009.
CAS Registry No. 174531-55-6, Entry date Mar. 26, 1996.
CAS Registry No. 3657-73-6, Entry date Nov. 16, 1984.
Database Registry, RN 1957154-25-4, 1956595-47-3, entered STN Jul. 21, 2016.
Database Registry, RN 1949800-28-5, entered STN Jul. 11, 2016.
Database Registry, RN 1952095-25-8, entered STN Jul. 14, 2016.
Database Registry, RN 1953046-94-0, 1952680-38, entered STN Jul. 15, 2016.
Dayakar et al., "Synthesis and antimycobacterial activity of 1H-1,2,3-triazolylisonicotinohydrazi," Indian Journal of Chemistry, Section B: Organic Chemistry Including Medicinal Chemistry 55B (7), (2016), 882-887 intermediates 9c to 9f.
Fundamentals of Medical Prevention. Educational and Methodological Manual for Students and Cadets of Professional Development Cycles of State Professional Educational Institutions. Novosibirsk, 2016, UDC 614.2-084, BBC 51.1(2)2, pp. 13-21, Available online https://rcmpnso.ru/profila/m_mater/docs/osnovi_med_pomoshi.pdf?ysclid=I5wi7xgplo450927514.

(56) References Cited

OTHER PUBLICATIONS

Krosig, U. et al., "Expanding the Genetic Alphabet: Pyrazine Nucleosides That Support a Donor-Donor-Acceptor Hydrogen-Bonding Pattern," Helv. Chim. Acta 2004, v.87, pp. 1299-1324.
Li, H.-L. et al., Exploring the effect of D61G mutation on SHP2 cause gain of function activity by a molecular dynamics study. J. Biomol. Struct. Dyn., Nov. 24, 2017, vol. 36, No. 14, pp. 3856-3868.
Mehta, V. et al., "Microwave-Assisted Palladium-Catalyzed Phosphonium Coupling of 2(1H)-Pyrazinones," J. Org. Chem. 2010, 75, 3, 976-979.
Perez et al., "Palladium-Catalyzed C,N-Cross Coupling Reactions of 3-Halo-2-aminopyridines," Organic Letters 13 (8): 2011; 1984-1987 compound 5 of Figure 2; compounds 12 and 13 of Scheme 2.
Pisaneschi, F. et al., "The 3S Enantiomer Drives Enolase Inhibitory Activity in SF2312 and Its Analogues", Molecules, 2019, vol. 24(13), 2510, p. 1-18.
Ran et. al., "Sticking It to Cancer with Molecular Glue forSHP2" Cancer Cell . Aug. 8, 2016;30(2):194-196.
Sansfacon et. al., "SHP-2 phosphatase contributes to KRAS-driven intestinal oncogenesis but prevents colitis-associated cancer development" Oncotarget. Oct. 4, 2016;7(40):65676-65695.
Tol, J. et al., "Chemotherapy, bevacizumab, and cetuximab in metastatic colorectal cancer", N Engl J Med, Feb. 5, 2009, vol. 360(6), pp. 563-572.
Yu, H. A. et al., "A phase ½ trial of ruxolitinib and erlotinib in patients with EGFR-mutant lung adenocarcinomas with acquired resistance to erlotinib", Journal of Thoracic Oncology, 2017, vol. 12(1), pp. 102-109.
Zefirov.O.N et al., "On the history of the emergence and development of the concept of bioisosterism," Vestn Mosk Un-Ta Ser 2 Chemistry, 2002, vol. 43(4), pp. 251-256.
Database Registry, RN 893806-50-3, entered STN Jul. 17, 2006.
Database Registry, RN 893807-90-4, entered STN Jul. 17, 2006.
Database Registry, RN 893808-63-4, entered STN Jul. 17, 2006.
Database Registry, RN 893810-11-2, entered STN Jul. 17, 2006.
9-(4-chlorophenyl)-5-(4-morpholinyl)tetrazolo[1,5-c]-thieno[3,2-e]pyrimidine, entered STN Jul. 17, 2006, 1 page.
9-(4-chlorophenyl)-5-(4-morpholinyl)thieno[3,2-e]-1,2,4-triazolo[4,3-c]pyrimidineentered STN Jul. 17, 2006, 1 page.
9-phenyl-5-(1-pyrrolidinyl)tetrazolo[1,5-c]thieno[3,2-e]pyrimidine, entered STN Jul. 17, 2006, 1 page.
9-phenyl-5-(1-pyrrolidinyl)thieno[3,2-e]-1,2,4-triazolo[4,3-c]pyrimidine, entered STN Jul. 17, 2006, 1 page.
Database Registry, RN 893294-18-3, entered STN Jul. 17, 2006, 1 page.
Database Registry, RN 893792-24-0, entered STN Jul. 17, 2006, 1 page.
Database Registry, RN 893792-68-2, entered STN Jul. 17, 2006, 1 page.
Database Registry, RN 893794-10-0, entered STN Jul. 17, 2006, 1 page.
Database Registry, RN 893795-14-7, entered STN Jul. 17, 2006, 1 page.
Database Registry, RN 893796-38-8, entered STN Jul. 17, 2006, 1 page.
Database Registry, RN 893796-42-4, entered STN Jul. 17, 2006, 1 page.
Database Registry, RN 893797-57-4, entered STN Jul. 17, 2006, 1 page.
Database Registry, RN 893797-61-0, entered STN Jul. 17, 2006, 1 page.
Database Registry, RN 893799-39-8, entered STN Jul. 17, 2006, 1 page.
Database Registry, RN 893799-43-4, entered STN Jul. 17, 2006, 1 page.
Database Registry, RN 893799-47-8, entered STN Jul. 17, 2006, 1 page.
Database Registry, RN 893801-34-8, entered STN Jul. 17, 2006, 1 page.
Database Registry, RN 893803-59-3, entered STN Jul. 17, 2006, 1 page.

* cited by examiner

POLYCYCLIC COMPOUNDS AS ALLOSTERIC SHP2 INHIBITORS

CROSS REFERENCE TO RELATED APPLICATIONS

This application is a continuation of International Patent Application No. PCT/US2018/065817, filed Dec. 14, 2018, which claims the benefit of U.S. Provisional Application No. 62/599,583, filed Dec. 15, 2017 and U.S. Provisional Application No. 62/678,891, filed May 31, 2018; the contents of each of which are incorporated herein by reference in their entireties.

FIELD OF THE DISCLOSURE

The present disclosure relates to inhibitors of protein tyrosine phosphatase SHP2 useful in the treatment of diseases or disorders. Specifically, the present disclosure is concerned with compounds and compositions inhibiting SHP2, methods of treating diseases associated with SHP2, and methods of synthesizing these compounds.

BACKGROUND OF THE DISCLOSURE

SH2 domain-containing protein tyrosine phosphatase-2 (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present disclosure fulfill the need for small molecules to that inhibit the activity of SHP2.

BRIEF SUMMARY

The present disclosure relates to compounds capable of inhibiting the activity of SHP2. The present disclosure further provides a process for the preparation of compounds, pharmaceutical preparations comprising such compounds and methods of using such compounds and compositions in the management of diseases or disorders associated with the aberrant activity of SHP2.

One aspect of the present disclosure relates to compounds of Formula I':

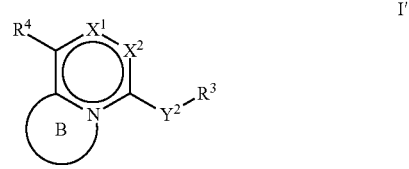

and pharmaceutically acceptable salts, prodrugs, solvates, hydrates, tautomers, and isomers thereof, wherein:

$R^4$ is H or

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —C(=$CH_2$)—, —$CH_2$—, or —S(O)—;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —($CR^a_2$)$_m$—, —O—, —C(O)—, —C($R^a$)$_2$NH—, —($CR^a_2$)$_m$O—, —C(O)N($R^a$)—, —N($R^a$)C(O)—, —S(O)$_2$N($R^a$)—, —N($R^a$)S(O)$_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —($CH_2$)$_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$ cycloalkyl, —$C_2$-$C_6$alkenyl, —($CH_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, —(CH$_2$)$_n$—R$^b$, or —(CH$_2$)$_n$C(O)NR$^5$R$^6$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^5$ and R$^6$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10;

provided that when X$^2$ is N and B ring is a monocyclic 5-membered heteroaryl containing 3-4 nitrogen atoms, then

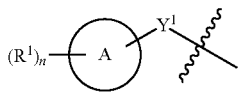

is not

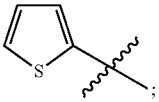 [SMILES: *c1cccs1]

and provided that when X$^1$ is N; X$^2$ is CH and Y$^1$ is NH; then R$^1$ is not C$_3$-C$_8$cycloalkyl or heteroaryl.

One aspect of the present disclosure relates to compounds of Formula I:

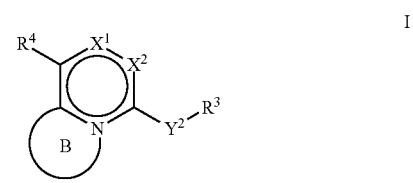

and pharmaceutically acceptable salts, prodrugs, solvates, hydrates, tautomers, and isomers thereof, wherein:

R$^4$ is H or

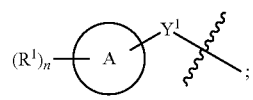

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

R$^1$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

Y$^1$ is —S—, a direct bond, —NH—, —S(O)$_2$—, —S(O)$_2$—NH—, —C(=CH$_2$)—, —CH$_2$—, or —S(O)—;

X$^1$ is N or CR$^2$;

X$^2$ is N or CH;

B, including the atoms at the points of attachment, is a monocyclic or polycyclic 5- to 12-membered heterocycle or a monocyclic or polycyclic 5- to 12-membered heteroaryl;

Y$^2$ is —NR$^a$—, —(CR$^a{}_2$)$_m$—, —C(O)—, —C(R$^a$)$_2$NH—, —(CR$^a{}_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the ring and the bond on the right side of the Y$^2$ moiety, as drawn, is bound to R$^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^2$ is independently —H, —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_nNH_2$, $(CH_2)_nOH$, —$COOR^b$, —$CONHR^b$, —$CONH(CH_2)_nCOOR^b$, —$NHCOOR^b$, —$CF_3$, —$CHF_2$, —$CH_2F$, or =O;

$R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

One aspect of the present disclosure relates to compounds of Formula II':

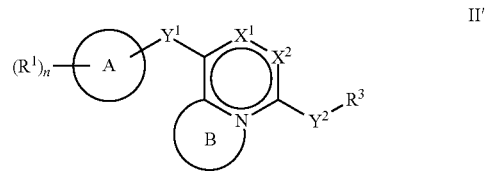

and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —$C(=CH_2)$—, —$CH_2$—, or —S(O)—;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —$(CR^a{}_2)_m$—, —O—, —C(O)—, —$C(R^a)_2NH$—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^2$ is independently —H, —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —C(O)$OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;

$R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10;

provided that when $X^2$ is N and B ring is a monocyclic 5-membered heteroaryl containing 3-4 nitrogen atoms, then

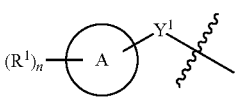

is not

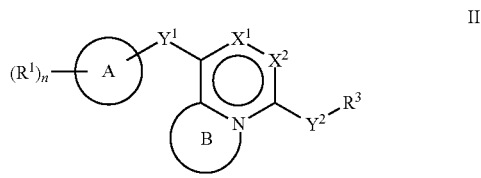

and provided that when $X^1$ is N; $X^2$ is CH and $Y^1$ is NH; then $R^1$ is not $C_3$-$C_8$cycloalkyl or heteroaryl.

One aspect of the present disclosure relates to compounds of Formula II:

II and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —C(=$CH_2$)—, —$CH_2$—, or —S(O)—;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —$N(R^a)C(O)O$—, —C(O)N($R^a$)O—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)$ $NR^5R^6$, $-NR^5S(O)R^6$, $-C(O)NR^5R^6$, $-NR^5C(O)R^6$, heterocycle, aryl, heteroaryl, $-(CH_2)_nOH$, $-C_1-C_6alkyl$, $-CF_3$, $-CHF_2$, or $-CH_2F$;

$R^2$ is independently $-H$, $-NH_2$, $-OR^b$, $-CN$, $-C_1-C_6alkyl$, $-C_2-C_6alkenyl$, $-C_4-C_8cycloalkenyl$, $-C_2-C_6alkynyl$, halogen, $-C(O)OR^b$, $-C_3-C_8cycloalkyl$, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more $-OH$, halogen, $-NO_2$, oxo, $-CN$, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, heterocycle, aryl, or heteroaryl;

$R^3$ is independently $-H$, $-C_1-C_6alkyl$, a 3- to 12-membered monocyclic or polycyclic heterocycle, a 5- to 12-membered spiroheterocycle, $C_3-C_8cycloalkyl$, or $-(CH_2)_n-R^b$, wherein each alkyl, spiroheterocycle, heterocycle, or cycloalkyl is optionally substituted with one or more $-C_1-C_6alkyl$, $-OH$, $-NH_2$, $-OR^b$, $-NHR^b$, $-(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more $-C_1-C_6alkyl$, halogen, $-OH$, $-OR^b$, $-NH_2$, $-NHR^b$, heteroaryl, heterocyclyl, $-(CH_2)_nNH_2$, $-(CH_2)_nOH$, $-COOR^b$, $-CONHR^b$, $-CONH(CH_2)_nCOOR^b$, $-NHCOOR^b$, $-CF_3$, $-CHF_2$, $-CH_2F$, or $=O$;

$R^3$ and $R^6$ are independently, at each occurrence, $-H$, $-C_1-C_6alkyl$, $-C_2-C_6alkenyl$, $-C_4-C_8cycloalkenyl$, $-C_2-C_6alkynyl$, $-C_3-C_8cycloalkyl$, a monocyclic or polycyclic 3- to 12-membered heterocycle, $-OR^7$, $-SR^7$, halogen, $-NR^7R^8$, $-NO_2$, $-CF_3$, or $-CN$;

$R^7$ and $R^8$ are independently, at each occurrence, $-H$, $-C_1-C_6alkyl$, $-C_2-C_6alkenyl$, $-C_4-C_8cycloalkenyl$, $-C_2-C_6alkynyl$, $-C_3-C_8cycloalkyl$, $-OR^b$, or a monocyclic or polycyclic 3- to 12-membered heterocycle, wherein each alkyl, alkenyl, cycloalkenyl, alkynyl, cycloalkyl, or heterocycle is optionally substituted with one or more $-OH$, $-SH$, $-NH_2$, $-NO_2$, or $-CN$;

m is independently 1, 2, 3, 4, 5 or 6; and n is independently 0, 1, 2, 3, 4, 5, 6, 7, 8, 9, or 10.

One aspect of the present disclosure relates to compounds of Formula III':

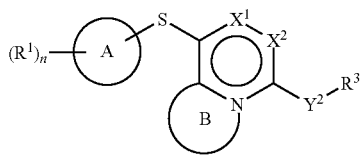

III' and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, $-H$, $-C_1-C_6alkyl$, $-C_2-C_6alkenyl$, $-C_4-C_8cycloalkenyl$, $-C_2-C_6alkynyl$, $-C_3-C_8cycloalkyl$, $-OH$, $-OR^6$, halogen, $-NO_2$, $-CN$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, $-C(O)R^5$, $-CO_2R^5$, $-C(O)NR^5R^6$, $-NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more $-OH$, halogen, $-NO_2$, oxo, $=O$, $-CN$, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, heterocycle, aryl, or heteroaryl;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is $-NR^a-$, $-(CR^a_2)_m-$, $-O-$, $-C(O)-$, $-C(R^a)_2NH-$, $-(CR^a_2)_mO-$, $-C(O)N(R^a)$, $-N(R^a)C(O)-$, $-S(O)_2N(R^a)-$, $-N(R^a)S(O)_2-$, $-N(R^a)C(O)N(R^a)-$, $-N(R^a)C(S)N(R^a)-$, $-C(O)O-$, $-OC(O)-$, $-OC(O)N(R^a)-$, $-N(R^a)C(O)O-$, $-C(O)N(R^a)O-$, $-N(R^a)C(S)-$, $-C(S)N(R^a)-$, or $-OC(O)O-$; wherein the bond on the left side of $Y^2$, as drawn, is bound to the ring and the bond on the right side of the $Y^2$ moiety, as drawn, is bound to $R^3$;

$R^a$ is independently, at each occurrence, $-H$, $-OH$, $-C_3-C_8cycloalkyl$, $-C_1-C_6alkyl$, 3- to 12-membered heterocyclyl, or $-(CH_2)_n$-aryl, wherein each alkyl or cycloalkyl is optionally substituted with one or more $-NH_2$, or wherein 2 $R^a$, together with the carbon atom to which they are both attached, can combine to form a 3- to 8-membered cycloalkyl;

$R^b$ is independently, at each occurrence, $-H$, $-OH$, $-C_1-C_6alkyl$, $-C_3-C_8cycloalkyl$, $-C_2-C_6alkenyl$, $-(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or $-(CH_2)_n$-aryl is optionally substituted with one or more $-OH$, halogen, $-NO_2$, oxo, $-CN$, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, $-C(O)NR^5R^6$, $-NR^5C(O)R^6$, heterocycle, aryl, heteroaryl, $-(CH_2)_nOH$, $-C_1-C_6alkyl$, $-CF_3$, $-CHF_2$, or $-CH_2F$;

$R^2$ is independently $-H$, $-NH_2$, $-OR^b$, $-CN$, $-C_1-C_6alkyl$, $-C_2-C_6alkenyl$, $-C_4-C_8cycloalkenyl$, $-C_2-C_6alkynyl$, halogen, $-C(O)OR^b$, $-C_3-C_8cycloalkyl$, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more $-OH$, halogen, $-NO_2$, oxo, $-R^5$, $-OR^5$, $-NR^5R^6$, $-SR^5$, $-S(O)_2NR^5R^6$, $-S(O)_2R^5$, $-NR^5S(O)_2NR^5R^6$, $-NR^5S(O)_2R^6$, $-S(O)NR^5R^6$, $-S(O)R^5$, $-NR^5S(O)NR^5R^6$, $-NR^5S(O)R^6$, heterocycle, aryl, or heteroaryl;

$R^3$ is independently $-H$, $-C_1-C_6alkyl$, a 3- to 12-membered monocyclic or polycyclic heterocycle, a 5- to 12-membered spiroheterocycle, $C_3-C_8cycloalkyl$, $-(CH_2)_n-R^b$, or $-(CH_2)_nC(O)NR^5R^6$, wherein each alkyl, spiroheterocycle, heterocycle, or cycloalkyl is optionally substituted with one or more $-C_1-C_6alkyl$, $-OH$, $-NH_2$, $-OR^b$, $-NHR^b$, $-(CH_2)_nOH$, heterocyclyl, or spiroheterocyclyl; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, optionally substituted heteroaryl, optionally substituted heterocyclyl, —(CH₂)ₙNH₂, —(CH₂)ₙOH, —COORᵇ, —CONHRᵇ, —CONH(CH₂)ₙCOORᵇ, —NHCOORᵇ, —O—C(O)—NR⁵R⁶, —CF₃, —CHF₂, —CH₂F, or =O; wherein the heteroaryl and heterocyclyl are optionally substituted with —CN;

R⁵ and R⁶ are independently, at each occurrence, —H, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, —CF₃, or —CN;

R⁷ and R⁸ are independently, at each occurrence, —H, —C₁-C₆alkyl, —C₂-C₆alkenyl, —C₄-C₈cycloalkenyl, —C₂-C₆alkynyl, —C₃-C₈cycloalkyl, —ORᵇ, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently 1, 2, 3, 4, 5 or 6; and n is independently 0, 1, 2, 3, 4, 5, 6, 7, 8, 9, or 10.

One aspect of the present disclosure relates to compounds of Formula III:

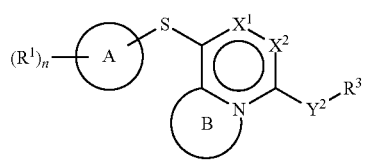

III and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

R¹ is independently, at each occurrence, —H, —C₁-C₆alkyl, —C₂-C₆alkenyl, —C₄-C₈cycloalkenyl, —C₂-C₆alkynyl, —C₃-C₈cycloalkyl, —OH, —OR⁶, halogen, —NO₂, —CN, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)R⁵, —CO₂R⁵, —C(O)NR⁵R⁶, —NR⁵C(O)R⁶, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO₂, oxo, =O, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

X is N or CR²;

X² is N or CH;

B, including the atoms at the points of attachment, is a monocyclic or polycyclic 5- to 12-membered heterocycle or a monocyclic or polycyclic 5- to 12-membered heteroaryl;

Y² is —NRᵃ—, —(CRᵃ₂)ₘ—, —C(O)—, —C(Rᵃ)₂NH—, —(CRᵃ₂)ₘO—, —C(O)N(Rᵃ)—, —N(Rᵃ)C(O)—, —S(O)₂N(Rᵃ)—, —N(Rᵃ)S(O)₂—, —N(Rᵃ)C(O)N(Rᵃ)—, —N(Rᵃ)C(S)N(Rᵃ)—, —C(O)O—, —OC(O)—, —OC(O)N(Rᵃ)—, —N(Rᵃ)C(O)O—, —C(O)N(Rᵃ)O—, —N(Rᵃ)C(S)—, —C(S)N(Rᵃ)—, or —OC(O)O—; wherein the bond on the left side of Y², as drawn, is bound to the ring and the bond on the right side of the Y² moiety, as drawn, is bound to R³;

Rᵃ is independently, at each occurrence, —H, —OH, —C₃-C₈cycloalkyl, —C₁-C₆alkyl, 3- to 12-membered heterocyclyl, or —(CH₂)ₙ-aryl, wherein each alkyl or cycloalkyl is optionally substituted with one or more —NH₂, or wherein 2 Rᵃ, together with the carbon atom to which they are both attached, can combine to form a 3- to 8-membered cycloalkyl;

Rᵇ is independently, at each occurrence, —H, —OH, —C₁-C₆alkyl, —C₃-C₈cycloalkyl, —C₂-C₆alkenyl, —(CH₂)ₙ-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH₂)ₙ-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O) NR⁵R⁶, —NR⁵S(O)R⁶, —C(O)NR⁵R⁶, —NR⁵C(O)R⁶, heterocycle, aryl, heteroaryl, —(CH₂)ₙOH, —C₁-C₆alkyl, —CF₃, —CHF₂, or —CH₂F;

R² is independently —H, —NH₂, —ORᵇ, —CN, —C₁-C₆alkyl, —C₂-C₆alkenyl, —C₄-C₈cycloalkenyl, —C₂-C₆alkynyl, halogen, —C(O)ORᵇ, —C₃-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O) NR⁵R⁶, —S(O)R⁵, —NR⁵S(O)NR⁵R⁶, —NR⁵S(O)R⁶, heterocycle, aryl, or heteroaryl;

R³ is independently —H, —C₁-C₆alkyl, a 3- to 12-membered monocyclic or polycyclic heterocycle, a 5- to 12-membered spiroheterocycle, C₃-C₈cycloalkyl, or —(CH₂)ₙ—Rᵇ, wherein each alkyl, spiroheterocycle, heterocycle, or cycloalkyl is optionally substituted with one or more —C₁-C₆alkyl, —OH, —NH₂, —ORᵇ, —NHRᵇ, —(CH₂)ₙOH, heterocyclyl, or spiroheterocyclyl; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, heteroaryl, heterocyclyl, —(CH₂)ₙNH₂, —(CH₂)ₙOH, —COORᵇ, —CONHRᵇ, —CONH(CH₂)ₙCOORᵇ, —NHCOORᵇ, —CF₃, —CHF₂, —CH₂F, or =O;

R⁵ and R⁶ are independently, at each occurrence, —H, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, —CF₃, or —CN;

R⁷ and R⁸ are independently, at each occurrence, —H, —C₁-C₆alkyl, —C₂-C₆alkenyl, —C₄-C₈cycloalkenyl, —C₂-C₆alkynyl, —C₃-C₈cycloalkyl, —ORᵇ, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently 1, 2, 3, 4, 5 or 6; and n is independently 0, 1, 2, 3, 4, 5, 6, 7, 8, 9, or 10.

One aspect of the present disclosure relates to compounds of Formula IV':

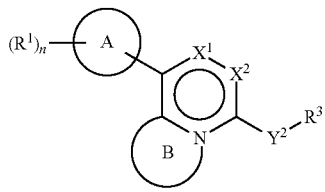

and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —$(CR^a_2)_m$—, —O—, —C(O)—, —$C(R^a)_2NH$—, —$(CR^a_2)_mO$—, —$C(O)N(R^a)$, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or $(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^2$ is independently —H, —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, —$(CH_2)_n$—$R^b$, or —$(CH_2)_nC(O)NR^5R^6$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_nOH$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;

$R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10;

provided that when $X^2$ is N and B ring is a monocyclic 5-membered heteroaryl containing 3-4 nitrogen atoms, then

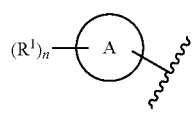

is not

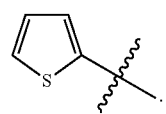 [SMILES: *c1cccs1]

.

One aspect of the present disclosure relates to compounds of Formula IV:

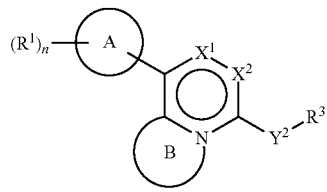

and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, ═O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —$(CR^a_2)_m$—, —C(O)—, —$C(R^a)_2$NH—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)$ $NR^5R^6$, —$NR^5S(O)R^6$, —$C(O)NR^5R^6$, —$NR^5C(O)R^6$, heterocycle, aryl, heteroaryl, —$(CH_2)_n$OH, —$C_1$-$C_6$alkyl, —$CF_3$, —$CHF_2$, or —$CH_2F$;

$R^2$ is independently —H, —$NH_2$, —$OR^b$, —CN, —$C_1$-$C_6$alkyl, —$C_2$-$C_6$alkenyl, —$C_4$-$C_8$cycloalkenyl, —$C_2$-$C_8$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)$ $NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —$(CH_2)_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, heteroaryl, heterocyclyl, —$(CH_2)_n NH_2$, —$(CH_2)_n OH$, —$COOR^b$, —$CONHR^b$, —$CONH(CH_2)_n COOR^b$, —$NHCOOR^b$, —$CF_3$, —$CHF_2$, —$CH_2F$, or ═O;

$R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

One aspect of the present disclosure relates to compounds of Formula V:

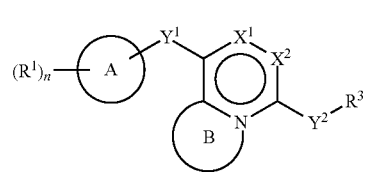

and pharmaceutically acceptable salts, prodrugs, solvates, hydrates, tautomers, and isomers thereof, wherein:

A is aryl or heteroaryl, wherein aryl and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

Y$^1$ is —S—, —O—, —NH—, or —CH$_2$—;

X$^1$ is N or CR$^2$;

X$^2$ is N or CH;

B, including the atoms at the points of attachment, is a monocyclic or polycyclic 5- to 12-membered heterocycle or a monocyclic or polycyclic 5- to 12-membered heteroaryl;

Y$^2$ is —NR$^a$—, —(CR$^a$$_2$)$_m$O—, —O—, or —C(O)N(R$^a$)—; wherein the bond on the left side of Y$^2$, as drawn, is bound to the ring and the bond on the right side of the Y$^2$ moiety, as drawn, is bound to R$^3$;

R$^a$ is independently, at each occurrence, —H or —C$_1$-C$_6$alkyl;

R$^b$ is independently, at each occurrence, —H, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$C(O)NR$^5$R$^6$, wherein each alkyl, spiroheterocycle, heterocycle, or cycloalkyl is optionally substituted with one or more —C$_1$-C$_6$alkyl, —OH, —OR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, optionally substituted heteroaryl, optionally substituted heterocyclyl, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^5$ and R$^6$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10;

provided that when X$^2$ is N and B ring is a monocyclic 5-membered heteroaryl containing 3-4 nitrogen atoms, then

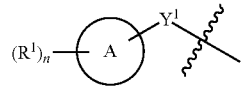

is not

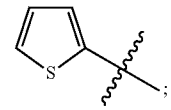

and provided that when X$^1$ is N; X$^2$ is CH and Y$^1$ is NH; then R$^1$ is not C$_3$-C$_8$cycloalkyl or heteroaryl.

One aspect of the present disclosure relates to compounds of Formula VI:

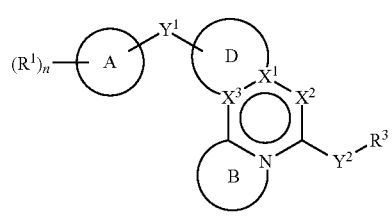

VI and pharmaceutically acceptable salts, prodrugs, solvates, hydrates, tautomers, and isomers thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

R$^1$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

Y$^1$ is —S—, a direct bond, —NH—, —S(O)$_2$—, —S(O)$_2$—NH—, —C(=CH$_2$)—, —CH$_2$—, or —S(O)—;

X$^1$ is N or C;

X$^2$ is N or CH;

X$^3$ is N or C;

B, including the atoms at the points of attachment, is a monocyclic or polycyclic 5- to 12-membered heterocycle or a monocyclic or polycyclic 5- to 12-membered heteroaryl;

D, including the atoms at the points of attachment, is a monocyclic 5- to 7-membered heterocycle or a monocyclic 5- to 7-membered heteroaryl;

Y$^2$ is —NR$^a$—, —(CR$^a_2$)$_m$—, —O—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the ring and the bond on the right side of the Y$^2$ moiety, as drawn, is bound to R$^3$;

R$^a$ is independently, at each occurrence, —H, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

R$^b$ is independently, at each occurrence, —H, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or (CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, or —(CH$_2$)$_n$—R$^b$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, —(CH$_2$)$_n$C(O)NR$^5$R$^6$, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^5$ and R$^6$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10.

Another aspect of the present disclosure relates to methods of treating a disease associated with SHP2 modulation in a subject in need thereof, comprising administering to the subject an effective amount of a compound of Formula I, I', II, II', III, III', IV, IV', V, or VI and pharmaceutically acceptable salts, prodrugs, solvates, hydrates, tautomers, and isomers thereof.

Another aspect of the present disclosure relates to methods of inhibiting SHP2. The method comprises administering to a patient in need thereof, an effective amount of a compound of Formula I, I', II, II', III, III', IV, IV', V, or VI, and pharmaceutically acceptable salts, prodrugs, solvates, hydrates, tautomers, and isomers thereof.

Another aspect of the present disclosure is directed to pharmaceutical compositions comprising a compound of Formula I, I', II, II', III, III', IV, IV', V, or VI, and pharmaceutically acceptable salts, prodrugs, solvates, hydrates, tautomers, and isomers thereof, and a pharmaceutically acceptable carrier. The pharmaceutically acceptable carrier can further comprise an excipient, diluent, or surfactant. The pharmaceutical composition can be effective for treating a disease associated with SHP2 modulation in a subject in need thereof.

Another aspect of the present disclosure relates to a compound of Formula I, I', II, II', III, III', IV, IV', V, or VI, and pharmaceutically acceptable salts, prodrugs, solvates, hydrates, tautomers, and isomers thereof, for use in treating or preventing a disease associated with SHP2 modulation.

Another aspect of the present disclosure relates to the use of a compound of Formula I, I', II, II', III, III', IV, IV', V, or VI, and pharmaceutically acceptable salts, prodrugs, solvates, hydrates, tautomers, and isomers thereof, in the manufacture of a medicament for treating or preventing a disease associated with SHP2 modulation.

The present disclosure also provides compounds that are useful in inhibiting SHP2.

DETAILED DESCRIPTION OF THE DISCLOSURE

The details of the present disclosure are set forth in the accompanying description below. Although methods and materials similar or equivalent to those described herein can be used in the practice or testing of the present disclosure, illustrative methods and materials are now described. Other features, objects, and advantages of the present disclosure will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which the present disclosure belongs. All patents and publications cited in this specification are incorporated herein by reference in their entireties.

Terms

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

By "optional" or "optionally," it is meant that the subsequently described event or circumstance may or may not occur, and that the description includes instances where the event or circumstance occurs and instances in which it does not. For example, "optionally substituted aryl" encompasses both "aryl" and "substituted aryl" as defined herein. It will be understood by those ordinarily skilled in the art, with respect to any group containing one or more substituents, that such groups are not intended to introduce any substitution or substitution patterns that are sterically impractical, synthetically non-feasible, and/or inherently unstable.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bonded to a halogen atom, a hydroxyl group, or any other substituent described herein. Thus the term "optionally substituted" means that a given chemical moiety has the potential to contain other functional groups, but does not necessarily have any further functional groups.

The term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—$C_1$-$C_6$alkyl, —$C_1$-$C_6$alkyl, —$OC_2$-$C_6$alkenyl, —$OC_2$-$C_6$alkynyl, —$C_2$-$C_6$alkenyl, —$C_2$-$C_6$alkynyl, —OH, —OP(O)(OH)$_2$, —OC(O)$C_1$-$C_6$alkyl, —C(O)$C_1$-$C_6$alkyl, —OC(O)O$C_1$-$C_6$alkyl, —NH$_2$, —NH($C_1$-$C_6$alkyl), —N($C_1$-$C_6$alkyl)$_2$, —S(O)$_2$—$C_1$-$C_6$alkyl, —S(O)NH$C_1$-$C_6$alkyl, and —S(O)N($C_1$-$C_6$alkyl)$_2$. The substituents can themselves be optionally substituted.

Unless otherwise specifically defined, "heteroaryl" means a monovalent or multivalent monocyclic aromatic radical or a polycyclic aromatic radical of 5 to 24 ring atoms, containing one or more ring heteroatoms selected from N, S, P, and O, the remaining ring atoms being C. Heteroaryl as herein defined also means a bicyclic heteroaromatic group wherein the heteroatom is selected from N, S, P, and O. The term also includes multiple condensed ring systems that have at least one such aromatic ring, which multiple condensed ring systems are further described below. The term also includes multiple condensed ring systems (e.g., ring systems comprising 2, 3 or 4 rings) wherein a heteroaryl group, as defined above, can be condensed with one or more rings selected from heteroaryls (to form for example a naphthyridinyl such as 1,8-naphthyridinyl), heterocycles, (to form for example a 1, 2, 3, 4-tetrahydronaphthyridinyl such as 1, 2, 3, 4-tetrahydro-1,8-naphthyridinyl), carbocycles (to form for example 5,6,7,8-tetrahydroquinolyl) and aryls (to form for example indazolyl) to form the multiple condensed ring system. The rings of the multiple condensed ring system can be connected to each other via fused, spiro and bridged bonds when allowed by valency requirements. It is to be understood that the individual rings of the multiple condensed ring system may be connected in any order relative to one another. It is also to be understood that the point of attachment of a multiple condensed ring system (as defined above for a heteroaryl) can be at any position of the multiple condensed ring system including a heteroaryl, heterocycle, aryl or carbocycle portion of the multiple condensed ring system and at any suitable atom of the multiple condensed ring system including a carbon atom and heteroatom (e.g., a nitrogen). The heteroaromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, dihydrobenzoxanyl, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzooxazolyl, benzoisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof.

"Alkyl" refers to a straight or branched chain saturated hydrocarbon. $C_1$-$C_6$alkyl groups contain 1 to 6 carbon atoms. Examples of a $C_1$-$C_6$alkyl group include, but are not limited to, methyl, ethyl, propyl, butyl, pentyl, isopropyl, isobutyl, sec-butyl and tert-butyl, isopentyl and neopentyl.

The term "alkenyl" means an aliphatic hydrocarbon group containing a carbon-carbon double bond and which may be straight or branched having about 2 to about 6 carbon atoms in the chain. Certain alkenyl groups have 2 to about 4 carbon atoms in the chain. Branched means that one or more lower alkyl groups such as methyl, ethyl, or propyl are attached to a linear alkenyl chain. Exemplary alkenyl groups include ethenyl, propenyl, n-butenyl, and i-butenyl. A $C_2$-$C_6$ alkenyl group is an alkenyl group containing between 2 and 6 carbon atoms.

The term "alkynyl" means an aliphatic hydrocarbon group containing a carbon-carbon triple bond and which may be straight or branched having about 2 to about 6 carbon atoms in the chain. Certain alkynyl groups have 2 to about 4 carbon atoms in the chain. Branched means that one or more lower alkyl groups such as methyl, ethyl, or propyl are attached to a linear alkynyl chain. Exemplary alkynyl groups include ethynyl, propynyl, n-butynyl, 2-butynyl, 3-methylbutynyl, and n-pentynyl. A $C_2$-$C_6$ alkynyl group is an alkynyl group containing between 2 and 6 carbon atoms.

The term "cycloalkyl" means monocyclic or polycyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl. A $C_3$-$C_8$ cycloalkyl is a cycloalkyl group containing between 3 and 8 carbon atoms. A cycloalkyl group can be fused (e.g., decalin) or bridged (e.g., norbornane).

The term "cycloalkenyl" means monocyclic, non-aromatic unsaturated carbon rings containing 4-18 carbon atoms. Examples of cycloalkenyl groups include, without limitation, cyclopentenyl, cyclohexenyl, cycloheptenyl, cyclooctenyl, and norborenyl. A $C_4$-$C_8$ cycloalkenyl is a cycloalkenyl group containing between 4 and 8 carbon atoms.

The terms "heterocyclyl" or "heterocycloalkyl" or "heterocycle" refer to monocyclic or polycyclic 3 to 24-membered rings containing carbon and heteroatoms selected from oxygen, phosphorus, nitrogen, and sulfur and wherein there are no delocalized 7n electrons (aromaticity) shared among the ring carbon or heteroatoms. Heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl. A heteroycyclyl or heterocyclalkyl ring can also be fused or bridged, e.g., can be a bicyclic ring.

In some embodiments "heterocyclyl" or "heterocycloalkyl" or "heterocycle" is a saturated, partially saturated or unsaturated, mono or bicyclic ring containing 3-24 atoms of which at least one atom is chosen from nitrogen, sulfur or oxygen, which may, unless otherwise specified, be carbon or nitrogen linked, wherein a —$CH_2$— group can optionally be replaced by a —C(O)— or a ring sulfur atom may be optionally oxidised to form the S-oxides. "Heterocyclyl" can be a saturated, partially saturated or unsaturated, mono or bicyclic ring containing 5 or 6 atoms of which at least one atom is chosen from nitrogen, sulfur or oxygen, which may, unless otherwise specified, be carbon or nitrogen linked, wherein a —$CH_2$— group can optionally be replaced by a —C(O)— or a ring sulfur atom may be optionally oxidised to form S-oxide(s). Non-limiting examples and suitable values of the term "heterocyclyl" are thiazolidinyl, pyrrolidinyl, pyrrolinyl, 2-pyrrolidonyl, 2,5-dioxopyrrolidinyl, 2-benzoxazolinonyl, 1,1-dioxotetrahydro thienyl, 2,4-dioxoimidazolidinyl, 2-oxo-1,3,4-(4-triazolinyl), 2-oxazolidinonyl, 5,6-dihydro uracilyl, 1,3-benzodioxolyl, 1,2,4-oxadiazolyl, 2-azabicyclo[2.2.1]heptyl, 4-thiazolidonyl, morpholino, 2-oxotetrahydrofuranyl, tetrahydrofuranyl, 2,3-dihydrobenzofuranyl, benzothienyl, tetrahydropyranyl, piperidyl, 1-oxo-1,3-dihydroisoindolyl, piperazinyl, thiomorpholino, 1,1-dioxothiomorpholino, tetrahydropyranyl, 1,3-dioxolanyl, homopiperazinyl, thienyl, isoxazolyl, imidazolyl, pyrrolyl, thiadiazolyl, isothiazolyl, 1,2,4-triazolyl, 1,3,4-triazolyl, pyranyl, indolyl, pyrimidyl, thiazolyl, pyrazinyl, pyridazinyl, pyridyl, 4-pyridonyl, quinolyl and 1-isoquinolonyl.

As used herein, the term "halo" or "halogen" means a fluoro, chloro, bromo, or iodo group.

The term "carbonyl" refers to a functional group comprising a carbon atom double-bonded to an oxygen atom. It can be abbreviated herein as "oxo", as C(O), or as C=O.

"Spirocycle" or "spirocyclic" means carbogenic bicyclic ring systems with both rings connected through a single atom. The ring can be different in size and nature, or identical in size and nature. Examples include spiropentane, spirohexane, spiroheptane, spirooctane, spirononane, or spirodecane. One or both of the rings in a spirocycle can be fused to another carbocyclic, heterocyclic, aromatic, or heteroaromatic ring. One or more of the carbon atoms in the spirocycle can be substituted with a heteroatom (e.g., O, N, S, or P). A $C_5$-$C_{12}$ spirocycle is a spirocycle containing between 5 and 12 carbon atoms. In some embodiments, a $C_5$-$C_{12}$ spirocycle is a spirocycle containing from 5 to 12 carbon atoms. One or more of the carbon atoms can be substituted with a heteroatom.

The term "spirocyclic heterocycle" "spiroheterocyclyl" or "spiroheterocycle" is understood to mean a spirocycle wherein at least one of the rings is a heterocycle (e.g., at least one of the rings is furanyl, morpholinyl, or piperadinyl). A spirocyclic heterocycle can contain between 5 and 12 atoms, at least one of which is a heteroatom selected from N, O, S and P. In some embodiments, a spirocyclic heterocycle can contain from 5 to 12 atoms, at least one of which is a heteroatom selected from N, O, S and P.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzoate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the present disclosure.

For example, compounds of the present disclosure can exist in tautomeric form. In some embodiments of Formula I, I', II, II', III, III', IV, IV', V, or VI, $X^1$ can be $CR^2$ and $R^2$ can be oxygen and $X^2$ can be nitrogen and tautomers of the compounds can exist in equilibrium:

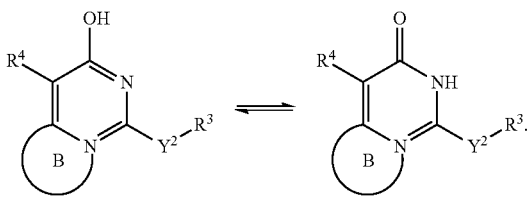

Compounds of the present disclosure can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the present disclosure can be replaced or substituted with isotopes of the atoms in natural or non-natural abundance. In some embodiments, the compound comprises at least one deuterium atom. For example, one or more hydrogen atoms in a compound of the present disclosure can be replaced or substituted by deuterium. In some embodiments, the compound comprises two or more deuterium atoms. In some embodiments, the compound comprises 1, 2, 3, 4, 5, 6, 7, 8, 9, 10, 11 or 12 deuterium atoms. Synthetic methods for including isotopes into organic compounds are known in the art.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

The term "solvate" refers to a complex of variable stoichiometry formed by a solute and solvent. Such solvents for the purpose of the present disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula I may have one or more asymmetric carbon atom and may occur as racemates, racemic mixtures and as individual enantiomers or diastereomers.

The term "stereoisomers" refers to the set of compounds which have the same number and type of atoms and share the same bond connectivity between those atoms, but differ in three dimensional structure. The term "stereoisomer" refers to any member of this set of compounds. For instance, a stereoisomer may be an enantiomer or a diastereomer.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomers. The term "diastereomer" refers to any member of this set of compounds. In some examples presented, the synthetic route may produce a single diastereomer or a mixture of diastereomers.

An "effective amount" when used in connection with a compound is an amount effective for treating or preventing a disease in a subject as described herein.

The term "carrier", as used in this disclosure, encompasses excipients and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "prevent" or "preventing" with regard to a subject refers to keeping a disease or disorder from afflicting the subject. Preventing includes prophylactic treatment. For instance, preventing can include administering to the subject a compound disclosed herein before a subject is afflicted with a disease and the administration will keep the subject from being afflicted with the disease.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

A "patient" or "subject" is a mammal, e.g., a human, mouse, rat, guinea pig, dog, cat, horse, cow, pig, or non-human primate, such as a monkey, chimpanzee, baboon or rhesus.

Compounds of Disclosed Formulae

In a first aspect, compounds of Formula I' are described:

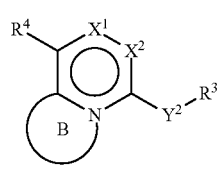

and pharmaceutically acceptable salts, prodrugs, solvates, hydrates, tautomers, or isomers thereof, wherein B, $X^1$, $X^2$, $R^3$, $R^4$, and $Y^2$ are described as above.

In another aspect, compounds of Formula I are described:

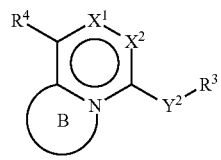

I and pharmaceutically acceptable salts, prodrugs, solvates, hydrates, tautomers, or isomers thereof, wherein B, $X^1$, $X^2$, $R^3$, $R^4$, and $Y^2$ are described as above.

In another aspect, compounds of the Formula II' are described:

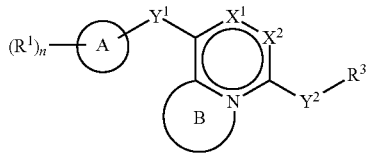

II' and pharmaceutically acceptable salts, prodrugs, solvates, hydrates, tautomers, or isomers thereof, wherein A, B, $X^1$, $X^2$, $R^1$, $R^3$, $Y^1$, $Y^2$, and n are described as above.

In another aspect, compounds of the Formula II are described:

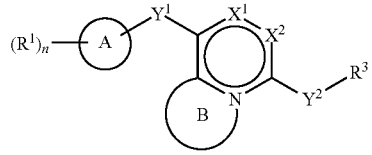

II and pharmaceutically acceptable salts, prodrugs, solvates, hydrates, tautomers, or isomers thereof, wherein A, B, $X^1$, $X^2$, $R^1$, $R^3$, $Y^1$, $Y^2$, and n are described as above.

In another aspect, compounds of the Formula III' are described:

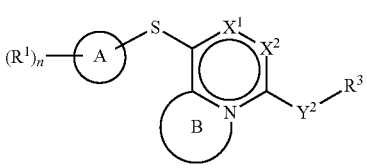

III' and pharmaceutically acceptable salts, prodrugs, solvates, hydrates, tautomers, or isomers thereof, wherein A, B, $X^1$, $X^2$, $R^1$, $R^3$, $Y^2$, and n are described as above.

In another aspect, compounds of the Formula III are described:

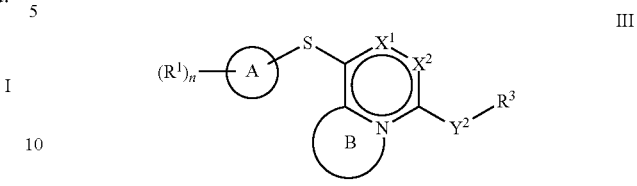

III and pharmaceutically acceptable salts, prodrugs, solvates, hydrates, tautomers, or isomers thereof, wherein A, B, $X^1$, $X^2$, $R^1$, $R^3$, $Y^2$, and n are described as above.

In another aspect, compounds of the Formula IV' are described:

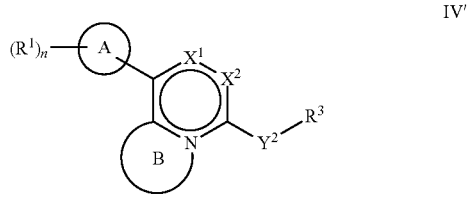

IV' and pharmaceutically acceptable salts, prodrugs, solvates, hydrates, tautomers, or isomers thereof, wherein A, B, $X^1$, $X^2$, $R^1$, $R^3$, $Y^2$, and n are described as above.

In another aspect, compounds of the Formula IV are described:

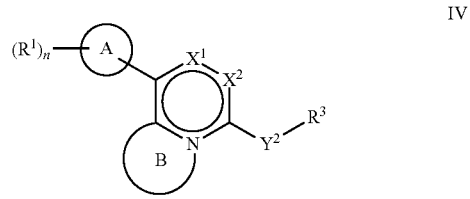

IV and pharmaceutically acceptable salts, prodrugs, solvates, hydrates, tautomers, or isomers thereof, wherein A, B, $X^1$, $X^2$, $R^1$, $R^3$, $Y^2$, and n are described as above.

In another aspect, compounds of the Formula V are described:

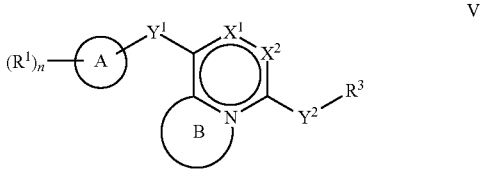

V and pharmaceutically acceptable salts, prodrugs, solvates, hydrates, tautomers, or isomers thereof, wherein A, B, $X^1$, $X^2$, $R^1$, $R^3$, $Y^1$, $Y^2$, and n are described as above.

In another aspect, compounds of the Formula VI are described:

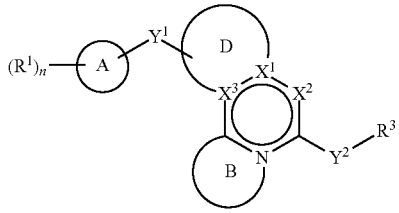

VI and pharmaceutically acceptable salts, prodrugs, solvates, hydrates, tautomers, or isomers thereof, wherein A, B, D, $X^1$, $X^2$, $X^3$, $R^1$, $R^3$, $Y^1$, $Y^2$, and n are described as above.

In certain embodiments of Formula I and I', the compound is of Formula I-A:

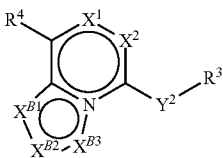

I-A and pharmaceutically acceptable salts, prodrugs, solvates, hydrates, tautomers, and isomers thereof, wherein $X^{B1}$ is N, CH, S, or O; $X^{B2}$ is N, CH, S, or O; and $X^{B3}$ is N, CH, S, or O.

In certain embodiments, $X^{B1}$ is N. In certain embodiments, $X^{B1}$ is CH. In certain embodiments, $X^{B1}$ is S. In certain embodiments, $X^{B1}$ is O. In certain embodiments, $X^{B2}$ is N. In certain embodiments, $X^{B2}$ is CH. In certain embodiments, $X^{B2}$ is S. In certain embodiments, $X^{B2}$ is O. In certain embodiments, $X^{B3}$ is N. In certain embodiments, $X^{B3}$ is CH. In certain embodiments, $X^{B3}$ is S. In certain embodiments, $X^{B3}$ is O.

In certain embodiments, $X^{B1}$ is N or CH; $X^{B2}$ is N or CH; and $X^{B3}$ is N or CH. In certain embodiments, $X^{B1}$ is N. In certain embodiments, $X^{B1}$ is CH. In certain embodiments, $X^{B2}$ is N. In certain embodiments, $X^{B2}$ is CH. In certain embodiments, $X^{B3}$ is N. In certain embodiments, $X^{B3}$ is CH.

In certain embodiments of Formula I-A,

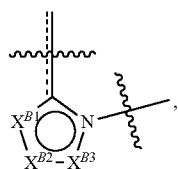

wherein ----- is a single bond or double bond to satisfy valency rules, is

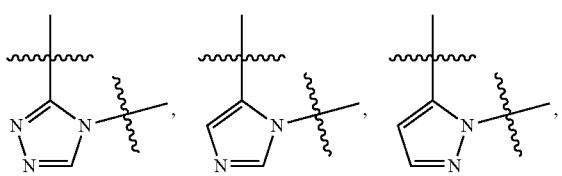

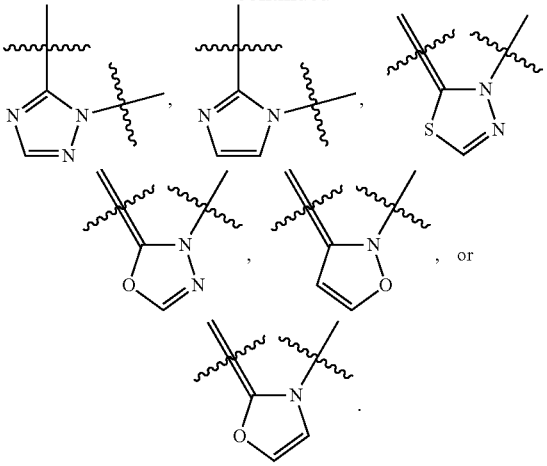

In certain embodiments of Formula I and I', the compound is of Formula I-B:

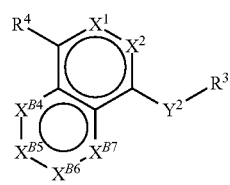

I-B and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments, $X^{B4}$ is N. In certain embodiments, $X^{B4}$ is CH. In certain embodiments, $X^{B5}$ is N. In certain embodiments, $X^{B5}$ is CH. In certain embodiments, $X^{B6}$ is N. In certain embodiments, $X^{B6}$ is CH. In certain embodiments, $X^{B7}$ is N. In certain embodiments, $X^{B7}$ is CH.

In certain embodiments of Formula I and I', the compound is of Formula I-C:

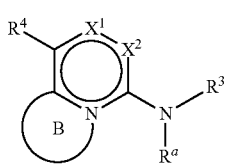

I-C and pharmaceutically acceptable salts, prodrugs, solvates, hydrates, tautomers, and isomers thereof.

In certain embodiments of Formula I and I', the compound is of Formula I-D:

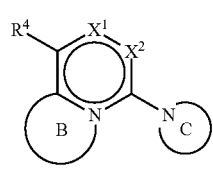

I-D and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with —$C_1$-$C_6$alkyl, —OH, or —$NH_2$.

In certain embodiments of Formula I-D, C ring, along with the nitrogen atom to which it is attached, is an optionally substituted 3- to 12-membered monocyclic heterocycle. In certain embodiments, C ring, along with the nitrogen atom to which it is attached, is an optionally substituted 3- to 12-membered polycyclic heterocycle. In certain embodiments, C ring, along with the nitrogen atom to which it is attached, is an optionally substituted 5- to 12-membered spiroheterocycle.

In certain embodiments of Formula I-D, C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is substituted with —$NH_2$.

In certain embodiments, C ring, along with the nitrogen atom to which it is attached, is an optionally substituted

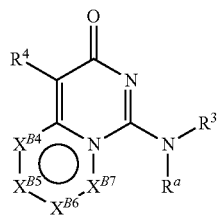

In certain embodiments, C ring, along with the nitrogen atom to which it is attached, is an optionally substituted

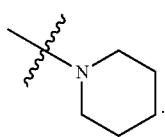

In certain embodiments of Formula I and I', the compound is of Formula I-E:

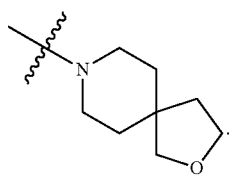 [SMILES: *N1CCC2(CCOC2)CC1]

I-E and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula I and I', the compound is of Formula I-F:

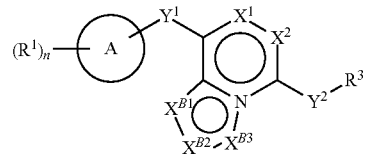

I-F and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula I and I', $R^4$ is H. In certain embodiments, $R^4$ is

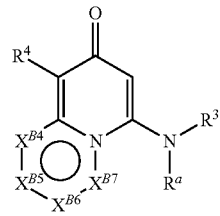

In certain embodiments of Formula II and II', the compound is of Formula II-A:

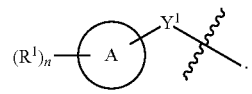

II-A and pharmaceutically acceptable salts, prodrugs, solvates, hydrates, tautomers, and isomers thereof, wherein $X^{B1}$ is N, CH, S, or O; $X^{B2}$ is N, CH, S, or O; and $X^{B3}$ is N, CH, S, or O.

In certain embodiments, $X^{B1}$ is N. In certain embodiments, $X^{B1}$ is CH. In certain embodiments, $X^{B1}$ is S. In certain embodiments, $X^{B1}$ is O. In certain embodiments, $X^{B2}$ is N. In certain embodiments, $X^{B2}$ is CH. In certain embodiments, $X^{B2}$ is S. In certain embodiments, $X^{B2}$ is O. In certain embodiments, $X^{B3}$ is N. In certain embodiments, $X^{B3}$ is CH. In certain embodiments, $X^{B3}$ is S. In certain embodiments, $X^{B3}$ is O.

In certain embodiments, $X^{B1}$ is N or CH; $X^{B2}$ is N or CH; and $X^{B3}$ is N or CH. In certain embodiments, $X^{B1}$ is N. In certain embodiments, $X^{B1}$ is CH. In certain embodiments, $X^{B2}$ is N. In certain embodiments, $X^{B2}$ is CH. In certain embodiments, $X^{B3}$ is N. In certain embodiments, $X^{B3}$ is CH.

In certain embodiments of Formula II-A,

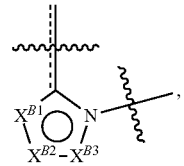

wherein ----- is a single bond or double bond to satisfy valency rules, is

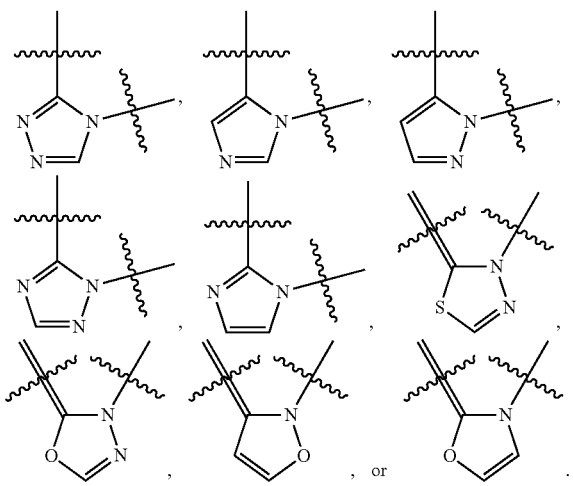

In certain embodiments of Formula II and II', the compound is of Formula II-B:

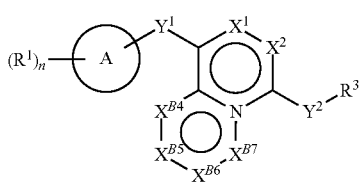

II-B and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments, $X^{B4}$ is N. In certain embodiments, $X^{B4}$ is CH. In certain embodiments, $X^{B5}$ is N. In certain embodiments, $X^{B5}$ is CH. In certain embodiments, $X^{B6}$ is N. In certain embodiments, $X^{B6}$ is CH. In certain embodiments, $X^{B7}$ is N. In certain embodiments, $X^{B7}$ is CH.

In certain embodiments of Formula II and II', the compound is of Formula II-C:

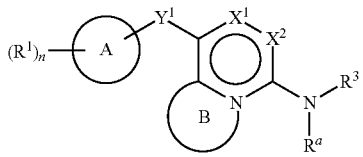

II-C and pharmaceutically acceptable salts, prodrugs, solvates, hydrates, tautomers, and isomers thereof.

In certain embodiments of Formula II and II', the compound is of Formula II-D:

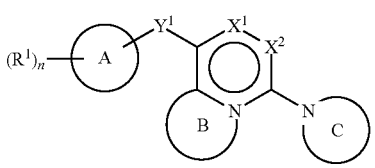

II-D and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with —$C_1$-$C_6$alkyl, —OH, or —$NH_2$.

In certain embodiments of Formula II-D, C ring, along with the nitrogen atom to which it is attached, is an optionally substituted 3- to 12-membered monocyclic heterocycle. In certain embodiments, C ring, along with the nitrogen atom to which it is attached, is an optionally substituted 3- to 12-membered polycyclic heterocycle. In certain embodiments, C ring, along with the nitrogen atom to which it is attached, is an optionally substituted 5- to 12-membered spiroheterocycle.

In certain embodiments of Formula II-D, C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is substituted with —$NH_2$.

In certain embodiments, C ring, along with the nitrogen atom to which it is attached, is an optionally substituted

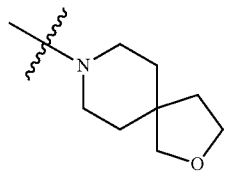

In certain embodiments, C ring, along with the nitrogen atom to which it is attached, is an optionally substituted

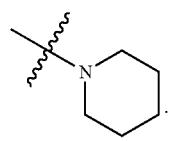 [SMILES: *N1CCCCC1]

In certain embodiments of Formula II and II', the compound is of Formula II-E:

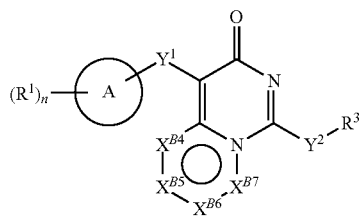

II-E and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula II and II', the compound is of Formula II-F:

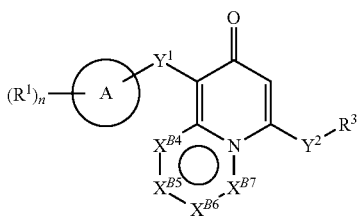

II-F and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula III and III', the compound is of Formula III-A:

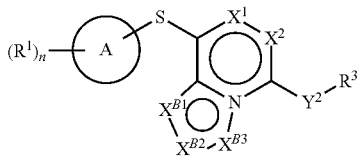

III-A and pharmaceutically acceptable salts, prodrugs, solvates, hydrates, tautomers, and isomers thereof, wherein $X^{B1}$ is N, CH, S, or O; $X^{B2}$ is N, CH, S, or O; and $X^{B3}$ is N, CH, S, or O.

In certain embodiments, $X^{B1}$ is N. In certain embodiments, $X^{B1}$ is CH. In certain embodiments, $X^{B1}$ is S. In certain embodiments, $X^{B1}$ is O. In certain embodiments, $X^{B2}$ is N. In certain embodiments, $X^{B2}$ is CH. In certain embodiments, $X^{B2}$ is S. In certain embodiments, $X^{B2}$ is O. In certain embodiments, $X^{B3}$ is N. In certain embodiments, $X^{B3}$ is CH. In certain embodiments, $X^{B3}$ is S. In certain embodiments, $X^{B3}$ is O.

In certain embodiments, $X^{B1}$ is N or CH; $X^{B2}$ is N or CH; and $X^{B3}$ is N or CH. In certain embodiments, $X^{B1}$ is N. In certain embodiments, $X^{B1}$ is CH. In certain embodiments, $X^{B2}$ is N. In certain embodiments, $X^{B2}$ is CH. In certain embodiments, $X^{B3}$ is N. In certain embodiments, $X^{B3}$ is CH.

In certain embodiments of Formula III-A,

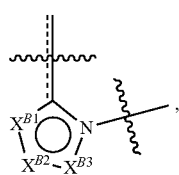

wherein ----- is a single bond or double bond to satisfy valency rules, is

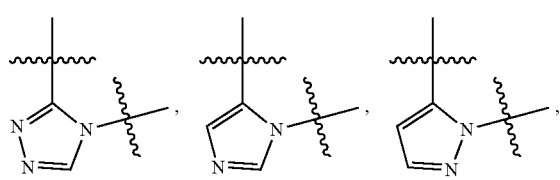

-continued

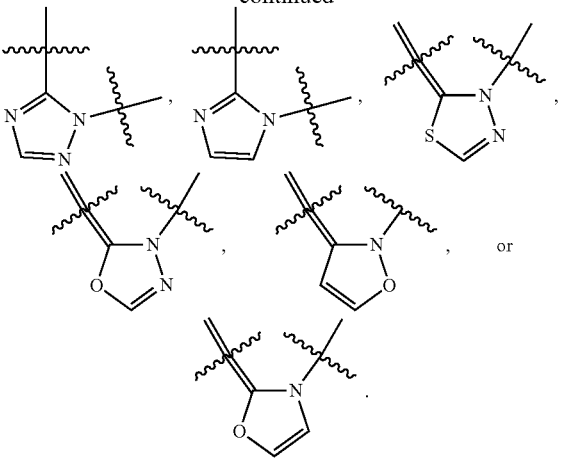

or

In certain embodiments of Formula III and III', the compound is of Formula III-B:

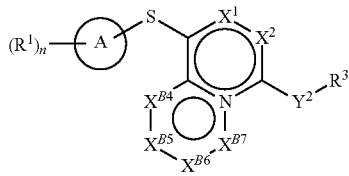

III-B and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments, $X^{B4}$ is N. In certain embodiments, $X^{B4}$ is CH. In certain embodiments, $X^{B5}$ is N. In certain embodiments, $X^{B5}$ is CH. In certain embodiments, $X^{B6}$ is N. In certain embodiments, $X^{B6}$ is CH. In certain embodiments, $X^{B7}$ is N. In certain embodiments, $X^{B7}$ is CH.

In certain embodiments of Formula III and III', the compound is of Formula III-C:

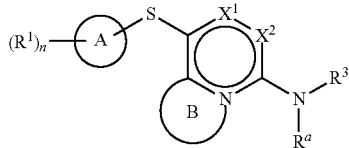

III-C and pharmaceutically acceptable salts, prodrugs, solvates, hydrates, tautomers, and isomers thereof.

In certain embodiments of Formula III and III', the compound is of Formula III-D:

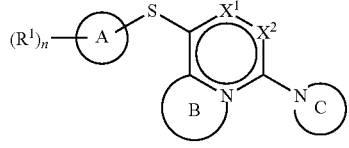

III-D and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with —$C_1$-$C_6$alkyl, —OH, or —$NH_2$.

In certain embodiments of Formula III-D, C ring, along with the nitrogen atom to which it is attached, is an optionally substituted 3- to 12-membered monocyclic heterocycle. In certain embodiments, C ring, along with the nitrogen atom to which it is attached, is an optionally substituted 3- to 12-membered polycyclic heterocycle. In certain embodiments, C ring, along with the nitrogen atom to which it is attached, is an optionally substituted 5- to 12-membered spiroheterocycle.

In certain embodiments of Formula III-D, C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is substituted with —$NH_2$.

In certain embodiments, C ring, along with the nitrogen atom to which it is attached, is an optionally substituted

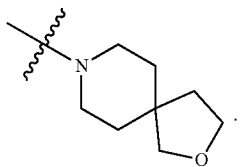 [SMILES: *N1CCC2(CCOC2)CC1]

In certain embodiments, C ring, along with the nitrogen atom to which it is attached, is an optionally substituted

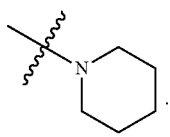 [SMILES: *N1CCCCC1]

In certain embodiments of Formula III and III', the compound is of Formula III-E:

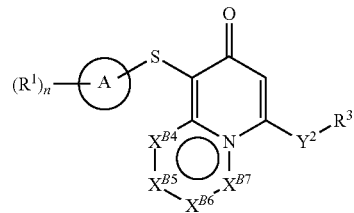

III-E and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula III and III', the compound is of Formula III-F:

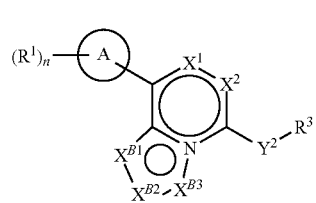

III-F and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula IV and IV', the compound is of Formula IV-A:

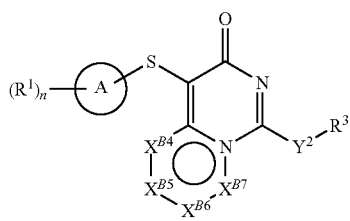

IV-A and pharmaceutically acceptable salts, prodrugs, solvates, hydrates, tautomers, and isomers thereof, wherein $X^{B1}$ is N, CH, S, or O; $X^{B2}$ is N, CH, S, or O; and $X^{B3}$ is N, CH, S, or O.

In certain embodiments, $X^{B1}$ is N. In certain embodiments, $X^{B1}$ is CH. In certain embodiments, $X^{B1}$ is S. In certain embodiments, $X^{B1}$ is O. In certain embodiments, $X^{B2}$ is N. In certain embodiments, $X^{B2}$ is CH. In certain embodiments, $X^{B2}$ is S. In certain embodiments, $X^{B2}$ is O. In certain embodiments, $X^{B3}$ is N. In certain embodiments, $X^{B3}$ is CH. In certain embodiments, $X^{B3}$ is S. In certain embodiments, $X^{B3}$ is O.

In certain embodiments, $X^{B1}$ is N or CH; $X^{B2}$ is N or CH; and $X^{B3}$ is N or CH. In certain embodiments, $X^{B1}$ is N. In certain embodiments, $X^{B1}$ is CH. In certain embodiments, $X^{B2}$ is N. In certain embodiments, $X^{B2}$ is CH. In certain embodiments, $X^{B3}$ is N. In certain embodiments, $X^{B3}$ is CH.

In certain embodiments of Formula IV-A,

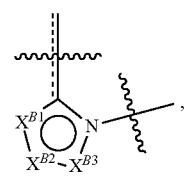

wherein ----- is a single bond or double bond to satisfy valency rules, is

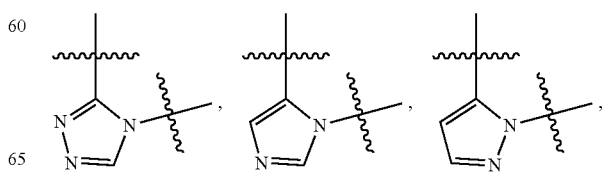

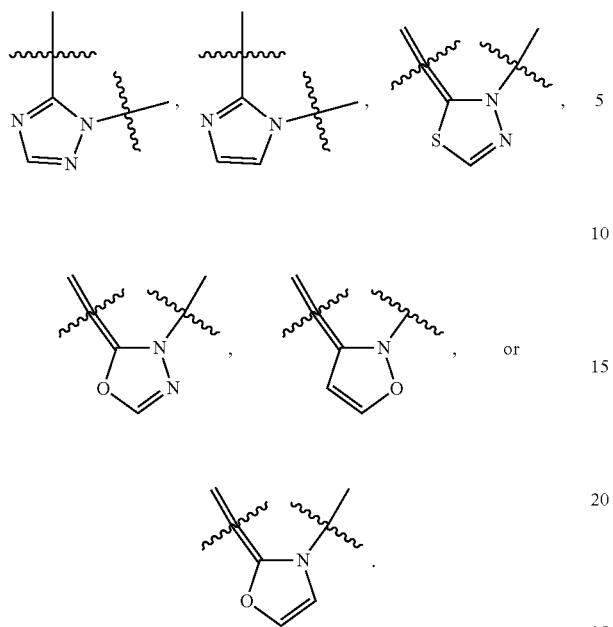

In certain embodiments of Formula IV and IV', the compound is of Formula IV-B:

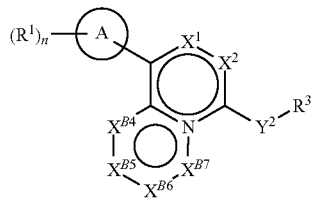

IV-B and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments, $X^{B4}$ is N. In certain embodiments, $X^{B4}$ is CH. In certain embodiments, $X^{B5}$ is N. In certain embodiments, $X^{B5}$ is CH. In certain embodiments, $X^{B6}$ is N. In certain embodiments, $X^{B6}$ is CH. In certain embodiments, $X^{B7}$ is N. In certain embodiments, $X^{B7}$ is CH.

In certain embodiments of Formula IV and IV', the compound is of Formula IV-C:

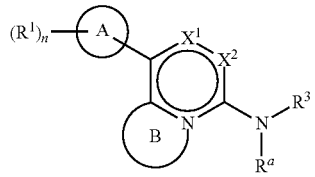

IV-C and pharmaceutically acceptable salts, prodrugs, solvates, hydrates, tautomers, and isomers thereof.

In certain embodiments of Formula IV and IV', the compound is of Formula IV-D:

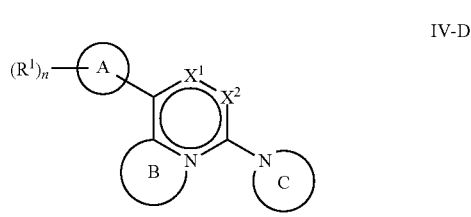

IV-D and pharmaceutically acceptable salts, prodrugs, solvates, hydrates, tautomers, and isomers thereof, wherein:

C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is optionally substituted with —$C_1$-$C_6$alkyl, —OH, or —$NH_2$.

In certain embodiments of Formula IV-D, C ring, along with the nitrogen atom to which it is attached, is an optionally substituted 3- to 12-membered monocyclic heterocycle. In certain embodiments, C ring, along with the nitrogen atom to which it is attached, is an optionally substituted 3- to 12-membered polycyclic heterocycle. In certain embodiments, C ring, along with the nitrogen atom to which it is attached, is an optionally substituted 5- to 12-membered spiroheterocycle.

In certain embodiments of Formula IV-D, C forms a 3- to 12-membered monocyclic heterocycle, 3- to 12-membered polycyclic heterocycle, or a 5- to 12-membered spiroheterocycle, along with the nitrogen atom to which it is attached, wherein the heterocycle or spiroheterocycle is substituted with —$NH_2$.

In certain embodiments, C ring, along with the nitrogen atom to which it is attached, is an optionally substituted

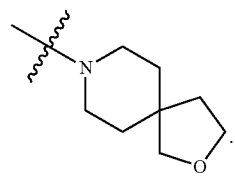 [SMILES: *N1CCC2(CCOC2)CC1]

In certain embodiments, C ring, along with the nitrogen atom to which it is attached, is an optionally substituted

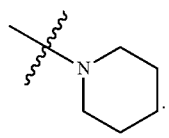

In certain embodiments of Formula IV and IV', the compound is of Formula IV-E:

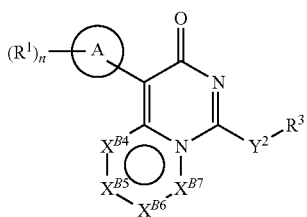

IV-E and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

In certain embodiments of Formula IV and IV', the compound is of Formula IV-F:

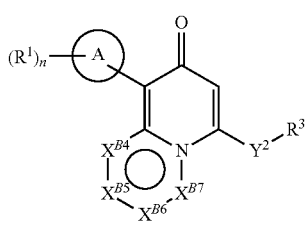

IV-F and pharmaceutically acceptable salts, prodrugs, solvates, hydrates, tautomers, and isomers thereof, wherein $X^{B4}$ is N or CH; $X^{B5}$ is N or CH; $X^{B6}$ is N or CH; and $X^{B7}$ is N or CH.

Certain embodiments of Formula I-IV and I'-IV' and V-VI are described below.

In certain embodiments, $Y^1$ is —S—. In certain embodiments, $Y^1$ is a direct bond. In certain embodiments, $Y^1$ is —NH—. In certain embodiments, $Y^1$ is —C(=CH$_2$)— or —CH$_2$—. In certain embodiments, $Y^1$ is —S(O)$_2$—, —S(O)$_2$—NH—, or —S(O)—.

In certain embodiments, $X^1$ is N. In certain embodiments, $X^1$ is $CR^2$. In certain embodiments, $R^2$ is —H, —NH$_2$, —OR$^b$, or —C$_1$-C$_6$alkyl. In certain embodiments, $R^2$ is —H, —NH$_2$, —OH, or —CH$_3$.

In certain embodiments, $X^2$ is N. In certain embodiments, $X^2$ is CH.

In certain embodiments, $X^1$ is N and $X^2$ is N. In certain embodiments, $X^1$ is N and $X^2$ is CH. In certain embodiments, $X^1$ is $CR^2$ and $X^2$ is N. In certain embodiments, $X^1$ is C and $X^2$ is $CR^2$. In certain embodiments, $R^2$ is —H, —NH$_2$, —OH, or —C$_1$-C$_6$alkyl.

In certain embodiments, $R^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, or heteroaryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O) NR$^5$R$^6$, —NR$^5$S(O)R$^6$, heterocycle, aryl, or heteroaryl.

In certain embodiments, $R^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 het-eroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O) NR$^5$R$^6$, —NR$^5$S(O)R$^6$, heterocycle, aryl, or heteroaryl.

In certain embodiments, if $R^2$ is aryl, then the aryl is optionally substituted with one or more —OH, halogen, —NO$_2$, oxo, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O) R$^6$, heterocycle, aryl, or heteroaryl.

In certain embodiments, $R^2$ is —H. In certain embodiments, $R^2$ is —NH$_2$. In certain embodiments, $R^2$ is OH. In certain embodiments, $R^2$ is CH$_3$. In certain embodiments, $R^2$ is OR$^b$. In certain embodiments, $R^2$ is —C$_1$-C$_6$alkyl. In certain embodiments, $R^2$ is —CN. In certain embodiments, $R^2$ is —C$_2$-C$_6$alkenyl. In certain embodiments, $R^2$ is —C$_4$-C$_8$cycloalkenyl. In certain embodiments, $R^2$ is —C$_2$-C$_6$alkynyl. In certain embodiments, $R^2$ is —C$_3$-C$_8$cycloalkyl. In certain embodiments, $R^2$ is aryl. In certain embodiments, $R^2$ is heterocyclyl containing 1-5 heteroatoms selected from the group consisting of N, S, P, or O. In one or more embodiments, $R^2$ is or heteroaryl containing 1-5 heteroatoms selected from the group consisting of N, S, P, or O.

In certain embodiments, B, including the atoms at the points of attachment, is a monocyclic or polycyclic 5- to 12-membered heterocycle. In certain embodiments, B, including the atoms at the points of attachment, is a monocyclic 5 to 6-membered heterocycle. In certain embodiments, B, including the atoms at the points of attachment, is a monocyclic 7 to 12-membered heterocycle.

In certain embodiments, B, including the atoms at the points of attachment, is a polycyclic 5- to 12-membered heterocyclyl. In certain embodiments, the heteroycyclyl ring is fused. In certain embodiments, the heterocyclyl ring is bridged.

In one or more embodiments, B, including the atoms at the points of attachment, is a monocyclic or polycyclic 5- to 12-membered heteroaryl. In certain embodiments, B, including the atoms at the points of attachment, is a monocyclic 5 to 6-membered heteroaryl. In certain embodiments, B, including the atoms at the points of attachment, is a monocyclic 7 to 12-membered heteroaryl.

In certain embodiments, B, including the atoms at the points of attachment, is a polycyclic 5- to 12-membered heteroaryl. In certain embodiments, the polycyclic het-eroaryl is a multiple condensed ring as described above. The rings of the multiple condensed ring system can be connected to each other via fused, spiro and bridged bonds when allowed by valency requirements.

In certain embodiments, wherein B, including the atoms at the points of attachment, is

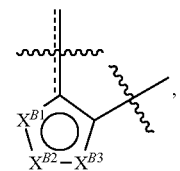

wherein $X^{B1}$ is N, CH, S, or O; $X^{B2}$ is N, CH, S, or O; $X^{B3}$ is N, CH, S, or O; and wherein ----- is a single bond or double bond to satisfy valency rules.

In certain embodiments, $X^{B1}$ is N. In certain embodiments, $X^{B1}$ is CH. In certain embodiments, $X^{B1}$ is S. In certain embodiments, $X^{B1}$ is O. In certain embodiments, $X^{B2}$ is N. In certain embodiments, $X^{B2}$ is CH. In certain embodiments, $X^{B2}$ is S. In certain embodiments, $X^{B2}$ is O. In certain embodiments, $X^{B3}$ is N. In certain embodiments, $X^{B3}$ is CH. In certain embodiments, $X^{B3}$ is S. In certain embodiments, $X^{B3}$ is O.

In certain embodiments, $X^{B1}$ is N or CH; $X^{B2}$ is N or CH; and $X^{B3}$ is N or CH. In certain embodiments, $X^{B1}$ is N. In certain embodiments, $X^{B1}$ is CH. In certain embodiments, $X^{B2}$ is N. In certain embodiments, $X^{B2}$ is CH. In certain embodiments, $X^{B3}$ is N. In certain embodiments, $X^{B3}$ is CH.

In certain embodiments, wherein B, including the atoms at the points of attachment, is

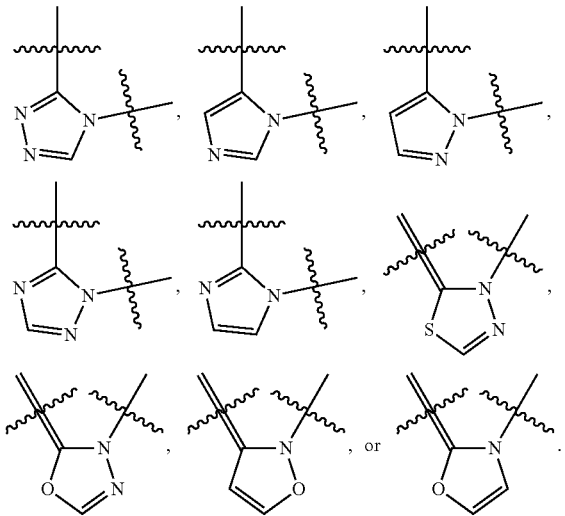

In certain embodiments, B, including the atoms at the points of attachment, is

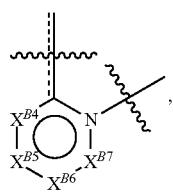

wherein $X^{B4}$ is N or CH; $X^{B5}$ is N or CH; $X^{B6}$ is N or CH; and $X^{B7}$ is N or CH; and wherein ----- is a single bond or double bond to satisfy valency rules.

In certain embodiments, $X^{B4}$ is N. In certain embodiments, $X^{B4}$ is CH. In certain embodiments, $X^{B5}$ is N. In certain embodiments, $X^{B5}$ is CH. In certain embodiments, $X^{B6}$ is N. In certain embodiments, $X^{B6}$ is CH. In certain embodiments, $X^{B7}$ is N. In certain embodiments, $X^{B7}$ is CH.

In certain embodiments, wherein B, including the atoms at the points of attachment, is

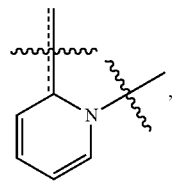

wherein ----- is a single bond or double bond to satisfy valency rules.

In certain embodiments of Formula VI, D, including the atoms at the points of attachment, is a monocyclic 5- to 7-membered heterocycle. In certain embodiments, D, including the atoms at the points of attachment, is a monocyclic 5 to 6-membered heterocycle.

In certain embodiments of Formula VI, D, including the atoms at the points of attachment, is a monocyclic 5- to 7-membered heteroaryl. In certain embodiments, D, including the atoms at the points of attachment, is a monocyclic 5 to 6-membered heteroaryl.

In certain embodiments of Formula VI, $X^3$ is N. In certain embodiments of Formula VI, $X^3$ is C.

In certain embodiments, A is a cycloalkyl. In certain embodiments, A is heterocycloalkyl. In certain embodiments, A is a monocyclic heterocycloalkyl. In certain embodiments, A is a bicyclic heterocycloalkyl. In certain embodiments, A is aryl. In certain embodiments, A is phenyl. In certain embodiments, A is heteroaryl. In certain embodiments, A is pyridyl.

In certain embodiments, A is 5- to 12-membered monocyclic heteroaryl. In certain embodiments, A is 5- to 12-membered polycyclic heteroaryl. In certain embodiments, A is 5- to 12-membered monocyclic aryl. In certain embodiments, A is 5- to 12-membered polycyclic aryl. In certain embodiments, A is 5- to 12-membered monocyclic heterocycloalkyl. In certain embodiments, A is 5- to 12-membered polycyclic heterocycloalkyl. In certain embodiments, A is 5- to 12-membered monocyclic cycloalkyl. In certain embodiments, A is 5- to 12-membered polycyclic cycloalkyl.

In certain embodiments, $R^1$ is independently —OH, —NO$_2$, —CN, halogen, or —NR$^5$R$^6$. In certain embodiments, n is 1. In certain embodiments, n is 2. In certain embodiments, n is 3. In certain embodiments, n is 4.

In certain embodiments, A, including $R^1$, is selected from the group consisting of

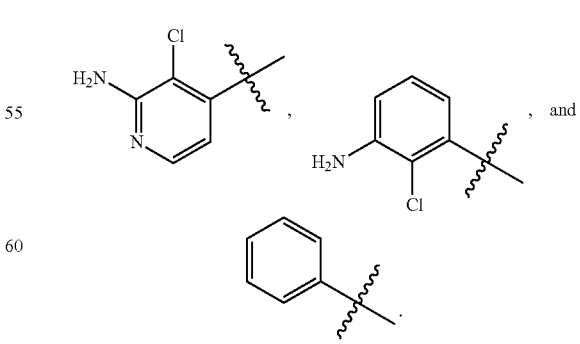

In certain embodiments, A, including $R^1$, is selected from the group consisting of

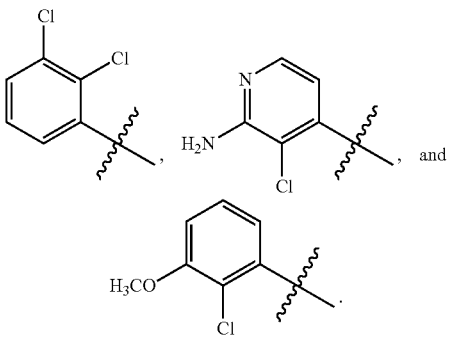

In certain embodiments, A, including $R^1$, is

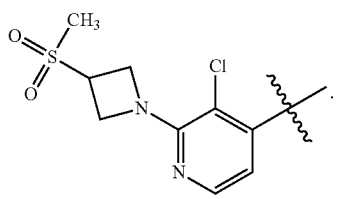 [SMILES: *c1ccnc(N2CC(S(C)(=O)=O)C2)c1Cl]

In certain embodiments, A, including $R^1$, is

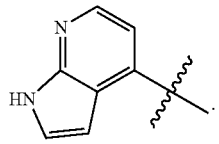

In certain embodiments, $Y^2$ is —$NR^a$—, —$(CR^a{}_2)_m$—, —$C(R^a)_2NH$—, —$(CR^a{}_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$C(O)O$—, —$OC(O)$—, —$OC(O)N(R^a)$—, —$N(R^a)C(O)O$—, —$C(O)N(R^a)O$—, —$N(R^a)C(S)$—, —$C(S)N(R^a)$—, or —$OC(O)O$—; wherein the bond on the left side of $Y^2$, as drawn, is bound to the ring and the bond on the right side of the $Y^2$ moiety, as drawn, is bound to $R^3$.

In certain embodiments, $Y^2$ is —$NR^a$—, —$(CR^a{}_2)_m$—, —$C(R^a)_2NH$—, —$(CR^a{}_2)_mO$—, —$S(O)_2N(R^a)$—, —$N(R^a)S(O)_2$—, —$N(R^a)C(S)N(R^a)$—, —$N(R^a)C(S)$—, or —$C(S)N(R^a)$—; wherein the bond on the left side of $Y^2$, as drawn, is bound to the ring and the bond on the right side of the $Y^2$ moiety, as drawn, is bound to $R^3$.

In certain embodiments, $Y^2$ is —$NR^a$—, —$C(R^a)_2NH$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —$OC(O)N(R^a)$—, —$N(R^a)C(O)O$—, —$C(O)N(R^a)O$—, —$N(R^a)C(S)$—, or —$C(S)N(R^a)$—; wherein the bond on the left side of $Y^2$, as drawn, is bound to the ring and the bond on the right side of the $Y^2$ moiety, as drawn, is bound to $R^3$.

In certain embodiments, $Y^2$ is —$NR^a$—. In certain embodiments, $Y^2$ is —$(CR^a{}_2)_m$—. In certain embodiments, $Y^2$ is —$C(O)$—. In certain embodiments, $Y^2$ is —$C(R^a)_2NH$— or —$(CR^a{}_2)_mO$—. In certain embodiments, $Y^2$ is —$C(O)N(R^a)$—, —$N(R^a)C(O)$—, —$S(O)_2N(R^a)$—, —$N(R^a)S(O)_2$—, —$N(R^a)C(S)$—, or —$C(S)N(R^a)$—. In certain embodiments, $Y^2$ is —$N(R^a)C(O)N(R^a)$—, —$N(R^a)C(S)N(R^a)$—, —$OC(O)N(R^a)$—, —$N(R^a)C(O)O$—, or —$C(O)N(R^a)O$—. In certain embodiments, $Y^2$ is —$C(O)O$—, —$OC(O)$—, or —$OC(O)O$—. In certain embodiments, $Y^2$ is —$O$—.

In certain embodiments, $R^a$ is —H. In certain embodiments, $R^a$ is —OH. In one or more embodiments, $R^a$ is —$C_3$-$C_8$cycloalkyl. In certain embodiments, $R^a$ is —$C_1$-$C_6$alkyl.

In certain embodiments, $R^3$ is —$C_1$-$C_6$alkyl. In certain embodiments, $R^3$ is 3- to 12-membered monocyclic or polycyclic heterocycle. In certain embodiments, $R^3$ is a 3- to 12-membered monocyclic heterocycle. In certain embodiments, $R^3$ is a 5- to 12-membered polycyclic heterocycle. In certain embodiments, $R^3$ is —$(CH_2)_nC(O)NR^5R^6$.

In certain embodiments, $R^3$ and $R^a$ together with the atom to which they are attached combine to form an optionally substituted 3- to 12-membered monocyclic heterocycle. In certain embodiments, $R^3$ and $R^a$ together with the atoms to which they are attached combine to form an optionally substituted 3- to 12-membered polycyclic heterocycle. In certain embodiments, $R^3$ and $R^a$ together with the atoms to which they are attached combine to form an optionally substituted 5- to 12-membered spiroheterocycle.

In certain embodiments, $R^3$ and $R^a$ together with the atom to which they are attached combine to form an optionally substituted

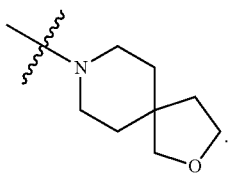 [SMILES: *N1CCC2(CCOC2)CC1]

In certain embodiments, $R^3$ and $R^a$ together with the atom to which they are attached combine to form an optionally substituted

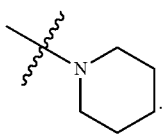

In certain embodiments, $R^3$ and $R^a$ together with the atom to which they are attached combine to form an optionally substituted

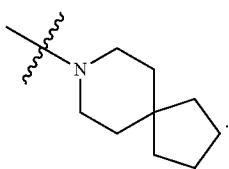 [SMILES: *N1CCC2(CCCC2)CC1]

In certain embodiments, $R^3$ and $R^a$ together with the atom to which they are attached combine to form a 3- to 12-membered monocyclic or polycyclic heterocycle or a 5- to 12-membered spiroheterocycle, wherein each heterocycle or spiroheterocycle is optionally substituted with one or more selected from the group consisting of $C_1$-$C_6$alkyl, —OH, halogen, —$NH_2$, —$NHR^b$, —$CF_3$, —$CHF_2$, or —$CH_2F$. In certain embodiments, the one or more substituent is selected from the group consisting of —$C_1$-$C_6$alkyl, halogen, —OH, —$OR^b$, —$NH_2$, —$NHR^b$, —$(CH_2)_nNH_2$, —$(CH_2)_nOH$, —$CF_3$, —$CHF_2$, —$CH_2F$, and =O. In certain embodiments, the one or more substituent is selected from the group consisting of $COOR^b$, —$CONHR^b$, —$CONH(CH_2)_nCOOR^b$, and —$NHCOOR^b$. In certain embodiments, the one or more substituent is —O—C(O)—$NR^5R^6$. In certain embodiments, the one or more substituent is an optionally substituted heteroaryl or optionally substituted heterocyclyl, wherein the heteroaryl and heterocyclyl are optionally substituted with —CN.

In certain embodiments, $R^3$ and $R^a$ together with the atom to which they are attached, and including the substituents, combine to form

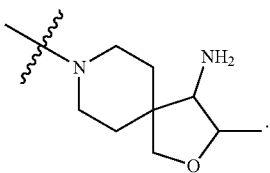 [SMILES: *N1CCC2(CC1)COC(C)C2N]

In certain embodiments, $R^3$ and $R^a$ together with the atom to which they are attached, and including the substituents, combine to form

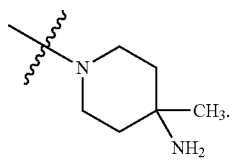 [SMILES: *N1CCC(C)(N)CC1]

In certain embodiments, $R^3$ and $R^a$ together with the atom to which they are attached combine to form

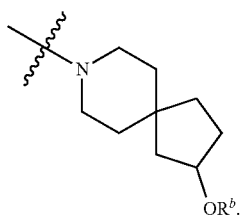

In certain embodiments, $R^3$ and $R^a$ together with the atom to which they are attached combine to form

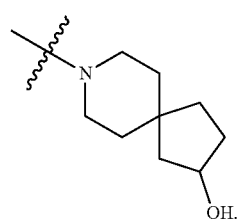 [SMILES: *N1CCC2(CCC(O)C2)CC1]

In certain embodiments, $R^3$ and $R^a$ together with the atom to which they are attached combine to form

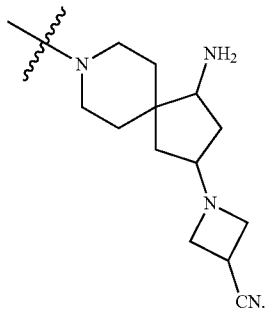 [SMILES: *N1CCC2(CC1)CC(N1CC(C#N)C1)CC2N]

In certain embodiments, $R^b$ is H. In one or more embodiments, $R^b$ is $C_1$-$C_6$ alkyl. In one or more embodiments, $R^b$ is —$C_1$-$C_6$cycloalkyl. In one or more embodiments, $R^b$ is —$C_2$-$C_6$alkenyl. In one or more embodiments, $R^b$ is heterocyclyl containing 1-5 heteroatoms selected from the group consisting of N, S, P, or O.

In certain embodiments, $R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN.

In certain embodiments, $R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN.

As described above, $R^7$ and $R^a$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN.

As described above, m is independently 1, 2, 3, 4, 5 or 6. In certain instances, m is 1. In certain instances, m is 2. In certain instances, m is 3. In certain instances, m is 4. In certain instances, m is 5. In certain instances, m is 6.

As described above, n is independently 0, 1, 2, 3, 4, 5, 6, 7, 8, 9, or 10. In certain instances, n is 0. In certain instances, n is 1. In certain instances, n is 2. In certain instances, n is 3. In certain instances, n is 4. In certain instances, n is 5. In certain instances, n is 6. In certain instances, n is 7. In certain instances, n is 8. In certain instances, n is 9. In certain instances, n is 10.

In one variation of Formula I, I', II, II', III, III', IV, IV', V, and VI, $X^1$ is $CR^2$; $R^2$ is H, —$NH_2$, —OH, or —$C_1$-$C_6$alkyl and B, including the atoms at the points of attachment, is a monocyclic 5 to 6-membered heteroaryl. In certain instances of Formula I, I', II, II', III, III', IV, IV', V, and VI, $X^1$ is $CR^2$; $R^2$ is H, —$NH_2$, —OH, or —$C_1$-$C_6$alkyl and B, including the atoms at the points of attachment, is a monocyclic 5-membered heteroaryl. In certain instances of Formula I, I', II, II', III, III', IV, IV', V, and VI, $X^1$ is $CR^2$; $R^2$ is H, —$NH_2$, —OH, or —$C_1$-$C_6$alkyl and B, including the atoms at the points of attachment, is a monocyclic 6-membered heteroaryl.

In one variation of Formula I, I', II, II', III, III', V, and VI, $Y^1$ is S and A is a cycloalkyl. In certain instances of Formula I, I', II, II', III, III', V, and VI, $Y^1$ is S and A is heterocycloalkyl. In certain instances of Formula I, I', II, II', III, III', V, and VI, $Y^1$ is S and A is aryl. In certain instances of Formula I, I', II, II', III, III', V, and VI, $Y^1$ is S and A is heteroaryl.

In one variation of Formula I, I', II, II', IV, IV', V, and VI, $Y^1$ is a direct bond and A is a cycloalkyl. In certain instances of Formula I, I', II, II', IV, IV', V, and VI, $Y^1$ is a direct bond and A is heterocycloalkyl. In certain instances of Formula I, I', II, II', IV, IV', V, and VI, $Y^1$ is a direct bond and A is aryl. In certain instances of Formula I, I', II, II', IV, IV', V, and VI, $Y^1$ is a direct bond and A is heteroaryl.

In one variation of Formula V, $Y^1$ is —S— and A ring is heteroaryl (e.g., pyridine). In certain instances, $Y^1$ is —S— and A ring is aryl. In certain embodiments, $Y^1$ is —S—; A ring is heteroaryl (e.g., pyridine); and $R^1$ is $NH_2$ and Cl. In certain embodiments, $Y^1$ is —S—; A ring is aryl; and $R^1$ is $NH_2$ and Cl.

In one variation of Formula V, $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —OH or —$(CH_2)_n$OH (e.g., —$CH_2$OH).

In one variation of Formula V, $Y^2$ is —$NR^a$—; $R^a$ is H; and $R^3$ is independently —$C_1$-$C_6$alkyl, wherein the alkyl is optionally substituted with one or more —OH.

In some embodiments, the compound of formula I or I', or a pharmaceutically acceptable salt, solvate, stereoisomer, or tautomer thereof, has one, two, or three or more of the following features:
a) $X^1$ is $CR^2$;
b) $R^2$ is —H, —$NH_2$, —OH, or —$CH_3$;
c) $X^2$ is N;
d) B, including the atoms at the points of attachment, is a monocyclic 5 to 6-membered heterocycle;
e) $Y^1$ is —S—;
f) A is aryl.

In some embodiments, the compound of formula I or I', or a pharmaceutically acceptable salt, solvate, stereoisomer, or tautomer thereof, has one, two, or three or more of the following features:
a) $X^1$ is $CR^2$;
b) $R^2$ is —H, —$NH_2$, —OH, or —$CH_3$;
c) $X^2$ is N;
d) B, including the atoms at the points of attachment, is a monocyclic 5 to 6-membered heterocycle;
e) $Y^1$ is direct bond;
f) A is aryl.

In some embodiments, the compound of formula I or I', or a pharmaceutically acceptable salt, solvate, stereoisomer, or tautomer thereof, has one, two, or three or more of the following features:
a) $X^1$ is $CR^2$;
b) $R^2$ is —H, —$NH_2$, —OH, or —$CH_3$;
c) $X^2$ is N;
d) B, including the atoms at the points of attachment, is a monocyclic 5 to 6-membered heterocycle;
e) $Y^1$ is —S—;
f) A is heteroaryl.

In some embodiments, the compound of formula I or I', or a pharmaceutically acceptable salt, solvate, stereoisomer, or tautomer thereof, has one, two, or three or more of the following features:
a) $X^1$ is $CR^2$;
b) $R^2$ is —H, —$NH_2$, —OH, or —$CH_3$;
c) $X^2$ is N;
d) B, including the atoms at the points of attachment, is a monocyclic 5 to 6-membered heterocycle;
e) $Y^1$ is direct bond;
f) A is heteroaryl.

In some embodiments, the compound of formula I or I', or a pharmaceutically acceptable salt, solvate, stereoisomer, or tautomer thereof, has one, two, or three or more of the following features:
a) $X^1$ is $CR^2$;
b) $R^2$ is —H, —$NH_2$, —OH, or —$CH_3$;
c) $X^2$ is N;
d) B, including the atoms at the points of attachment, is a monocyclic 5 to 6-membered heterocycle;
e) $Y^2$ is —$NR^a$—
f) $R^3$ and $R^a$ together with the atoms to which they are attached combine to form an optionally substituted 5- to 12-membered spiroheterocycle.

In some embodiments, the compound of formula I or I', or a pharmaceutically acceptable salt, solvate, stereoisomer, or tautomer thereof, has one, two, or three or more of the following features:
a) $X^1$ is $CR^2$;
b) $R^2$ is —H, —$NH_2$, —OH, or —$CH_3$;
c) $X^2$ is N;
d) B, including the atoms at the points of attachment, is a monocyclic 5 to 6-membered heterocycle;
e) $Y^2$ is —$NR^a$—;
f) $R^3$ and $R^a$ together with the atoms to which they are attached combine to form an optionally substituted 3- to 12-membered heterocycle.

The present disclosure provides a compound, and pharmaceutically acceptable salts, solvates, stereoisomers, and tautomers thereof, selected from the group consisting of:

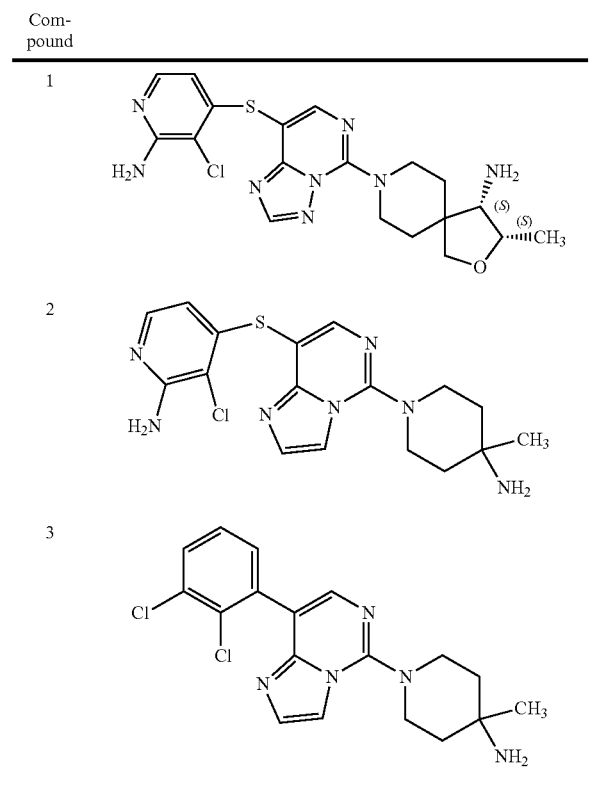

| Compound | |
|---|---|
| 1 | |
| 2 | |
| 3 | |

| Compound | |
|---|---|
| 4 | 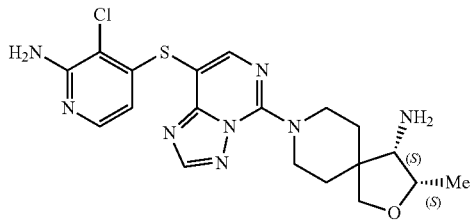 |
| 5 | 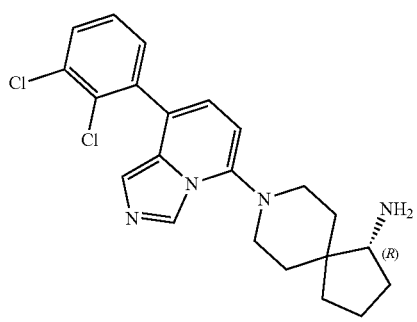 |
| 6 | 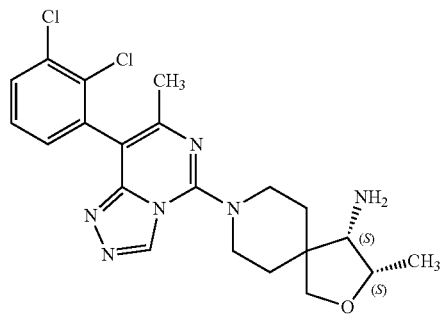 |
| 7 | 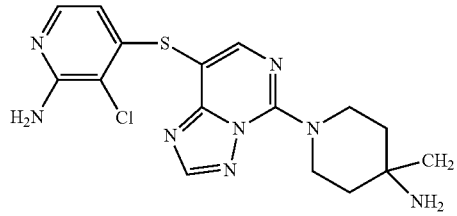 |
| 8 | 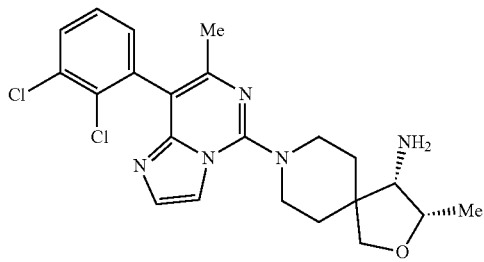 [SMILES: Cc1nc(N2CCC3(CC2)CO[C@@H](C)[C@H]3N)n2ccnc2c1-c1cccc(Cl)c1Cl] |
| Compound | |
|---|---|
| 9 | 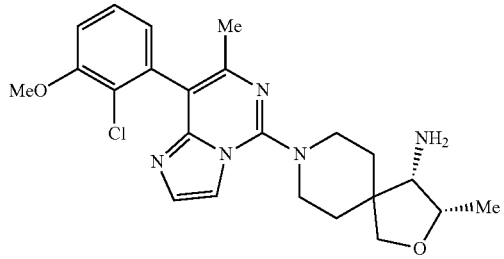 [SMILES: COc1cccc(-c2c(C)nc(N3CCC4(CC3)CO[C@@H](C)[C@H]4N)n3ccnc23)c1Cl] |
The present disclosure provides a compound, and pharmaceutically acceptable salts, solvates, stereoisomers, and tautomers thereof, selected from the group consisting of:
(1)
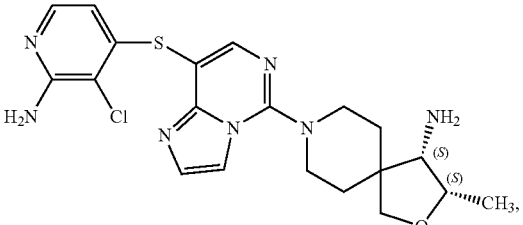
(2)
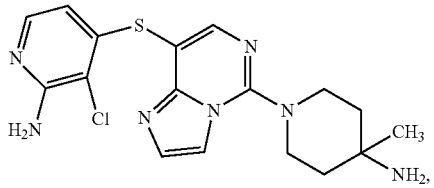
(3)
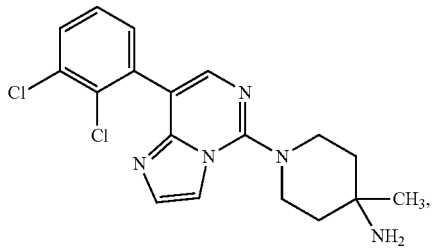
(4)
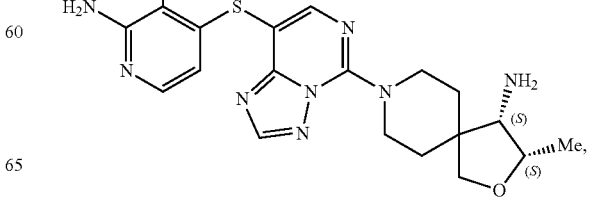

(5)
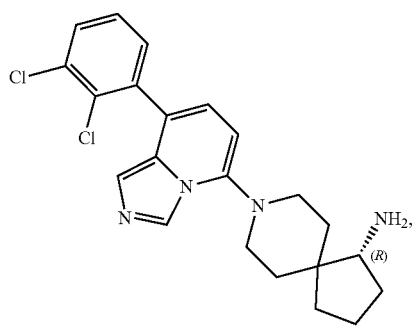
(6)
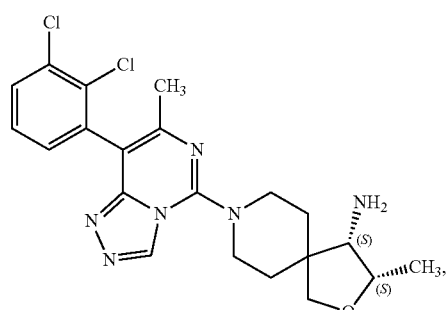
(7)
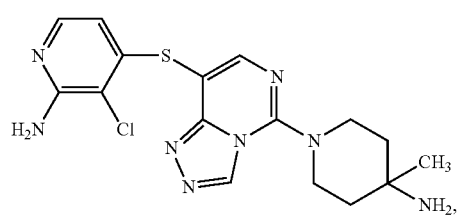
(8)
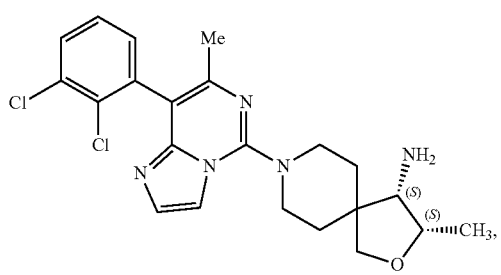
(9)
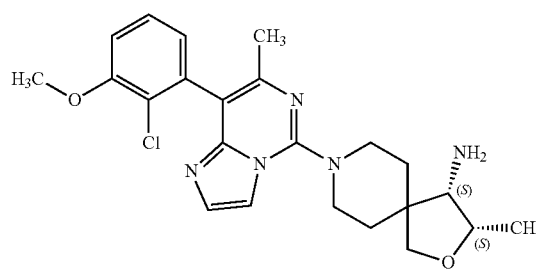
(10)
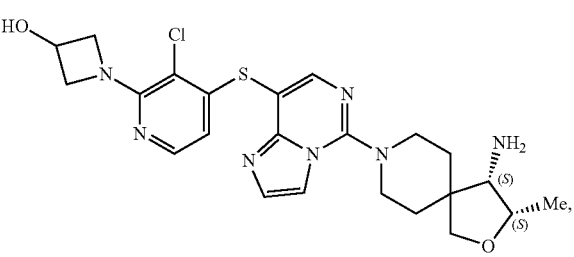
(11)
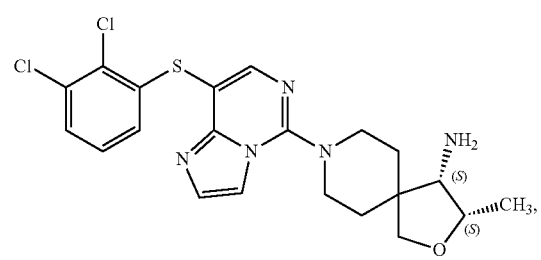
(12)
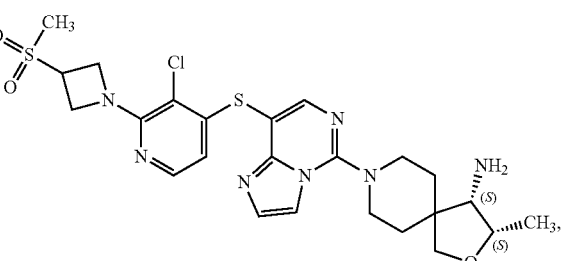
(13)
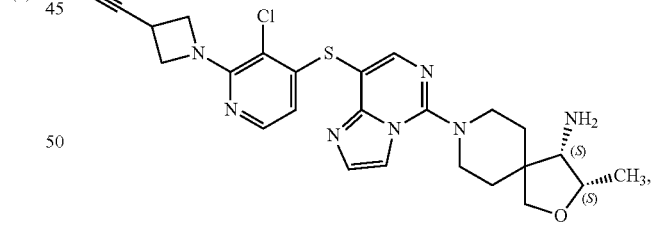
(14)
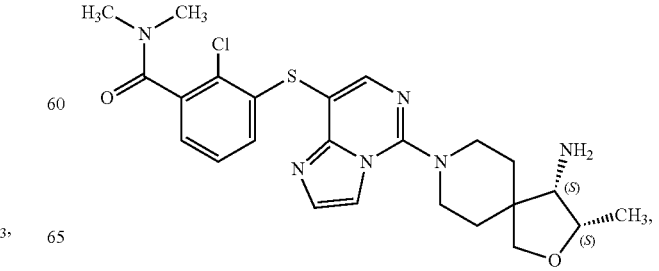

-continued

-continued

(38)
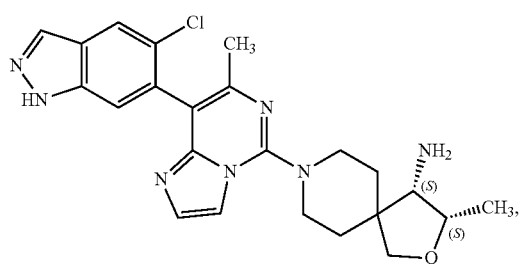
(39)
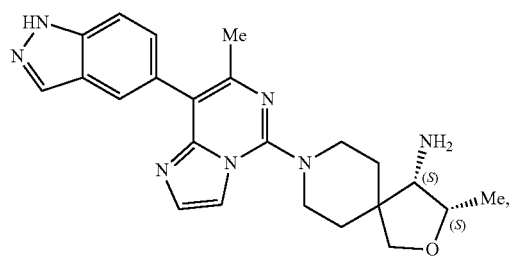
(40)
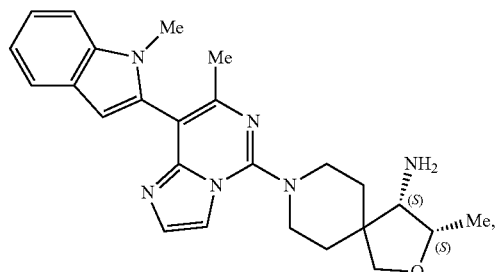
(41)
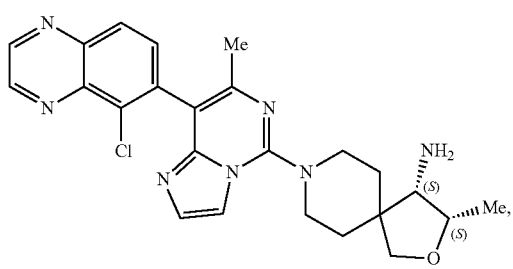
(42)
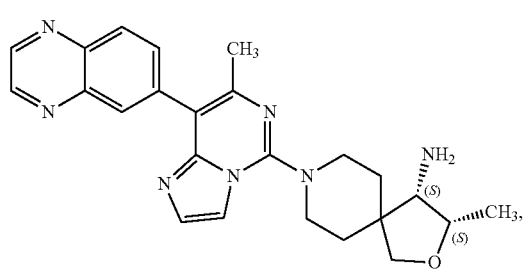
(43)
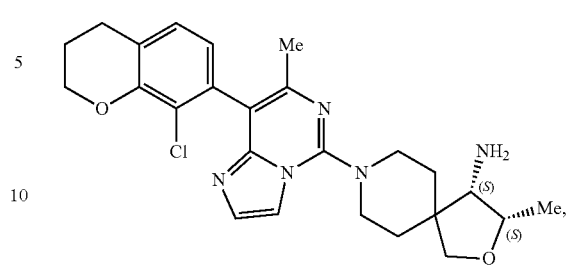
(44)
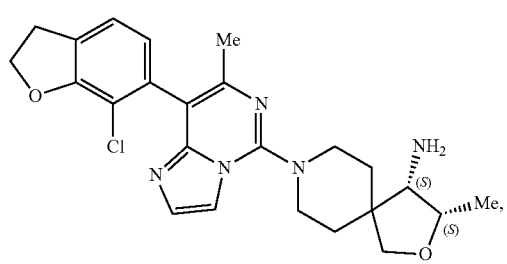
(45)
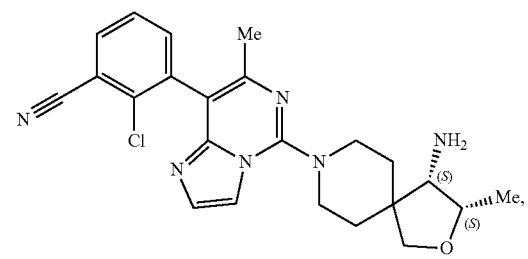
(46)
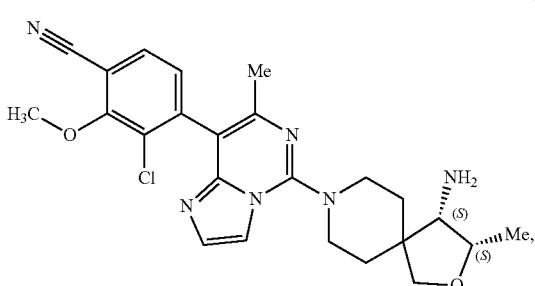
(47)
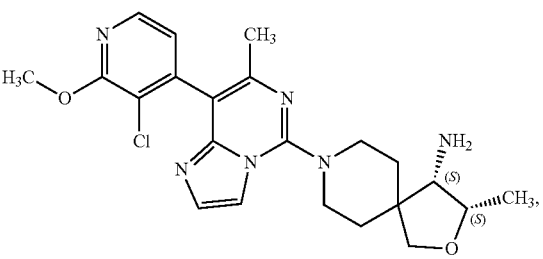

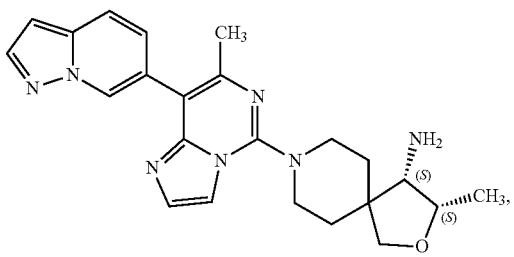
(48)
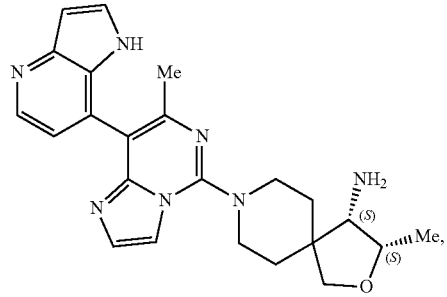
(53)
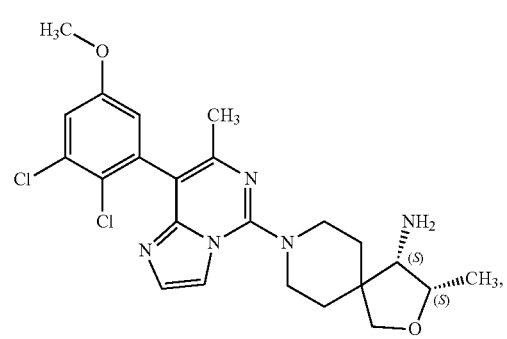
(49)
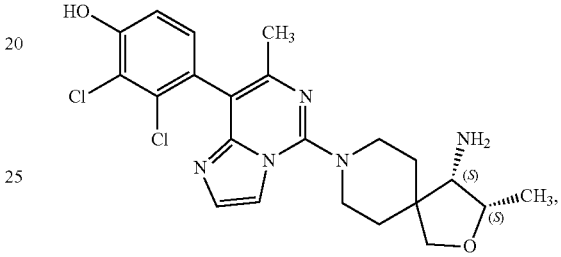
(54)
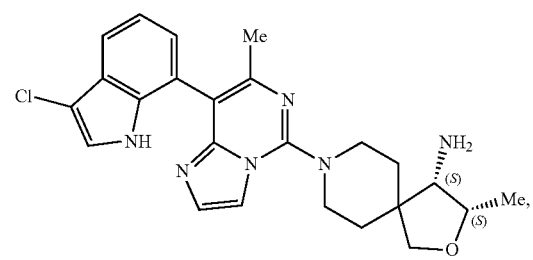
(50)
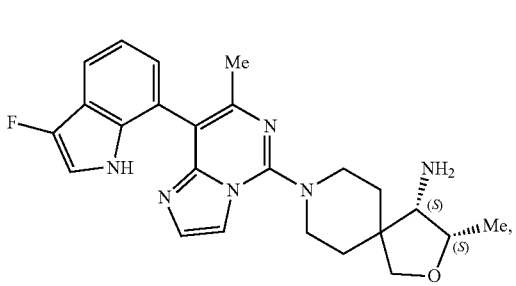
(55)
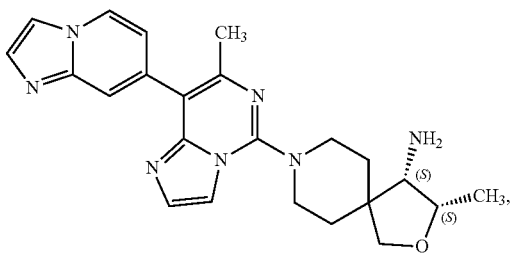
(51)
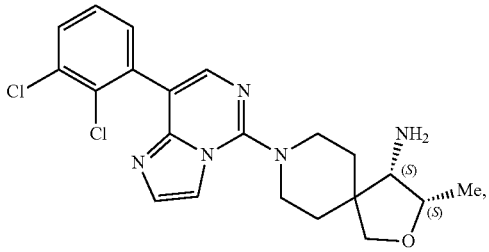
(56)
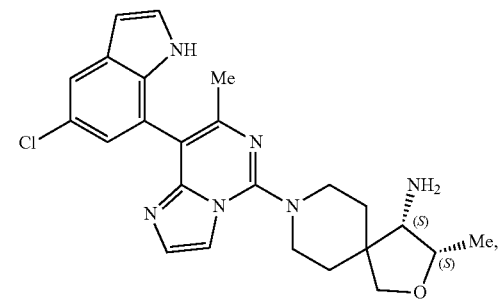
(52)
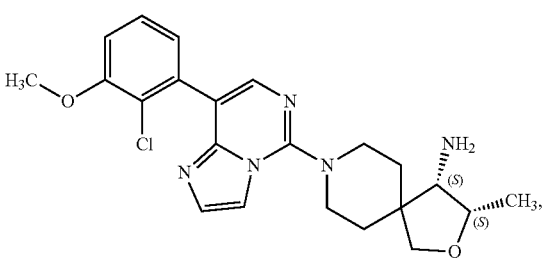
(57)

-continued
(58)
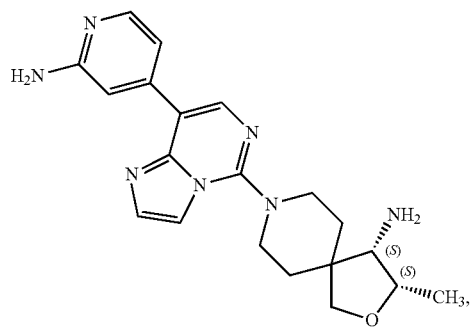
(59)
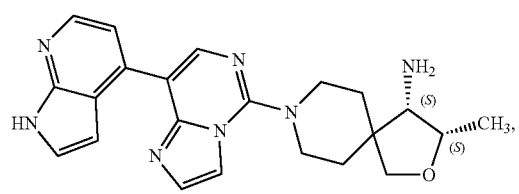
(60)
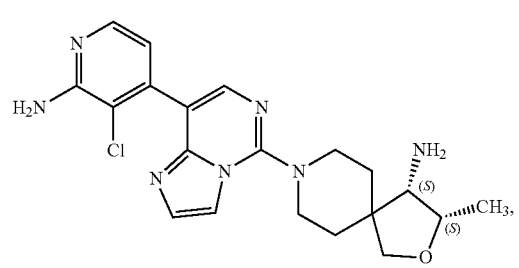
(61)
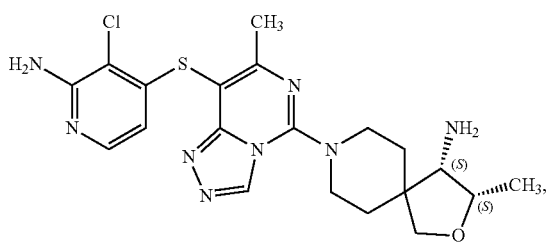
(62)
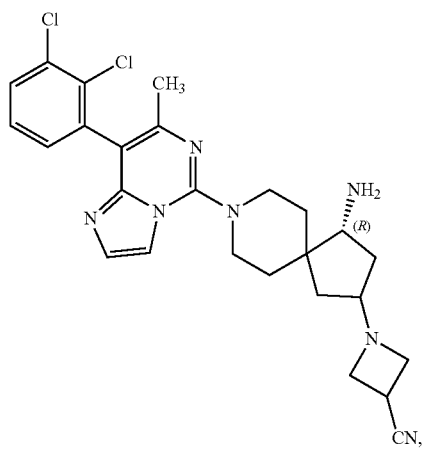
-continued
(63)
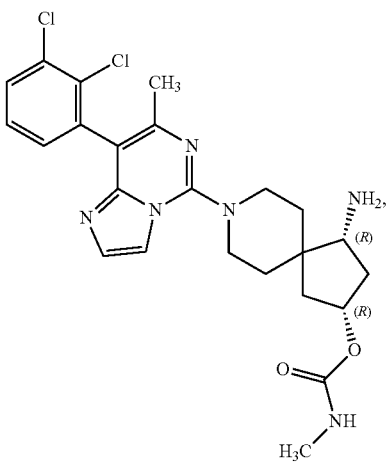
(64)
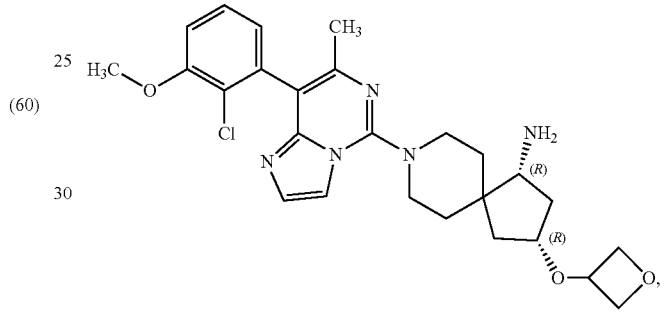
(65)
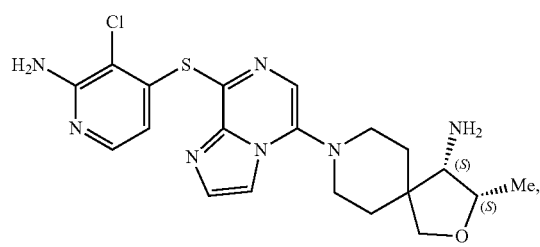
(66)
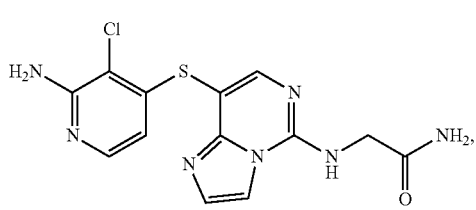
(67)
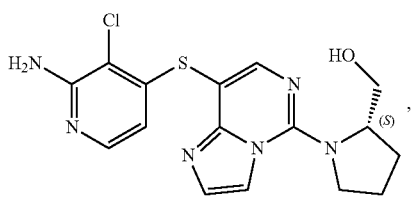

-continued
(68)
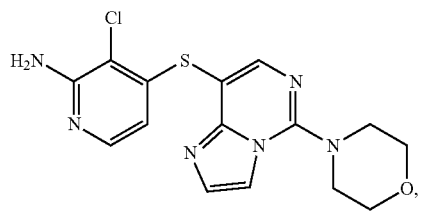
(69)
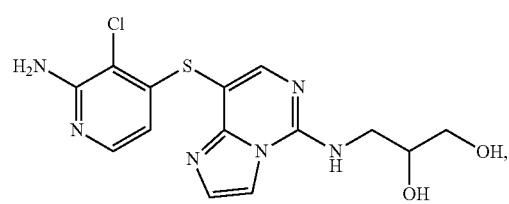
(70)
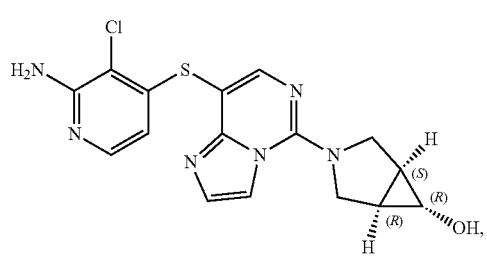
(71)
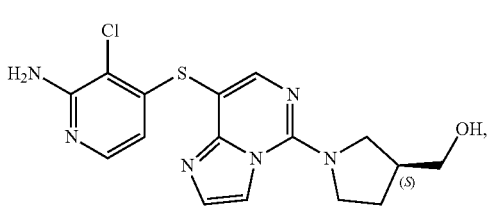
(72)
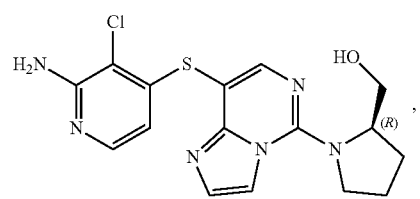
(73)
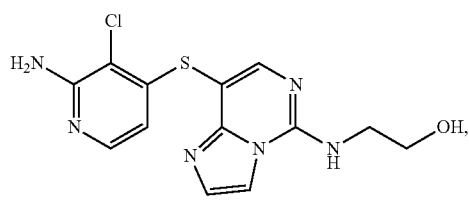
(74)
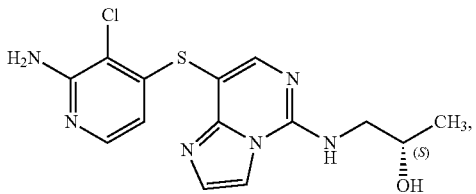
-continued
(75)
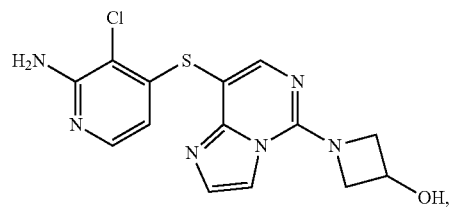
(76)
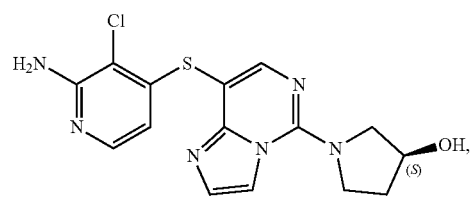
(77)
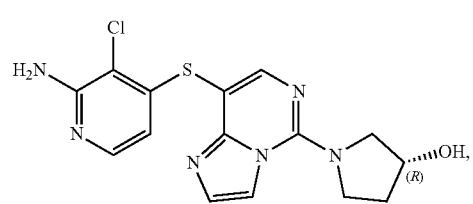
(78)
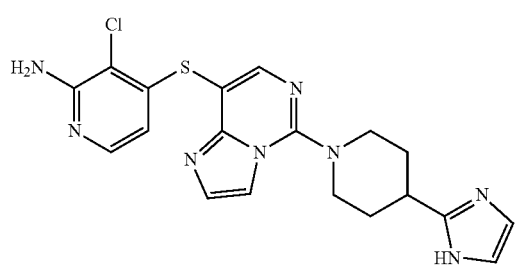
(79)
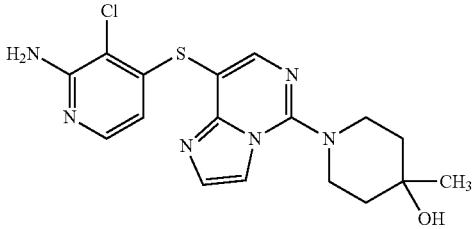
(80)
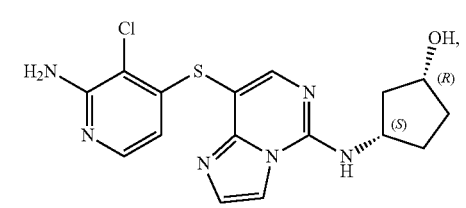
(81)
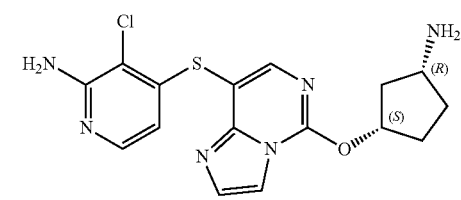

67

-continued (82)

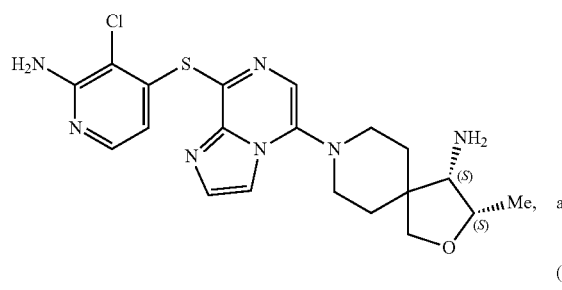

and (83)

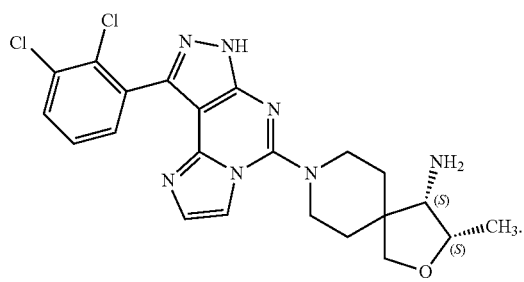

Methods of Synthesizing the Disclosed Compounds

The compounds of the present disclosure may be made by a variety of methods, including standard chemistry. Suitable synthetic routes are depicted in the schemes given below.

The compounds of any of the formulae described herein may be prepared by methods known in the art of organic synthesis as set forth in part by the following synthetic schemes and examples. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of Formula I, I', II, II', III, III', IV, IV', V, or VI.

Those skilled in the art will recognize if a stereocenter exists in any of the compounds of the present disclosure. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

Preparation of Compounds

The compounds described herein may be made from commercially available starting materials or synthesized using known organic, inorganic, and/or enzymatic processes.

The compounds of the present disclosure can be prepared in a number of ways well known to those skilled in the art

68 of organic synthesis. By way of example, compounds of the disclosure can be synthesized using the methods described below, together with synthetic methods known in the art of synthetic organic chemistry, or variations thereon as appreciated by those skilled in the art. These methods include but are not limited to those methods described below.

Scheme 1. General synthesis of 8-(phenylthio)imidazo[1,2-c]pyrimidin-5-amine (or an alternative bi-cyclic structure)

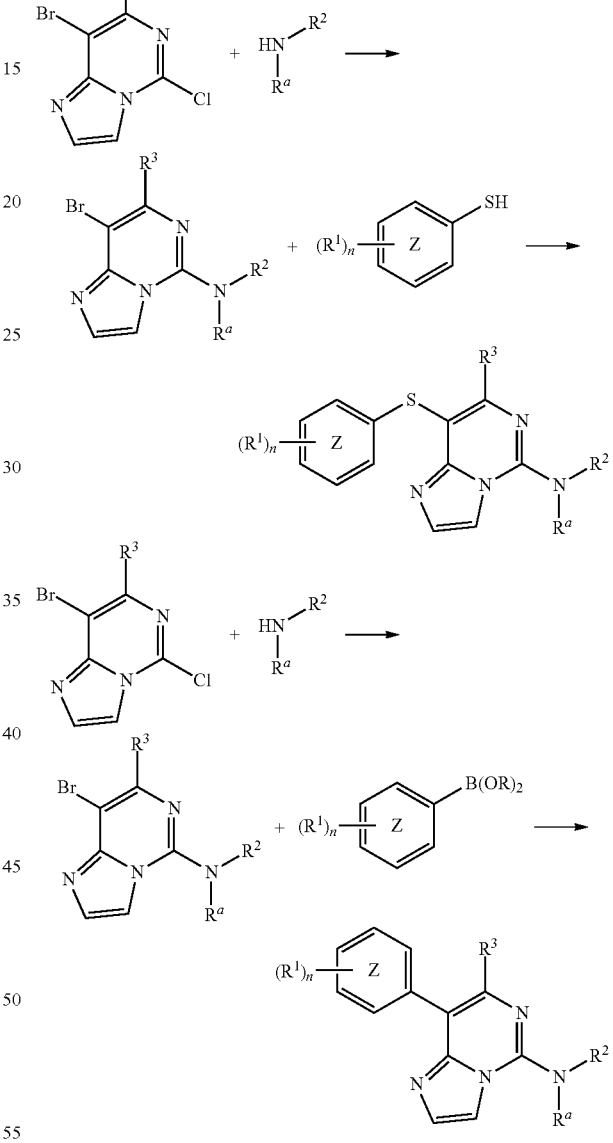

A general synthesis of 8-(phenylthio)imidazopyrimidin-5-amines is outlined in Scheme 1. In the scheme, Z ring refers to an aryl or heteroaryl ring. 8-bromo-5-chloroimidazo[1,2-c]pyrimidine (or an alternative bi-cyclic structure) can be coupled to a substituted primary or secondary amine to give 8-bromoimidazo[1,2-c]pyrimidine-5-amine. The resulting intermediate can be coupled to a substituted aryl- or heteroaryl-thiol in the presence of a copper catalyst (e.g., CuI) or under SNAr conditions. Alternatively, the resulting intermediate can be coupled to an appropriately substituted aryl or heteroaryl boronic acid in the presence of Pd catalyst.

Additional deprotection and/or functionalization steps can be required to produce the final compound.

Methods of Using the Disclosed Compounds

Another aspect of the present disclosure relates to a method of treating a disease associated with SHP2 modulation in a subject in need thereof. The method involves administering to a patient in need of treatment for diseases or disorders associated with SHP2 modulation an effective amount of a compound of Formula I, I', II, II', III, III', IV, IV', V, or VI. In an embodiment, the disease can be, but is not limited to Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In addition, SHP2 plays a role in transducing signals originating from immune checkpoint molecules, including but not limited to programmed cell death protein 1 (PD-1) and cytotoxic T-lymphocyte-associated protein 4 (CTLA-4). In this context, modulation of SHP2 function can lead to immune activation, specifically anti-cancer immune responses.

Another aspect of the present disclosure is directed to a method of inhibiting SHP2. The method involves administering to a patient in need thereof an effective amount of Formula I, I', II, II', III, III', IV, IV', V, or VI.

The present disclosure relates to compositions capable of modulating the activity of (e.g., inhibiting) SHP2. The present disclosure also relates to the therapeutic use of such compounds.

The disclosed compound can be administered in effective amounts to treat or prevent a disorder and/or prevent the development thereof in subjects.

Another aspect of the present disclosure relates to a compound of Formula I, I', II, II', III, III', IV, IV', V, or VI, or a pharmaceutically acceptable salt, hydrate, solvate, prodrug, stereoisomer, or tautomer thereof, for use in treating or preventing a disease associated with SHP2 modulation. In some embodiments, the disease is Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

In another aspect, the present disclosure relates to the use of a compound of Formula I, I', II, II', III, III', IV, IV', V, or VI, or a pharmaceutically acceptable salt, hydrate, solvate, prodrug, stereoisomer, or tautomer thereof, in the manufacture of a medicament for treating or preventing a disease.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compounds or pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a compound of the disclosure and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algiic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described for instance in U.S. Pat. No. 5,262,564, the contents of which are hereby incorporated by reference.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parental injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the present disclosure relates to a pharmaceutical composition comprising a compound of the present disclosure and a pharmaceutically acceptable carrier. The pharmaceutically acceptable carrier can further include an excipient, diluent, or surfactant.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXEMPLARY EMBODIMENTS

Some embodiments of this disclosure are Embodiment I, as follows:

Embodiment I-1. A compound of the Formula II:

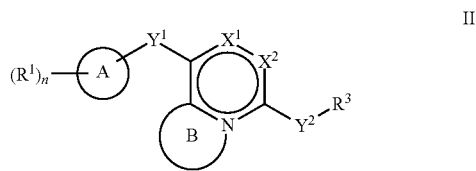

II or a pharmaceutically acceptable salt, prodrug, solvate, hydrate, tautomer, or isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2$$R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —C(=$CH_2$)—, —$CH_2$—, or —S(O)—;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —$(CR^a_2)_m$—, —C(O)—, —$C(R^a)_2$NH—, —$(CR^a_2)_mO$—, —C(O)N($R^a$)—, —N($R^a$)C(O)—, —$S(O)_2N(R^a)$—, —N($R^a$)$S(O)_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, —C(O)NR⁵R⁶, —NR⁵C(O)R⁶, heterocycle, aryl, heteroaryl, —(CH₂)ₙOH, —C₁-C₆alkyl, —CF₃, —CHF₂, or —CH₂F;

R² is independently —H, —NH₂, —ORᵇ, —CN, —C₁-C₆alkyl, —C₂-C₆alkenyl, —C₄-C₈cycloalkenyl, —C₂-C₆alkynyl, halogen, —C(O)ORᵇ, —O-C₈cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO₂, oxo, —CN, —R⁵, —OR⁵, —NR⁵R⁶, —SR⁵, —S(O)₂NR⁵R⁶, —S(O)₂R⁵, —NR⁵S(O)₂NR⁵R⁶, —NR⁵S(O)₂R⁶, —S(O)NR⁵R⁶, —S(O)R⁵, —NR⁵S(O)NR⁵R⁶, —NR⁵S(O)R⁶, heterocycle, aryl, or heteroaryl;

R³ is independently —H, —C₁-C₆alkyl, a 3- to 12-membered monocyclic or polycyclic heterocycle, a 5- to 12-membered spiroheterocycle, C₃-C₈cycloalkyl, or —(CH₂)ₙ—Rᵇ, wherein each alkyl, spiroheterocycle, heterocycle, or cycloalkyl is optionally substituted with one or more —C₁-C₆alkyl, —OH, —NH₂, —ORᵇ, —NHRᵇ, —(CH₂)ₙOH, heterocyclyl, or spiroheterocyclyl; or R³ can combine with Rᵃ to form a 3- to 12-membered monocyclic or polycyclic heterocycle or a 5- to 12-membered spiroheterocycle, wherein each heterocycle or spiroheterocycle is optionally substituted with one or more —C₁-C₆alkyl, halogen, —OH, —ORᵇ, —NH₂, —NHRᵇ, heteroaryl, heterocyclyl, —(CH₂)ₙNH₂, —(CH₂)ₙOH, —COORᵇ, —CONHRᵇ, —CONH(CH₂)ₙCOORᵇ, —NHCOORᵇ, —CF₃, —CHF₂, —CH₂F, or =O;

R⁵ and R⁶ are independently, at each occurrence, —H, —C₁-C₆alkyl, —C₂-C₆alkenyl, —C₄-C₈cycloalkenyl, —C₂-C₆alkynyl, —C₃-C₈cycloalkyl, a monocyclic or polycyclic 3- to 12-membered heterocycle, —OR⁷, —SR⁷, halogen, —NR⁷R⁸, —NO₂, —CF₃, or —CN;

R⁷ and R⁸ are independently, at each occurrence, —H, —C₁-C₆alkyl, —C₂-C₆alkenyl, —C₄-C₈cycloalkenyl, —C₂-C₆alkynyl, —C₃-C₈cycloalkyl, —ORᵇ, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH₂, —NO₂, or —CN;

m is independently 1, 2, 3, 4, 5 or 6; and n is independently 0, 1, 2, 3, 4, 5, 6, 7, 8, 9, or 10.

Embodiment I-2. The compound of Embodiment I-1, wherein Y¹ is —S—.

Embodiment I-3. The compound of Embodiment I-1, wherein Y¹ is a direct bond.

Embodiment I-4. The compound of any one of Embodiments I-1 to I-3, wherein X¹ is N.

Embodiment I-5. The compound of any one of Embodiments I-1 to I-3, wherein X¹ is CR².

Embodiment I-6. The compound of Embodiment I-5, wherein R² is —H, —NH₂, —OH, or —C₁-C₆alkyl.

Embodiment I-7. The compound of any one of Embodiments I-1 to I-3, wherein X² is N.

Embodiment I-8. The compound of any one of Embodiments I-1 to I-3, wherein X² is CH.

Embodiment I-9. The compound of any one of Embodiments I-1 to I-3, wherein X¹ is N and X² is N.

Embodiment I-10. The compound of any one of Embodiments I- to I-3, wherein X¹ is N and X² is CH.

Embodiment I-11. The compound of any one of Embodiments I-1 to I-3, wherein X¹ is CR² and X² is N.

Embodiment I-12. The compound of any one of Embodiments I-1 to I-3, wherein X¹ is CR² and X² is CH.

Embodiment I-13. The compound of any one of Embodiments I-11 to I-12, wherein R² is —H, —NH₂, —OH, or —C₁-C₆alkyl.

Embodiment I-14. The compound of any one of Embodiments I-1 to I-13, wherein B, including the atoms at the points of attachment, is a monocyclic 5- to 12-membered heteroaryl.

Embodiment I-15. The compound of any one of Embodiments I-1 to I-14, wherein B, including the atoms at the points of attachment, is

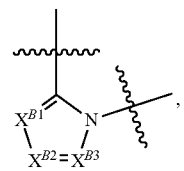

wherein $X^{B1}$ is N, CH, S, or O; $X^{B2}$ is N, CH, S, or O; and $X^{B3}$ is N, CH, S, or O.

Embodiment I-16. The compound of any one of Embodiments I-1 to I-14, wherein B, including the atoms at the points of attachment, is

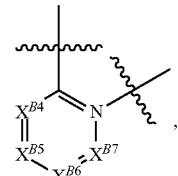

wherein $X^{B4}$ is N or CH; $X^{B5}$ is N or CH; $X^{B6}$ is N or CH; and $X^{B7}$ is N or CH.

Embodiment I-17. The compound of any of one of Embodiments I-1 to I-16, wherein A is cycloalkyl.

Embodiment I-18. The compound of any of one of Embodiments I-1 to I-16, wherein A is heterocycloalkyl.

Embodiment I-19. The compound of any of one of Embodiments I-1 to I-16, wherein A is aryl.

Embodiment I-20. The compound of any of one of Embodiments I-1 to I-16, wherein A is phenyl.

Embodiment I-21. The compound of any of one of Embodiments I-1 to I-16, wherein A is heteroaryl.

Embodiment I-22. The compound of any of one of Embodiments I-1 to I-16, wherein A is pyridyl.

Embodiment I-23. The compound of any one of Embodiments I-1 to I-22, wherein R¹ is independently —OH, —NO₂, —CN, halogen, or —NR⁵R⁶.

Embodiment I-24. The compound of any of one of Embodiments I-1 to I-23, wherein Y² is —NRᵃ—.

Embodiment I-25. The compound of any of one of Embodiments I-1 to I-23, wherein Y² is —(CRᵃ₂)ₘ—.

Embodiment I-26. The compound of any of one of Embodiments I-1 to I-25, wherein Rᵃ is —H.

Embodiment I-27. The compound of any of one of Embodiments I-1 to I-25, wherein Rᵃ is —C₁-C₆alkyl.

Embodiment I-28. The compound of any of one of Embodiments I-1 to I-27, wherein R³ is —C₁-C₆alkyl.

Embodiment I-29. The compound of any of one of Embodiments I-1 to I-27, wherein R³ is 3- to 12-membered monocyclic or polycyclic heterocycle.

Embodiment I-30. The compound of any of one of Embodiments I-1 to I-27, wherein R³ is a 3- to 12-membered monocyclic heterocycle.

Embodiment I-31. The compound of any of one of Embodiments I-1 to I-27, wherein R³ is a 5- to 12-membered polycyclic heterocycle.

Embodiment I-32. The compound of any of one of Embodiments I-1 to I-25, wherein R³ and R$^a$ together with the atom to which they are attached combine to form a 3- to 12-membered monocyclic heterocycle.

Embodiment I-33. The compound of any of one of Embodiments I-1 to I-25, wherein R³ and R$^a$ together with the atoms to which they are attached combine to form a 3- to 12-membered polycyclic heterocycle.

Embodiment I-34. The compound of any of one of Embodiments I-1 to I-25, wherein R³ and R$^a$ together with the atoms to which they are attached combine to form a 5- to 12-membered spiroheterocycle.

Embodiment I-35. The compound of any of one of Embodiments I-32 to I-34, wherein heterocycle or spirocycle formed by R³ and R$^a$ is substituted with one or more substituents selected from the group consisting of C$_1$-C$_6$alkyl, —OH, halogen, —NH$_2$, —NHR$^b$, —CF$_3$, —CHF$_2$, or —CH$_2$F.

Embodiment I-36. A compound, or a pharmaceutically acceptable salt, solvate, stereoisomer, or tautomer thereof, selected from the group consisting of:

| Compound | |
|---|---|
| 1 | 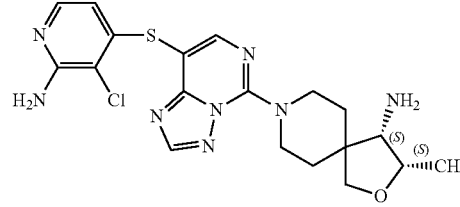 |
| 2 | 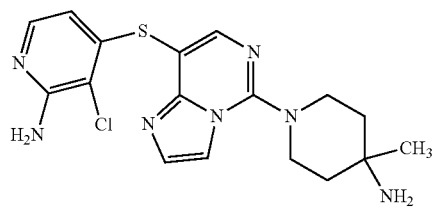 [SMILES: CC1(N)CCN(c2ncc(Sc3ccnc(N)c3Cl)c3nccn23)CC1] |
| 3 | 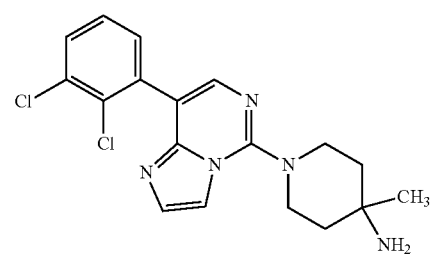 [SMILES: CC1(N)CCN(c2ncc(-c3cccc(Cl)c3Cl)c3nccn23)CC1] |
| 4 | 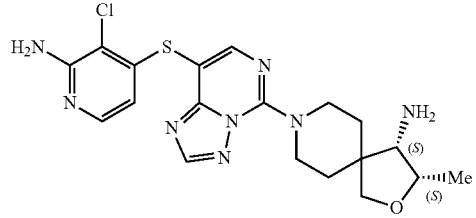 |
| 5 | 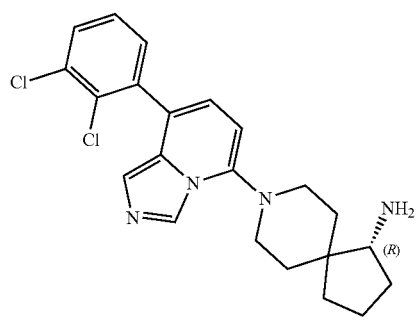 |
| 6 | 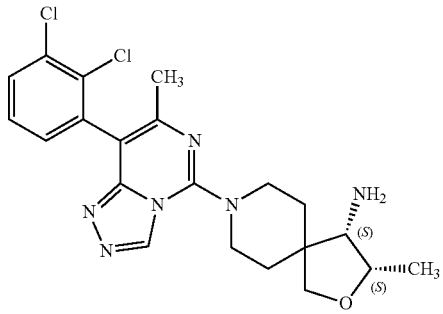 |
| 7 | 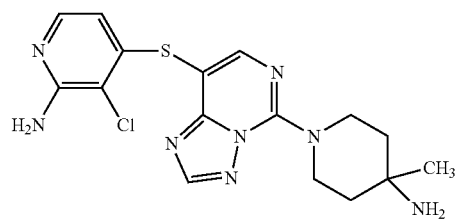 |
| 8 | 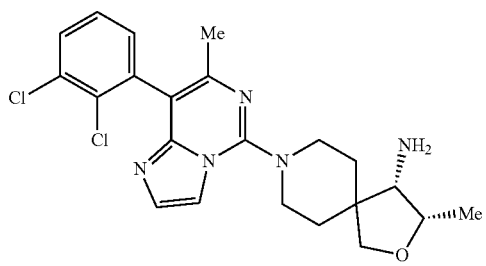 [SMILES: Cc1nc(N2CCC3(CC2)CO[C@@H](C)[C@H]3N)n2ccnc2c1-c1cccc(Cl)c1Cl] |

| Compound | |
|---|---|
| 9 | 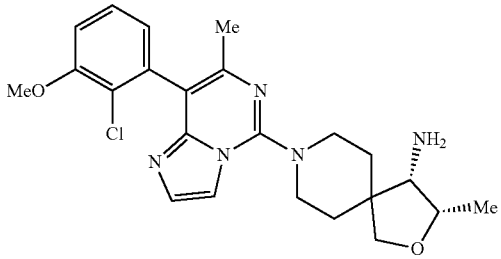 [SMILES: COc1cccc(-c2c(C)nc(N3CCC4(CC3)CO[C@@H](C)[C@H]4N)n3ccnc23)c1Cl] |

Embodiment I-37. A pharmaceutical composition comprising a compound of any one of Embodiments I-1 to I-36, or a pharmaceutically acceptable salt, prodrug, solvate, hydrate, tautomer, or isomer thereof, and a pharmaceutically acceptable carrier.

Embodiment I-38. A method of treating a disease associated with SHP2 modulation in a subject in need thereof, comprising administering to the subject an effective amount of a compound of any one of Embodiments I-1 to I-36, or a pharmaceutically acceptable salt, prodrug, solvate, hydrate, tautomer, or isomer thereof.

Embodiment I-39. The method of Embodiment I-38, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment I-40. A compound of any one of Embodiments I-1 to I-36 for use in treating or preventing a disease associated with SHP2 modulation.

Embodiment I-41. Use of a compound of any one of Embodiments I-1 to I-36 in the manufacture of a medicament for treating or preventing a disease associated with SHP2 modulation.

Some embodiments of this disclosure are Embodiment II, as follows:

Embodiment II-1. A compound of the Formula II':

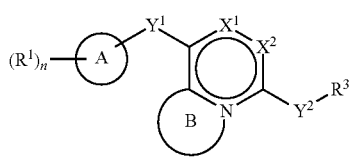

II' or a pharmaceutically acceptable salt, prodrug, solvate, hydrate, tautomer, or isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —$S(O)_2NR^5R^6$, —$S(O)_2$$R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)R^5$, —$CO_2R^5$, —$C(O)NR^5R^6$, —$NR^5C(O)R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$Y^1$ is —S—, a direct bond, —NH—, —$S(O)_2$—, —$S(O)_2$—NH—, —C(=$CH_2$)—, —$CH_2$—, or —S(O)—;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —($CR^a_2$)$_m$—, —O—, —C(O)—, —C($R^a$)$_2$NH—, —($CR^a_2$)$_m$O—, —C(O)N($R^a$)y, —N($R^a$)C(O)—, —$S(O)_2$N($R^a$)—, —N($R^a$)$S(O)_2$—, —N($R^a$)C(O)N($R^a$)—, —N($R^a$)C(S)N($R^a$)—, —C(O)O—, —OC(O)—, —OC(O)N($R^a$)—, —N($R^a$)C(O)O—, —C(O)N($R^a$)O—, —N($R^a$)C(S)—, —C(S)N($R^a$)—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —($CH_2$)$_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —($CH_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —($CH_2$)$_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)$$NR^5R^6$, —$NR^5S(O)R^6$, —$C(O)NR^5R^6$, —$NR^5C(O)R^6$, heterocycle, aryl, heteroaryl, —($CH_2$)$_n$OH, —$C_1$-$C_6$alkyl, —$CF_3$, —$CHF_2$, or —$CH_2F$;

$R^2$ is independently —H, —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —$R^5$, —$OR^5$, —$NR^5R^6$, —$SR^5$, —$S(O)_2NR^5R^6$, —$S(O)_2$$R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, —($CH_2$)$_n$—$R^b$, or —($CH_2$)$_n$C(O)$NR^5R^6$, wherein each alkyl, spiroheterocycle, heterocycle, or cycloalkyl is optionally substituted with one or more —$C_1$-$C_6$alkyl, —OH, —$NH_2$, —$OR^b$, —$NHR^b$, —($CH_2$)$_n$OH, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^5$ and R$^6$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^{11}$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10;

provided that when X$^2$ is N and B ring is a monocyclic 5-membered heteroaryl containing 3-4 nitrogen atoms, then

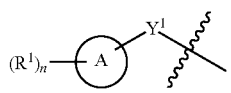

is not

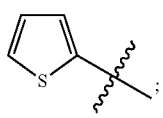 [SMILES: *c1cccs1]

and provided that when X$^1$ is N; X$^2$ is CH and Y$^1$ is NH; then R$^1$ is not C$_3$-C$_8$cycloalkyl or heteroaryl.

Embodiment II-2. The compound of Embodiment II-1, wherein Y$^1$ is —S—.

Embodiment II-3. The compound of Embodiment II-1, wherein Y$^1$ is a direct bond.

Embodiment II-4. The compound of any one of Embodiments II-1 to II-3, wherein X$^1$ is N.

Embodiment II-5. The compound of any one of Embodiments II-1 to II-3, wherein X$^1$ is CR$^2$.

Embodiment II-6. The compound of Embodiment II-5, wherein R$^2$ is —H, —NH$_2$, —OH, or —C$_1$-C$_6$alkyl.

Embodiment II-7. The compound of any one of Embodiments II-1 to II-3, wherein X$^2$ is N.

Embodiment II-8. The compound of any one of Embodiments II-1 to II-3, wherein X$^2$ is CH.

Embodiment II-9. The compound of any one of Embodiments II-1 to II-3, wherein X$^1$ is N and X$^2$ is N.

Embodiment II-10. The compound of any one of Embodiments II-1 to II-3, wherein X$^1$ is N and X$^2$ is CH.

Embodiment LI-11. The compound of any one of Embodiments II-1 to II-3, wherein X$^1$ is CR$^2$ and X$^2$ is N.

Embodiment II-12. The compound of any one of Embodiments II-I to II-3, wherein X$^1$ is CR$^2$ and X$^2$ is CH.

Embodiment II-13. The compound of any one of Embodiments II-11 to II-12, wherein R$^2$ is —H, —NH$_2$, —OH, or —C$_1$-C$_6$alkyl.

Embodiment II-14. The compound of any one of Embodiments II-1 to II-13, wherein B, including the atoms at the points of attachment, is a monocyclic 5- to 12-membered heteroaryl.

Embodiment II-15. The compound of any one of Embodiments II-1 to II-14, wherein B, including the atoms at the points of attachment, is

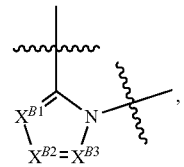

wherein X$^{B1}$ is N, CH, S, or O; X$^{B2}$ is N, CH, S, or O; and X$^{B3}$ is N, CH, S, or O.

Embodiment II-16. The compound of any one of Embodiments II-1 to II-14, wherein B, including the atoms at the points of attachment, is

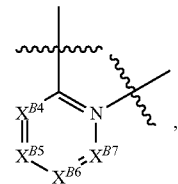

wherein X$^{B4}$ is N or CH; X$^{B5}$ is N or CH; X$^{B6}$ is N or CH; and X$^{B7}$ is N or CH.

Embodiment II-17. The compound of any of one of Embodiments II-1 to II-16, wherein A is cycloalkyl.

Embodiment II-18. The compound of any of one of Embodiments II-1 to II-16, wherein A is heterocycloalkyl.

Embodiment II-19. The compound of any of one of Embodiments II-1 to II-16, wherein A is aryl.

Embodiment II-20. The compound of any of one of Embodiments II-1 to II-16, wherein A is phenyl.

Embodiment II-21. The compound of any of one of Embodiments II-1 to II-16, wherein A is heteroaryl.

Embodiment II-22. The compound of any of one of Embodiments II-1 to II-16, wherein A is pyridyl.

Embodiment II-23. The compound of any one of Embodiments II-1 to II-22, wherein R$^1$ is independently —OH, —NO$_2$, —CN, halogen, or —NR$^5$R$^6$.

Embodiment II-24. The compound of any of one of c Embodiments II-1 to II-23, wherein Y$^2$ is —NR$^a$—.

Embodiment II-25. The compound of any of one of Embodiments II-1 to II-23, wherein Y$^2$ is —(CR$^a_2$)$_m$—.

Embodiment II-26. The compound of any of one of Embodiments II-1 to II-25, wherein R$^a$ is —H.

Embodiment II-27. The compound of any of one of Embodiments II-1 to II-25, wherein R$^a$ is —C$_1$-C$_6$alkyl.

Embodiment II-28. The compound of any of one of Embodiments II-1 to II-27, wherein R$^3$ is —C$_1$-C$_6$alkyl.

Embodiment II-29. The compound of any of one of Embodiments II-1 to II-27, wherein R$^3$ is 3- to 12-membered monocyclic or polycyclic heterocycle.

Embodiment II-30. The compound of any of one of Embodiments II-1 to II-27, wherein R$^3$ is a 3- to 12-membered monocyclic heterocycle.

Embodiment II-31. The compound of any of one of Embodiments II-1 to II-27, wherein $R^3$ is a 5- to 12-membered polycyclic heterocycle.

Embodiment II-32. The compound of any of one of Embodiments II-1 to II-25, wherein $R^3$ and $R^a$ together with the atom to which they are attached combine to form a 3- to 12-membered monocyclic heterocycle.

Embodiment II-33. The compound of any of one of Embodiments II-1 to II-25, wherein $R^3$ and $R^a$ together with the atoms to which they are attached combine to form a 3- to 12-membered polycyclic heterocycle.

Embodiment II-34. The compound of any of one of Embodiments II-1 to II-25, wherein $R^3$ and $R^a$ together with the atoms to which they are attached combine to form a 5- to 12-membered spiroheterocycle.

Embodiment II-35. The compound of any of one of Embodiments II-32 to II-34, wherein heterocycle or spirocycle formed by $R^3$ and $R^a$ is substituted with one or more substituents selected from the group consisting of $C_1$-$C_6$alkyl, —OH, halogen, —NH$_2$, —NHR$^b$, —CF$_3$, —CHF$_2$, or —CH$_2$F.

Embodiment II-36. A compound, or a pharmaceutically acceptable salt, solvate, stereoisomer, or tautomer thereof, selected from the group consisting of:

| Compound | |
|---|---|
| 1 | [structure] |
| 2 | [structure] |
| 3 | [structure] |
| 4 | [structure] |
| 5 | [structure] |
| 6 | [structure] |
| 7 | [structure] |
| 8 | [structure] |
| 9 | [structure] |

Embodiment II-37. A compound, or a pharmaceutically acceptable salt, solvate, stereoisomer, or tautomer thereof, selected from the group consisting of:

(1)
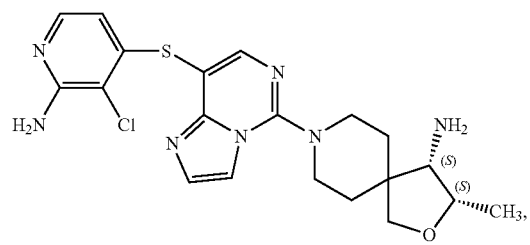
(2)
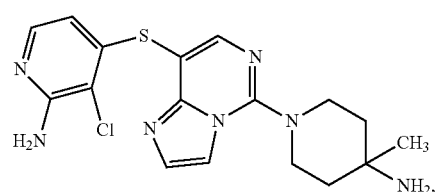
(3)
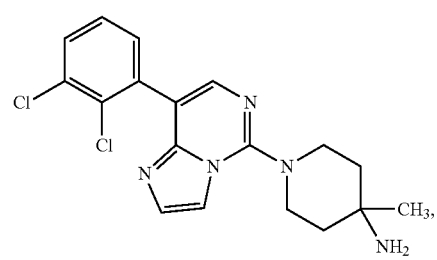
(4)
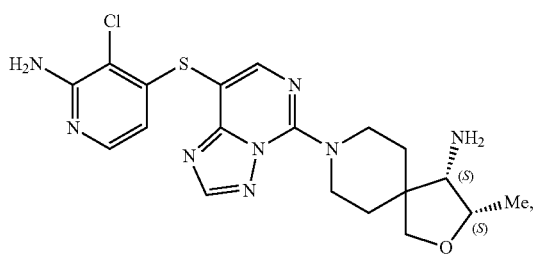
(5)
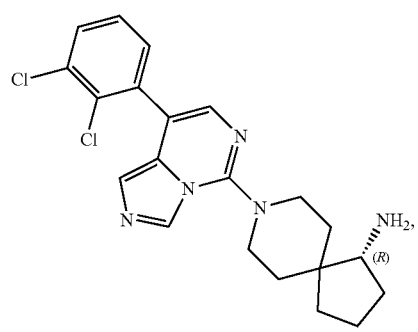
(6)
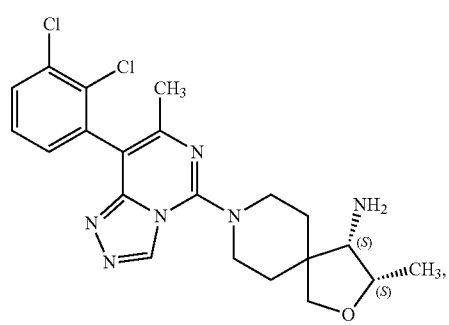
-continued
(7)
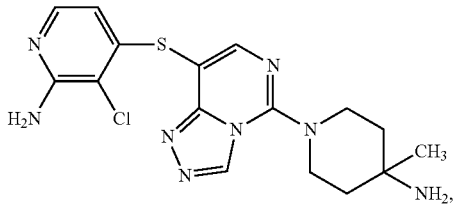
(8)
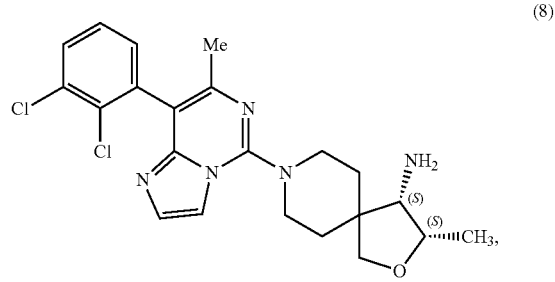
(9)
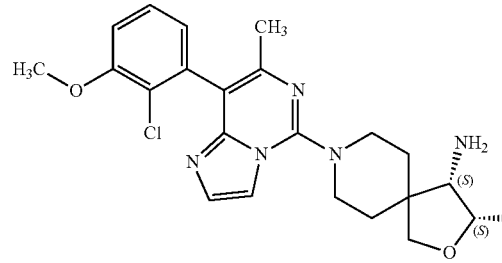
(10)
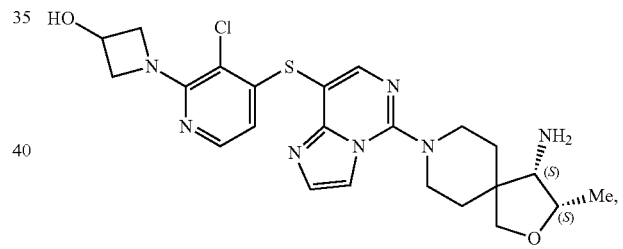
(11)
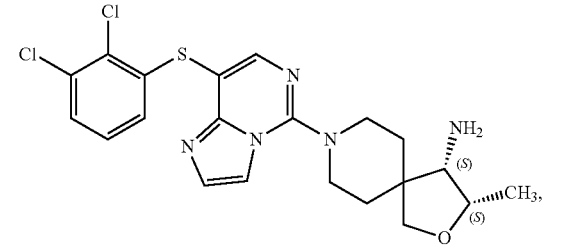
(12)
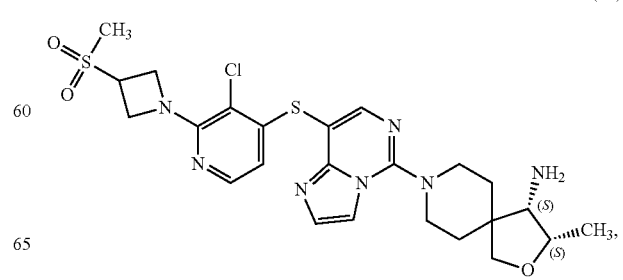

(13)
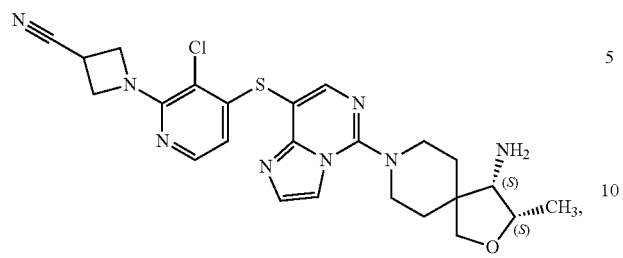
(14)
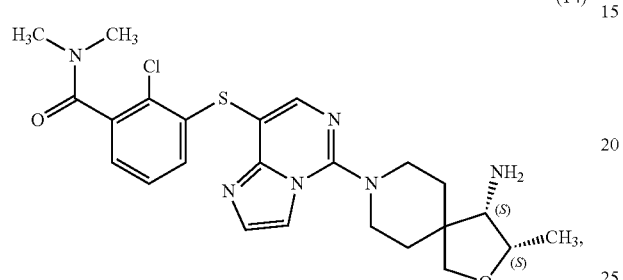
(15)
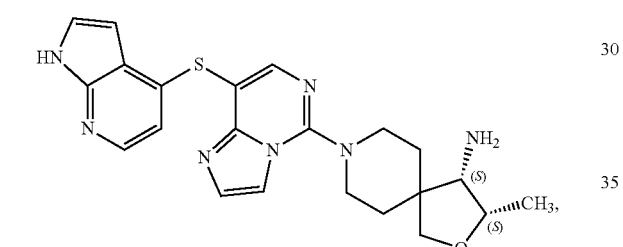
(16)
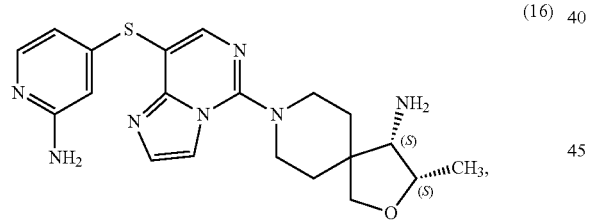
(17)
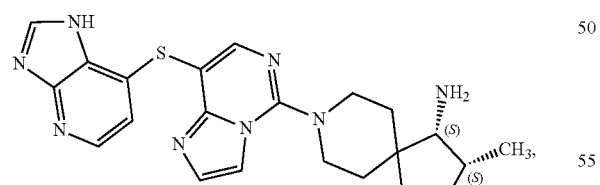
(18)
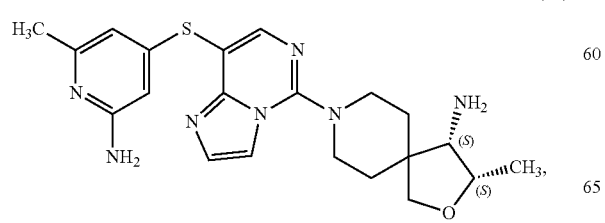
(19)
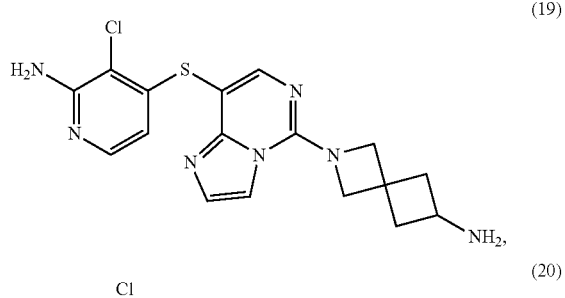
(20)
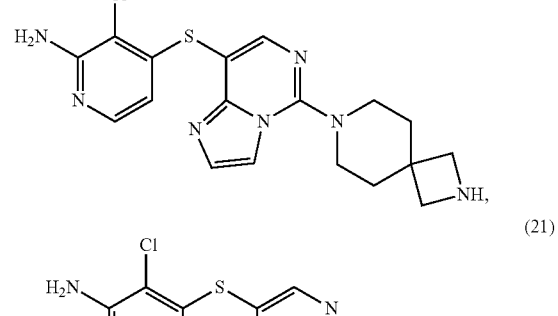
(21)
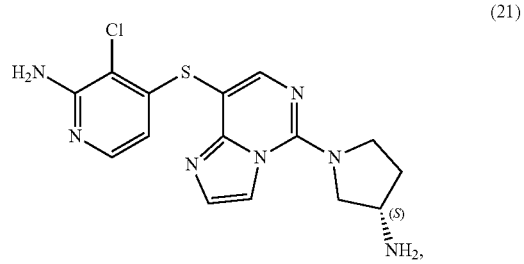
(22)
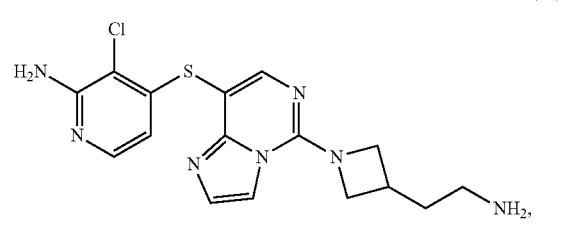
(23)
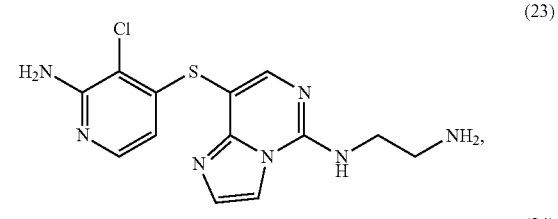
(24)
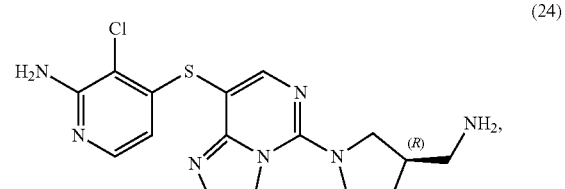
(25)
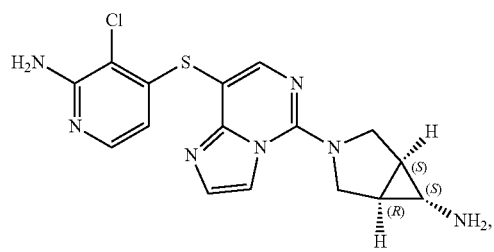

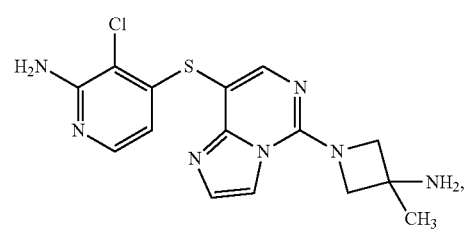
(26)
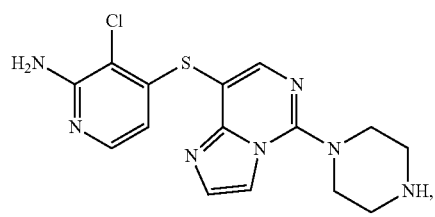
(27)
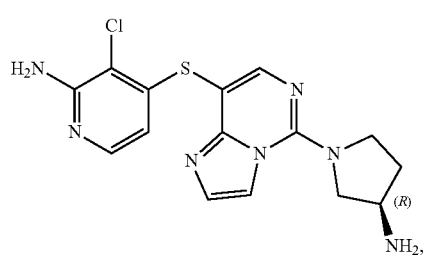
(28)
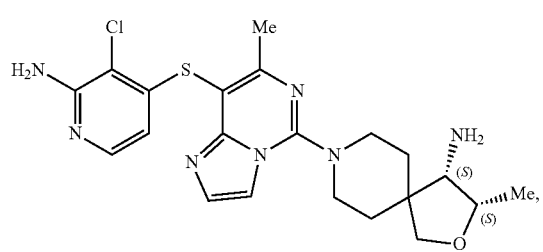
(29)
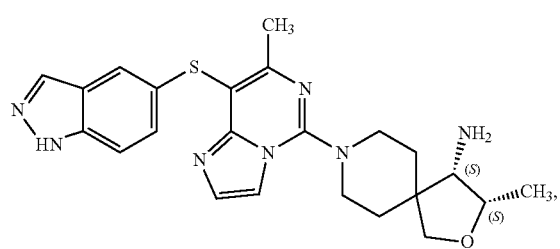
(30)
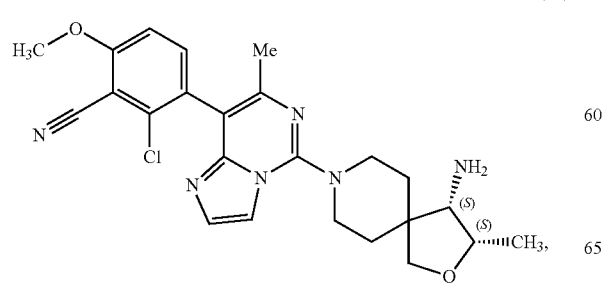
(31)
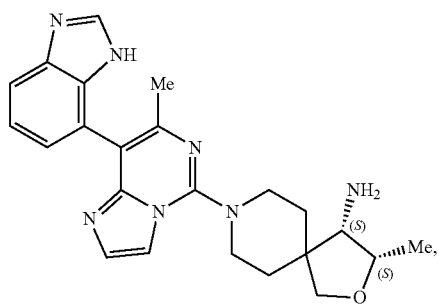
(32)
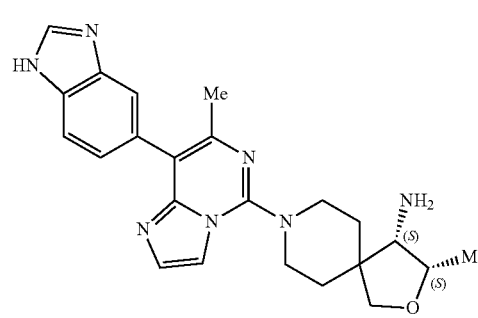
(33)
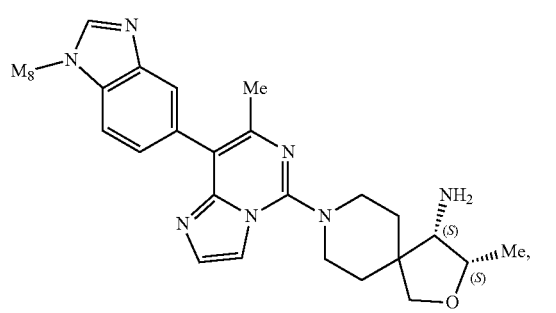
(34)
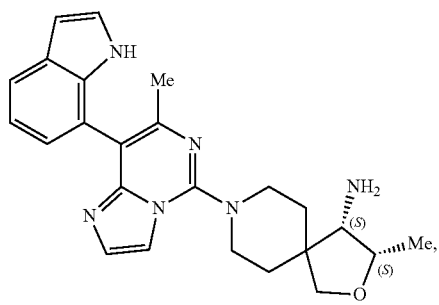
(35)
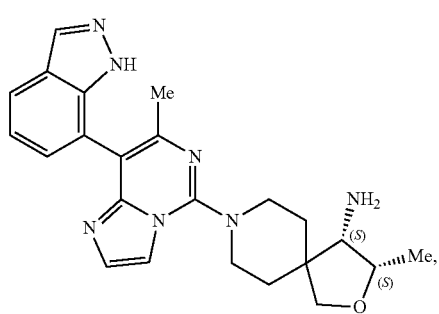
(36)

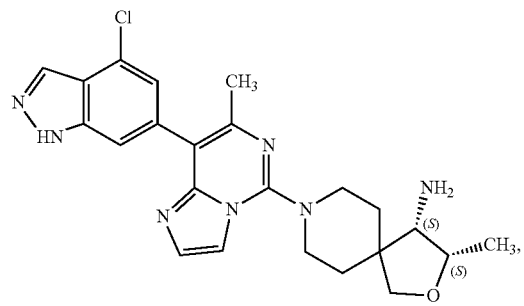
(37)
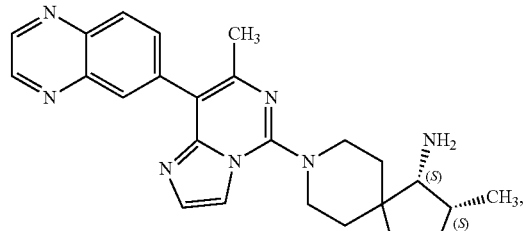
(42)
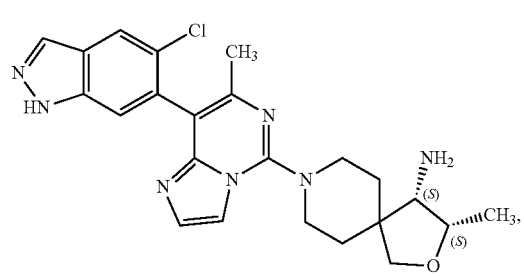
(38)
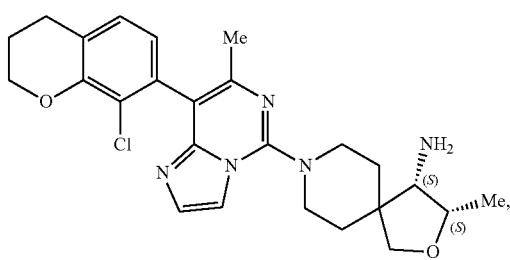
(43)
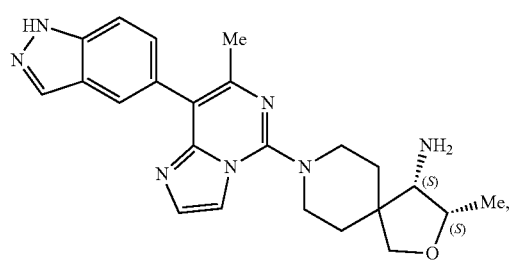
(39)
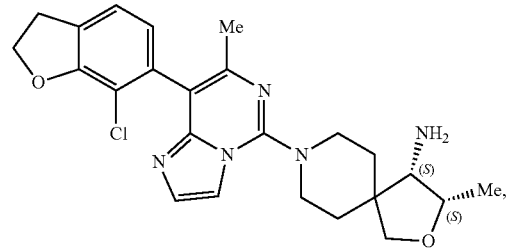
(44)
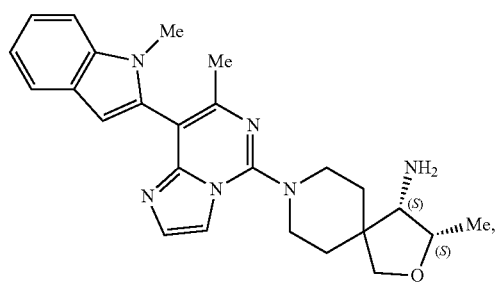
(40)
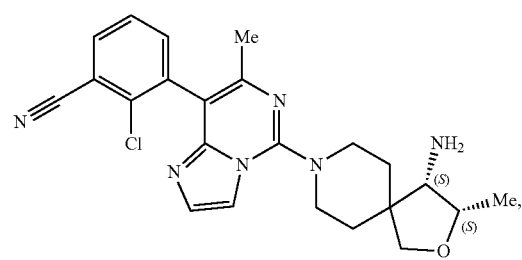
(45)
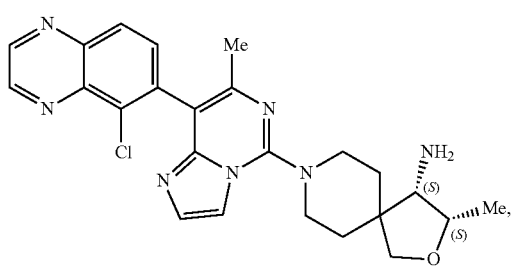
(41)
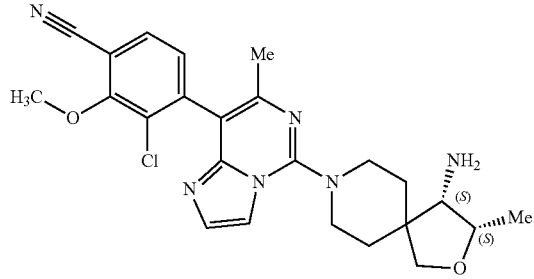
(46)

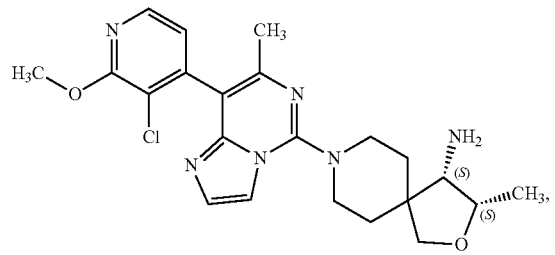
(47)
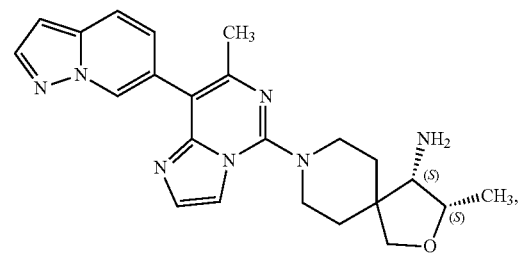
(48)
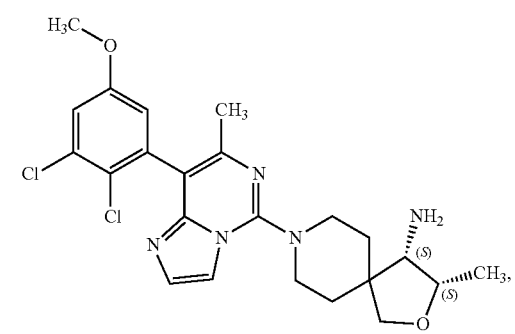
(49)
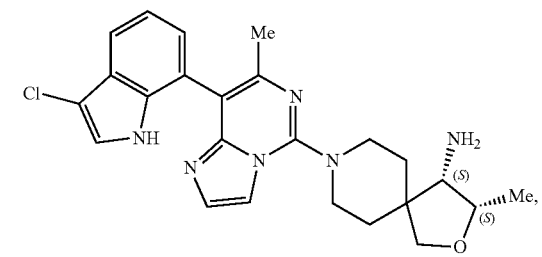
(50)
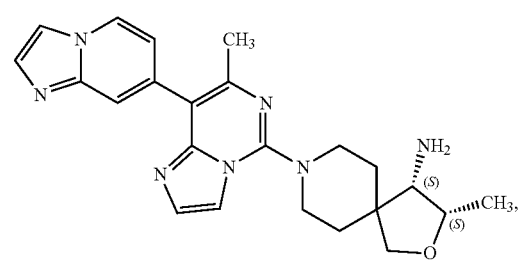
(51)
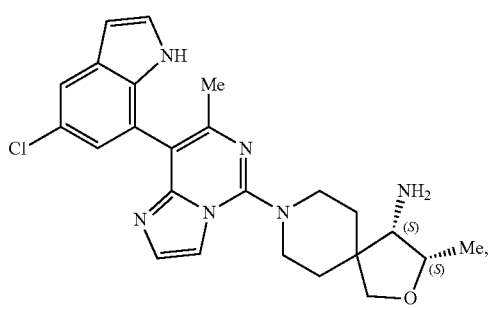
(52)
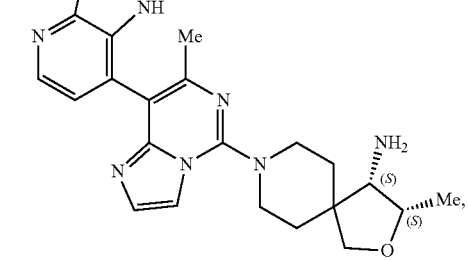
(53)
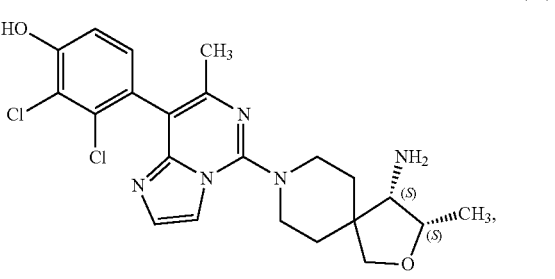
(54)
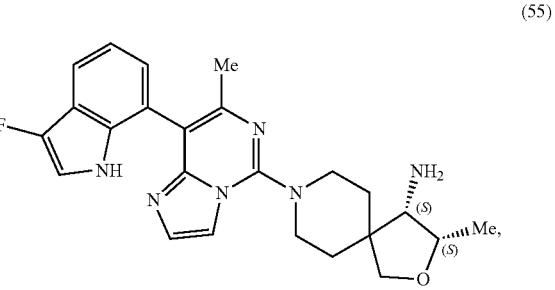
(55)
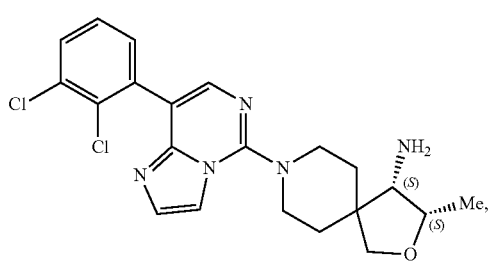
(56)

-continued
(57)
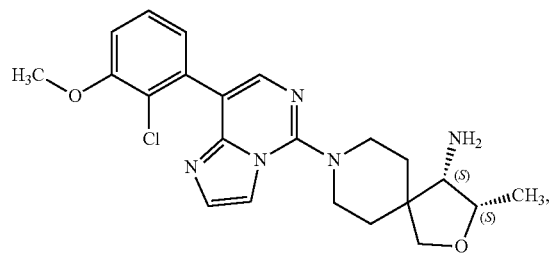
(58)
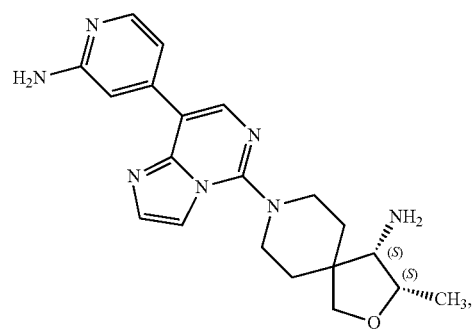
(59)
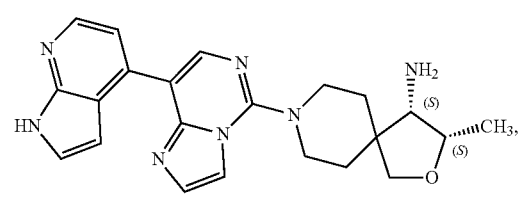
(60)
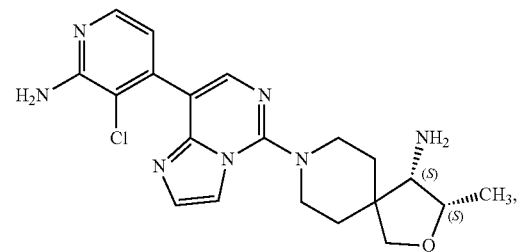
(61)
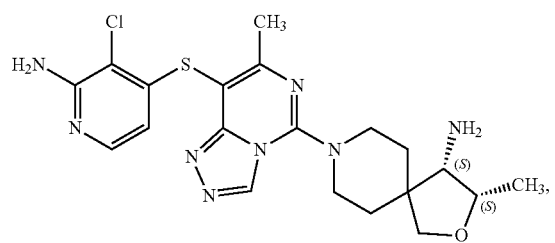
-continued
(62)
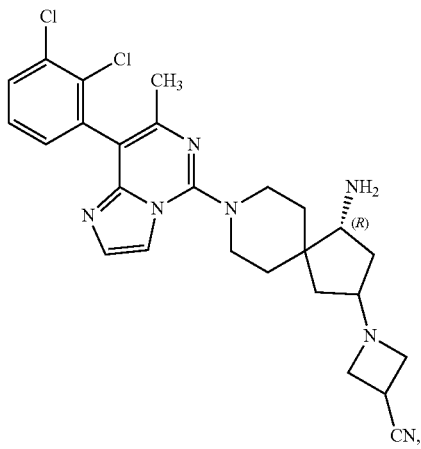
(63)
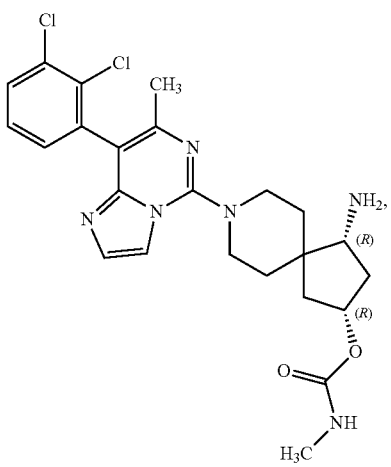
(64)
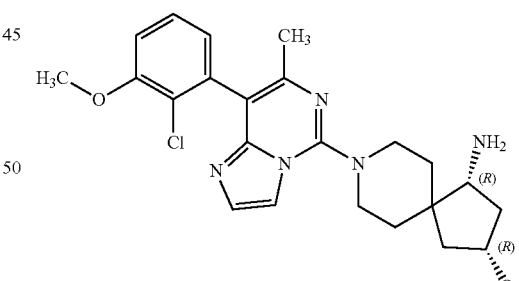
(65)
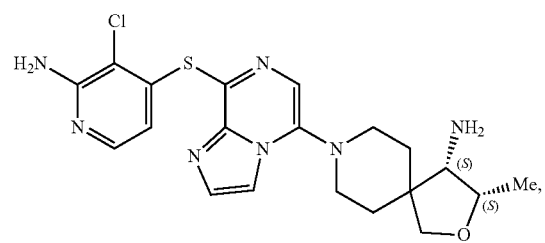

-continued
(66)
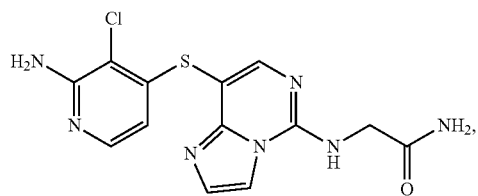
(67)
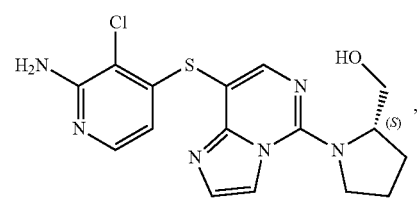
(68)
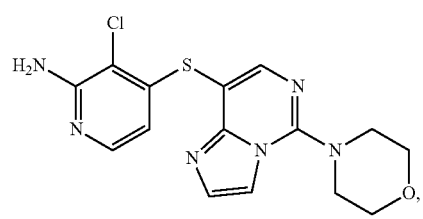
(69)
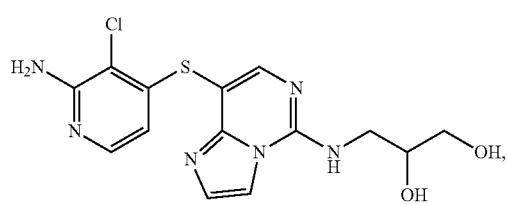
(70)
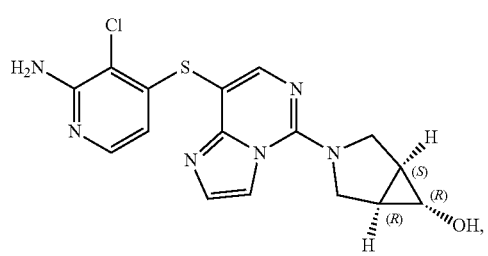
(71)
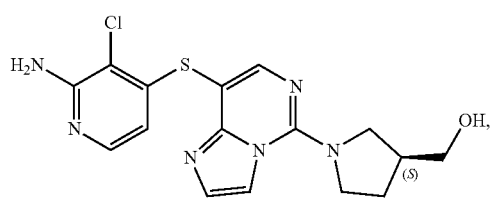
(72)
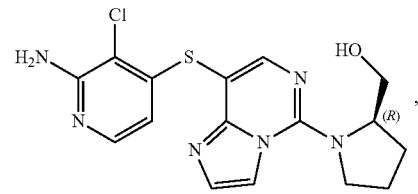
-continued
(73)
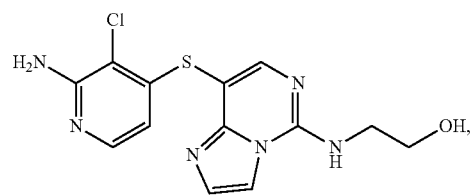
(74)
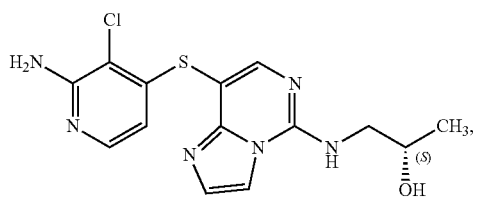
(75)
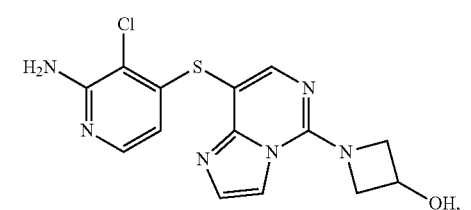
(76)
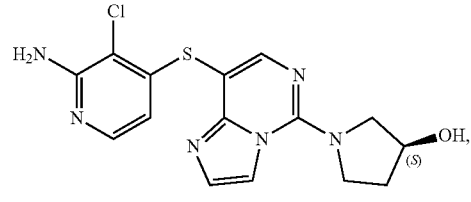
(77)
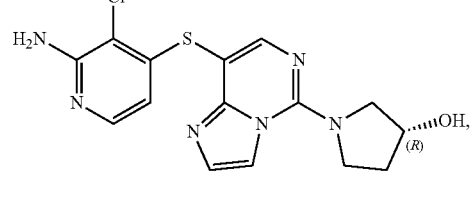
(78)
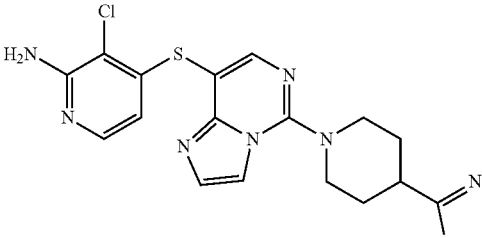
(79)
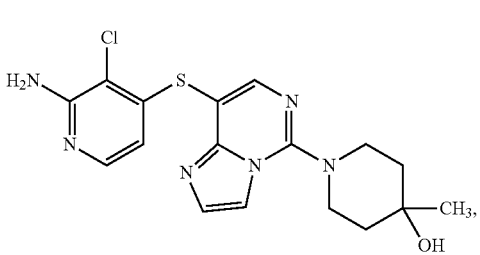

(80)

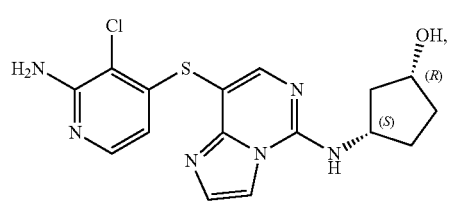

(81)

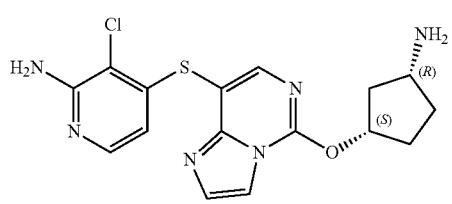

(82)

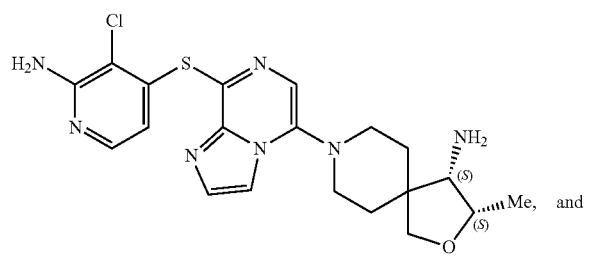

(83)

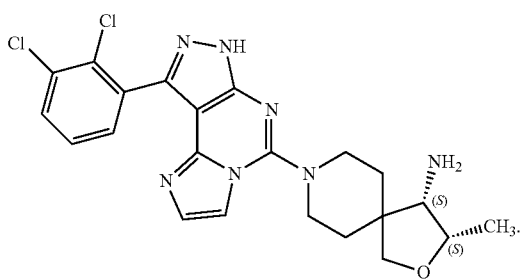

Embodiment II-38. A pharmaceutical composition comprising a compound of any one of Embodiments II-1 to II-37, or a pharmaceutically acceptable salt, prodrug, solvate, hydrate, tautomer, or isomer thereof, and a pharmaceutically acceptable carrier.

Embodiment II-39. A method of treating a disease associated with SHP2 modulation in a subject in need thereof, comprising administering to the subject an effective amount of a compound of any one of Embodiments II-1 to II-37, or a pharmaceutically acceptable salt, prodrug, solvate, hydrate, tautomer, or isomer thereof.

Embodiment II-40. The method of Embodiment II-39, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-41. A compound of any one of Embodiments II-1 to II-37, or a pharmaceutically acceptable salt, prodrug, solvate, hydrate, tautomer, or isomer thereof, for use as a medicament.

Embodiment II-42. A compound of any one of Embodiments II-1 to II-37, or a pharmaceutically acceptable salt, prodrug, solvate, hydrate, tautomer, or isomer thereof, for use in treating or preventing a disease associated with SHP2 modulation.

Embodiment II-43. Use of a compound of any one of Embodiments II-1 to II-37, or a pharmaceutically acceptable salt, prodrug, solvate, hydrate, tautomer, or isomer thereof, in the manufacture of a medicament for treating or preventing a disease associated with SHP2 modulation.

Embodiment II-44. A method of treating a disease associated with SHP2 modulation in a subject in need thereof, comprising administering to the subject an effective amount of a pharmaceutical composition of Embodiment II-38.

Embodiment II-45. The method of Embodiment II-44, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment II-46. A pharmaceutical composition of Embodiment II-38 for use as a medicament.

Embodiment II-47. A pharmaceutical composition of Embodiment II-38 for use in treating or preventing a disease associated with SHP2 modulation.

Embodiment II-48. Use of a pharmaceutical composition of Embodiment II-38 in the manufacture of a medicament for treating or preventing a disease associated with SHP2 modulation.

Some embodiments of this disclosure are Embodiment III, as follows:

Embodiment III-1. A compound of the Formula II':

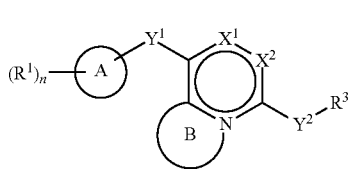

II' or a pharmaceutically acceptable salt, prodrug, solvate, hydrate, tautomer, or isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

$R^1$ is independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —OH, —$OR^6$, halogen, —$NO_2$, —CN, —$NR^5R^6$, —$SR^5$, —S(O)$_2NR^5R^6$, —S(O)$_2$$R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, —C(O)$R^5$, —$CO_2R^5$, —C(O)$NR^5R^6$, —$NR^5$C(O)$R^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —$NO_2$, oxo, =O, —CN, —$R^5$, —$OR^5$, —$NR^5R^6$, —$SR^5$, —S(O)$_2NR^5R^6$, —S(O)$_2R^5$, —$NR^5$S(O)$_2NR^5R^6$, —$NR^5$S(O)$_2R^6$, —S(O)$NR^5R^6$, —S(O)$R^5$, —$NR^5$S(O)$NR^5R^6$, —$NR^5$S(O)$R^6$, heterocycle, aryl, or heteroaryl;

$Y^1$ is —S—, a direct bond, —NH—, —S(O)$_2$—, —S(O)$_2$—NH—, —C(=CH$_2$)—, —CH$_2$—, or —S(O)—;

$X^1$ is N or $CR^2$;

$X^2$ is N or CH;

B, including the atoms at the points of attachment, is a monocyclic or polycyclic 5- to 12-membered heterocycle or a monocyclic or polycyclic 5- to 12-membered heteroaryl;

$Y^2$ is —$NR^a$—, —(CR$^a_2$)$_m$—, —O—, —C(O)—, —C(R$^a$)$_2$NH—, —(CR$^a_2$)$_m$O—, —C(O)N(R$^a$)—, —N(R$^a$)C(O)—, —S(O)$_2$N(R$^a$)—, —N(R$^a$)S(O)$_2$—, —N(R$^a$)C(O)

N(R$^a$)—, —N(R$^a$)C(S)N(R$^a$)—, —C(O)O—, —OC(O)—, —OC(O)N(R$^a$)—, —N(R$^a$)C(O)O—, —C(O)N(R$^a$)O—, —N(R$^a$)C(S)—, —C(S)N(R$^a$)—, or —OC(O)O—; wherein the bond on the left side of Y$^2$, as drawn, is bound to the ring and the bond on the right side of the Y$^2$ moiety, as drawn, is bound to R$^3$;

R$^a$ is independently, at each occurrence, —H, —OH, —C$_3$-C$_8$cycloalkyl, —C$_1$-C$_6$alkyl, 3- to 12-membered heterocyclyl, or —(CH$_2$)$_n$-aryl, wherein each alkyl or cycloalkyl is optionally substituted with one or more —NH$_2$, or wherein 2 R$^a$, together with the carbon atom to which they are both attached, can combine to form a 3- to 8-membered cycloalkyl;

R$^b$ is independently, at each occurrence, —H, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

R$^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —NO$_2$, oxo, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ is independently —H, —C$_1$-C$_6$alkyl, a 3- to 12-membered monocyclic or polycyclic heterocycle, a 5- to 12-membered spiroheterocycle, C$_3$-C$_8$cycloalkyl, —(CH$_2$)$_n$—R$^b$, or —(CH$_2$)$_n$C(O)NR$^5$R$^6$, wherein each alkyl, spiroheterocycle, heterocycle, or cycloalkyl is optionally substituted with one or more —C$_1$-C$_6$alkyl, —OH, —NH$_2$, —OR$^b$, —NHR$^b$, —(CH$_2$)$_n$OH, heterocyclyl, or spiroheterocyclyl; or R$^3$ can combine with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —O—C(O)—NR$^5$R$^6$, —CF$_3$, —CHF$_2$, —CH$_2$F, or =O; wherein the heteroaryl and heterocyclyl are optionally substituted with —CN;

R$^5$ and R$^6$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10;

provided that when X$^2$ is N and B ring is a monocyclic 5-membered heteroaryl containing 3-4 nitrogen atoms, then

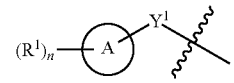

is not

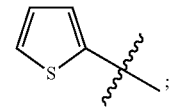

and provided that when X$^1$ is N; X$^2$ is CH and Y$^1$ is NH; then R$^1$ is not C$_3$-C$_8$cycloalkyl or heteroaryl.

Embodiment III-2.A compound of the Formula VI:

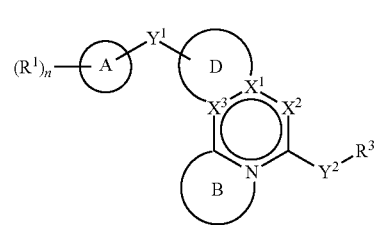

VI or a pharmaceutically acceptable salt, prodrug, solvate, hydrate, tautomer, or isomer thereof, wherein:

A is cycloalkyl, heterocycloalkyl, aryl, or heteroaryl, wherein cycloalkyl, heterocycloalkyl, aryl, and heteroaryl are 5- to 12-membered monocyclic or 5- to 12-membered polycyclic;

R$^1$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, heteroaryl, or oxo, wherein each alkyl, alkenyl, cycloalkenyl, alkynyl, cycloalkyl, heterocyclyl, spiroheterocyclyl, or heteroaryl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

Y$^1$ is —S—, a direct bond, —NH—, —S(O)$_2$—, —S(O)$_2$—NH—, —C(=CH$_2$)—, —CH$_2$—, or —S(O)—;

X$^1$ is N or C;

X$^2$ is N or CH;

X$^3$ is N or C;

B, including the atoms at the points of attachment, is a monocyclic or polycyclic 5- to 12-membered heterocycle or a monocyclic or polycyclic 5- to 12-membered heteroaryl;

D, including the atoms at the points of attachment, is a monocyclic 5- to 7-membered heterocycle or a monocyclic 5- to 7-membered heteroaryl;

$Y^2$ is —$NR^a$—, —$(CR^a_2)_m$—, —O—, —C(O)—, —$C(R^a)_2NH$—, —$(CR^a_2)_mO$—, —$C(O)N(R^a)$—, —$N(R^a)C(O)$—, —$S(O)_2N(R^a)$—, —$N(R^a)S(O)_2$—, —$N(R^a)C(O)N(R^a)$—, —$N(R^a)C(S)N(R^a)$—, —C(O)O—, —OC(O)—, —$OC(O)N(R^a)$—, —$N(R^a)C(O)O$—, —$C(O)N(R^a)O$—, —$N(R^a)C(S)$—, —$C(S)N(R^a)$—, or —OC(O)O—; wherein the bond on the left side of $Y^2$, as drawn, is bound to the ring and the bond on the right side of the $Y^2$ moiety, as drawn, is bound to $R^3$;

$R^a$ is independently, at each occurrence, —H, —OH, —$C_3$-$C_8$cycloalkyl, —$C_1$-$C_6$alkyl, 3- to 12-membered heterocyclyl, or —$(CH_2)_n$-aryl, wherein each alkyl or cycloalkyl is optionally substituted with one or more —$NH_2$, or wherein 2 $R^a$, together with the carbon atom to which they are both attached, can combine to form a 3- to 8-membered cycloalkyl;

$R^b$ is independently, at each occurrence, —H, —OH, —$C_1$-$C_6$alkyl, —$C_3$-$C_8$cycloalkyl, —$C_2$-$C_6$alkenyl, —$(CH_2)_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —$(CH_2)_n$-aryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, —$C(O)NR^5R^6$, —$NR^5C(O)R^6$, heterocycle, aryl, heteroaryl, —$(CH_2)_nOH$, —$C_1$-$C_6$alkyl, —$CF_3$, —$CHF_2$, or —$CH_2F$;

$R^2$ is independently —H, —$NH_2$, —$OR^b$, —CN, —$C_1$-$C_6$alkyl, —$C_2$-$C_6$alkenyl, —$C_4$-$C_8$cycloalkenyl, —$C_2$-$C_6$alkynyl, halogen, —$C(O)OR^b$, —$C_3$-$C_8$cycloalkyl, aryl, heterocyclyl containing 1-5 heteroatoms selected from the group consisting of N, S, P, and O, or heteroaryl containing 1-5 heteroatoms selected from the group consisting of N, S, P, and O; wherein each alkyl, alkenyl, cycloalkenyl, alkynyl, cycloalkyl, heterocyclyl, aryl, or heteroaryl is optionally substituted with one or more —OH, halogen, —$NO_2$, oxo, —CN, —$R^5$, —$OR^5$, —$NR^5R^6$, —$SR^5$, —$S(O)_2NR^5R^6$, —$S(O)_2R^5$, —$NR^5S(O)_2NR^5R^6$, —$NR^5S(O)_2R^6$, —$S(O)NR^5R^6$, —$S(O)R^5$, —$NR^5S(O)NR^5R^6$, —$NR^5S(O)R^6$, heterocycle, aryl, or heteroaryl;

$R^3$ is independently —H, —$C_1$-$C_6$alkyl, a 3- to 12-membered monocyclic or polycyclic heterocycle, a 5- to 12-membered spiroheterocycle, $C_3$-$C_8$cycloalkyl, or —$(CH_2)_n$—$R^b$, wherein each alkyl, spiroheterocycle, heterocycle, or cycloalkyl is optionally substituted with one or more —$C_1$-$C_6$alkyl, —OH, —$NH_2$, —$OR^5$, —$NHR^b$, —$(CH_2)_nOH$, —$(CH_2)_nC(O)NR^5R^6$, heterocyclyl, or spiroheterocyclyl; or $R^3$ can combine with $R^a$ to form a 3- to 12-membered monocyclic or polycyclic heterocycle or a 5- to 12-membered spiroheterocycle, wherein each heterocycle or spiroheterocycle is optionally substituted with one or more —$C_1$-$C_6$alkyl, halogen, —OH, —$OR^b$, —$NH_2$, —$NHR^b$, optionally substituted heteroaryl, optionally substituted heterocyclyl, —$(CH_2)_nNH_2$, —$(CH_2)_nOH$, —$COOR^b$, —$CONHR^b$, —$CONH(CH_2)_nCOOR^b$, —$NHCOOR^b$, —O—C(O)—$NR^5R^6$, —$CF_3$, —$CHF_2$, —$CH_2F$, or =O; wherein the heteroaryl and heterocyclyl are optionally substituted with —CN;

$R^5$ and $R^6$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, a monocyclic or polycyclic 3- to 12-membered heterocycle, —$OR^7$, —$SR^7$, halogen, —$NR^7R^8$, —$NO_2$, —$CF_3$, or —CN;

$R^7$ and $R^8$ are independently, at each occurrence, —H, —$C_1$-$C_6$alkyl, —$C_2$-$C_6$alkenyl, —$C_4$-$C_8$cycloalkenyl, —$C_2$-$C_6$alkynyl, —$C_3$-$C_8$cycloalkyl, —$OR^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —$NH_2$, —$NO_2$, or —CN;

m is independently 1, 2, 3, 4, 5 or 6; and n is independently 0, 1, 2, 3, 4, 5, 6, 7, 8, 9, or 10.

Embodiment III-3. The compound of Embodiment III-1 or III-2, wherein $Y^1$ is —S—.

Embodiment III-4. The compound of Embodiment III-1 or III-2, wherein $Y^1$ is a direct bond.

Embodiment III-5. The compound of any one of Embodiments III-1 to III-4, wherein $X^1$ is N.

Embodiment III-6. The compound of any one of Embodiments III-1 to III-4, wherein $X^1$ is $CR^2$.

Embodiment III-7. The compound of Embodiment III-6, wherein $R^2$ is —H, —$NH_2$, —OH, or —$C_1$-$C_6$alkyl.

Embodiment III-8. The compound of any one of Embodiments III-1 to III-4, wherein $X^2$ is N.

Embodiment III-9. The compound of any one of Embodiments III-1 to III-4, wherein $X^2$ is CH.

Embodiment III-10. The compound of any one of Embodiments III-1 to III-4, wherein $X^1$ is N and $X^2$ is N.

Embodiment III-11. The compound of any one of Embodiments III-1 to III-4, wherein $X^1$ is N and $X^2$ is CH.

Embodiment III-12. The compound of any one of Embodiments III-1 to III-4, wherein $X^1$ is $CR^2$ and $X^2$ is N.

Embodiment III-13. The compound of any one of Embodiments III-1 to III-4, wherein $X^1$ is $CR^2$ and $X^2$ is CH.

Embodiment III-14. The compound of any one of Embodiments III-12 to III-13, wherein $R^2$ is —H, —$NH_2$, —OH, or —$C_1$-$C_6$alkyl.

Embodiment III-15. The compound of any one of Embodiments III-1 to III-14, wherein B, including the atoms at the points of attachment, is a monocyclic 5- to 12-membered heteroaryl.

Embodiment III-16. The compound of any one of Embodiments III-1 to III-15, wherein B, including the atoms at the points of attachment, is

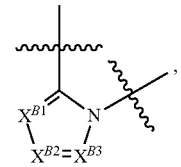

wherein $X^{B1}$ is N, CH, S, or O; $X^{B2}$ is N, CH, S, or O; and $X^{B3}$ is N, CH, S, or O.

Embodiment III-17. The compound of any one of Embodiments III-1 to III-15, wherein B, including the atoms at the points of attachment, is

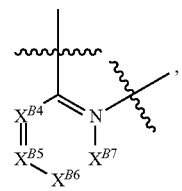

wherein $X^{B4}$ is N or CH; $X^{B5}$ is N or CH; $X^{B6}$ is N or CH; and $X^{B7}$ is N or CH.

Embodiment III-18. The compound of any of one of Embodiments III-1 to III-17, wherein A is cycloalkyl.

Embodiment III-19. The compound of any of one of Embodiments III-1 to III-17, wherein A is heterocycloalkyl.

Embodiment III-20. The compound of any of one of Embodiments III-1 to III-17, wherein A is aryl.

Embodiment III-21. The compound of any of one of Embodiments III-1 to III-17, wherein A is phenyl.

Embodiment III-22. The compound of any of one of Embodiments III-1 to III-17, wherein A is heteroaryl.

Embodiment III-23. The compound of any of one of Embodiments III-1 to III-17, wherein A is pyridyl.

Embodiment III-24. The compound of any one of Embodiments III-1 to III-23, wherein $R^1$ is independently —OH, —NO$_2$, —CN, halogen, or —NR$^5$R$^6$.

Embodiment III-25. The compound of any of one of Embodiments III-1 to III-24, wherein $Y^2$ is —NR$^a$—.

Embodiment III-26. The compound of any of one of Embodiments III-1 to III-24, wherein $Y^2$ is —(CR$^a{}_2$)$_m$—.

Embodiment III-27. The compound of any of one of Embodiments III-1 to III-26, wherein R$^a$ is —H.

Embodiment III-28. The compound of any of one of Embodiments III-1 to III-26, wherein R$^a$ is —C$_1$-C$_6$alkyl.

Embodiment III-29. The compound of any of one of Embodiments III-1 to III-28, wherein $R^3$ is —C$_1$-C$_6$alkyl.

Embodiment III-30. The compound of any of one of Embodiments III-1 to III-28, wherein $R^3$ is 3- to 12-membered monocyclic or polycyclic heterocycle.

Embodiment III-31. The compound of any of one of Embodiments III-1 to III-28, wherein $R^3$ is a 3- to 12-membered monocyclic heterocycle.

Embodiment III-32. The compound of any of one of Embodiments III-1 to III-28, wherein $R^3$ is a 5- to 12-membered polycyclic heterocycle.

Embodiment III-33. The compound of any of one of Embodiments III-1 to III-26, wherein $R^3$ and R$^a$ together with the atom to which they are attached combine to form a 3- to 12-membered monocyclic heterocycle.

Embodiment III-34. The compound of any of one of Embodiments III-1 to III-26, wherein $R^3$ and R$^a$ together with the atoms to which they are attached combine to form a 3- to 12-membered polycyclic heterocycle.

Embodiment III-35. The compound of any of one of Embodiments III-1 to III-26, wherein $R^3$ and R$^a$ together with the atoms to which they are attached combine to form a 5- to 12-membered spiroheterocycle.

Embodiment III-36. The compound of any of one of Embodiments III-33 to III-35, wherein heterocycle or spirocycle formed by $R^3$ and R$^a$ is substituted with one or more substituents selected from the group consisting of C$_1$-C$_6$alkyl, —OH, halogen, —NH$_2$, —NHR$^b$, —CF$_3$, —CHF$_2$, or —CH$_2$F.

Embodiment III-37. A compound, or a pharmaceutically acceptable salt, solvate, stereoisomer, or tautomer thereof, selected from the group consisting of:

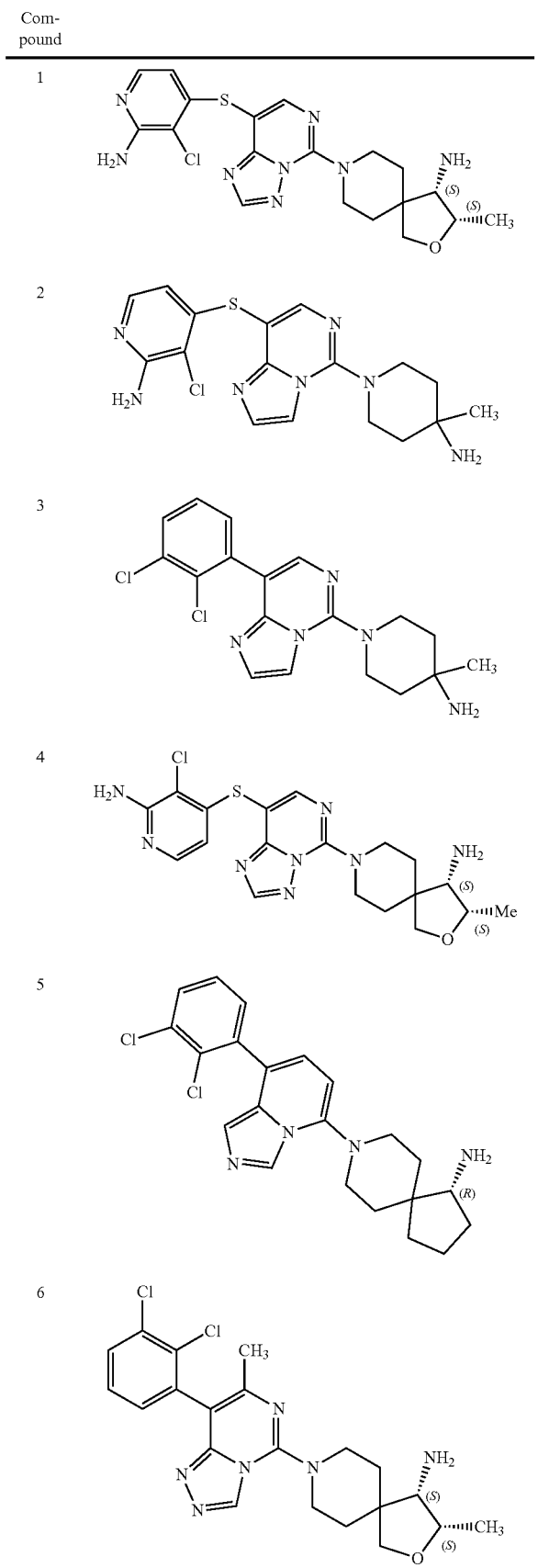

| Compound | |
|---|---|
| 7 | 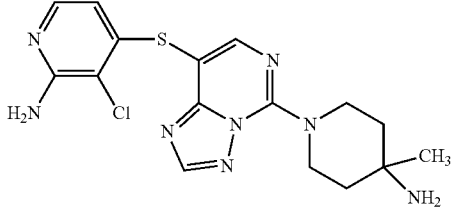 [SMILES: CC1(N)CCN(c2ncc(Sc3ccnc(N)c3Cl)c3ncnn23)CC1] |
| 8 | 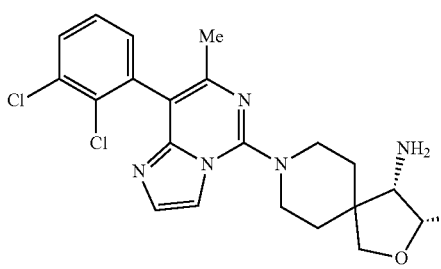 |
| 9 | 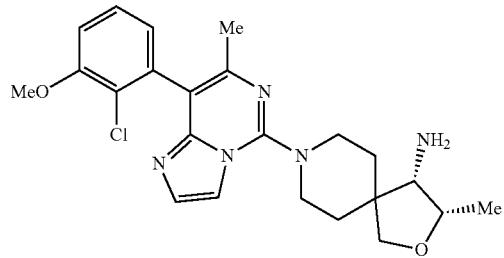 [SMILES: COc1cccc(-c2c(C)nc(N3CCC4(CC3)CO[C@@H](C)[C@H]4N)n3ccnc23)c1Cl] |
Embodiment III-38. A compound, or a pharmaceutically acceptable salt, solvate, stereoisomer, or tautomer thereof, selected from the group consisting of:
(1)
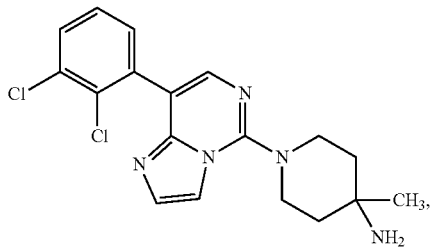
(2)
(3)
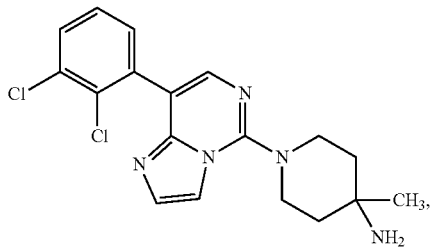
(4)
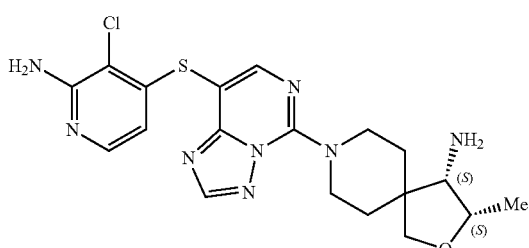
(5)
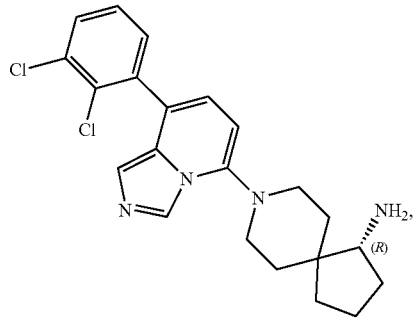
(6)
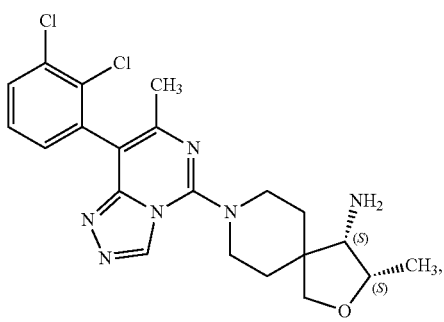
(7)
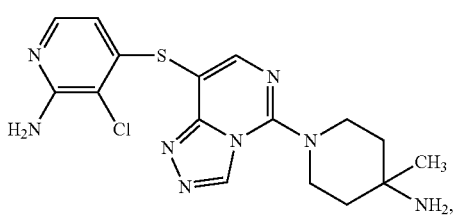

(8)
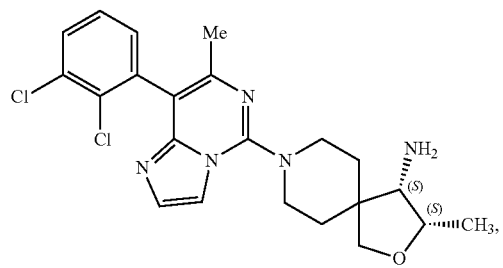
(13)
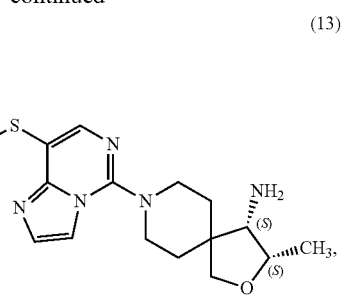
(9)
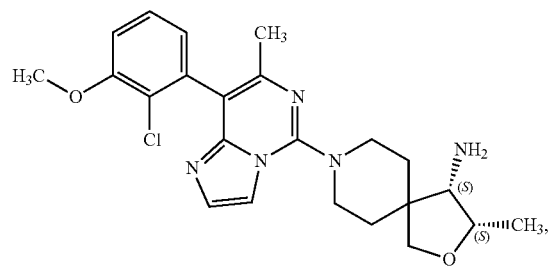
(14)
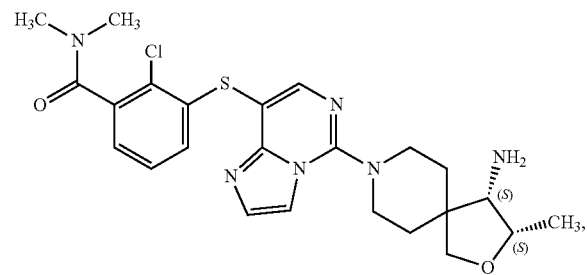
(10)
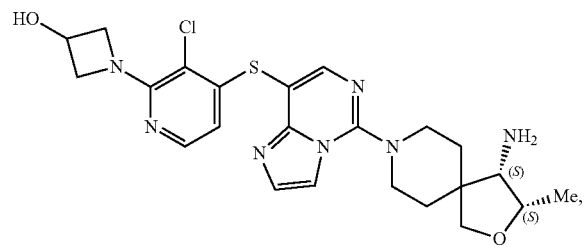
(15)
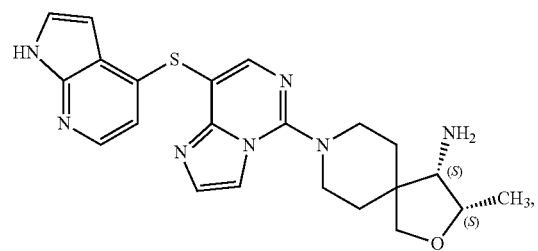
(11)
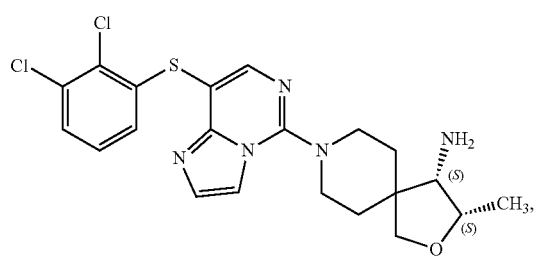
(16)
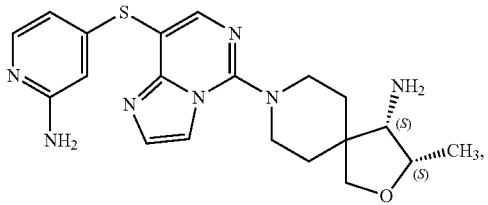
(17)
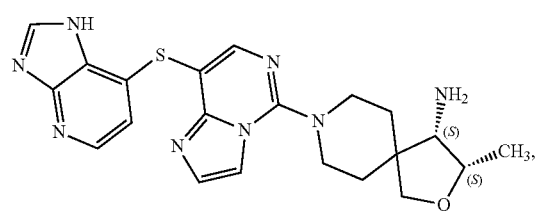
(12)
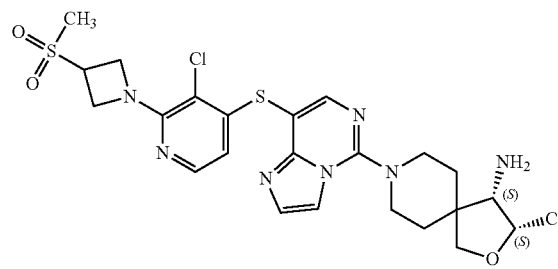
(18)
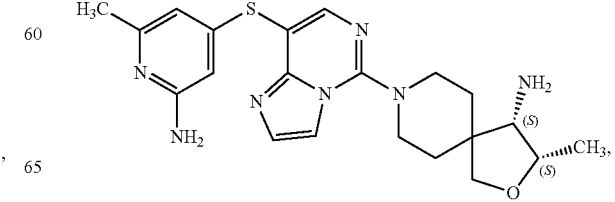

(19) 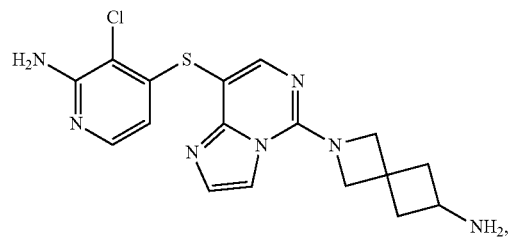
(20) 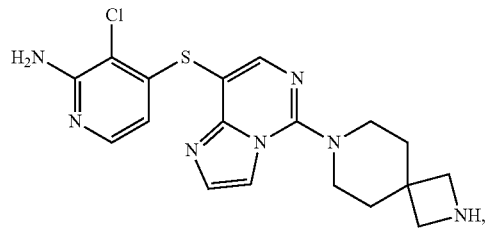
(21) 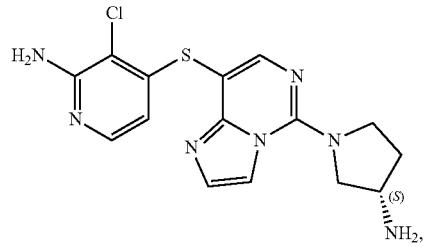
(22) 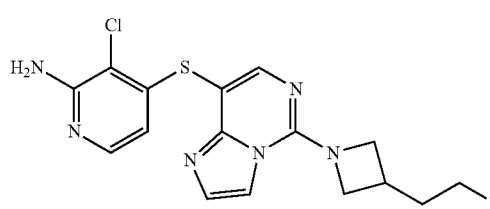
(23) 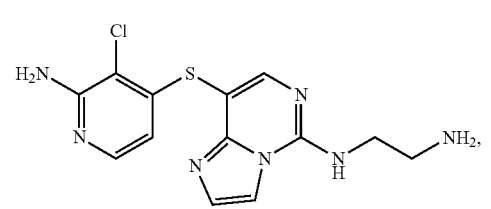
(24) 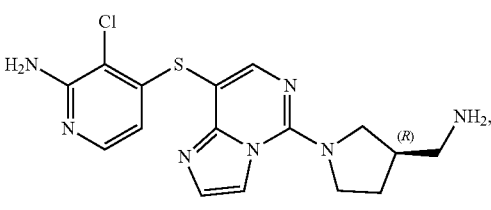
(25) 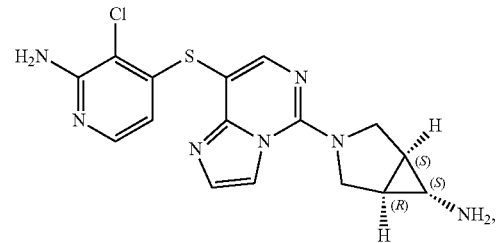
(26) 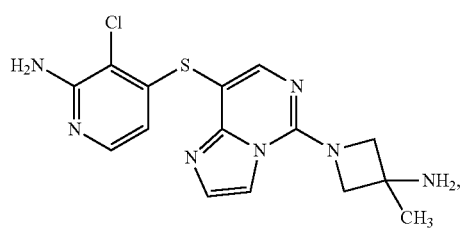
(27) 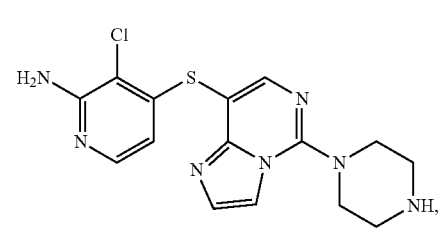
(28) 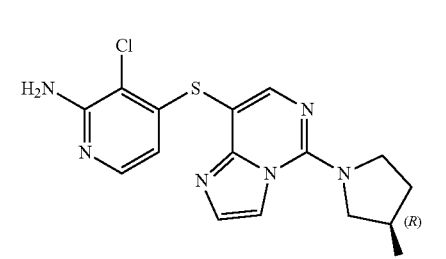
(29) 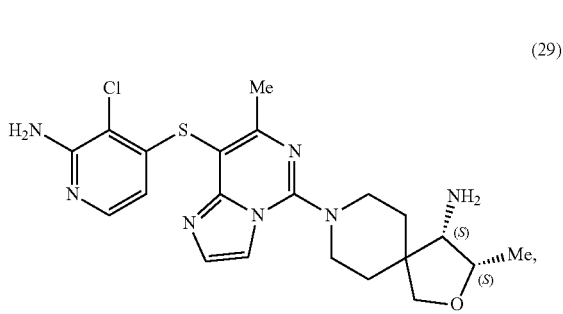
(30) 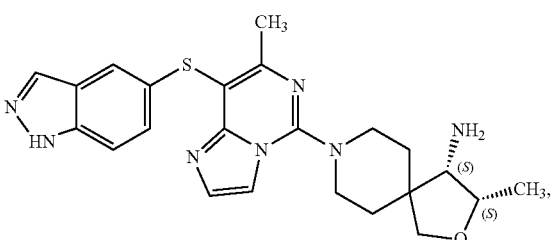
(31) 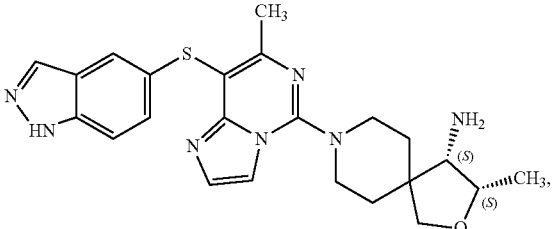

(32)
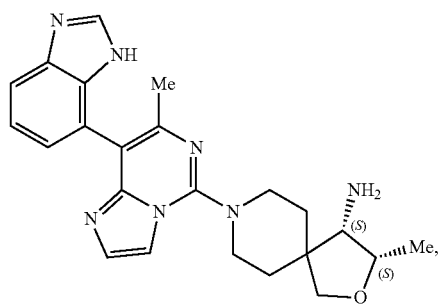
(33)
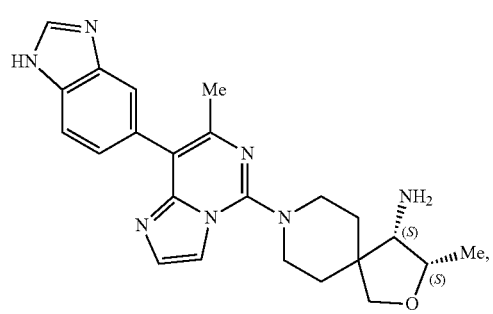
(34)
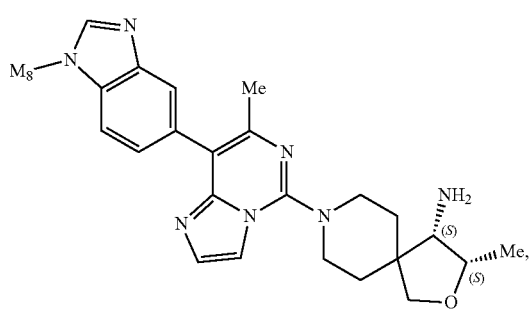
(35)
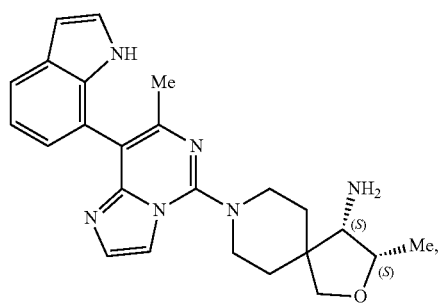
(36)
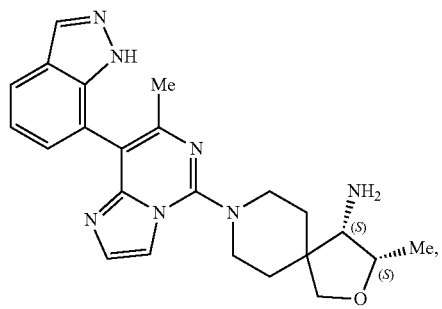
(37)
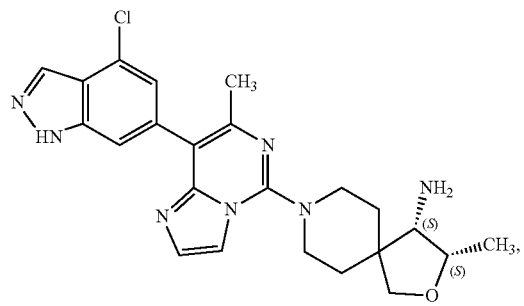
(38)
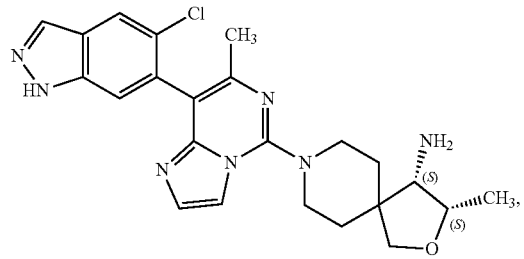
(39)
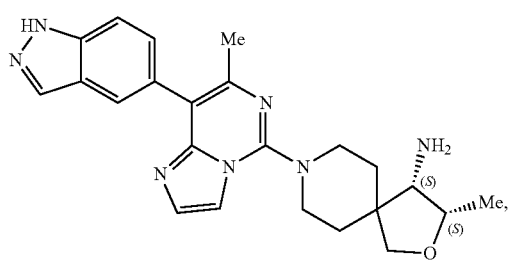
(40)
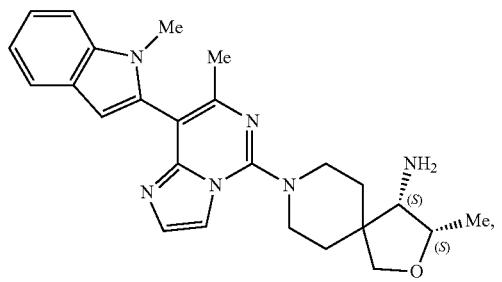
(41)
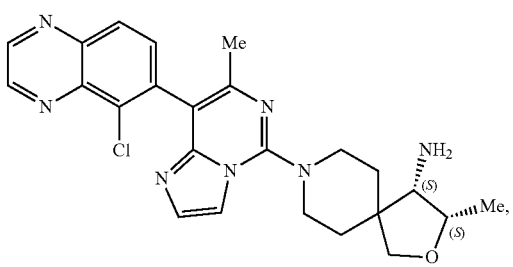

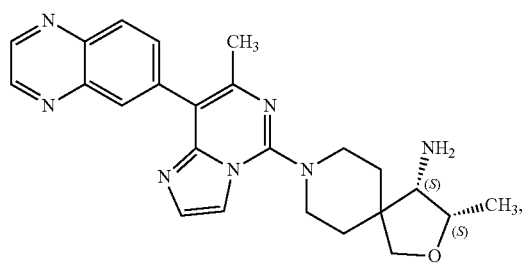
(42)
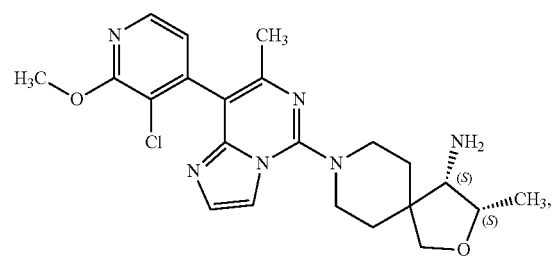
(47)
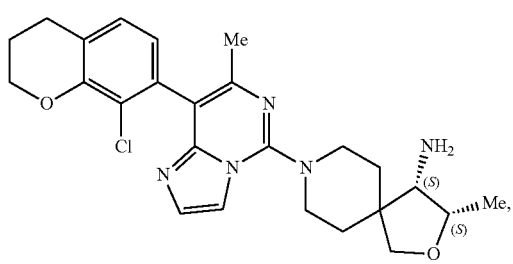
(43)
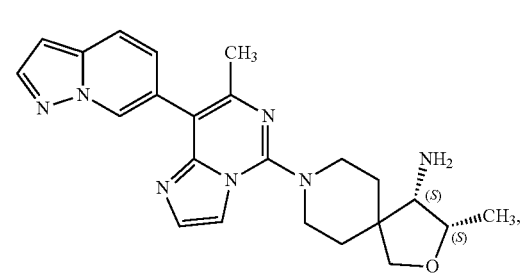
(48)
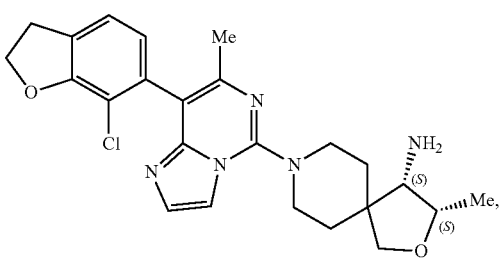
(44)
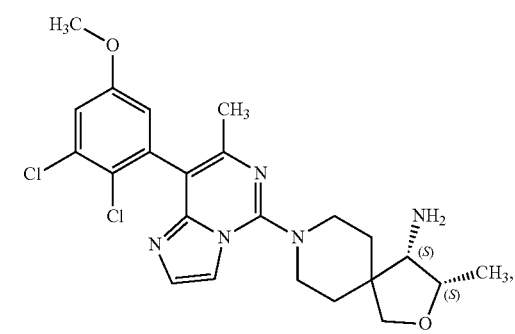
(49)
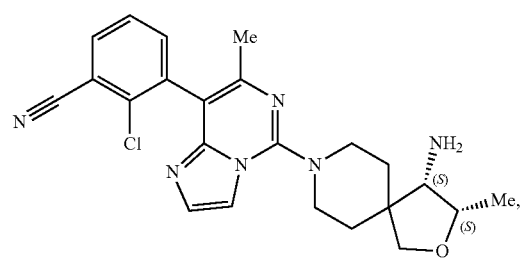
(45)
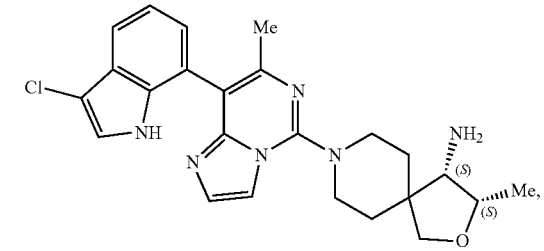
(50)
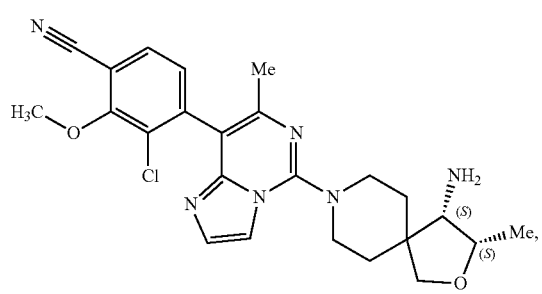
(46)
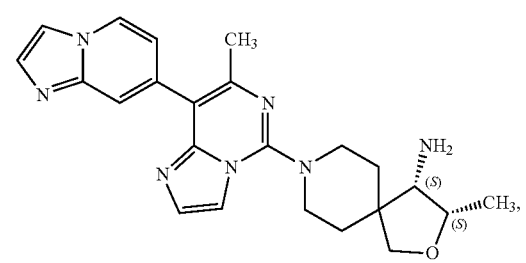
(51)

(52)
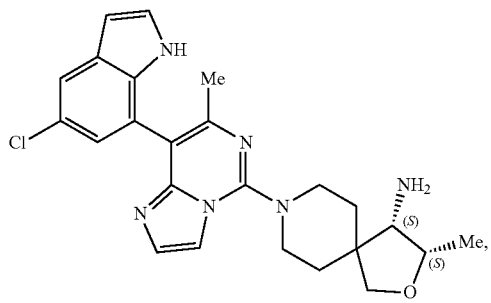
(53)
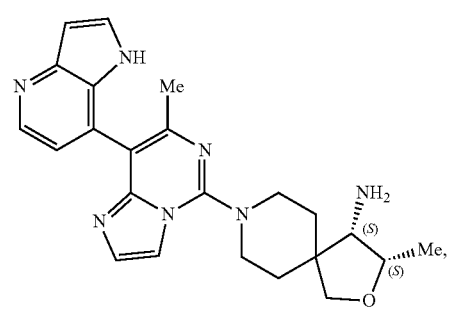
(54)
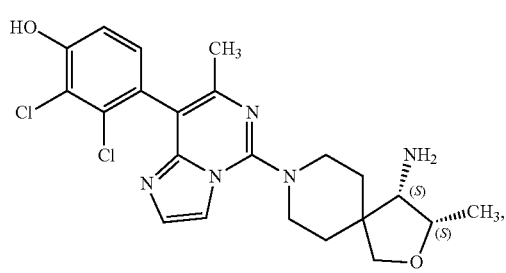
(55)
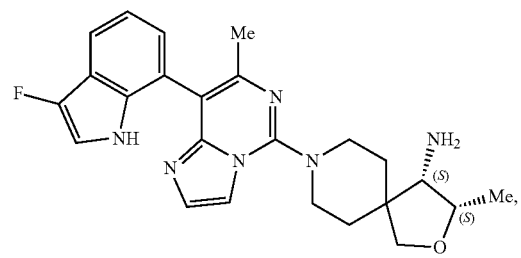
(56)
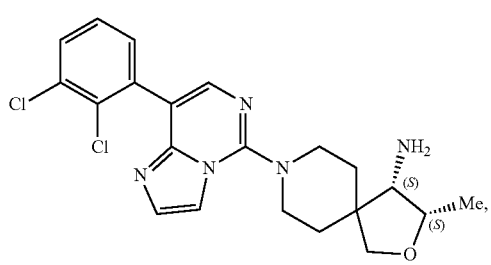
(57)
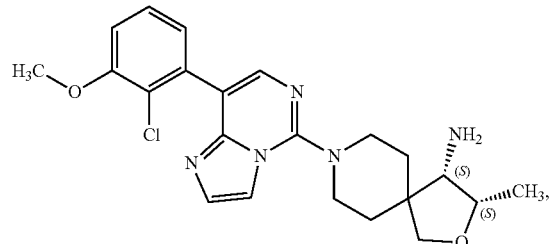
(58)
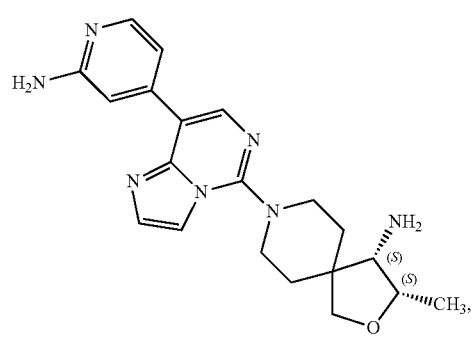
(59)
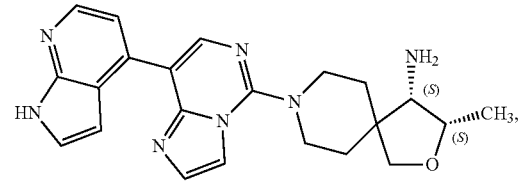
(60)
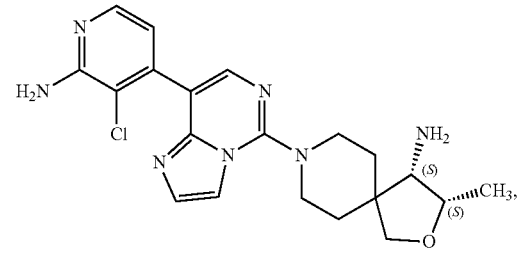
(61)
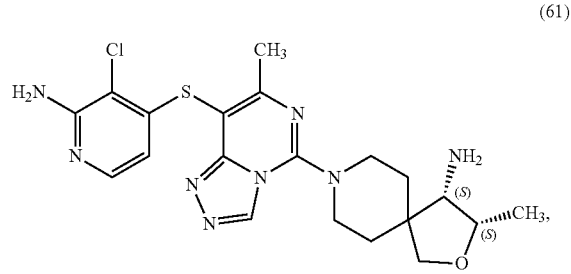

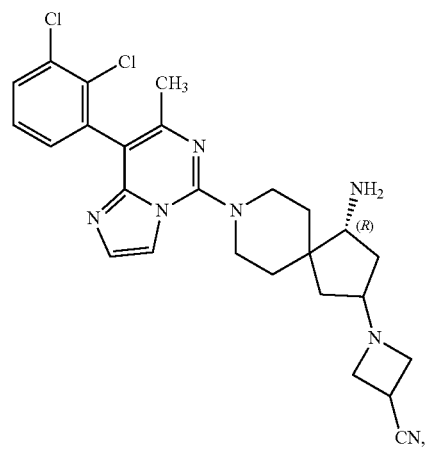
(62)
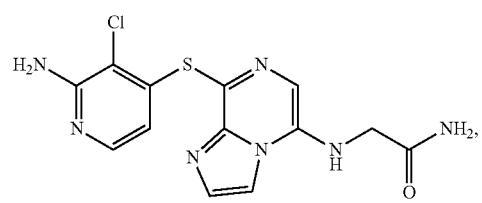
(66)
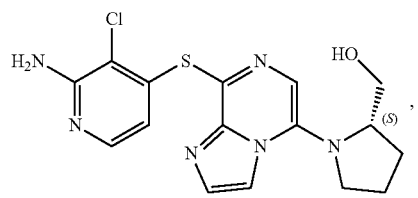
(67)
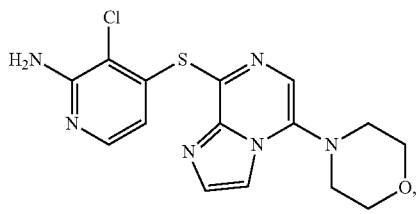
(68)
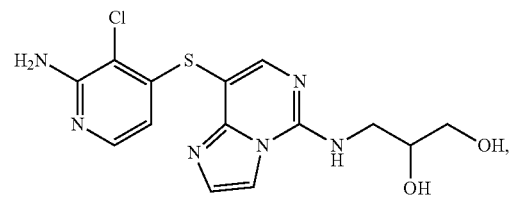
(69)
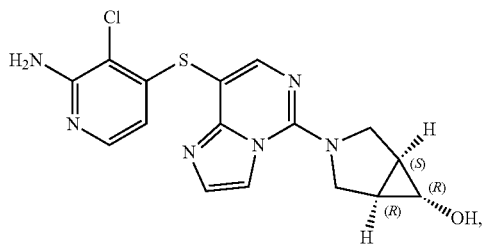
(70)
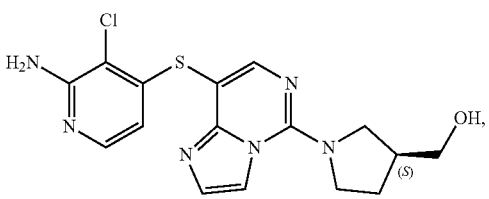
(71)
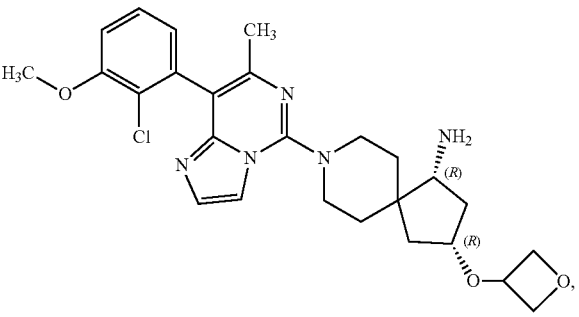
(63), (64), (65)
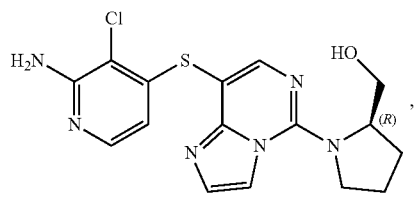
(72)

-continued

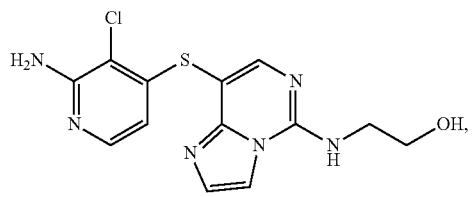
(73)

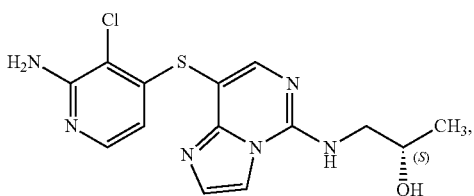
(74)

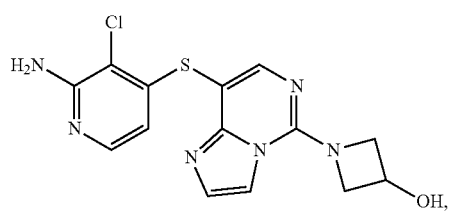
(75)

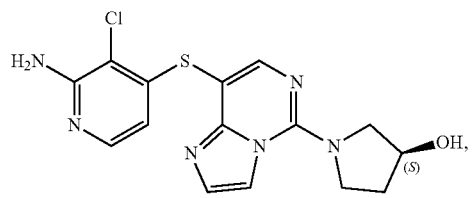
(76)

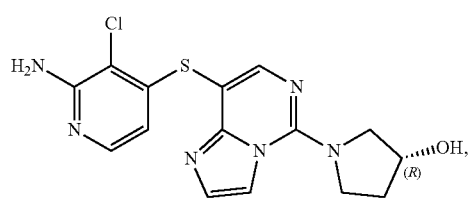
(77)

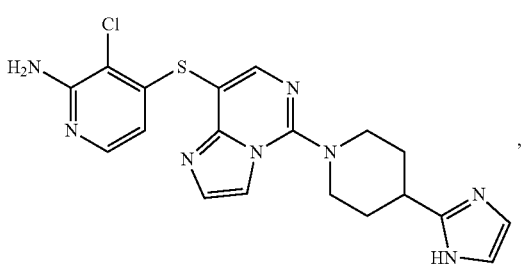
(78)

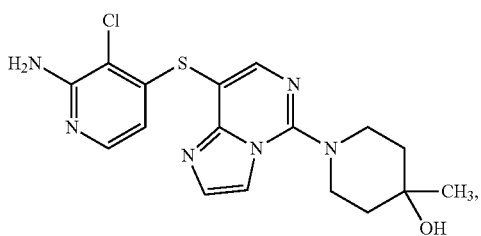
(79)

-continued

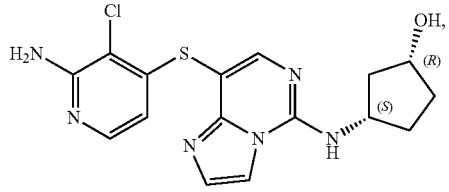
(80)

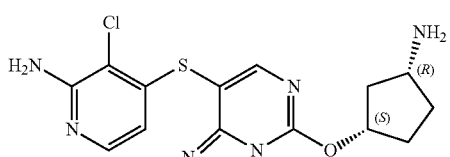
(81)

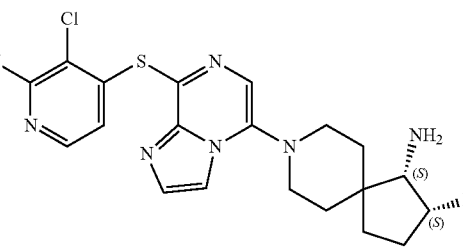
(82)

and

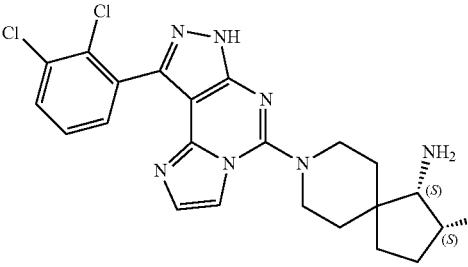
(83)

Embodiment III-39. A pharmaceutical composition comprising a compound of any one of Embodiments III-1 to III-38, or a pharmaceutically acceptable salt, prodrug, solvate, hydrate, tautomer, or isomer thereof, and a pharmaceutically acceptable carrier.

Embodiment III-40. A method of treating a disease associated with SHP2 modulation in a subject in need thereof, comprising administering to the subject an effective amount of a compound of any one of Embodiments III-1 to III-38, or a pharmaceutically acceptable salt, prodrug, solvate, hydrate, tautomer, or isomer thereof.

Embodiment III-41. The method of Embodiment III-40, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment III-42. A compound of any one of Embodiments III-1 to III-38, or a pharmaceutically acceptable salt, prodrug, solvate, hydrate, tautomer, or isomer thereof, for use as a medicament.

Embodiment III-43. A compound of any one of Embodiments III-1 to III-38, or a pharmaceutically acceptable salt, prodrug, solvate, hydrate, tautomer, or isomer thereof, for use in treating or preventing a disease associated with SHP2 modulation.

Embodiment III-44. Use of a compound of any one of Embodiments III-1 to III-38, or a pharmaceutically acceptable salt, prodrug, solvate, hydrate, tautomer, or isomer thereof, in the manufacture of a medicament for treating or preventing a disease associated with SHP2 modulation.

Embodiment III-45. A method of treating a disease associated with SHP2 modulation in a subject in need thereof, comprising administering to the subject an effective amount of a pharmaceutical composition of Embodiment III-39.

Embodiment III-46. The method of Embodiment III-45, wherein the disease is selected from Noonan Syndrome, Leopard Syndrome, juvenile myelomonocytic leukemias, neuroblastoma, melanoma, acute myeloid leukemia and cancers of the breast, lung and colon.

Embodiment III-47. A pharmaceutical composition of Embodiment III-39 for use as a medicament.

Embodiment III-48. A pharmaceutical composition of Embodiment III-39 for use in treating or preventing a disease associated with SHP2 modulation.

Embodiment III-49. Use of a pharmaceutical composition of Embodiment III-39 in the manufacture of a medicament for treating or preventing a disease associated with SHP2 modulation.

EXAMPLES

The disclosure is further illustrated by the following examples and synthesis examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Definitions used in the following examples and elsewhere herein are:
$CH_2Cl_2$, DCM Methylene chloride, Dichloromethane
$CH_3CN$, MeCN Acetonitrile
CuI Copper (I) iodide
DIPEA Diisopropylethyl amine
DMF N,N-Dimethylformamide
EtOAc Ethyl acetate
hr hour
$H_2O$ Water
HCl Hydrochloric acid
$K_3PO_4$ Potassium phosphate (tribasic)
MeOH Methanol
$Na_2SO_4$ Sodium sulfate
NMP N-methyl pyrrolidone
Pd(dppf)Cl$_2$ [1,1'-Bis(diphenylphosphino)ferrocene]dichloropalladium(II)

Example 1. Synthesis of (3S,4S)-8-{8-[(2-amino-3-chloropyridin-4-yl)sulfanyl]imidazo[1,2-c]pyrimidin-5-yl}-3-methyl-2-oxa-8-azaspiro[4.5]decan-4-amine (Compound 1)

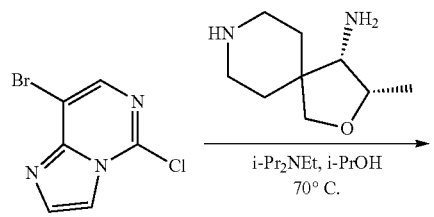

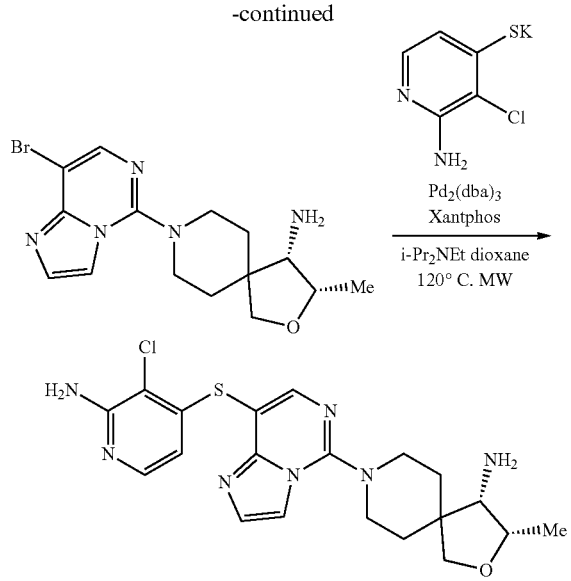

Step 1. Synthesis of (3S,4S)-8-{8-bromoimidazo[1,2-c]pyrimidin-5-yl}-3-methyl-2-oxa-8-azaspiro[4.5]decan-4-amine To a solution of 8-bromo-5-chloro-imidazo[1,2-c]pyrimidine (0.50 g, 2.15 mmol) in isopropanol (10 mL) was added (3S,4S)-3-methyl-2-oxa-8-azaspiro[4.5]decan-4-amine (0.44 g, 2.1 mmol, HCl salt) and N,N-diisopropylethylamine (3.74 mL, 21.5 mmol) at room temperature. (Huang, Y et al. *J. Med. Chem.* 2017, 60, 2215.) The reaction was heated to 70° C. for 3 h. Upon completion, the reaction mixture was concentrated under reduced pressure and the resulting residue was purified silica gel column chromatography (0-20% MeOH/DCM) to afford (3S,4S)-8-{8-bromoimidazo[1,2-c]pyrimidin-5-yl}-3-methyl-2-oxa-8-azaspiro[4.5]decan-4-amine (0.65 g, 83% yield). $^1$H NMR (500 MHz, Methanol-$d_4$) δ 7.96 (s, 1H), 7.82 (d, J=1.7 Hz, 1H), 7.66 (d, J=1.6 Hz, 11H), 4.45-4.21 (m, 1H), 3.99 (dt, J=9.2, 1.1 Hz, 1H), 3.88 (dd, J=9.3, 0.8 Hz, 11H), 3.87-3.76 (m, 1H), 3.49 (t, J=3.9 Hz, 1H), 3.28-3.10 (m, 3H), 2.06 (tdd, J=11.1, 7.0, 3.9 Hz, 2H), 1.95 (ddt, J=13.6, 4.9, 2.6 Hz, 1H), 1.86-1.69 (m, 1H), 1.33 (dd, J=6.6, 1.2 Hz, 3H). LC-MS (ESI): m/z: [M+H]$^+$ calculated for $C_{15}H_{21}BrN_5O$: 366.1; found 366.3.

Step 2. Synthesis of (3S,4S)-8-{8-[(2-amino-3-chloropyridin-4-yl)sulfanyl]imidazo[1,2-c]pyrimidin-5-yl}-3-methyl-2-oxa-8-azaspiro[4.5]decan-4-amine (3S,4S)-8-{8-bromoimidazo[1,2-c]pyrimidin-5-yl}-3-methyl-2-oxa-8-azaspiro[4.5]decan-4-amine (100 mg, 273 µmol), 3-chloro-4-(potassiosulfanyl)pyridin-2-amine (81.2 mg, 409 µmol), [5-(diphenylphosphanyl)-9,9-dimethyl-9H-xanthen-4-yl]diphenylphosphane (known as XantPhos) (31.5 mg, 54.6 µmol), tris(dibenzylideneacetone) dipalladium (24.9 mg, 27.3 µmol) and a Teflon coated magnetic stir bar were sequentially added to a 5 mL microwave vial. The vial was capped, and then sparged with nitrogen gas for 3 minutes. To this vial was then added dioxane (2.7 mL), which had been sparged with nitrogen gas for 45 minutes, followed by the addition of N,N-diisopropylethylamine (63.3 µL, 364 µmol). This heterogeneous mixture was then heated in a microwave at 120° C. for 2 h. The reaction was filtered over a pad of celite, washed with 20% MeOH/DCM. The filtrate was concentrated under reduced pressure and the resulting residue was purified via silica gel chromatography (0-20% MeOH/DCM). Purification by prep-HPLC (1-30% CH$_3$CN/H$_2$O with 0.1% formic acid) afforded (3S,4S)-8-{8-[(2-amino-3-chloropyridin-4-yl)sulfanyl]imidazo[1,2-c]pyrimidin-5-yl}-3-methyl-2-oxa-8-azaspiro[4.5]decan-4-amine (45.2 mg, 37% yield) as a formic acid salt. $^1$H NMR (500 MHz, Methanol-d$_4$) δ 8.47 (s, 1H), 8.05 (s, 1H), 7.82 (d, J=1.6 Hz, 1H), 7.58 (d, J=1.6 Hz, 1H), 7.49 (d, J=5.6 Hz, 1H), 5.87 (d, J=5.6 Hz, 1H), 4.32 (qd, J=6.5, 4.2 Hz, 1H), 4.08-3.93 (m, 3H), 3.89 (d, J=9.1 Hz, 1H), 3.45 (d, J=4.2 Hz, 1H), 3.41-3.34 (m, 1H), 3.30-3.24 (m, 1H), 2.07 (ddt, J=14.6, 11.0, 3.7 Hz, 2H), 2.01-1.91 (m, 1H), 1.88-1.76 (m, 1H), 1.33 (d, J=6.5 Hz, 3H). LC-MS (ESI): m/z: [M+H]$^+$ calculated for C$_{20}$H$_{25}$ClN$_7$OS: 446.1; found 446.3.

Example 2. Synthesis of 4-{[5-(4-amino-4-methylpiperidin-1-yl)imidazo[1,2-c]pyrimidin-8-yl]sulfanyl}-3-chloropyridin-2-amine (Compound 2)

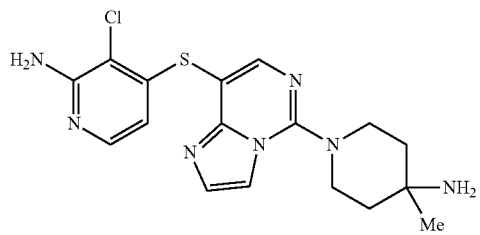 [SMILES: CC1(N)CCN(c2ncc(Sc3ccnc(N)c3Cl)c3nccn23)CC1]

4-{[5-(4-amino-4-methylpiperidin-1-yl)imidazo[1,2-c]pyrimidin-8-yl]sulfanyl}-3-chloropyridin-2-amine was synthesized in a manner similar to Example 1, except (3S,4S)-3-methyl-2-oxa-8-azaspiro[4.5]decan-4-amine was substituted with tert-butyl (4-methylpiperidin-4-yl)carbamate. $^1$H NMR (500 MHz, Methanol-d$_4$) δ 8.51 (s, 1H), 8.07 (s, 1H), 7.84 (d, J=1.6 Hz, 1H), 7.59 (d, J=1.6 Hz, 1H), 7.49 (d, J=5.5 Hz, 1H), 5.87 (d, J=5.5 Hz, 1H), 3.96 (dt, J=14.1, 4.6 Hz, 2H), 3.54 (ddd, J=13.7, 10.1, 3.2 Hz, 2H), 2.13-2.04 (m, 2H), 2.03-1.95 (m, 2H), 1.53 (s, 3H). LC-MS (ESI): m/z: [M+H] calculated for C$_{17}$H$_{21}$ClN$_7$S: 390.1; found 390.3.

Example 3. Synthesis of 1-[8-(2,3-dichlorophenyl)imidazo[1,2-c]pyrimidin-5-yl]-4-methylpiperidin-4-amine (Compound 3)

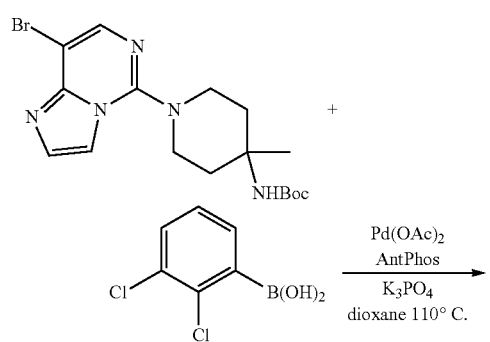

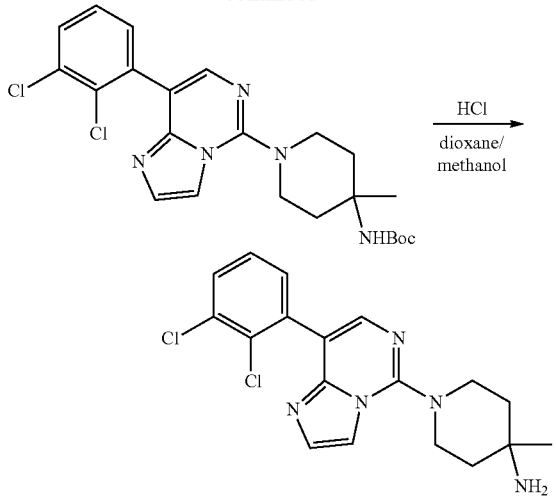

Step 1. Synthesis of tert-butyl N-{1-[8-(2,3-dichlorophenyl)imidazo[1,2-c]pyrimidin-5-yl]-4-methylpiperidin-4-yl}carbamate tert-Butyl N-(1-{8-bromoimidazo[1,2-c]pyrimidin-5-yl}-4-methylpiperidin-4-yl)carbamate (75 mg, 182 μmol), (2,3-dichlorophenyl)boronic acid (48 mg, 254 μmol), tripotassium phosphate (115 mg, 546 μmol, 3.0 equiv), AntPhos (13.4 mg, 36.4 μmol), palladium(II) acetate (4.1 mg, 18.2 μmol) were mixed with dioxane (1.81 mL) and the vial was sparged with nitrogen for 45 minutes. The solution was heated to 110° C. for 2.5 h. Upon completion, the reaction was allowed to cool to room temperature, and AntPhos (26.8 mg, 72.8 μmol, 0.4 equiv), palladium(II) acetate (4.08 mg, 18.2 μmol, 0.1 equiv), and (2,3-dichlorophenyl)boronic acid (24.2 mg, 127 μmol, 0.7 equiv) were added. The reaction was heated to 110° C. for an additional 2.5 h. The solution was filtered through celite, and washed with 20% MeOH/CH$_2$Cl$_2$. Purification by column chromatography afforded tert-butyl N-{1-[8-(2,3-dichlorophenyl)imidazo[1,2-c]pyrimidin-5-yl]-4-methylpiperidin-4-yl}carbamate (52.7 mg, 61% yield). $^1$H NMR (500 MHz, Chloroform-d) δ 7.78 (s, 1H), 7.63 (d, J=1.5 Hz, 1H), 7.54 (dd, J=8.0, 1.6 Hz, 1H), 7.49 (d, J=1.5 Hz, 1H), 7.42 (dd, J=7.7, 1.6 Hz, 1H), 7.31 (t, J=7.9 Hz, 1H), 4.47 (s, 1H), 3.64 (dt, J=13.6, 4.4 Hz, 2H), 3.40 (ddd, J=13.4, 10.5, 2.8 Hz, 2H), 2.27 (d, J=13.8 Hz, 2H), 1.85 (ddd, J=14.1, 10.6, 3.9 Hz, 2H), 1.61-1.32 (m, 12H). LC-MS (ESI): m/z: [M+H]$^+$ calculated for C$_{23}$H$_{28}$Cl$_2$N$_5$O$_2$: 476.2; found 476.4.

Step 2. Synthesis of 1-[8-(2,3-dichlorophenyl)imidazo[1,2-c]pyrimidin-5-yl]-4-methylpiperidin-4-amine To a solution of tert-butyl N-{1-[8-(2,3-dichlorophenyl)imidazo[1,2-c]pyrimidin-5-yl]-4-methylpiperidin-4-yl}carbamate (52 mg, 109 μmol) in MeOH (2 mL) was added hydrogen chloride (4 M in dioxane, 1 mL) at room temperature. The reaction was allowed to stir for 4 h at room temperature. The solvent was removed under reduced pressure and purification by prep-HPLC afforded 1-[8-(2,3-dichlorophenyl)imidazo[1,2-c]pyrimidin-5-yl]-4-methylpiperidin-4-amine (3.6 mg, 9% yield) as a formic acid salt. $^1$H NMR (500 MHz, Methanol-d$_4$) δ 8.47 (s, 1H), 7.81 (d, J=1.6

Hz, 1H), 7.76 (s, 1H), 7.69-7.63 (m, 1H), 7.59 (d, J=1.5 Hz, 1H), 7.42 (d, J=1.0 Hz, 1H), 7.41 (s, 1H), 3.87 (dt, J=14.0, 4.5 Hz, 2H), 3.47 (ddd, J=13.7, 10.3, 3.2 Hz, 2H), 2.13 (ddd, J=14.0, 10.2, 4.0 Hz, 2H), 2.01 (dt, J=13.8, 3.9 Hz, 2H), 1.55 (s, 3H). LC-MS (ESI): m/z: [M+H] calculated for $C_{18}H_{20}Cl_2N_5$: 376.1; found 376.4.

Example 4. Synthesis of (3S,4S)-8-{8-[(2-amino-3-chloropyridin-4-yl)sulfanyl]-[1,2,4]triazolo[1,5-c]pyrimidin-5-yl}-3-methyl-2-oxa-8-azaspiro[4.5]decan-4-amine (Compound 4)

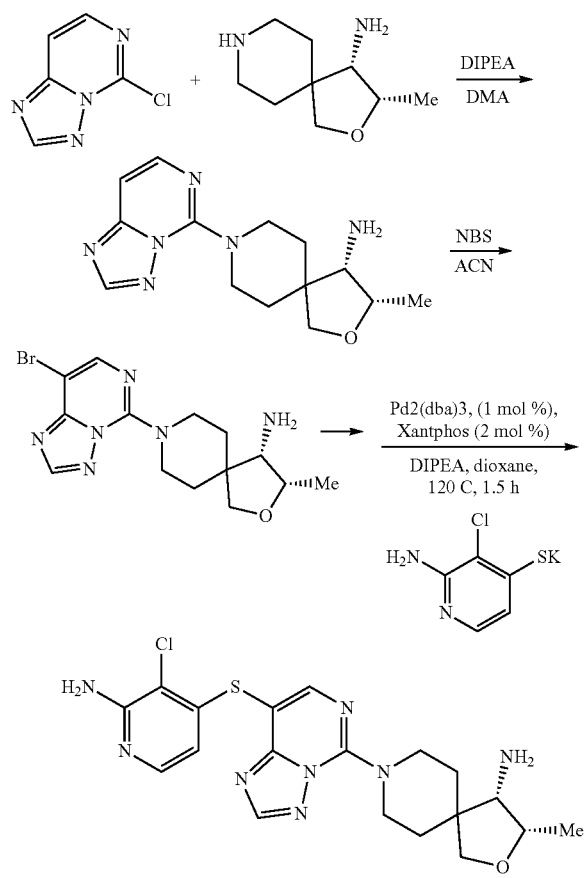

Step 1. Synthesis of (3S,4S)-8-([1,2,4]triazolo[1,5-c]pyrimidin-5-yl)-3-methyl-2-oxa-8-azaspiro[4.5]decan-4-amine To a solution of 5-chloro-[1,2,4]triazolo[1,5-c]pyrimidine (120 mg, 776 μmol) in DMA (3.88 mL) was added (3S,4S)-3-methyl-2-oxa-8-azaspiro[4.5]decan-4-amine bis hydrochloride (277 mg, 1.16 mmol) and DIPEA (675 μL, 3.88 mmol). The reaction mixture was stirred in a capped vial at 90° C. for 1 h. The resulting mixture was concentrated under reduced pressure and the crude residue was carried onto the next step without any further purification. LCMS (ESI): m/z: [M+H] calculated for $C_{14}H_{21}N_6O$: 289.2; found 289.3.

Step 2. Synthesis of (3S,4S)-8-(8-bromo-[1,2,4]triazolo[1,5-c]pyrimidin-5-yl)-3-methyl-2-oxa-8-azaspiro[4.5]decan-4-amine To a solution of the crude (3S,4S)-8-([1,2,4]triazolo[1,5-c]pyrimidin-5-yl)-3-methyl-2-oxa-8-azaspiro[4.5]decan-4-amine (50 mg, 173 μmol) in CH$_3$CN (865 μL) was added N-bromosuccinimide (61.5 mg, 346 μmol). The reaction mixture was stirred at room temperature in a capped vial for 1 h. The resulting mixture was concentrated under reduced pressure and purified by column chromatography (10:1 DCM:MeOH) to yield the desired product (3S,4S)-8-(8-bromo-[1,2,4]triazolo[1,5-c]pyrimidin-5-yl)-3-methyl-2-oxa-8-azaspiro[4.5]decan-4-amine (110 mg, 299 μmol, 79%). LCMS (ESI): m/z: [M+H] calculated for $C_{14}H_{20}BrN_6O$: 367.1; found 367.0.

Step 3. Synthesis of (3S,4S)-8-{8-[(2-amino-3-chloropyridin-4-yl)sulfanyl]-[1,2,4]triazolo[1,5-c]pyrimidin-5-yl}-3-methyl-2-oxa-8-azaspiro[4.5]decan-4-amine To a microwave vial was added (3S,4S)-8-(8-bromo-[1,2,4]triazolo[1,5-c]pyrimidin-5-yl)-3-methyl-2-oxa-8-azaspiro[4.5]decan-4-amine (110 mg, 299 μmol), 3-chloro-4-(potassiosulfanyl)pyridin-2-amine (89.0 mg, 448 μmol), Pd$_2$(dba)$_3$ (27.3 mg, 29.9 μmol), Xantphos (34.6 mg, 59.8 μmol), and DIPEA (154 μL, 897 μmol). The mixture was evacuated under house vac for 15 min before adding degassed dioxane (1.49 mL). The reaction mixture was purged with N$_2$ and evacuated three times before subjecting it to microwave conditions for 1.5 h at 130° C. The resulting reaction mixture was filtered through a pad of celite and the filtrate was concentrated under reduced pressure. The residue was purified by prep HPLC (5-30% ACN+0.1% formic acid/H2O+0.1% formic acid) to yield the desired product (3S,4S)-8-{8-[(2-amino-3-chloropyridin-4-yl)sulfanyl]-[1,2,4]triazolo[1,5-c]pyrimidin-5-yl}-3-methyl-2-oxa-8-azaspiro[4.5]decan-4-amine (30.0 mg, 84.9%) as the formic acid salt. $^1$H NMR (500 MHz, Methanol-d$_4$) δ 8.53 (s, 1H), 8.36 (s, 1H), 8.21 (s, 1H), 7.54 (d, J=5.5 Hz, 1H), 5.95 (d, J=5.5 Hz, 1H), 4.87 (s, 2H), 4.30 (s, 1H), 3.98 (d, J=8.8 Hz, 1H), 3.84 (d, J=9.0 Hz, 2H), 3.78-3.63 (m, 2H), 1.97 (d, J=20.5 Hz, 3H), 1.85 (d, J=45.8 Hz, 1H), 1.30 (d, J=7.3 Hz, 3H). LCMS (ESI): m/z: [M+H] calculated for $C_{19}H_{24}ClN_8OS$: 447.1; found 447.4.

Example 5. Synthesis of (1R)-8-[8-(2,3-dichlorophenyl)imidazo[1,5-a]pyridin-5-yl]-8-azaspiro[4.5]decan-1-amine (Compound 5)

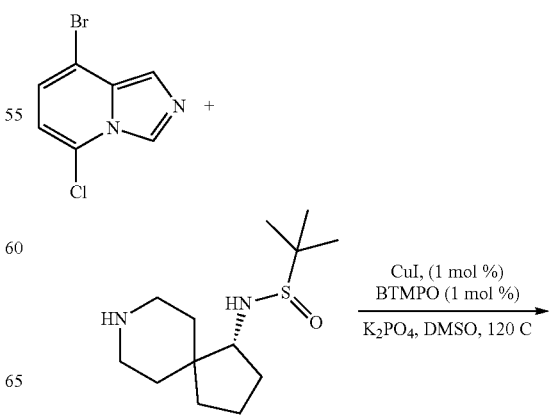

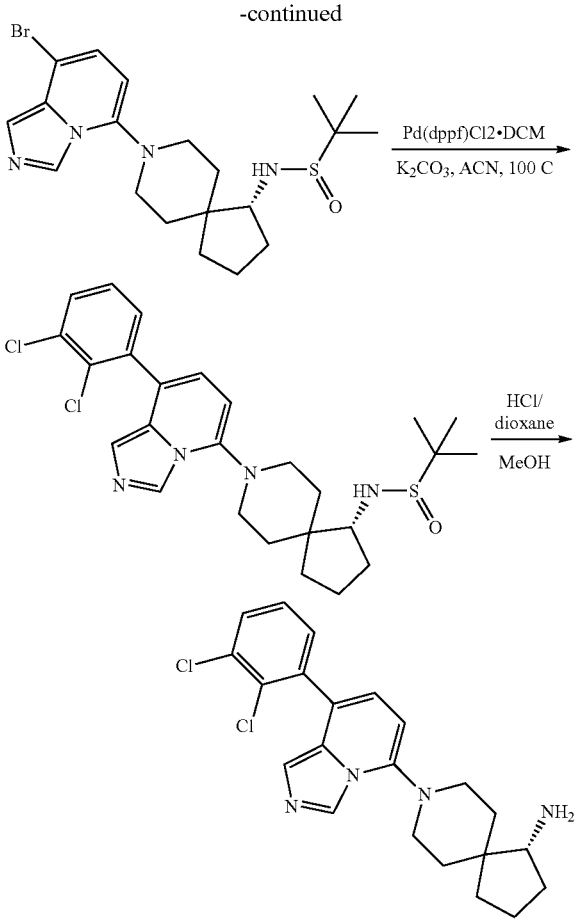

Step 1. Synthesis of N—((R)-8-(8-bromoimidazo[1,5-a]pyridin-5-yl)-8-azaspiro[4.5]decan-1-yl)-2-methylpropane-2-sulfinamide To a reaction vial was added 8-bromo-5-chloroimidazo[1,5-a]pyridine (50.0 mg, 216 μmol), 2-methyl-N—((R)-8-azaspiro[4.5]decan-1-yl)propane-2-sulfinamide (83.7 mg, 324 μmol), CuI (4.11 mg, 21.6 μmol), BTMPO (9.08 mg, 21.6 μmol), and K₃PO₄ (137 mg, 648 μmol). The vial was evacuated and filled with N₂ three times before adding in DMSO (1 mL). The reaction was stirred in the capped vial overnight at 120° C. The resulting reaction mixture was diluted with EtOAc and H₂O, and the aqueous layer was extracted three times with EtOAc. The combined organic layers were washed with brine. The resulting organic layer was dried over MgSO₄, filtered, and concentrated under reduced pressure. The residue was purified by column chromatography (0-10% MeOH/DCM) to yield the desired product N—((R)-8-(8-bromoimidazo[1,5-a]pyridin-5-yl)-8-azaspiro[4.5]decan-1-yl)-2-methylpropane-2-sulfinamide (68.0 mg, 149 μmol, 69.4%). LCMS (ESI): m/z: [M+H] calculated for $C_{20}H_{29}BrN_4OS$: 453.1; found 452.9.

Step 2. Synthesis of N—((R)-8-(8-(2,3-dichlorophenyl)imidazo[1,5-a]pyridin-5-yl)-8-azaspiro[4.5]decan-1-yl)-2-methylpropane-2-sulfinamide To a reaction vial was added N—((R)-8-(8-bromoimidazo[1,5-a]pyridin-5-yl)-8-azaspiro[4.5]decan-1-yl)-2-methylpropane-2-sulfinamide (37 mg, 81.5 μmol), (2,3-dichlorophenyl)boronic acid (23.2 mg, 122 μmol), Pd(dppf)Cl₂·CH₂Cl₂ (13.3 mg, 16.3 μmol), and K₂CO₃ (22.5 mg, 163 μmol). The mixture was evacuated and filled with N₂ three times before adding in degassed CH₃CN (815 μL). The reaction was stirred at 100° C. for 2 h. The resulting mixture was filtered through a pad of celite. The filtrate was concentrated under reduced pressure and purified by column chromatography (0-100% EtOAc/Heptane followed by 0-10% MeOH/DCM) to yield the desired product. LCMS (ESI): m/z: [M+H] calculated for $C_{26}H_{33}Cl_2N_4OS$: 519.1; found 519.0.

Step 3. Synthesis of (1R)-8-[8-(2,3-dichlorophenyl)imidazo[1,5-a]pyridin-5-yl]-8-azaspiro[4.5]decan-1-amine To a solution of N—((R)-8-(8-(2,3-dichlorophenyl)imidazo[1,5-a]pyridin-5-yl)-8-azaspiro[4.5]decan-1-yl)-2-methylpropane-2-sulfinamide (10 mg, 19.2 μmol) in methanol (1 mL) was added 4M HCl (14.4 μL, 57.6 μmol) in dioxane. The reaction mixture was stirred at 35° C. for 1 h. The resulting reaction mixture was concentrated under reduced pressure and the residue was purified by prep HPLC (Biotage) using 5-35% ACN+0.1% formic acid/H₂O+0.1% formic acid to yield the desired product (1R)-8-[8-(2,3-dichlorophenyl)imidazo[1,5-a]pyridin-5-yl]-8-azaspiro[4.5]decan-1-amine (3.00 mg, 7.22 μmol, 37.6%) as the formic acid salt. ¹H NMR (500 MHz, Methanol-d₄) δ 8.28 (s, 1H), 7.66 (dd, J=6.5, 3.1 Hz, 1H), 7.45-7.37 (m, 2H), 7.07 (s, 1H), 6.86 (d, J=7.2 Hz, 1H), 6.43 (d, J=7.1 Hz, 11H), 4.59 (s, 1H), 3.46 (d, J=29.9 Hz, 2H), 3.36 (d, J=7.9 Hz, 1H), 3.06 (t, J=12.1 Hz, 3H), 2.14-1.98 (m, 1H), 1.98-1.63 (m, 7H), 1.31 (s, 1H). LCMS (ESI): m/z: [M+H] calculated for $C_{22}H_{25}Cl_2N_4$: 415.1; found 415.3.

Example 6. Synthesis of (3S,4S)-8-[8-(2,3-dichlorophenyl)-7-methyl-[1,2,4]triazolo[4,3-c]pyrimidin-5-yl]-3-methyl-2-oxa-8-azaspiro[4.5]decan-4-amine (Compound 6)

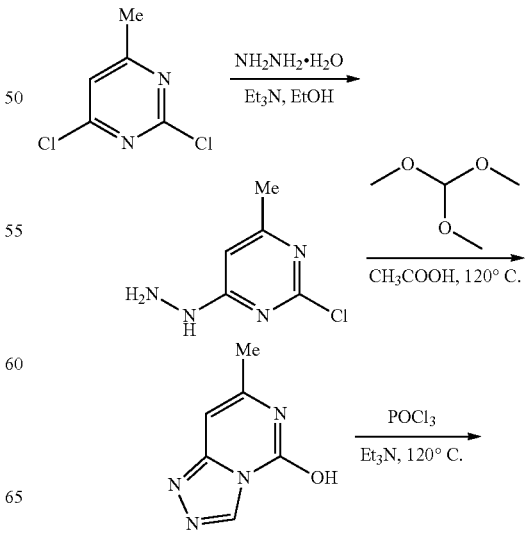

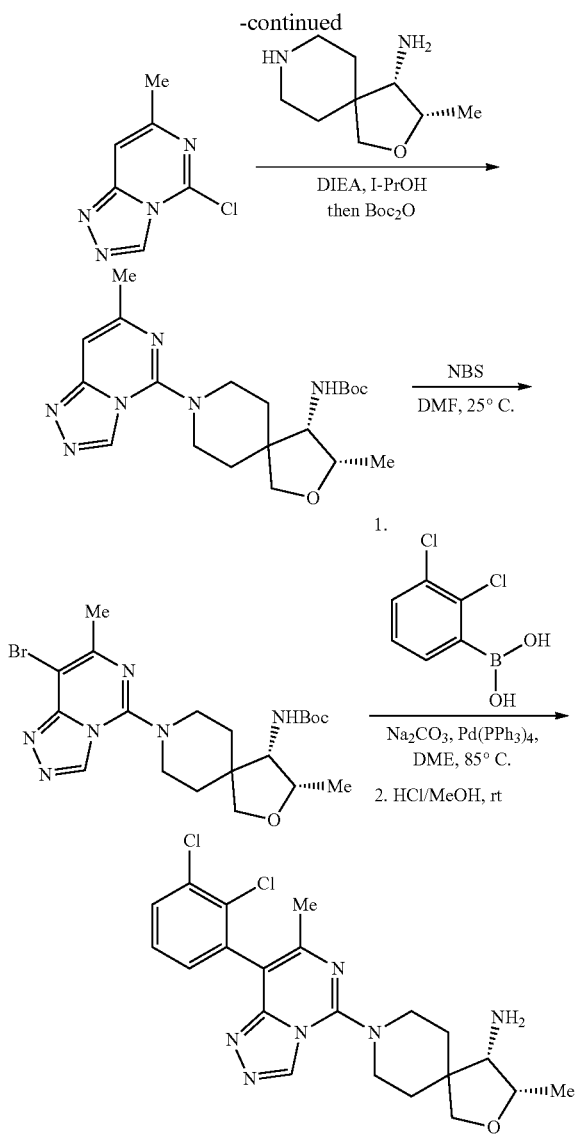

4]triazolo[4,3-c]pyrimidin-5-ol (0.7 g, 4.62 mmol, 73.2% yield) as a gray solid. $^1$H NMR (400 MHz, DMSO-d$_6$) δ 12.01 (br s, 1H), 8.32 (s, 1H), 6.58 (s, 1H), 2.26 (s, 3H).

Step 3. Synthesis of 5-chloro-7-methyl-[1,2,4]triazolo[4,3-c]pyrimidine

To a solution of 7-methyl-[1,2,4]triazolo[4,3-c]pyrimidin-5-ol (0.7 g, 4.66 mmol) in POCl$_3$ (14 ml, 151 mmol) was added TEA (1.4 ml). The mixture was stirred at 120° C. for 2 h and then concentrated under reduced pressure. The viscous residue was adjusted to pH=8 by addition of aqueous NaHCO$_3$. Then the mixture was extracted with EtOAc. The combined organic layers were washed with brine, dried over Na$_2$SO$_4$ and concentrated to give 5-chloro-7-methyl-[1,2,4]triazolo[4,3-c]pyrimidine (0.6 g, 3.56 mmol, 76.3% yield) as a yellow solid. LCMS (ESI): m/z: [M+H] calculated for C$_6$H$_6$ClN$_4$: 169.0; found 169.1; $^1$H NMR (400 MHz, DMSO-d$_6$) δ 8.68 (s, 1H), 7.79 (d, J=0.8 Hz, 1H), 2.52 (d, J=0.8 Hz, 3H).

Step 4. Synthesis of tert-butyl N-[(3S,4S)-3-methyl-8-(7-methyl-[1,2,4]triazolo[4,3-c]pyrimidin-5-yl)-2-oxa-8-azaspiro[4.5]decan-4-yl]carbamate To a solution of 5-chloro-7-methyl-[1,2,4]triazolo[4,3-c]pyrimidine (315 mg, 1.87 mmol) and (3S,4S)-3-methyl-2-oxa-8-azaspiro[4.5]decan-4-amine bis-hydrochloride (454 mg, 1.87 mmol) in i-PrOH (8 ml) was added DIPEA (2.6 ml, 15.0 mmol). The mixture was stirred at 75° C. for 2 h. The reaction was cooled to 25° C. and tert-butyl carbonate (489 mg, 2.24 mmol) was added drop wise. The mixture was stirred at room temperature for 1 h and then concentrated under reduced pressure. The crude residue was purified by column chromatography to give tert-butyl N-[(3S,4S)-3-methyl-8-(7-methyl-[1,2,4]triazolo[4,3-c]pyrimidin-5-yl)-2-oxa-8-azaspiro[4.5]decan-4-yl]carbamate (0.6 g, 1.49 mmol, 80% yield) as a white solid. LCMS (ESI): m/z [M+H] calculated for C$_{20}$H$_{31}$N$_6$O$_3$: 403.2; found 403.3; $^1$H NMR (400 MHz, DMSO-d$_6$) δ 8.40 (s, 1H), 7.02 (t, J=5.2 Hz, 2H), 4.2-4.1 (m, 2H), 3.98-3.87 (m, 2H), 3.7-3.68 (m, 1H), 3.54 (d, J=8.4 Hz, 1H), 3.52 (d, J=8.4 Hz, 1H), 2.36 (s, 3H), 1.78-1.67 (m, 3H), 1.62-1.54 (m, 1H), 1.39 (s, 9H), 1.02 (d, J=6.0 Hz, 2H).

Step 5. Synthesis of tert-butyl N-[(3S,4S)-8-(8-bromo-7-methyl-[1,2,4]triazolo[4,3-c]pyrimidin-5-yl)-3-methyl-2-oxa-8-azaspiro[4.5]decan-4-yl]carbamate To a solution of tert-butyl N-[(3S,4S)-3-methyl-8-(7-methyl-[1,2,4]triazolo[4,3-c]pyrimidin-5-yl)-2-oxa-8-azaspiro[4.5]decan-4-yl]carbamate (0.6 g, 1.49 mmol) in DMF (6 ml) was added NBS (318 mg, 1.79 mmol). The reaction was stirred at 25° C. for 1.5 h before aq.Na$_2$S$_2$O$_3$ (50 ml) was added and the mixture was and extracted with EtOAc. The combined organic layers were washed with brine and dried over Na$_2$SO$_4$. The solvent was removed under reduced pressure and the residue was purified by column chromatography to give tert-butyl N-[(3S,4S)-8-(8-bromo-7-methyl-[1,2,4]triazolo[4,3-c]pyrimidin-5-yl)-3-methyl-2-oxa-8-azaspiro[4.5]decan-4-yl]carbamate (480 mg, 0.94 mmol, 63% yield) as a white solid. LCMS (ESI): m/z [M+H] calculated for C$_{20}$H$_{30}$BrN$_6$O$_3$: 481.2; found 481.1; $^1$H NMR (400 MHz, DMSO-d$_6$) δ 8.46 (s, 1H), 7.01 (d, J=10.4 Hz, 11H), 4.20-4.14 (m, 2H), 4.04-4.01 (m, 2H), 3.89 (dd, J=5.2, 10.4 Hz, 1H), 3.83-3.74 (m, 1H), 3.69 (d, Step 1. Synthesis of (2-chloro-6-methyl-pyrimidin-4-yl) hydrazine To a solution of 2,4-dichloro-6-methyl-pyrimidine (10 g, 61.35 mmol) in EtOH (100 ml) was added TEA (9.4 ml, 67.5 mmol), followed by NH$_2$NH$_2$H$_2$O (4.21 ml, 85% purity, 73.6 mmol) at 0° C. drop wise. The mixture was stirred at 25° C. for 8 h and then filtered. The filtrate was concentrated under reduced pressure and the crude residue was purified by C18 reverse phase column to give (2-chloro-6-methyl-pyrimidin-4-yl) hydrazine (1.4 g, 8.83 mmol, 14.4% yield) as a white solid. $^1$H NMR (400 MHz, DMSO-d$_6$) δ 8.75 (br s, 1H), 6.59 (br s, 1H), 4.51 (br s, 1H), 2.20 (s, 3H).

Step 2. Synthesis of 7-methyl-[1,2,4]triazolo[4,3-c]pyrimidin-5-ol

To a solution of (2-chloro-6-methyl-pyrimidin-4-yl)hydrazine (1 g, 6.31 mmol) in trimethoxymethane (20 ml, 182 mmol) was added acetic acid (2 ml). The mixture was stirred at 120° C. for 10 h and then filtered. The filtrate was concentrated under reduced pressure to give 7-methyl-[1,2, J=8.4 Hz, 1H), 3.53 (d, J=8.4 Hz, 1H), 1.78-1.66 (m, 3H), 1.63-1.53 (m, 1H), 1.39 (s, 9H), 1.02 (d, J=6.0 Hz, 3H).

Step 6. Synthesis of (3S,4S)-8-[8-(2,3-dichlorophenyl)-7-methyl-[1,2,4]triazolo[4,3-c]pyrimidin-5-yl]-3-methyl-2-oxa-8-azaspiro[4.5]decan-4-amine To a solution of tert-butyl N-[(3S,4S)-8-(8-bromo-7-methyl-[1,2,4]triazolo[4,3-c]pyrimidin-5-yl)-3-methyl-2-oxa-8-azaspiro[4.5]decan-4-yl]carbamate (80 mg, 0.17 mmol) and (2,3-dichlorophenyl)boronic acid (48 mg, 0.25 mmol) in DME (0.8 ml) and H$_2$O (0.13 ml) was added Na$_2$CO$_3$ (35 mg, 0.33 mmol), then Pd(PPh$_3$)$_4$ (19 mg, 0.016 mmol) was added to the reaction mixture. The mixture was stirred at 100° C. for 1 h and then diluted with EtOAc (5 ml) and the solvent was removed under reduced pressure. The crude residue was purified by silica gel chromatography and the product was dissolved in MeOH (1.5 ml) and HCl (1.5 ml, 4 M in dioxane) was added. The mixture was stirred at 25° C. for 1 h and then concentrated under reduced pressure to give (3S,4S)-8-[8-(2,3-dichlorophenyl)-7-methyl-[1,2,4]triazolo[4,3-c]pyrimidin-5-yl]-3-methyl-2-oxa-8-azaspiro[4.5]decan-4-amine (8.5 mg, 0.017 mmol, 10% yield). $^1$H NMR (400 MHz, Methanol-d$_4$) δ 10.66 (s, 1H), 9.71 (d, J=8.30 Hz, 1H), 9.49-9.43 (m, 1H), 9.37 (d, J=7.90 Hz, 1H), 6.96 (s, 2H), 6.32 (d, J=4.40 Hz, 1H), 6.02 (d, J=9.20 Hz, 1H), 5.91 (d, J=9.60 Hz, 11H), 5.58-5.49 (m, 4H), 4.98-4.84 (m, 1H), 4.26 (s, 3H), 4.01 (d, J=16.20 Hz, 3H), 3.80 (d, J=12.30 Hz, 1H), 3.32 (d, J=6.60 Hz, 3H). LCMS (ESI): m/z [M+H] calculated for C$_{21}$H$_{25}$Cl$_2$N$_6$O: 447.1; found 447.3.

Example 7. Synthesis of 4-{[5-(4-amino-4-methylpiperidin-1-yl)-[1,2,4]triazolo[4,3-c]pyrimidin-8-yl]sulfanyl}-3-chloropyridin-2-amine (Compound 7)

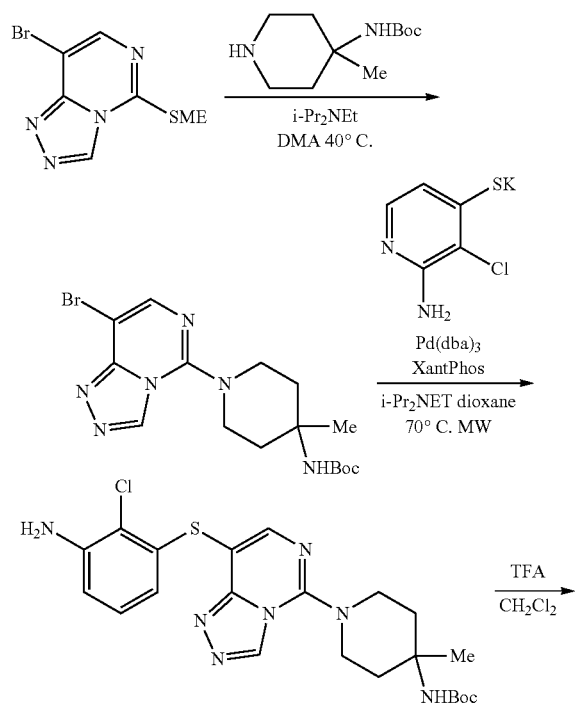

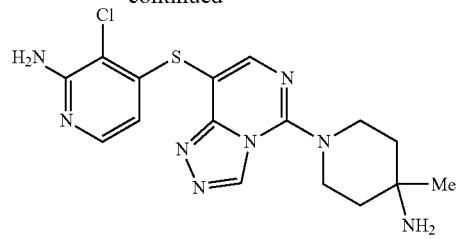

Step 1. Synthesis of tert-butyl N-(1-{8-bromo-[1,2,4]triazolo[4,3-c]pyrimidin-5-yl}-4-methylpiperidin-4-yl)carbamate To a solution of 8-bromo-5-(methylsulfanyl)-[1,2,4]triazolo[4,3-c]pyrimidine (250 mg, 1.01 mmol) in dimethylacetamide (5.05 mL) was added tert-butyl N-(4-methylpiperidin-4-yl)carbamate (432 mg, 2.02 mmol) followed by N,N-diisopropylethylamine (878 μL, 5.05 mmol). This solution was heated to 40° C. for 17 h, and the reaction was concentrated under reduced pressure. The resulting residue was purified via column chromatography to deliver tert-butyl N-(1-{8-bromo-[1,2,4]triazolo[4,3-c]pyrimidin-5-yl}-4-methylpiperidin-4-yl)carbamate (310 mg, 74% yield) as a solid. $^1$H NMR (500 MHz, Chloroform-d) δ 8.76 (s, 1H), 7.82 (s, 1H), 4.43 (s, 1H), 3.76-3.56 (m, 2H), 3.44 (ddd, J=13.5, 10.7, 2.9 Hz, 2H), 2.25 (d, J=14.2 Hz, 2H), 1.79 (ddd, J=14.3, 10.7, 3.9 Hz, 2H), 1.44 (s, 12H). LC-MS (ESI): m/z: [M+H]$^+$ calculated for C$_{16}$H$_{24}$BrN$_6$O$_2$: 411.1; found 411.2.

Step 2. Synthesis of tert-butyl N-(1-{8-[(2-amino-3-chloropyridin-4-yl)sulfanyl]-[1,2,4]triazolo[4,3-c]pyrimidin-5-yl}-4-methylpiperidin-4-yl)carbamate To a 5 mL microwave vial was added tert-butyl N-(1-{8-bromo-[1,2,4]triazolo[4,3-c]pyrimidin-5-yl}-4-methylpiperidin-4-yl)carbamate (75 mg, 182 μmol), 3-chloro-4-(potassiosulfanyl)pyridin-2-amine (54.2 mg, 273 μmol), XantPhos (21.0 mg, 36.4 μmol), tris(dibenzylideneacetone)dipalladium (16.6 mg, 18.2 μmol) and a Teflon coated magnetic stir bar. The vial was then capped and the headspace was then purged with nitrogen gas for 3 min. To the mixture of solids was then added dioxane (1.81 mL) that had been sparged with nitrogen gas for 45 minutes, followed by N,N-diisopropylethylamine (63.3 μL, 364 μmol). The heterogeneous solution was then placed in the microwave at 70° C. for 90 mins. The resulting mixture was filtered through a pad of celite, washed with 20% MeOH/CH$_2$Cl$_2$ to elute off the product. The filtrate was then concentrated under reduced pressure and the residue was purified via column chromatography to deliver tert-butyl N-(1-{8-[(2-amino-3-chloropyridin-4-yl)sulfanyl]-[1,2,4]triazolo[4,3-c]pyrimidin-5-yl}-4-methylpiperidin-4-yl)carbamate (40 mg, 44% yield). $^1$H NMR (500 MHz, Chloroform-d) δ 8.80 (s, 1H), 7.94 (s, 1H), 7.62 (d, J=5.6 Hz, 1H), 6.01 (d, J=5.6 Hz, 1H), 5.18 (s, 2H), 4.46 (s, 1H), 3.86 (dt, J=13.7, 4.3 Hz, 2H), 3.60 (ddd, J=13.6, 10.7, 2.9 Hz, 2H), 2.44-2.24 (m, 2H), 1.82 (ddd, J=14.2, 10.6, 3.9 Hz, 2H), 1.46 (s, 12H). LC-MS (ESI): m/z: [M+H]$^+$ calculated for C$_{21}$H$_{28}$ClN$_8$O$_2$S: 491.2; found 491.1.

Step 3. Synthesis of 4-{[5-(4-amino-4-methylpiperidin-1-yl)-[1,2,4]triazolo[4,3-c]pyrimidin-8-yl]sulfanyl}-3-chloropyridin-2-amine To a solution of tert-butyl N-(1-{8-[(2-amino-3-chloropyridin-4-yl)sulfanyl]-[1,2,4]triazolo[4,3-c]pyrimidin-5- yl}-4-methylpiperidin-4-yl)carbamate (40 mg, 81.4 μmol) in DCM (2 mL) was added trifluoroacetic acid (1 mL, 12.9 mmol) at room temperature. After stirring at room temperature for 30 minutes, the reaction was concentrated under reduced pressure. The residue was directly purified via preparatory HPLC (1-10% CH$_3$CN/H$_2$O with 0.1% formic acid) to afford 4-{[5-(4-amino-4-methylpiperidin-1-yl)-[1,2,4]triazolo[4,3-c]pyrimidin-8-yl]sulfanyl}-3-chloropyridin-2-amine (9.5 mg, 30% yield) as a formic acid salt. $^1$H NMR (500 MHz, Methanol-d$_4$) δ 9.32 (s, 1H), 8.52 (s, 1H), 8.05 (s, 1H), 7.53 (d, J=5.6 Hz, 1H), 6.03 (d, J=5.6 Hz, 1H), 4.09 (dt, J=14.9, 5.0 Hz, 2H), 3.68 (ddd, J=13.7, 9.7, 3.6 Hz, 2H), 2.01 (dtd, J=19.2, 14.6, 14.1, 7.0 Hz, 4H), 1.52 (s, 3H). LC-MS (ESI): m/z [M+H]+ calculated for C$_{16}$H$_{20}$ClN$_8$S: 391.1; found 391.2.

Example 8. Synthesis of (3S,4S)-8-[8-(2,3-dichlorophenyl)-7-methylimidazo[1,2-c]pyrimidin-5-yl]-3-methyl-2-oxa-8-azaspiro[4.5]decan-4-amine

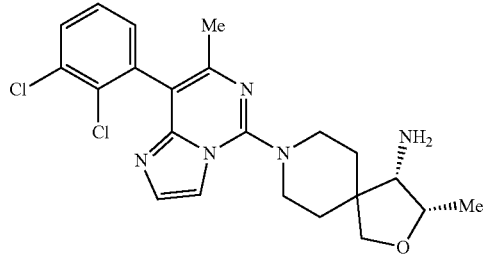 [SMILES: Cc1nc(N2CCC3(CC2)CO[C@@H](C)[C@H]3N)n2ccnc2c1-c1cccc(Cl)c1Cl]

(3S,4S)-8-[8-(2,3-dichlorophenyl)-7-methylimidazo[1,2-c]pyrimidin-5-yl]-3-methyl-2-oxa-8-azaspiro[4.5]decan-4-amine was synthesized in a manner similar to Example 15, except $^1$H-indazol-6-ylboronic acid was substituted with 2,3-dichlorophenylboronic acid. $^1$H NMR (500 MHz, Methanol-d$_4$) δ 7.75 (d, J=1.7 Hz, 1H), 7.68 (dd, J=8.1, 1.6 Hz, 1H), 7.54 (d, J=1.7 Hz, 1H), 7.45 (t, J=7.9 Hz, 1H), 7.32 (dd, J=7.6, 1.5 Hz, 1H), 4.33 (dtd, J=7.0, 6.0, 3.9 Hz, 1H), 4.02 (d, J=9.2 Hz, 1H), 3.99-3.87 (m, 3H), 3.53 (d, J=4.1 Hz, 1H), 3.30-3.18 (m, 2H), 2.21 (s, 3H), 2.10 (tdd, J=13.2, 6.9, 3.5 Hz, 2H), 1.99 (d, J=13.7 Hz, 1H), 1.83 (dt, J=13.1, 2.3 Hz, 1H), 1.35 (d, J=6.5 Hz, 3H). LC-MS (ESI): m/z [M+H]$^+$ calculated for C$_{22}$H$_{26}$Cl$_2$N$_5$O: 446.1; found 446.3.

Example 9. Synthesis of (3S,4S)-8-[8-(2-chloro-3-methoxyphenyl)-7-methylimidazo[1,2-c]pyrimidin-5-yl]-3-methyl-2-oxa-8-azaspiro[4.5]decan-4-amine

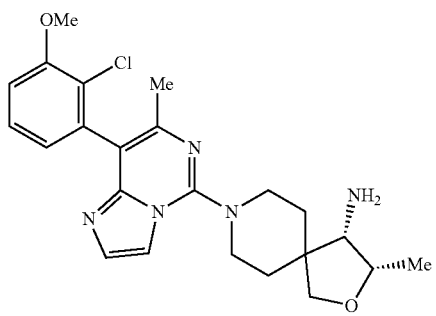 [SMILES: COc1cccc(-c2c(C)nc(N3CCC4(CC3)CO[C@@H](C)[C@H]4N)n3ccnc23)c1Cl]

(3S,4S)-8-[8-(2-chloro-3-methoxyphenyl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 2-chloro-3-methoxyphenylboronic acid. $^1$H NMR (500 MHz, Methanol-d$_4$) δ 8.57 (s, 1H), 7.70 (d, J=1.6 Hz, 1H), 7.45 (d, J=1.5 Hz, 1H), 7.41 (dd, J=8.3, 7.6 Hz, 1H), 7.20 (dd, J=8.4, 1.4 Hz, 1H), 6.94 (dd, J=7.6, 1.4 Hz, 1H), 4.35-4.20 (m, 1H), 3.97 (s, 3H), 3.95 (d, J=9.1 Hz, 1H), 3.82 (d, J=8.8 Hz, 1H), 3.81-3.74 (m, 2H), 3.32-3.17 (m, 2H), 2.19 (s, 3H), 2.07 (tdd, J=14.2, 9.4, 5.1 Hz, 2H), 1.90 (d, J=13.5 Hz, 1H), 1.83 (d, J=13.6 Hz, 1H), 1.29 (d, J=6.5 Hz, 3H). LC-MS (ESI): m/z: [M+H]+ calculated for C$_{23}$H$_{29}$ClN$_5$O$_2$ 442.2; found 442.4.

Example 10. 1-[4-({5-[(3S,4S)-4-amino-3-methyl-2-oxa-8-azaspiro[4.5]decan-8-yl]imidazo[1,2-c]pyrimidin-8-yl}sulfanyl)-3-chloropyridin-2-yl]azetidin-3-ol

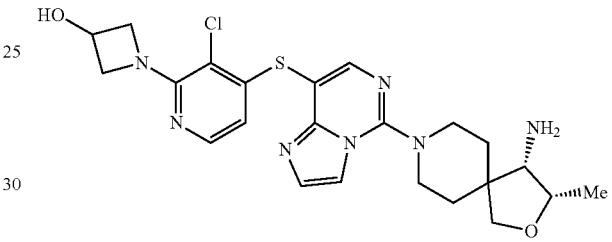

1-[4-({5-[(3S,4S)-4-amino-3-methyl-2-oxa-8-azaspiro[4.5]decan-8-yl]imidazo[1,2-c]pyrimidin-8-yl}sulfanyl)-3-chloropyridin-2-yl]azetidin-3-ol was synthesized in a manner similar to Example 1, except 3-chloro-4-(potassiosulfanyl)pyridin-2-amine was substituted with 1-(3-chloro-4-sulfanylpyridin-2-yl)azetidin-3-ol. $^1$H NMR (500 MHz, Methanol-d$_4$) δ 8.56 (s, 1H), 8.06 (s, 1H), 7.85 (d, J=1.6 Hz, 1H), 7.63 (d, J=5.5 Hz, 1H), 7.58 (d, J=1.6 Hz, 1H), 5.97 (d, J=5.5 Hz, 1H), 4.63 (tt, J=6.6, 4.7 Hz, 1H), 4.52-4.46 (m, 2H), 4.34-4.26 (m, 1H), 4.02 (ddd, J=9.1, 4.8, 1.2 Hz, 2H), 3.98-3.88 (m, 3H), 3.82 (d, J=8.8 Hz, 1H), 3.44 (ddd, J=13.4, 10.3, 3.1 Hz, 1H), 3.40-3.34 (m, 1H), 3.20 (d, J=4.7 Hz, 1H), 2.05 (dddd, J=21.3, 14.0, 10.1, 3.8 Hz, 2H), 1.89 (d, J=13.9 Hz, 1H), 1.82 (d, J=13.6 Hz, 1H), 1.29 (d, J=6.5 Hz, 3H). LCMS (ESI): m/z: [M+H] calculated for C$_{23}$H$_{29}$ClN$_7$O$_2$S 502.2; found 502.3.

Example 11. Synthesis of (3S,4S)-8-{8-[(2,3-dichlorophenyl)sulfanyl]imidazo[1,2-c]pyrimidin-5-yl}-3-methyl-2-oxa-8-azaspiro[4.5]decan-4-amine

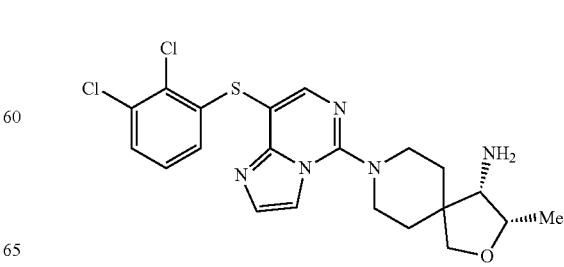

(3S,4S)-8-{8-[(2,3-dichlorophenyl)sulfanyl]imidazo[1,2-c]pyrimidin-5-yl}-3-methyl-2-oxa-8-azaspiro[4.5]decan-4-amine was synthesized in a manner similar to Example 1, except 3-chloro-4-(potassiosulfanyl)pyridin-2-amine was substituted with 2,3-dichlorobenzene-1-thiol. $^1$H NMR (500 MHz, Methanol-$d_4$) δ 8.55 (s, 1H), 8.03 (s, 1H), 7.84 (d, J=1.6 Hz, 1H), 7.58 (d, J=1.6 Hz, 1H), 7.32 (dd, J=8.0, 1.4 Hz, 1H), 7.05 (t, J=8.1 Hz, 1H), 6.69 (dd, J=8.1, 1.4 Hz, 1H), 4.31 (qd, J=6.5, 4.5 Hz, 1H), 4.01-3.87 (m, 3H), 3.84 (d, J=8.9 Hz, 1H), 3.40 (ddd, J=13.5, 10.5, 3.0 Hz, 1H), 3.29 (dd, J=8.7, 3.7 Hz, 1H), 2.13-1.99 (m, 2H), 1.92 (d, J=13.5 Hz, 1H), 1.82 (dd, J=12.0, 3.2 Hz, 1H), 1.30 (d, J=6.5 Hz, 3H). LCMS (ESI): m/z: [M+H] calculated for $C_{21}H_{25}Cl_2N_5OS$ 464.1; found 464.0.

Example 12. Synthesis of (3S,4S)-8-(8-{[3-chloro-2-(3-methanesulfonylazetidin-1-yl)pyridin-4-yl]sulfanyl}imidazo[1,2-c]pyrimidin-5-yl)-3-methyl-2-oxa-8-azaspiro[4.5]decan-4-amine

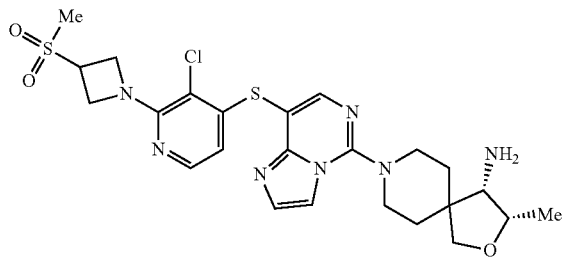 [SMILES: C[C@@H]1OCC2(CCN(c3ncc(Sc4ccnc(N5CC(S(C)(=O)=O)C5)c4Cl)c4nccn34)CC2)[C@@H]1N]

(3S,4S)-8-(8-{[3-chloro-2-(3-methanesulfonylazetidin-1-yl)pyridin-4-yl]sulfanyl}imidazo[1,2-c]pyrimidin-5-yl)-3-methyl-2-oxa-8-azaspiro[4.5]decan-4-amine was synthesized in a manner similar to Example 1, except 3-chloro-4-(potassiosulfanyl)pyridin-2-amine was substituted with 3-chloro-2-(3-(methylsulfonyl)azetidin-1-yl)pyridine-4-thiol. $^1$H NMR (400 MHz, Methanol-$d_4$) δ 8.06 (s, 1H) 7.83 (s, 1H) 7.67 (d, J=5.26 Hz, 1H) 7.57 (s, 1H) 6.02 (d, J=5.26 Hz, 1H) 4.59-4.45 (m, 4H) 4.35-4.26 (m, 2H) 4.03-3.90 (m, 3H) 3.86 (d, J=9.21 Hz, 1H) 3.48 (s, 3H) 3.01 (s, 3H) 2.13-1.75 (m, 4H) 1.30 (d, J=6.58 Hz, 3H). LCMS (ESI): m/z: [M+H] calculated for $C_{24}H_{31}ClN_7O_3S_2$: 564.2; found 564.1

Example 13. Synthesis of 1-[4-({5-[(3S,4S)-4-amino-3-methyl-2-oxa-8-azaspiro[4.5]decan-8-yl]imidazo[1,2-c]pyrimidin-8-yl}sulfanyl)-3-chloropyridin-2-yl]azetidine-3-carbonitrile

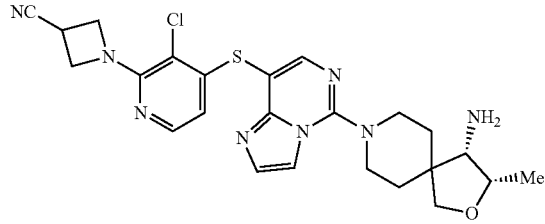 [SMILES: C[C@@H]1OCC2(CCN(c3ncc(Sc4ccnc(N5CC(C#N)C5)c4Cl)c4nccn34)CC2)[C@@H]1N]

1-[4-({5-[(3S,4S)-4-amino-3-methyl-2-oxa-8-azaspiro[4.5]decan-8-yl]imidazo[1,2-c]pyrimidin-8-yl}sulfanyl)-3-chloropyridin-2-yl]azetidine-3-carbonitrile was synthesized in a manner similar to Example 1, except 3-chloro-4-(potassiosulfanyl)pyridin-2-amine was substituted with 1-(3-chloro-4-mercapto-2-pyridinyl)-3-azetidinecarbonitrile. $^1$H NMR (400 MHz, Methanol-$d_4$) δ 8.06 (s, 1H) 7.83 (d, J=1.75 Hz, 1H) 7.67 (d, J=5.70 Hz, 1H) 7.57 (d, J=1.32 Hz, 1H) 6.04 (d, J=5.70 Hz, 1H) 4.55-4.48 (m, 2H) 4.39-4.29 (m, 3H) 4.03-3.92 (m, 3H) 3.86 (d, J=9.21 Hz, 1H) 3.78-3.64 (m, 1H) 3.51-3.35 (m, 3H) 2.15-1.73 (m, 4H) 1.30 (d, J=6.14 Hz, 3H). LCMS (ESI): m/z: [M+H] calculated for $C_{24}H_{28}ClN_8OS$: 511.2; found 511.1.

Example 14. Synthesis of 3-({5-[(3S,4S)-4-amino-3-methyl-2-oxa-8-azaspiro[4.5]decan-8-yl]imidazo[1,2-c]pyrimidin-8-yl}sulfanyl)-2-chloro-N,N-dimethylbenzamide

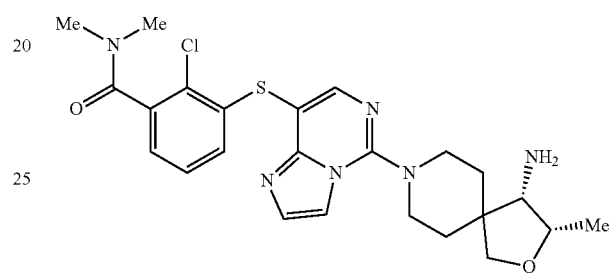

3-({5-[(3S,4S)-4-amino-3-methyl-2-oxa-8-azaspiro[4.5]decan-8-yl]imidazo[1,2-c]pyrimidin-8-yl}sulfanyl)-2-chloro-N,N-dimethylbenzamide was synthesized in a manner similar to Example 1, except 3-chloro-4-(potassiosulfanyl)pyridin-2-amine was substituted with 3-dimethylamide-2-chloro-1-thiol. $^1$H NMR (400 MHz, DMSO-$d_6$) δ 8.34 (br s, 4H) 8.00 (s, 1H) 7.84 (d, J=1.34 Hz, 1H) 7.56 (d, J=1.47 Hz, 1H) 7.14-7.19 (m, 1H) 7.08-7.12 (m, 1H) 6.76 (dd, J=8.01, 1.65 Hz, 1H) 4.05-4.14 (m, 1H) 3.70 (br d, J=8.31 Hz, 4H) 3.53 (br d, J=8.31 Hz, 1H) 2.97 (d, J=5.01 Hz, 1H) 2.80 (s, 3H) 2.61-2.65 (m, 1H) 1.95 (br s, 1H) 1.83 (br s, 1H) 1.68 (br d, J=19.32 Hz, 2H) 1.10 (d, J=6.36 Hz, 3H). LCMS (ESI): m/z: [M+H] calculated for $C_{24}H_{30}ClN_6O_2S$: 501.2; found 501.1.

Example 15. Synthesis of (3S,4S)-3-methyl-8-(8-{1H-pyrrolo[2,3-b]pyridin-4-ylsulfanyl}imidazo[1,2-c]pyrimidin-5-yl)-2-oxa-8-azaspiro[4.5]decan-4-amine

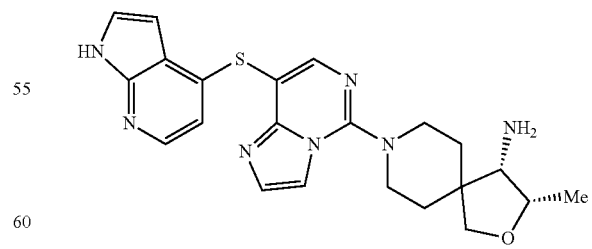

(3S,4S)-3-methyl-8-(8-{1H-pyrrolo[2,3-b]pyridin-4-ylsulfanyl}imidazo[1,2-c]pyrimidin-5-yl)-2-oxa-8-azaspiro[4.5]decan-4-amine was synthesized in a manner similar to Example 1, except 3-chloro-4-(potassiosulfanyl)pyridin-2-amine was substituted with 4-sulfanyl-1H-pyrrolo[2,3-b]

pyridine. ¹H NMR (400 MHz, Methanol-d₄) δ 8.06 (s, 1H), 7.88 (d, J=5.5 Hz, 1H), 7.84-7.82 (m, 1H), 7.56 (s, 1H), 7.39 (d, J=3.3 Hz, 1H), 6.57 (d, J=3.5 Hz, 1H), 6.49 (d, J=5.3 Hz, 1H), 4.30-4.24 (m, 1H), 3.94-3.82 (m, 3H), 3.77 (d, J=9.0 Hz, 1H), 3.41 (br t, J=10.7 Hz, 2H), 3.12 (br d, J=5.1 Hz, 1H), 2.09-1.97 (m, 2H), 1.90-1.75 (m, 2H), 1.27-1.22 (m, 3H). LCMS (ESI): m/z: [M−H] calculated for $C_{22}H_{26}N_7OS$: 436.2; found 436.1.

Example 16. Synthesis of (3S,4S)-8-{8-[(2-amino-pyridin-4-yl)sulfanyl]imidazo[1,2-c]pyrimidin-5-yl}-3-methyl-2-oxa-8-azaspiro[4.5]decan-4-amine

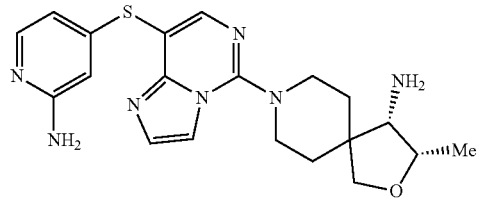 [SMILES: C[C@@H]1OCC2(CCN(c3ncc(Sc4ccnc(N)c4)c4nccn34)CC2)[C@@H]1N]

(3S,4S)-8-{8-[(2-aminopyridin-4-yl)sulfanyl]imidazo[1,2-c]pyrimidin-5-yl}-3-methyl-2-oxa-8-azaspiro[4.5]decan-4-amine was synthesized in a manner similar to Example 1, except 3-chloro-4-(potassiosulfanyl)pyridin-2-amine was substituted with 4-(potassiosulfanyl)pyridin-2-amine. ¹H NMR (400 MHz, Methanol-d₄) δ 8.40 (br s, 1H), 8.06 (s, 1H), 7.82 (s, 1H), 7.64 (d, J=5.7 Hz, 1H), 7.61 (s, 1H), 6.36 (br d, J=4.4 Hz, 1H), 6.23 (s, 1H), 4.37-4.26 (m, 1H), 4.04-3.86 (m, 4H), 3.50-3.43 (m, 1H), 3.28-3.09 (m, 2H), 2.11-1.91 (m, 3H), 1.81 (br d, J=14.8 Hz, 1H), 1.33 (d, J=6.4 Hz, 3H). LCMS (ESI): m/z: [M−H] calculated for $C_{20}H_{26}N_7OS$: 412.2; found 412.1.

Example 17. Synthesis of (3S,4S)-8-(8-{1H-imidazo[4,5-b]pyridin-7-ylsulfanyl}imidazo[1,2-c]pyrimidin-5-yl)-3-methyl-2-oxa-8-azaspiro[4.5]decan-4-amine

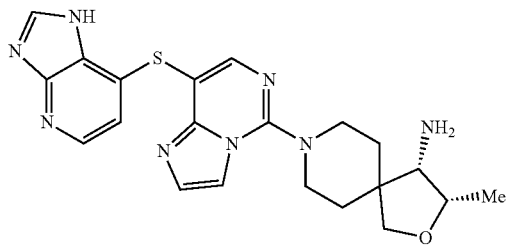 [SMILES: C[C@@H]1OCC2(CCN(c3ncc(Sc4ccnc5nc[nH]c45)c4nccn34)CC2)[C@@H]1N]

(3S,4S)-8-(8-{1H-imidazo[4,5-b]pyridin-7-ylsulfanyl}imidazo[1,2-c]pyrimidin-5-yl)-3-methyl-2-oxa-8-azaspiro[4.5]decan-4-amine was synthesized in a manner similar to Example 1, except (3S,4S)-3-methyl-2-oxa-8-azaspiro[4.5]decan-4-amine was substituted with 7-sulfanyl-1H-imidazo[4,5-b]pyridine. ¹H NMR (400 MHz, Methanol-d₄) δ 8.48 (br s, 1H), 8.38 (s, 1H), 8.13 (s, 1H), 8.02 (d, J=5.3 Hz, 1H), 7.84 (d, J=1.3 Hz, 1H), 7.57 (d, J=1.5 Hz, 1H), 6.59 (br d, J=4.4 Hz, 1H), 4.36-4.26 (m, 1H), 4.06-3.86 (m, 4H), 3.48-3.35 (m, 2H), 3.27 (br s, 1H), 2.15-2.02 (m, 2H), 1.99-1.92 (m, 1H), 1.82 (br d, J=13.6 Hz, 1H), 1.32 (d, J=6.5 Hz, 3H). LCMS (ESI): m/z: [M−H] calculated for $C_{21}H_{25}N_8OS$: 437.2; found 437.1.

Example 18. Synthesis of (3S,4S)-8-{8-[(2-amino-6-methylpyridin-4-yl)sulfanyl]imidazo[1,2-c]pyrimidin-5-yl}-3-methyl-2-oxa-8-azaspiro[4.5]decan-4-amine

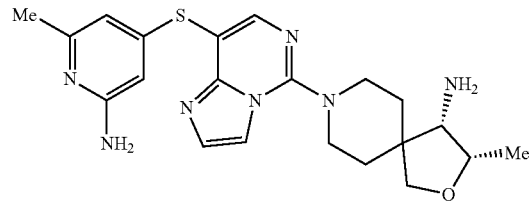 [SMILES: Cc1cc(Sc2cnc(N3CCC4(CC3)CO[C@@H](C)[C@H]4N)n3ccnc23)cc(N)n1]

(3S,4S)-8-{8-[(2-amino-6-methylpyridin-4-yl)sulfanyl]imidazo[1,2-c]pyrimidin-5-yl}-3-methyl-2-oxa-8-azaspiro[4.5]decan-4-amine was synthesized in a manner similar to Example 1, except 3-chloro-4-(potassiosulfanyl)pyridin-2-amine was substituted with 2-amino-6-methyl-pyridine-4-thiol. ¹H NMR (400 MHz, Methanol-d₄) δ 8.48 (br d, J=1.7 Hz, 1H), 8.06 (s, 1H), 7.83 (d, J=1.3 Hz, 11H), 7.61 (d, J=1.3 Hz, 1H), 6.34 (s, 1H), 6.08 (s, 1H), 4.32 (br dd, J=4.4, 6.2 Hz, 11H), 4.04-3.85 (m, 4H), 3.49-3.41 (m, 1H), 3.36 (br s, 2H), 2.25 (s, 3H), 2.12-1.90 (m, 3H), 1.82 (br d, J=13.1 Hz, 1H), 1.33 (d, J=6.4 Hz, 3H). LCMS (ESI): m/z: [M−H] calculated for $C_{21}H_{28}N_7OS$: 426.2; found 426.2.

Example 19. Synthesis of 2-{8-[(2-amino-3-chloro-pyridin-4-yl)sulfanyl]imidazo[1,2-c]pyrimidin-5-yl}-2-azaspiro[3.3]heptan-6-amine

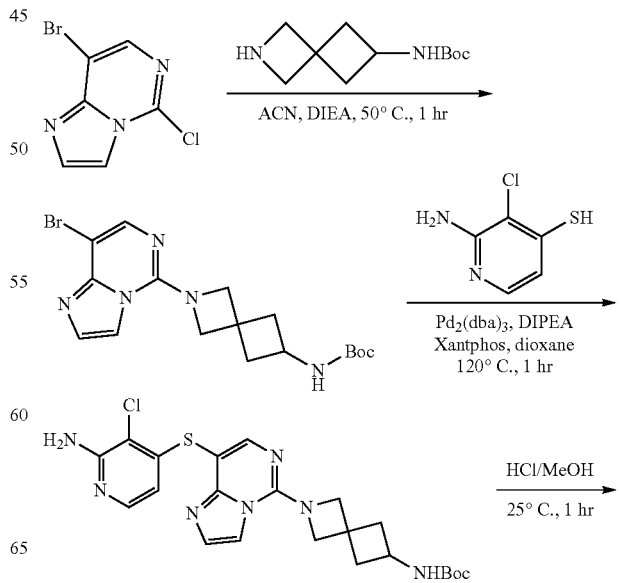

-continued

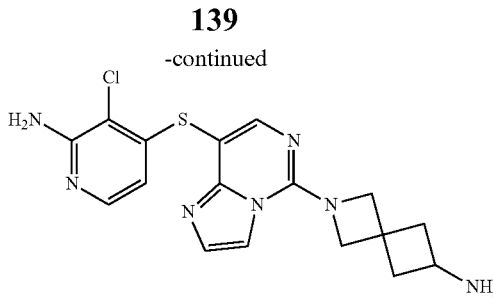

Step 1. Synthesis of tert-butyl N-[2-(8-bromoimidazo[1,2-c]pyrimidin-5-yl)-2-azaspiro[3.3]heptan-6-yl]carbamate To a solution of 8-bromo-5-chloro-imidazo[1,2-c]pyrimidine (150 mg, 645 umol, 1 eq) in AcCN (3 mL) was added DIEA (416 mg, 3.23 mmol, 561 μt) and tert-butyl N-(2-azaspiro[3.3]heptan-6-yl)carbamate (205 mg, 967 μmol) The mixture was stirred at 50° C. for 1 h. The reaction mixture was filtered and concentrated under reduced pressure and the remaining residue was purified by column chromatography to afford tert-butyl N-[2-(8-bromoimidazo[1,2-c]pyrimidin-5-yl)-2-azaspiro[3.3]heptan-6-yl]carbamate (210 mg, 514 μmol, 79% yield) as a yellow solid. $^1$H NMR (400 MHz, Methanol-$d_4$) δ 7.81 (d, J=1.54 Hz, 1H) 7.77 (s, 1H) 7.53 (d, J=1.54 Hz, 1H) 4.51 (s, 2H) 4.37 (s, 2H) 4.01-3.87 (m, 1H) 2.64-2.59 (m, 3H) 2.27-2.14 (m, 2H) 1.43 (s, 9H).

Step 2. Synthesis of tert-butyl N-[2-[8-[(2-amino-3-chloro-4-pyridyl)sulfanyl]imidazo[1,2-c]pyrimidin-5-yl]-2-azaspiro[3.3]heptan-6-yl]carbamate To a solution of tert-butyl N-[2-(8-bromoimidazo[1,2-c]pyrimidin-5-yl)-2-azaspiro[3.3] heptan-6-yl]carbamate (210 mg, 514 μmol) in dioxane (3 mL) was added 2-amino-3-chloro-pyridine-4-thiol (165 mg, 1.03 mmol), DIEA (199 mg, 1.54 mmol, 268 μL), Xantphos (178 mg, 308 μmol) and Pd$_2$(dba)$_3$ (141 mg, 154 μmol). The reaction mixture was stirred at 120° C. for 1 h. The reaction mixture was filtered and concentrated under reduced pressure and the resulting residue was purified by silica gel chromatography to afford tert-butyl N-[2-[8-[(2-amino-3-chloro-4-pyridyl)sulfanyl] imidazo[1,2-c]pyrimidin-5-yl]-2-azaspiro[3.3]heptan-6-yl] carbamate (112 mg, 229 μmol, 44% yield) as a yellow solid. LCMS (ESI): m/z: [M+H] calculated for C$_{22}$H$_{27}$ClN$_7$O$_2$S: 488.2; found 488.1.

Step 3. 2-{8-[(2-amino-3-chloropyridin-4-yl)sulfanyl]imidazo[1,2-c]pyrimidin-5-yl}-2-azaspiro[3.3]heptan-6-amine A mixture of tert-butyl N-[2-[8-[(2-amino-3-chloro-4-pyridyl)sulfanyl]imidazo[1,2-c]pyrimidin-5-yl]-2-azaspiro [3.3]heptan-6-yl]carbamate (111 mg, 227 μmol) in HCl/MeOH (10 mL) was stirred at 25° C. for 1 h. The reaction mixture was concentrated under reduced pressure and the remaining residue was purified by pre-HPLC to afford 2-{8-[(2-amino-3-chloropyridin-4-yl)sulfanyl]imidazo[1,2-c]pyrimidin-5-yl}-2-azaspiro[3.3]heptan-6-amine (35 mg, 79 μmol, 34% yield) as a white solid. $^1$H NMR (400 MHz, Methanol-$d_4$) δ 8.48 (s, 1H) 7.93 (s, 1H) 7.84 (d, J=1.71 Hz, 1H) 7.54-7.45 (m, 2H) 5.89 (d, J=5.50 Hz, 1H) 4.69 (s, 2H) 4.59 (s, 2H) 3.85-3.77 (m, 1H) 2.91-2.72 (m, 2H) 2.59-2.42 (m, 2H). LCMS (ESI): m/z: [M+H] calculated for Chemical Formula: C$_7$H$_{19}$ClN$_7$S: 388.1; found 388.1.

Example 20. Synthesis of 3-chloro-4-[(5-{2,7-diazaspiro[3.5]nonan-7-yl}imidazo[1,2-c]pyrimidin-8-yl)sulfanyl]pyridin-2-amine

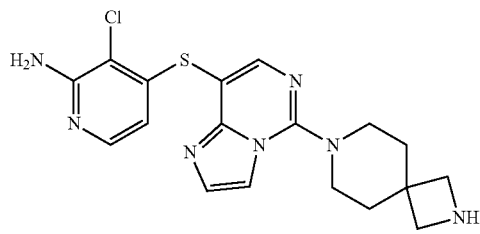 [SMILES: Nc1nccc(Sc2cnc(N3CCC4(CC3)CNC4)n3ccnc23)c1Cl]

3-chloro-4-[(5-{2,7-diazaspiro[3.5]nonan-7-yl}imidazo [1,2-c]pyrimidin-8-yl)sulfanyl]pyridin-2-amine was synthesized in a manner similar to Example 19, except tert-butyl N-(2-azaspiro[3.3]heptan-6-yl)carbamate was substituted with tert-butyl 2,7-diazaspiro[3.5]nonane-2-carboxylate. $^1$H NMR (400 MHz, Methanol-$d_4$) δ 8.54 (s, 1H) 8.04 (s, 1H) 7.82 (d, J=1.54 Hz, 1H) 7.57 (s, 1H) 7.48 (d, J=5.51 Hz, 1H) 5.86 (d, J=5.51 Hz, 1H) 3.96 (s, 4H) 3.62-3.54 (m, 4H) 2.18-2.10 (m, 4H). LCMS (ESI): m/z: [M+H] calculated for C$_{18}$H$_{21}$ClN$_7$S: 402.1; found 402.1.

Example 21. Synthesis of 4-({5-[(3S)-3-aminopyrrolidin-1-yl]imidazo[1,2-c]pyrimidin-8-yl}sulfanyl)-3-chloropyridin-2-amine

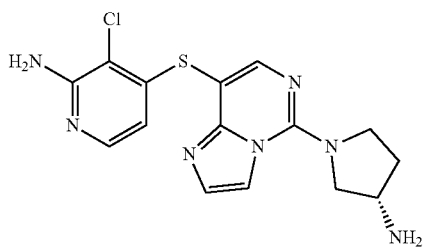 [SMILES: Nc1nccc(Sc2cnc(N3CC[C@H](N)C3)n3ccnc23)c1Cl]

4-({5-[(3S)-3-aminopyrrolidin-1-yl]imidazo[1,2-c]pyrimidin-8-yl}sulfanyl)-3-chloropyridin-2-amine was synthesized in a manner similar to Example 19, except tert-butyl N-(2-azaspiro[3.3]heptan-6-yl)carbamate was substituted with tert-butyl N-[(3S)-pyrrolidin-3-yl]carbamate. $^1$H NMR (400 MHz, Methanol-$d_4$) δ 8.16 (d, J=1.7 Hz, 1H), 7.92 (s, 1H) 7.49 (d, J=5.6 Hz, 1H) 7.47 (d, J=1.7 Hz, 1H) 5.89 (d, J=5.5 Hz, 1H), 4.18-4.24 (m, 3H), 3.90-3.96 (m, 3H), 2.40-2.47 (m, 2H), 2.13-2.18 (m, 2H). LCMS (ESI): m/z: [M+H] calculated for C$_{15}$H$_{17}$SN$_7$Cl: 362.1; found 362.0.

Example 22. Synthesis of 4-({5-[3-(2-aminoethyl)azetidin-1-yl]imidazo[1,2-c]pyrimidin-8-yl}sulfanyl)-3-chloropyridin-2-amine

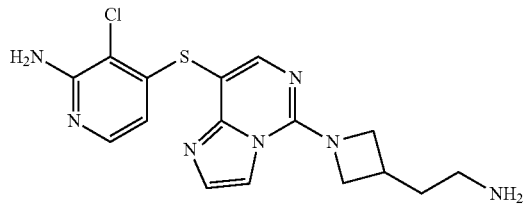 [SMILES: NCCC1CN(c2ncc(Sc3ccnc(N)c3Cl)c3nccn23)C1]

4-({5-[3-(2-aminoethyl)azetidin-1-yl]imidazo[1,2-c]pyrimidin-8-yl}sulfanyl)-3-chloropyridin-2-amine was synthesized in a manner similar to Example 19, except tert-butyl N-(2-azaspiro[3.3]heptan-6-yl)carbamate was substituted with 2-(azetidin-3-yl)ethanamine. $^1$H NMR (400 MHz, Methanol-$d_4$) δ 8.45 (br s, 1H), 7.94 (s, 1H), 7.86 (d, J=1.7 Hz, 1H), 7.51 (d, J=5.6 Hz, 1H), 7.48 (d, J=1.6 Hz, 1H), 5.90 (d, J=5.6 Hz, 1H), 4.76 (t, J=8.6 Hz, 2H), 4.30 (dd, J=5.6, 8.8 Hz, 2H), 3.08-2.87 (m, 3H), 2.13 (q, J=7.7 Hz, 2H). LCMS (ESI): m/z: [M+H] calculated for $C_{16}H_{19}ClN_7S$: 376.1; found 376.1.

Example 23. Synthesis of N1-{8-[(2-amino-3-chloropyridin-4-yl)sulfanyl]imidazo[1,2-c]pyrimidin-5-yl}ethane-1,2-diamine

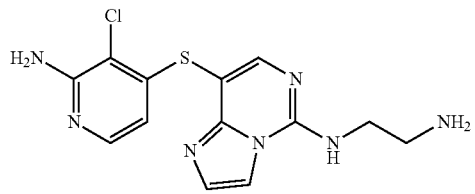 [SMILES: NCCNc1ncc(Sc2ccnc(N)c2Cl)c2nccn12]

N1-{8-[(2-amino-3-chloropyridin-4-yl)sulfanyl]imidazo[1,2-c]pyrimidin-5-yl}ethane-1,2-diamine was synthesized in a manner similar to Example 19, except tert-butyl N-(2-azaspiro[3.3]heptan-6-yl)carbamate was substituted with N-Boc-ethylenediamine. $^1$H NMR (500 MHz, Methanol-$d_4$) δ 8.47 (s, 2H), 8.02 (s, 1H), 7.93 (d, J=1.6 Hz, 11H), 7.55 (d, J=1.6 Hz, 1H), 7.51 (d, J=5.6 Hz, 1H), 5.90 (d, J=5.6 Hz, 1H), 3.99 (t, J=5.7 Hz, 2H). LCMS (ESI): m/z: [M+H] calculated for $C_{13}H_{15}ClN_7S$: 336.1; found 336.3.

Example 24. Synthesis of 4-({5-[(3R)-3-(aminomethyl)pyrrolidin-1-yl]imidazo[1,2-c]pyrimidin-8-yl}sulfanyl)-3-chloropyridin-2-amine

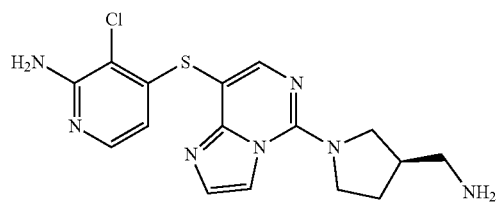 [SMILES: NC[C@H]1CCN(c2ncc(Sc3ccnc(N)c3Cl)c3nccn23)C1]

4-({5-[(3R)-3-(aminomethyl)pyrrolidin-1-yl]imidazo[1,2-c]pyrimidin-8-yl}sulfanyl)-3-chloropyridin-2-amine was synthesized in a manner similar to Example 19, except tert-butyl N-(2-azaspiro[3.3]heptan-6-yl)carbamate was substituted with N-[(3S)-pyrrolidin-3-ylmethyl](tert-butoxy)carboximidic acid. $^1$H NMR (500 MHz, Methanol-$d_4$) δ 8.19 (d, J=1.9 Hz, 1H), 8.11 (d, J=1.4 Hz, 11H), 7.95 (d, J=2.8 Hz, 1H), 7.51 (d, J=5.6 Hz, 11H), 7.48 (d, J=1.6 Hz, 1H), 5.95 (dd, J=9.4, 5.6 Hz, 11H), 4.25-4.15 (m, 2H), 4.11 (td, J=10.2, 9.4, 7.1 Hz, 11H), 3.80 (dd, J=10.8, 8.1 Hz, 1H), 3.23-3.09 (m, 2H), 2.76-2.66 (m, 11H), 2.38 (dq, J=9.0, 5.0, 3.8 Hz, 1H), 2.01-1.80 (m, 1H). LCMS (ESI): m/z: [M+H] calculated for $C_{16}H_{19}ClN_7S$: 376.9; found 376.4.

Example 25. Synthesis of (1R,5S,6R)-3-{8-[(2-amino-3-chloropyridin-4-yl)sulfanyl]imidazo[1,2-c]pyrimidin-5-yl}-3-azabicyclo[3.1.0]hexan-6-amine

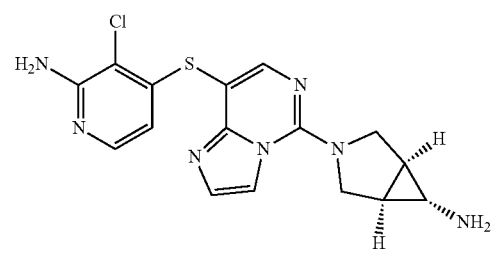 [SMILES: Nc1nccc(Sc2cnc(N3C[C@@H]4[C@@H](N)[C@@H]4C3)n3ccnc23)c1Cl]

(1R,5S,6R)-3-{8-[(2-amino-3-chloropyridin-4-yl)sulfanyl]imidazo[1,2-c]pyrimidin-5-yl}-3-azabicyclo[3.1.0]hexan-6-amine was synthesized in a manner similar to Example 19, except tert-butyl N-(2-azaspiro[3.3]heptan-6-yl)carbamate was substituted with N-[(1R,5S,6S)-3-azabicyclo[3.1.0]hexan-6-yl](tert-butoxy)carboximidic acid. $^1$H NMR (500 MHz, Methanol-$d_4$) δ 8.25 (d, J=1.9 Hz, 1H), 8.03 (s, 1H), 7.57-7.47 (m, 2H), 6.18 (d, J=6.6 Hz, 1H), 4.51 (d, J=11.1 Hz, 2H), 4.16 (dt, J=11.4, 2.0 Hz, 2H), 2.60 (t, J=2.4 Hz, 1H), 2.29 (dt, J=3.9, 1.8 Hz, 2H). LCMS (ESI): m/z: [M+H] calculated for $C_{16}H_7ClN_7S$: 374.9; found 374.4.

Example 26. Synthesis of 4-{[5-(3-amino-3-methylazetidin-1-yl)imidazo[1,2-c]pyrimidin-8-yl]sulfanyl}-3-chloropyridin-2-amine

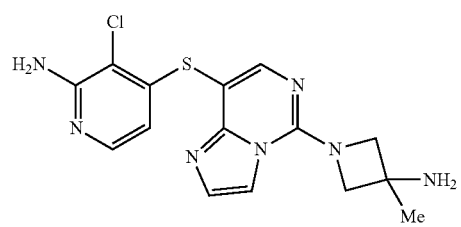 [SMILES: CC1(N)CN(c2ncc(Sc3ccnc(N)c3Cl)c3nccn23)C1]

4-{[5-(3-amino-3-methylazetidin-1-yl)imidazo[1,2-c]pyrimidin-8-yl]sulfanyl}-3-chloropyridin-2-amine was synthesized in a manner similar to Example 19, except tert-butyl N-(2-azaspiro[3.3]heptan-6-yl)carbamate was substituted with N-(3-methylazetidin-3-yl)(tert-butoxy)carboximidic acid hydrochloride. $^1$H NMR (500 MHz, Methanol-$d_4$) δ 8.09 (s, 1H), 7.91 (d, J=1.7 Hz, 1H), 7.59 (d, J=1.7 Hz, 1H), 7.53 (d, J=6.7 Hz, 1H), 6.21 (d, J=6.7 Hz, 1H), 4.74 (d, J=10.0 Hz, 2H), 4.67 (d, J=10.0 Hz, 2H), 1.79 (s, 3H). LCMS (ESI): m/z: [M+H] calculated for $C_{15}H_7ClN_7S$: 362.9; found 362.2.

Example 27. Synthesis of 3-chloro-4-{[5-(piperazin-1-yl)imidazo[1,2-c]pyrimidin-8-yl]sulfanyl}pyridin-2-amine

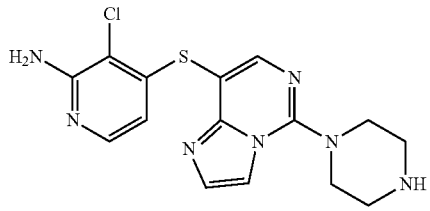 [SMILES: Nc1nccc(Sc2cnc(N3CCNCC3)n3ccnc23)c1Cl]

3-chloro-4-{[5-(piperazin-1-yl)imidazo[1,2-c]pyrimidin-8-yl]sulfanyl}pyridin-2-amine was synthesized in a manner similar to Example 19, except tert-butyl N-(2-azaspiro[3.3]heptan-6-yl)carbamate was substituted with tert-butyl piperazine-1-carboxylate. $^1$H NMR (500 MHz, Methanol-d$_4$) δ 8.19 (s, 1H), 8.01 (d, J=1.7 Hz, 1H), 7.66 (d, J=1.6 Hz, 1H), 7.52 (d, J=6.4 Hz, 1H), 6.15 (d, J=6.4 Hz, 1H), 3.92 (t, J=5.1 Hz, 4H), 3.54 (t, J=5.1 Hz, 5H). LCMS (ESI) m/z: [M+H]: calculated for $C_{15}H_{17}ClN_7S$: 362.9; found 362.3.

Example 28. Synthesis of 4-({5-[(3R)-3-aminopyrrolidin-1-yl]imidazo[1,2-c]pyrimidin-8-yl}sulfanyl)-3-chloropyridin-2-amine

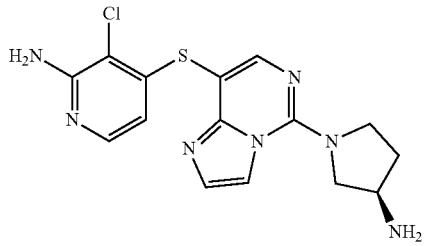 [SMILES: Nc1nccc(Sc2cnc(N3CC[C@@H](N)C3)n3ccnc23)c1Cl]

4-({5-[(3R)-3-aminopyrrolidin-1-yl]imidazo[1,2-c]pyrimidin-8-yl}sulfanyl)-3-chloropyridin-2-amine was synthesized in a manner similar to Example 19, except tert-butyl N-(2-azaspiro[3.3]heptan-6-yl)carbamate was substituted with tert-butyl N-[(3R)-pyrrolidin-3-yl]carbamate. $^1$H NMR (400 MHz, Methanol-d$_4$) δ 8.52-8.38 (m, 2H), 8.17 (d, J=1.5 Hz, 1H), 7.94 (s, 1H), 7.52-7.47 (m, 2H), 5.89 (d, J=5.5 Hz, 1H), 4.31-4.17 (m, 3H), 4.08-3.95 (m, 2H), 2.51 (br dd, J=5.7, 13.7 Hz, 1H), 2.23 (br d, J=4.4 Hz, 1H). LCMS (ESI): m/z: [M+H] calculated for $C_5H_{17}ClN_7S$: 362.1; found 362.2.

Example 29. Synthesis of (3S,4S)-8-{8-[(2-amino-3-chloropyridin-4-yl)sulfanyl]-7-methylimidazo[1,2-c]pyrimidin-5-yl}-3-methyl-2-oxa-8-azaspiro[4.5]decan-4-amine

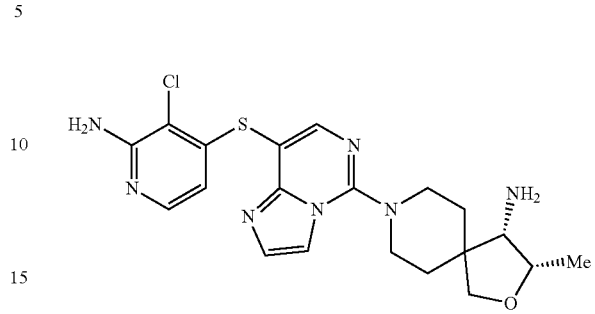

(3S,4S)-8-{8-[(2-amino-3-chloropyridin-4-yl)sulfanyl]-7-methylimidazo[1,2-c]pyrimidin-5-yl}-3-methyl-2-oxa-8-azaspiro[4.5]decan-4-amine was synthesized in a manner similar to Example 1, except (3S,4S)-8-{8-bromoimidazo[1,2-c]pyrimidin-5-yl}-3-methyl-2-oxa-8-azaspiro[4.5]decan-4-amine was substituted with (3S,4S)-8-{8-[(2-amino-3-chloropyridin-4-yl)sulfanyl]-7-methylimidazo[1,2-c]pyrimidin-5-yl}-3-methyl-2-oxa-8-azaspiro[4.5]decan-4-yl. $^1$H NMR (500 MHz, Methanol-d$_4$) δ 8.44 (s, 3H), 7.76 (d, J=1.6 Hz, 1H), 7.52 (t, J=1.2 Hz, 1H), 5.80 (d, J=5.5 Hz, 1H), 4.38-4.31 (m, 1H), 4.02 (t, J=11.5 Hz, 3H), 3.92 (d, J=9.2 Hz, 1H), 3.50 (d, J=4.2 Hz, 1H), 3.31-3.25 (m, 1H), 2.58 (s, 3H), 2.16-2.05 (m, 2H), 1.99 (d, J=13.8 Hz, 1H), 1.84 (d, J=13.2 Hz, 1H), 1.36 (d, J=6.5 Hz, 3H). LCMS (ESI): m/z: [M+H] calculated for $C_{21}H_{27}ClN_7OS$: 460.2; found 460.3.

Example 30. Synthesis of (3S,4S)-8-[8-(2H-indazol-6-yl)-7-methylimidazo[1,2-c]pyrimidin-5-yl]-3-methyl-2-oxa-8-azaspiro[4.5]decan-4-amine

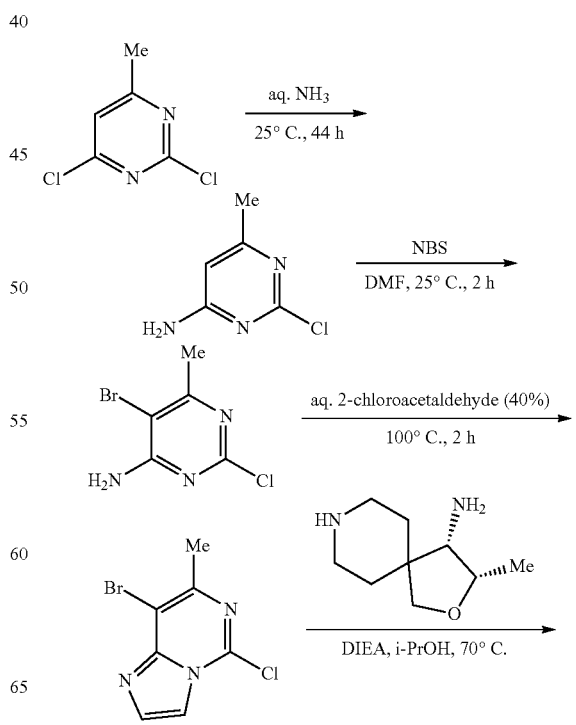

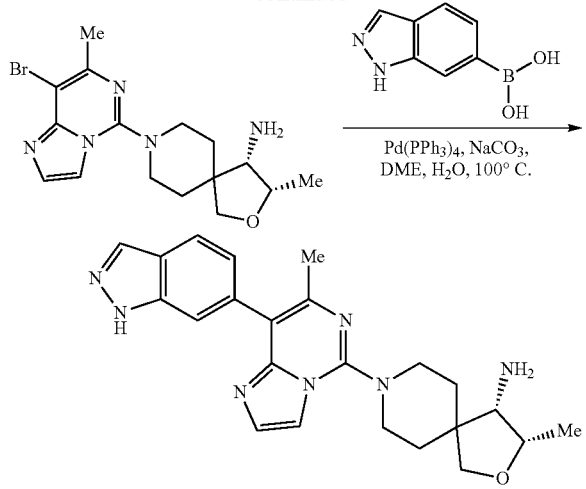

Step 1. Synthesis of 2-chloro-6-methyl-pyrimidin-4-amine

A mixture of 2,4-dichloro-6-methyl-pyrimidine (40 g, 245 mmol) in $NH_3 \cdot H_2O$ (500 mL) was stirred at 25° C. for 44 h. The crude product was filtered and the resulting solution was concentrated under reduced pressure. The remaining residue was purified by silica gel chromatography to afford 2-chloro-6-methyl-pyrimidin-4-amine (10.4 g, 72.4 mmol, 30% yield) as a white solid. LCMS (ESI): m/z: [M+H] calculated for $C_5H_7ClN_3$: 144.0; found 144.3.

Step 2. Synthesis of 5-bromo-2-chloro-6-methyl-pyrimidin-4-amine

To a solution of 2-chloro-6-methyl-pyrimidin-4-amine (13 g, 91 mol) in DMF (130 mL) was added NBS (24.2 g, 136 mmol) at 15° C., and the mixture was stirred at 15° C. for 2 h. The mixture was quenched by the addition of a saturated solution of $Na_2SO_3$ (130 mL) and ice water (130 mL). The resulting mixture was stirred for 5 min and the mixture was filtered to afford 5-bromo-2-chloro-6-methyl-pyrimidin-4-amine (16 g, 72 mmol, 79% yield) as a white solid LCMS (ESI): m/z: [M+H] calculated for $C_5H_6BrClN_3$: 223.9; found 223.8.

Step 3. Synthesis of 8-bromo-5-chloro-7-methyl-imidazo[1,2-c]pyrimidine

A mixture of 5-bromo-2-chloro-6-methyl-pyrimidin-4-amine (8 g, 36 mmol) in 2-chloroacetaldehyde (160 mL) was stirred at 100° C. for 0.5 h. The resulting residue was purified by column chromatography to afford 8-bromo-5-chloro-7-methyl-imidazo [1,2-c]pyrimidine (3.5 g, 14.2 mmol, 40% yield) as a white solid. LCMS (ESI): m/z: [M+H] calculated for $C_7H_6BrClN_3$: 247.9; found 248.1.

Step 4. Synthesis of (3S,4S)-8-(8-bromo-7-methyl-imidazo[1,2-c]pyrimidin-5-yl)-3-methyl-2-oxa-8-azaspiro[4.5]decan-4-amine A solution of 8-bromo-5-chloro-7-methyl-imidazo[1,2-c]pyrimidine (300 mg, 1.2 mmol), (3S,4S)-3-methyl-2-oxa-8-azaspiro[4.5]decan-4-amine (249 mg, 1.5 mmol) and DIPEA (1.6 g, 12.2 mmol, 2.1 mL) in i-PrOH (3 mL) was stirred at 70° C. for 3 h. The mixture was cooled to 25° C. and then concentrated under reduced pressure. The resulting residue was purified by column chromatography to afford (3S,4S)-8-(8-bromo-7-methyl-imidazo[1,2-c]pyrimidin-5-yl)-3-methyl-2-oxa-8-azaspiro[4.5]decan-4-amine (400 mg, 1 mmol, 86% yield) as a white solid. LCMS (ESI): m/z: [M+H] calculated for $C_{16}H_{23}BrN_5O$: 380.1; found 380.2.

Step 5. Synthesis of (3S,4S)-8-[8-(2H-indazol-6-yl)-7-methylimidazo[1,2-c]pyrimidin-5-yl]-3-methyl-2-oxa-8-azaspiro[4.5]decan-4-amine To a solution of 1H-indazol-6-ylboronic acid (64 mg, 394 μmol) and (3S,4S)-8-(8-bromo-7-methyl-imidazo[1,2-c]pyrimidin-5-yl)-3-methyl-2-oxa-8-azaspiro[4.5]decan-4-amine (100 mg, 263 μmol) in DME (1 mL) and $H_2O$ (0.2 mL) was added $Na_2CO_3$ (56 mg, 526 μmol) and $Pd(PPh_3)_4$ (30 mg, 26 μmol) under $N_2$ at 25° C. The mixture was stirred at 100° C. for 3 h. The mixture was cooled to 25° C. and the mixture was filtered. The resulting solution was concentrated under reduced pressure and the resulting residue was purified by prep-HPLC to afford (3S,4S)-8-[8-(2H-indazol-6-yl)-7-methylimidazo[1,2-c]pyrimidin-5-yl]-3-methyl-2-oxa-8-azaspiro[4.5]decan-4-amine (8.5 mg, 20.2 μmol, 8% yield) as a white solid. $^1$H NMR (400 MHz, Methanol-$d_4$) δ 8.43 (s, 1H), 8.12 (s, 1H), 7.89 (d, J=8.70 Hz, 1H), 7.70 (s, 1H), 7.58 (s, 1H), 7.48 (s, 1H), 7.17 (d, J=7.60 Hz, 1H), 4.33 (s, 1H), 4.00 (d, J=9.30 Hz, 1H), 3.92-3.82 (m, 3H), 3.48 (s, 1H), 3.23-3.17 (m, 2H), 2.33 (s, 3H), 2.13-2.07 (m, 2H), 1.99-1.96 (m, 1H), 1.82 (d, J=12.80 Hz, 1H), 1.34 (d, J=6.00 Hz, 3H). LCMS (ESI): m/z: [M+H] calculated for $C_{23}H_{28}N_7O$: 418.2; found 418.4.

Example 31. Synthesis of 3-{5-[(3S,4S)-4-amino-3-methyl-2-oxa-8-azaspiro[4.5]decan-8-yl]-7-methyl-imidazo[1,2-c]pyrimidin-8-yl}-2-chloro-6-methoxy-benzonitrile

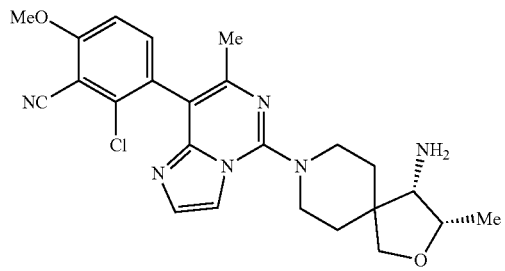 [SMILES: COc1ccc(-c2c(C)nc(N3CCC4(CC3)CO[C@@H](C)[C@H]4N)n3ccnc23)c(Cl)c1C#N]

3-{5-[(3S,4S)-4-amino-3-methyl-2-oxa-8-azaspiro[4.5] decan-8-yl]-7-methylimidazo[1,2-c]pyrimidin-8-yl}-2-chloro-6-methoxybenzonitrile was synthesized in a manner similar to Example 15, except 1H-indazol-6-ylboronic acid was substituted with 2-chloro-3-cyano-4-methoxyphenylboronic acid. $^1$H NMR (500 MHz, Methanol-$d_4$) δ 8.50 (s, 1H), 7.70 (d, J=1.6 Hz, 1H), 7.58 (d, J=8.8 Hz, 1H), 7.47 (d, J=1.6 Hz, 1H), 7.29 (d, J=8.8 Hz, 1H), 4.34-4.28 (m, 1H), 4.06 (s, 3H), 3.98 (d, J=9.0 Hz, 1H), 3.92-3.81 (m, 3H), 3.39 (d, J=4.3 Hz, 1H), 3.28-3.16 (m, 2H), 2.20 (s, 3H), 2.13-2.02 (m, 2H), 1.94 (d, J=13.9 Hz, 1H), 1.81 (d, J=13.3 Hz, 1H), 1.31 (d, J=6.5 Hz, 3H). LC-MS (ESI): m/z: [M+H] calculated for $C_{24}H_{28}ClN_6O_2$: 467.2; found 467.4.

Example 32. Synthesis of (3S,4S)-8-[8-(1H-1,3-benzodiazol-4-yl)-7-methylimidazo[1,2-c]pyrimidin-5-yl]-3-methyl-2-oxa-8-azaspiro[4.5]decan-4-amine

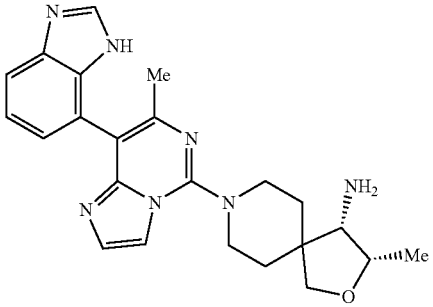 [SMILES: Cc1nc(N2CCC3(CC2)CO[C@@H](C)[C@H]3N)n2ccnc2c1-c1cccc2nc[nH]c12]

(3S,4S)-8-[8-(1H-1,3-benzodiazol-4-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 1H-benzimidazol-4-yl boronic acid. $^1$H NMR (500 MHz, Methanol-$d_4$) δ 8.48 (s, 1H), 8.08 (s, 1H), 7.73-7.61 (m, 2H), 7.47-7.33 (m, 2H), 7.23 (dd, J=7.4, 1.1 Hz, 1H), 4.38-4.20 (m, 1H), 3.95 (d, J=9.0 Hz, 1H), 3.81 (dd, J=23.1, 11.6 Hz, 3H), 3.33 (s, 1H), 3.26-3.12 (m, 2H), 2.19 (s, 3H), 2.05 (s, 2H), 1.91 (d, J=13.7 Hz, 1H), 1.79 (d, J=13.1 Hz, 1H), 1.28 (d, J=6.5 Hz, 3H). LCMS (ESI): m/z: [M+H] calculated for $C_{23}H_{28}N_7O$: 418.2; found 418.6.

Example 33. Synthesis of (3S,4S)-8-[8-(1H-1,3-benzodiazol-6-yl)-7-methylimidazo[1,2-c]pyrimidin-5-yl]-3-methyl-2-oxa-8-azaspiro[4.5]decan-4-amine

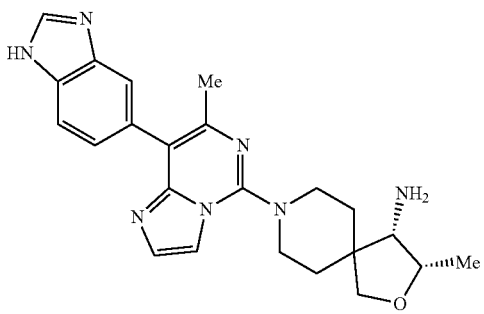 [SMILES: Cc1nc(N2CCC3(CC2)CO[C@@H](C)[C@H]3N)n2ccnc2c1-c1ccc2[nH]cnc2c1]

(3S,4S)-8-[8-(1H-1,3-benzodiazol-6-yl)-7-methylimidazo[1,2-c]pyrimidin-5-yl]-3-methyl-2-oxa-8-azaspiro[4.5]decan-4-amine was synthesized in a manner similar to Example 5, except 1H-indazol-6-ylboronic acid was substituted with 1H-benzimidazole-5-boronic acid. $^1$H NMR (500 MHz, Methanol-$d_4$) δ 8.25 (s, 2H), 8.21 (s, 1H), 7.67 (dd, J=8.3, 0.8 Hz, 1H), 7.63 (d, J=1.6 Hz, 11H), 7.59 (t, J=1.1 Hz, 1H), 7.41 (d, J=1.5 Hz, 1H), 7.24 (dd, J=8.3, 1.6 Hz, 1H), 4.36-4.20 (m, 1H), 3.94 (d, J=9.1 Hz, 1H), 3.89-3.73 (m, 3H), 3.45 (d, J=4.1 Hz, 1H), 3.12 (dt, J=26.5, 12.0 Hz, 2H), 2.26 (s, 3H), 2.12-1.87 (m, 3H), 1.76 (d, J=12.6 Hz, 1H), 1.28 (d, J=6.5 Hz, 3H). LCMS (ESI): m/z: [M+H] calculated for $C_{23}H_{28}N_7O$: 418.2; found 418.5.

Example 34. Synthesis of (3S,4S)-3-methyl-8-[7-methyl-8-(1-methyl-1H-indazol-5-yl)imidazo[1,2-c]pyrimidin-5-yl]-2-oxa-8-azaspiro[4.5]decan-4-amine

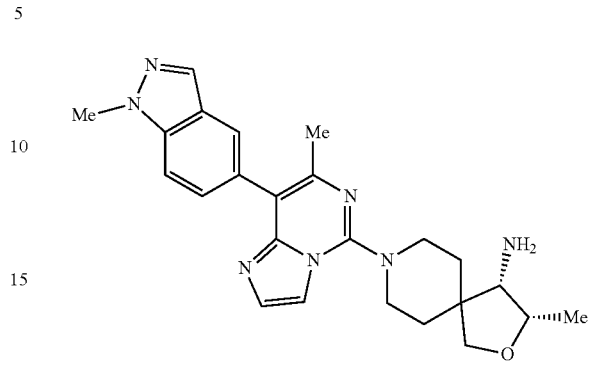

(3S,4S)-3-methyl-8-[7-methyl-8-(1-methyl-1H-indazol-5-yl)imidazo[1,2-c]pyrimidin-5-yl]-2-oxa-8-azaspiro[4.5]decan-4-amine was synthesized in a manner similar to Example 15, except 1H-indazol-6-ylboronic acid was substituted with 1-methyl-1H-indazole-5-boronic acid. $^1$H NMR (500 MHz, Methanol-$d_4$) δ 8.43 (s, 1H), 8.03 (d, J=1.0 Hz, 1H), 7.76 (dd, J=1.6, 0.9 Hz, 1H), 7.66 (d, J=1.6 Hz, 11H), 7.64 (dt, J=8.7, 0.9 Hz, 1H), 7.45 (d, J=1.5 Hz, 1H), 7.42 (dd, J=8.7, 1.6 Hz, 1H), 4.36-4.25 (m, 1H), 4.10 (s, 3H), 3.97 (d, J=9.1 Hz, 1H), 3.87 (d, J=9.1 Hz, 11H), 3.81 (dd, J=17.9, 13.3 Hz, 3H), 3.44 (d, J=4.1 Hz, 1H), 3.25-3.09 (m, 1H), 2.29 (s, 3H), 2.06 (t, J=12.1 Hz, 2H), 1.94 (d, J=13.7 Hz, 11H), 1.79 (d, J=13.3 Hz, 1H), 1.30 (d, J=6.5 Hz, 3H). LCMS (ESI): m/z: [M+H] calculated for $C_{24}H_{30}N_7O$: 432.2; found 432.5.

Example 35. Synthesis of (3S,4S)-8-[8-(1H-indol-7-yl)-7-methylimidazo[1,2-c]pyrimidin-5-yl]-3-methyl-2-oxa-8-azaspiro[4.5]decan-4-amine

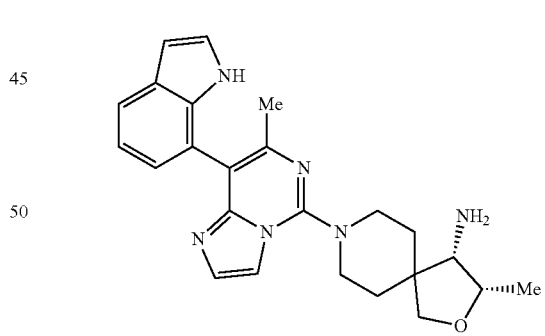

(3S,4S)-8-[8-(1H-indol-7-yl)-7-methylimidazo[1,2-c]pyrimidin-5-yl]-3-methyl-2-oxa-8-azaspiro[4.5]decan-4-amine was synthesized in a manner similar to Example 15, except $^1$H-indazol-6-ylboronic acid was substituted with Indole-7-boronic acid. $^1$H NMR (500 MHz, Methanol-$d_4$) δ 8.38 (s, 1H), 7.67 (d, J=1.6 Hz, 1H), 7.61 (dd, J=7.9, 1.1 Hz, 1H), 7.39 (d, J=1.5 Hz, 1H), 7.16-7.09 (m, 2H), 7.04 (dd, J=7.2, 1.1 Hz, 1H), 6.48 (d, J=3.1 Hz, 1H), 4.35-4.26 (m, 11H), 3.98 (d, J=9.1 Hz, 11H), 3.88 (d, J=9.1 Hz, 1H), 3.86-3.78 (m, 3H), 3.46 (d, J=4.1 Hz, 1H), 3.20 (t, J=12.4 Hz, 1H), 2.18 (s, 3H), 2.06 (d, J=8.1 Hz, 2H), 1.97 (d, J=13.6

Hz, 1H), 1.81 (d, J=12.8 Hz, 1H), 1.31 (d, J=6.5 Hz, 3H). LCMS (ESI): m/z: [M+H] calculated for $C_{24}H_{29}N_6O$: 417.23; found 417.5.

Example 36. (3S,4S)-8-[8-(2H-indazol-7-yl)-7-methylimidazo[1,2-c]pyrimidin-5-yl]-3-methyl-2-oxa-8-azaspiro[4.5]decan-4-amine

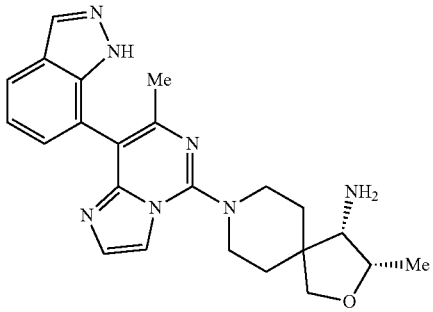 [SMILES: Cc1nc(N2CCC3(CC2)CO[C@@H](C)[C@H]3N)n2ccnc2c1-c1cccc2cn[nH]c12]

(3S,4S)-8-[8-(2H-indazol-7-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 1H-Indazol-7-ylboronic acid. $^1$H NMR (500 MHz, Methanol-$d_4$) δ 8.45 (s, 2H), 8.09 (s, 1H), 7.85 (dd, J=8.1, 1.0 Hz, 11H), 7.69 (d, J=1.6 Hz, 1H), 7.40 (d, J=1.6 Hz, 1H), 7.35 (dd, J=7.0, 1.0 Hz, 1H), 7.27 (dd, J=8.1, 7.0 Hz, 1H), 4.30 (dd, J=6.6, 4.3 Hz, 1H), 3.97 (d, J=8.9 Hz, 1H), 3.87 (d, J=9.0 Hz, 2H), 3.83 (d, J=13.4 Hz, 1H), 3.40 (d, J=4.2 Hz, 1H), 3.25-3.12 (m, 3H), 2.21 (s, 3H), 2.06 (t, J=11.4 Hz, 2H), 1.95 (d, J=14.0 Hz, 1H), 1.81 (d, J=13.2 Hz, 1H), 1.30 (d, J=6.5 Hz, 3H). LCMS (ESI): m/z: [M+H] calculated for $C_{23}H_{28}N_7O$: 418.2; found 418.4.

Example 37. Synthesis of (3S,4S)-8-[8-(4-chloro-2H-indazol-6-yl)-7-methylimidazo[1,2-c]pyrimidin-5-yl]-3-methyl-2-oxa-8-azaspiro[4.5]decan-4-amine

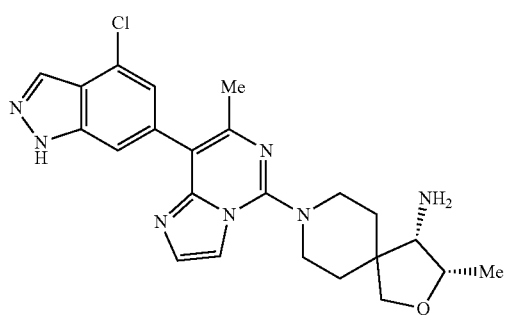 [SMILES: Cc1nc(N2CCC3(CC2)CO[C@@H](C)[C@H]3N)n2ccnc2c1-c1cc(Cl)c2cn[nH]c2c1]

(3S,4S)-8-[8-(4-chloro-2H-indazol-6-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with (4-chloro-1H-indazol-6-yl)boronic acid. $^1$H NMR (400 MHz, Methanol-$d_4$) δ 8.53 (br s, 1H) 8.16 (s, 1H) 7.70 (s, 1H) 7.50 (br d, J=17.73 Hz, 2H) 7.19 (s, 1H) 4.27-4.36 (m, 1H) 3.98 (br d, J=9.05 Hz, 1H) 3.78-3.91 (m, 3H) 3.41 (br d, J=2.93 Hz, 1H) 3.12-3.26 (m, 2H) 3.12-3.26 (m, 1H) 2.34 (s, 3H) 2.08 (br t, J=11.86 Hz, 2H) 1.94 (br d, J=13.33 Hz, 1H) 1.82 (br d, J=13.08 Hz, 1H) 1.32 (br d, J=6.36 Hz, 3H). LCMS (ESI): m/z: [M+H] calculated for $C_{23}H_{27}ClN_7O$: 452.2; found 452.1.

Synthesis of (4-chloro-1H-indazol-6-yl)boronic acid

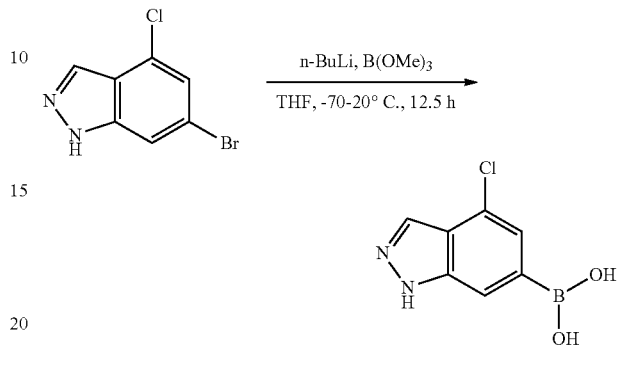

A solution of n-BuLi (2.5 M, 423.37 uL) was added dropwise to a mixture of 6-bromo-4-chloro-1H-indazole (70 mg, 302 μmol) in THF (1 mL) at −70° C. under $N_2$. The mixture was stirred at −70° C. for 0.5 h, after which a solution of B(OMe)$_3$ (63 mg, 605 μmol) in THF (1 mL) was added. The mixture was slowly allowed to warm to 20° C. and stirred at 20° C. for 12 h. The reaction mixture was then quenched by addition 1N HCl until pH=2 was attained. The mixture was extracted with EtOAc (10 mL×3) and the combined organic layers were washed with aqueous NaCl (10 mL×2), dried over $Na_2SO_4$, filtered and concentrated under reduced pressure to afford (4-chloro-1H-indazol-6-yl)boronic acid (100 mg, crude) as white solid. LCMS (ESI): m/z: [M−H] calculated for $C_7H_5BClN_2O_2$: 195.2; found 195.0.

Example 38. Synthesis of (3S,4S)-8-[8-(5-chloro-2H-indazol-6-yl)-7-methylimidazo[1,2-c]pyrimidin-5-yl]-3-methyl-2-oxa-8-azaspiro[4.5]decan-4-amine

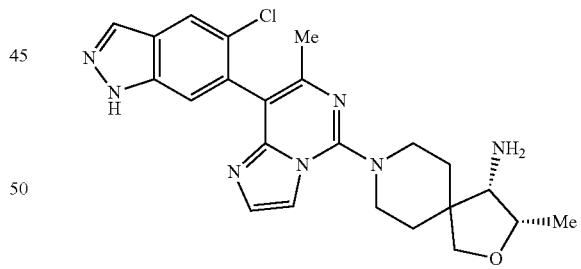

(3S,4S)-8-[8-(5-chloro-2H-indazol-6-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 5-chloro-6-(4,4,5,5-tetramethyl-1,3,2-dioxaborolan-2-yl)-1H-indazole. $^1$H NMR (400 MHz, Methanol-$d_4$) δ 8.11 (s, 1H) 8.02 (s, 1H) 7.71 (s, 1H) 7.54 (s, 1H) 7.45 (d, J=1.34 Hz, 1H) 4.27-4.36 (m, 1H) 3.98 (d, J=9.05 Hz, 1H) 3.87 (br d, J=9.05 Hz, 3H) 3.17-3.26 (m, 4H) 2.21 (s, 3H) 2.02-2.15 (m, 2H) 2.02-2.15 (m, 2H) 1.94 (br d, J=14.18 Hz, 1H) 1.82 (br d, J=13.33 Hz, 1H) 1.31 (d, J=6.48 Hz, 3H). LCMS (ESI): m/z: [M+H] calculated for $C_{23}H_{27}ClN_7O$: 452.2; found 452.0.

Synthesis of 5-chloro-6-(4,4,5,5-tetramethyl-1,3,2-dioxaborolan-2-yl)-1H-indazole

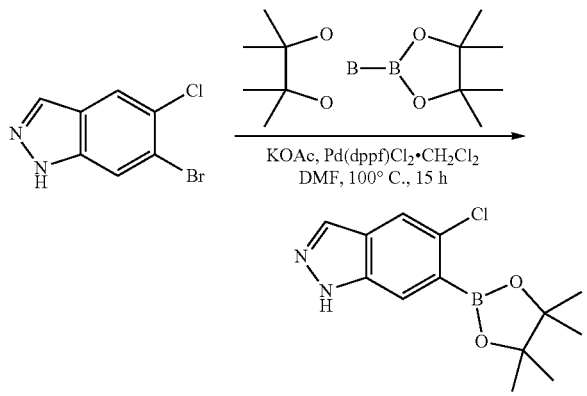

To a solution of 6-bromo-5-chloro-1H-indazole (100 mg, 432 μmol, 1 eq) in DMF (2 mL) was added 4,4,5,5-tetramethyl-2-(4,4,5,5-tetramethyl-1,3,2-dioxaborolan-2-yl)-1,3,2-dioxaborolane (187 mg, 734 μmol), Pd(dppf)Cl$_2$·CH$_2$Cl$_2$ (35 mg, 43 μmol) and KOAc (127 mg, 1.3 mmol, 3 eq). The mixture was stirred at 100° C. for 15 h. The reaction mixture was concentrated under reduced pressure and the resulting residue was purified by column chromatography to afford 5-chloro-6-(4,4,5,5-tetramethyl-1,3,2-dioxaborolan-2-yl)-1H-indazole (130 mg, crude) as yellow oil. LCMS (ESI): m/z: [M+H] calculated for C$_{13}$H$_{17}$BClN$_2$O$_2$: 279.1; found 278.9.

Example 39. Synthesis of (3S,4S)-8-[8-(2H-indazol-5-yl)-7-methylimidazo[1,2-c]pyrimidin-5-yl]-3-methyl-2-oxa-8-azaspiro[4.5]decan-4-amine

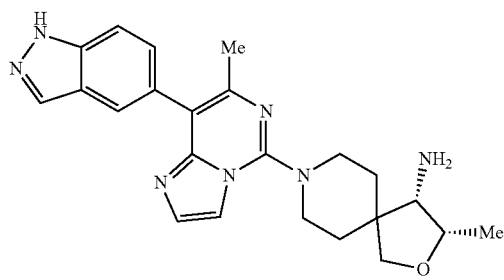 [SMILES: Cc1nc(N2CCC3(CC2)CO[C@@H](C)[C@H]3N)n2ccnc2c1-c1ccc2[nH]ncc2c1]

(3S,4S)-8-[8-(2H-indazol-5-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 1H-Indazole-5-boronic acid. $^1$H NMR (500 MHz, Methanol-d$_4$) δ 8.41 (s, 2H), 8.06 (d, J=1.0 Hz, 1H), 7.77 (t, J=1.1 Hz, 1H), 7.67-7.58 (m, 2H), 7.42 (d, J=1.1 Hz, 1H), 7.37 (dd, J=8.6, 1.5 Hz, 1H), 4.28 (s, 1H), 3.95 (d, J=9.1 Hz, 1H), 3.90-3.74 (m, 3H), 3.43 (s, 1H), 3.23-3.07 (m, 1H), 2.28 (s, 3H), 2.13-1.87 (m, 3H), 1.77 (d, J=12.9 Hz, 1H), 1.29 (d, J=6.4 Hz, 3H). LCMS (ESI): m/z: [M+H] calculated for C$_{23}$H$_{28}$N$_7$O: 418.2; found 418.2.

Example 40. Synthesis of (3S,4S)-3-methyl-8-[7-methyl-8-(1-methyl-1H-indol-2-yl)imidazo[1,2-c]pyrimidin-5-yl]-2-oxa-8-azaspiro[4.5]decan-4-amine

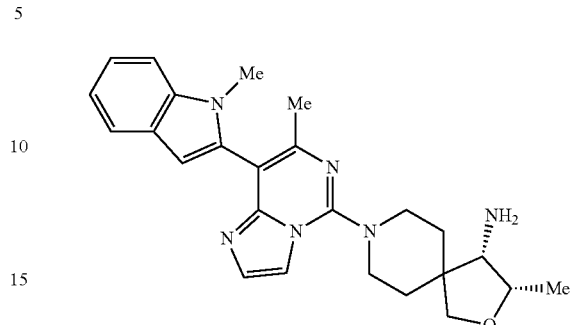

(3S,4S)-3-methyl-8-[7-methyl-8-(1-methyl-1H-indol-2-yl)imidazo[1,2-c]pyrimidin-5-yl]-2-oxa-8-azaspiro[4.5]decan-4-amine was synthesized in a manner similar to Example 15, except 1H-indazol-6-ylboronic acid was substituted with N-methylindole-2-boronic acid. $^1$H NMR (500 MHz, Methanol-d$_4$) δ 7.67 (d, J=1.6 Hz, 1H), 7.54 (dt, J=7.9, 1.0 Hz, 1H), 7.42 (d, J=1.6 Hz, 1H), 7.38 (dt, J=8.3, 1.0 Hz, 1H), 7.16 (ddd, J=8.3, 7.1, 1.2 Hz, 1H), 7.03 (ddd, J=8.0, 7.1, 1.0 Hz, 1H), 6.47 (d, J=0.8 Hz, 1H), 4.32-4.19 (m, 1H), 3.92 (d, J=8.9 Hz, 1H), 3.87-3.74 (m, 3H), 3.47 (s, 4H), 3.24-3.13 (m, 1H), 2.29 (s, 3H), 2.12-1.96 (m, 2H), 1.87 (d, J=13.8 Hz, 1H), 1.77 (d, J=13.5 Hz, 1H), 1.25 (d, J=6.6 Hz, 4H). LCMS (ESI): m/z: [M+H] calculated for C$_{25}$H$_{31}$N$_6$O: 431.2; found 431.1.

Example 41. Synthesis of (3S,4S)-8-[8-(5-chloroquinoxalin-6-yl)-7-methylimidazo[1,2-c]pyrimidin-5-yl]-3-methyl-2-oxa-8-azaspiro[4.5]decan-4-amine

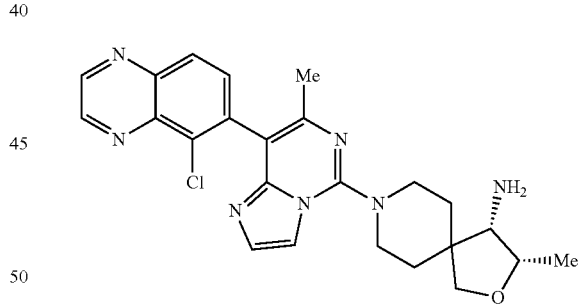

(3S,4S)-8-[8-(5-chloroquinoxalin-6-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 5-chloro-6-(4,4,5,5-tetramethyl-1,3,2-dioxaborolan-2-yl)-Quinoxaline. $^1$H NMR (500 MHz, Methanol-d$_4$) δ 9.08-9.03 (m, 2H), 8.22 (d, J=8.6 Hz, 1H), 7.84 (d, J=8.6 Hz, 1H), 7.77 (d, J=1.5 Hz, 1H), 7.51 (d, J=1.5 Hz, 1H), 4.42-4.30 (m, 1H), 4.10-3.87 (m, 5H), 3.55-3.49 (m, 1H), 3.32-3.15 (m, 1H), 2.28 (s, 3H), 2.14 (dt, J=18.3, 13.5 Hz, 3H), 2.02 (d, J=13.7 Hz, 1H), 1.87 (d, J=13.0 Hz, 1H), 1.37 (d, J=6.5 Hz, 3H). LCMS (ESI): m/z: [M+H] calculated for C$_{24}$H$_{27}$ClN$_7$O: 464.2; found 464.4.

Example 42. Synthesis of (3S,4S)-3-methyl-8-[7-methyl-8-(1-methyl-1H-indol-2-yl)imidazo[1,2-c]pyrimidin-5-yl]-2-oxa-8-azaspiro[4.5]decan-4-amine

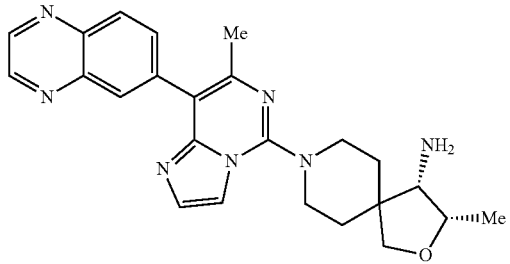 [SMILES: Cc1nc(N2CCC3(CC2)CO[C@@H](C)[C@H]3N)n2ccnc2c1-c1ccc2nccnc2c1]

(3S,4S)-3-methyl-8-[7-methyl-8-(1-methyl-1H-indol-2-yl)imidazo[1,2-c]pyrimidin-5-yl]-2-oxa-8-azaspiro[4.5]decan-4-amine was synthesized in a manner similar to Example 15, except 1H-indazol-6-ylboronic acid was substituted with Quinoxaline-6-boronic acid. 1H NMR (500 MHz, Methanol-$d_4$) δ 8.98 (q, J=2.0 Hz, 2H), 8.53 (s, 1H), 8.26 (d, J=8.7 Hz, 1H), 8.20 (d, J=1.9 Hz, 1H), 7.96 (dd, J=8.6, 1.9 Hz, 1H), 7.77 (d, J=1.6 Hz, 1H), 7.53 (d, J=1.6 Hz, 1H), 4.41-4.26 (m, 1H), 4.02 (d, J=9.0 Hz, 1H), 3.90 (t, J=12.6 Hz, 3H), 3.43 (d, J=4.2 Hz, 1H), 3.32-3.15 (m, 1H), 2.41 (s, 3H), 2.11 (t, J=12.5 Hz, 2H), 1.98 (d, J=13.5 Hz, 1H), 1.85 (d, J=13.1 Hz, 1H), 1.34 (d, J=6.4 Hz, 3H). LCMS (ESI): m/z: [M+H] calculated for $C_{24}H_{28}N_7O$ 430.5; found 430.1.

Example 43. Synthesis of (3S,4S)-8-[8-(8-chloro-3,4-dihydro-2H-1-benzopyran-7-yl)-7-methylimidazo[1,2-c]pyrimidin-5-yl]-3-methyl-2-oxa-8-azaspiro[4.5]decan-4-amine

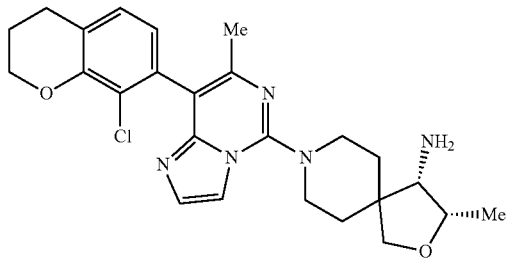 [SMILES: Cc1nc(N2CCC3(CC2)CO[C@@H](C)[C@H]3N)n2ccnc2c1-c1ccc2c(c1Cl)OCCC2]

(3S,4S)-8-[8-(8-chloro-3,4-dihydro-2H-1-benzopyran-7-yl)-7-methylimidazo[1,2-c]pyrimidin-5-yl]-3-methyl-2-oxa-8-azaspiro[4.5]decan-4-amine. was synthesized in a manner similar to Example 15, except 1H-indazol-6-ylboronic acid was substituted 2-(8-Chlorochroman-7-yl)-4,4,5,5-tetramethyl-1,3,2-dioxaborolane. $^1$H NMR (500 MHz, Methanol-$d_4$) δ 8.56 (s, 1H), 7.72 (d, J=1.6 Hz, 1H), 7.50 (d, J=1.5 Hz, 1H), 7.21-7.12 (m, 1H), 6.83 (d, J=7.7 Hz, 1H), 4.38 (td, J=6.6, 3.6 Hz, 3H), 4.05 (d, J=9.1 Hz, 1H), 3.91 (dd, J=30.8, 12.9 Hz, 3H), 3.50 (d, J=4.2 Hz, 1H), 3.34-3.18 (m, 2H), 2.96 (t, J=6.5 Hz, 2H), 2.25 (s, 3H), 2.22-2.08 (m, 4H), 2.01 (d, J=13.9 Hz, 1H), 1.88 (d, J=13.4 Hz, 1H), 1.39 (d, J=6.5 Hz, 3H). LCMS (ESI): m/z: [M+H] calculated for $C_{25}H_{31}ClN_5O_2$: 468.21; found 468.4.

Example 44. Synthesis of (3S,4S)-8-[8-(7-chloro-2,3-dihydro-1-benzofuran-6-yl)-7-methylimidazo[1,2-c]pyrimidin-5-yl]-3-methyl-2-oxa-8-azaspiro[4.5]decan-4-amine

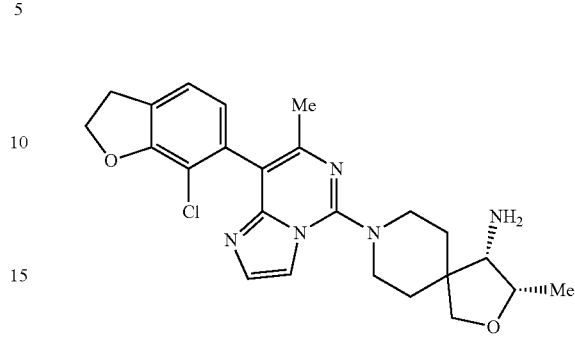

(3S,4S)-8-[8-(7-chloro-2,3-dihydro-1-benzofuran-6-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 2-(7-chloro-2,3-dihydrobenzofuran-6-yl)-4,4,5,5-tetramethyl-1,3,2-dioxaborolane. 1H NMR (500 MHz, Methanol-$d_4$) δ 8.54 (s, 1H), 7.74 (d, J=1.5 Hz, 11H), 7.52 (d, J=1.6 Hz, 1H), 7.32 (dt, J=7.3, 1.2 Hz, 11H), 6.87 (d, J=7.5 Hz, 11H), 4.78 (t, J=8.8 Hz, 2H), 4.39 (q, J=6.4, 5.8 Hz, 1H), 4.06 (d, J=9.1 Hz, 1H), 3.93 (dd, J=27.7, 13.3 Hz, 3H), 3.55-3.41 (m, 3H), 3.30 (dd, J=27.7, 15.0 Hz, 2H), 2.27 (s, 3H), 2.23-2.10 (m, 2H), 2.02 (d, J=13.8 Hz, 1H), 1.89 (d, J=13.2 Hz, 1H), 1.40 (d, J=6.5 Hz, 3H). LCMS (ESI): m/z: [M+H] calculated for $C_{24}H_{29}ClN_5O_2$: 454.19; found 454.4.

Example 45. Synthesis of 3-{5-[(3S,4S)-4-amino-3-methyl-2-oxa-8-azaspiro[4.5]decan-8-yl]-7-methyl-imidazo[1,2-c]pyrimidin-8-yl}-2-chlorobenzonitrile

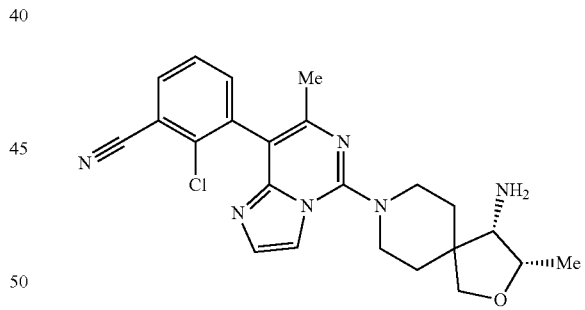

3-{5-[(3S,4S)-4-amino-3-methyl-2-oxa-8-azaspiro[4.5]decan-8-yl]-7-methylimidazo[1,2-c]pyrimidin-8-yl}-2-chlorobenzonitrile was synthesized in a manner similar to Example 15, except 1H-indazol-6-ylboronic acid was substituted with 2-chloro3-cyanophenylboronic acid. $^1$H NMR (500 MHz, Methanol-$d_4$) δ 8.40 (s, 2H), 7.95 (dd, J=7.7, 1.7 Hz, 1H), 7.73 (d, J=1.6 Hz, 11H), 7.69 (dd, J=7.8, 1.8 Hz, 1H), 7.64 (t, J=7.7 Hz, 11H), 7.50 (d, J=1.6 Hz, 1H), 4.41-4.29 (m, 1H), 4.06-3.85 (m, 5H), 3.50 (dd, J=4.2, 1.4 Hz, 1H), 3.30-3.15 (m, 2H), 2.21 (s, 3H), 2.18-2.04 (m, 2H), 1.99 (d, J=13.8 Hz, 1H), 1.83 (d, J=13.0 Hz, 1H), 1.35 (d, J=6.5 Hz, 3H). LCMS (ESI): m/z: [M+H] calculated for $C_{23}H_{26}ClN_6O$: 437.2; found 437.4.

Example 46. Synthesis of 4-{5-[(3S,4S)-4-amino-3-methyl-2-oxa-8-azaspiro[4.5]decan-8-yl]-7-methyl-imidazo[1,2-c]pyrimidin-8-yl}-3-chloro-2-methoxy-benzonitrile

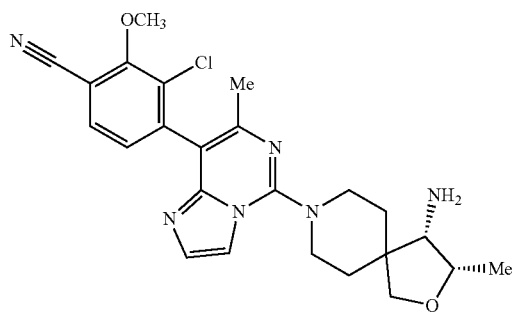 [SMILES: COc1c(C#N)ccc(-c2c(C)nc(N3CCC4(CC3)CO[C@@H](C)[C@H]4N)n3ccnc23)c1Cl]

4-{5-[(3S,4S)-4-amino-3-methyl-2-oxa-8-azaspiro[4.5]decan-8-yl]-7-methylimidazo[1,2-c]pyrimidin-8-yl}-3-chloro-2-methoxybenzonitrile was synthesized in a manner similar to Example 15, except 1H-indazol-6-ylboronic acid was substituted with (2-chloro-4-cyano-3-methoxyphenyl) boronic acid. $^1$H NMR (500 MHz, Methanol-d$_4$) δ 8.52 (s, 1H), 7.77 (d, J=8.0 Hz, 1H), 7.73 (d, J=1.6 Hz, 1H), 7.50 (d, J=1.6 Hz, 1H), 7.30 (d, J=8.0 Hz, 1H), 4.38-4.29 (m, 1H), 4.13 (s, 3H), 4.03-3.97 (m, 1H), 3.96-3.83 (m, 3H), 3.41 (d, J=4.2 Hz, 1H), 3.31-3.17 (m, 2H), 2.22 (s, 3H), 2.16-2.03 (m, 2H), 1.96 (d, J=13.9 Hz, 1H), 1.84 (d, J=13.3 Hz, 11H), 1.34 (d, J=6.5 Hz, 3H). LCMS (ESI): m/z: [M+H] calculated for C$_{24}$H$_{28}$ClN$_6$O$_2$ 467.2; found 467.4.

Example 47. Synthesis of (3S,4S)-8-[8-(3-chloro-2-methoxypyridin-4-yl)-7-methylimidazo[1,2-c]pyrimidin-5-yl]-3-methyl-2-oxa-8-azaspiro[4.5]decan-4-amine

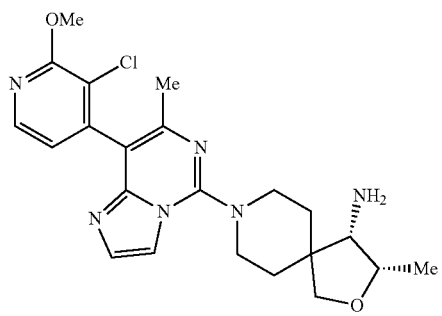 [SMILES: COc1nccc(-c2c(C)nc(N3CCC4(CC3)CO[C@@H](C)[C@H]4N)n3ccnc23)c1Cl]

(3S,4S)-8-[8-(3-chloro-2-methoxypyridin-4-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 3-chloro-2-methoxy-4-pyridinyl boronic acid. $^1$H NMR (500 MHz, Methanol-d$_4$) δ 8.18 (d, J=5.0 Hz, 1H), 7.73 (d, J=1.6 Hz, 1H), 7.47 (d, J=1.6 Hz, 1H), 6.97 (d, J=5.1 Hz, 1H), 4.29 (qd, J=6.4, 4.9 Hz, 1H), 3.93 (d, J=8.7 Hz, 1H), 3.85-3.70 (m, 2H), 3.42-3.34 (m, 1H), 3.27 (dd, J=13.3, 10.2 Hz, 1H), 3.12 (m, 1H), 2.05 (dddd, J=31.1, 14.2, 9.5, 4.0 Hz, 2H), 1.91-1.79 (m, 2H), 1.27 (d, J=6.5 Hz, 3H). LCMS (ESI): m/z: [M+H] calculated for C$_{22}$H$_{28}$ClN$_6$O$_2$ 443.2; found 443.3.

Example 48. Synthesis of (3S,4S)-3-methyl-8-(7-methyl-8-pyrazolo[1,5-a]pyridin-6-yl-imidazo[1,2-c]pyrimidin-5-yl)-2-oxa-8-azaspiro[4.5]decan-4-amine

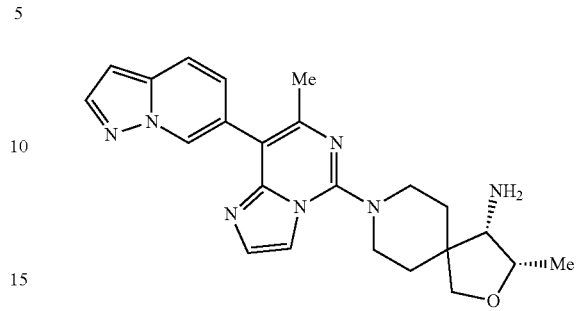

(3S,4S)-3-methyl-8-(7-methyl-8-pyrazolo[1,5-a]pyridin-6-yl-imidazo[1,2-c]pyrimidin-5-yl)-2-oxa-8-azaspiro[4.5]decan-4-amine was synthesized in a manner similar to Example 15, except 1H-indazol-6-ylboronic acid was substituted with 6-(4,4,5,5-tetramethyl-1,3,2-dioxaborolan-2-yl)pyrazolo[1,5-a]pyridine. $^1$H NMR (400 MHz, Methanol-d$_4$) δ 8.60 (s, 1H) 8.50 (br s, 1H) 8.02 (d, J=2.32 Hz, 1H) 7.78 (d, J=9.05 Hz, 1H) 7.71 (d, J=1.22 Hz, 1H) 7.50 (d, J=1.10 Hz, 1H) 7.25 (d, J=9.05 Hz, 1H) 6.69 (d, J=1.96 Hz, 1H) 4.28-4.36 (m, 1H) 3.99 (d, J=9.05 Hz, 1H) 3.80-3.91 (m, 3H) 3.41 (d, J=4.16 Hz, 1H) 3.15-3.27 (m, 2H) 2.40 (s, 3H) 2.02-2.13 (m, 2H) 1.91-1.99 (m, 1H) 1.82 (br d, J=13.45 Hz, 1H) 1.32 (d, J=6.60 Hz, 3H). LCMS (ESI): m/z: [M+H] calculated for C$_{23}$H$_{28}$N$_7$O: 418.2; found 418.2.

Example 49. Synthesis of (3S,4S)-8-[8-(2,3-dichloro-5-methoxyphenyl)-7-methylimidazo[1,2-c]pyrimidin-5-yl]-3-methyl-2-oxa-8-azaspiro[4.5]decan-4-amine

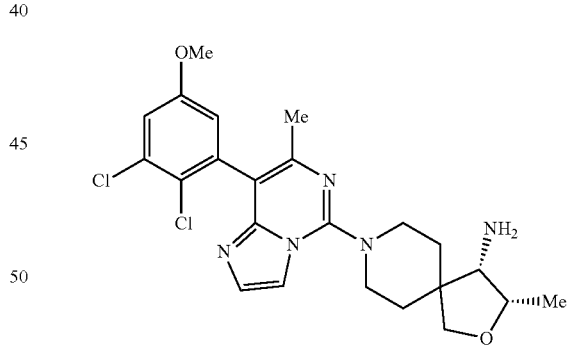

(3S,4S)-8-[8-(2,3-dichloro-5-methoxyphenyl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 2-(2,3-dichloro-5-methoxy-phenyl)-4,4,5,5-tetramethyl-1,3,2-dioxaborolane. $^1$H NMR (400 MHz, DMSO-d$_6$) δ 8.51 (s, 1H) 7.68 (s, 1H) 7.45 (d, J=1.2 Hz, 1H) 7.23 (d, J=3.2 Hz, 1H) 6.88 (d, J=2.8 Hz, 1H) 4.31-4.28 (m, 1H) 3.96 (d, J=8.8 Hz, 1H) 3.86-3.82 (m, 5H) 3.45-3.34 (m, 1H) 3.30-3.19 (m, 3H) 2.20 (s, 3H) 2.08-2.04 (m, 2H) 1.94-1.90 (m, 1H) 1.82-1.78 (m, 1H) 1.29 (d, J=6.4 Hz, 3H). LCMS (ESI): m/z: [M+H] calculated for C$_{23}$H$_{28}$Cl$_2$N$_5$O$_2$: 476.2; found 476.2.

Example 50. Synthesis of (3S,4S)-8-[8-(3-chloro-1H-indol-7-yl)-7-methylimidazo[1,2-c]pyrimidin-5-yl]-3-methyl-2-oxa-8-azaspiro[4.5]decan-4-amine

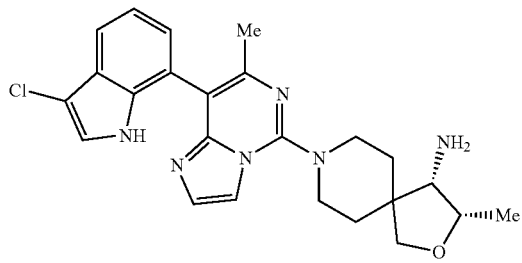 [SMILES: Cc1nc(N2CCC3(CC2)CO[C@@H](C)[C@H]3N)n2ccnc2c1-c1cccc2c(Cl)c[nH]c12]

(3S,4S)-8-[8-(3-chloro-1H-indol-7-yl)-7-methylimidazo[1,2-c]pyrimidin-5-yl]-3-methyl-2-oxa-8-azaspiro[4.5]decan-4-amine amine was synthesized in a manner similar to Example 15, except 1H-indazol-6-ylboronic acid was substituted with 3-chloro-7-(4,4,5,5-tetramethyl-1,3,2-dioxaborolan-2-yl)-1H-indole. $^1$H NMR (500 MHz, Methanol-d$_4$) δ 8.51 (s, 2H), 7.69 (d, J=1.6 Hz, 1H), 7.63-7.57 (m, 1H), 7.40 (d, J=1.6 Hz, 1H), 7.24 (t, J=7.6 Hz, 1H), 7.19-7.12 (m, 2H), 4.60 (s, 1H), 4.36-4.25 (m, 1H), 3.96 (d, J=8.9 Hz, 1H), 3.82 (dd, J=24.3, 11.5 Hz, 3H), 3.44 (s, 1H), 3.16 (s, 1H), 2.19 (s, 3H), 2.07 (d, J=12.0 Hz, 2H), 1.93 (d, J=7.5 Hz, 1H), 1.82 (d, J=12.6 Hz, 1H), 1.28 (d, J=2.3 Hz, 5H). LCMS (ESI): m/z: [M+H] calculated for C$_{24}$H$_{28}$ClN$_6$O 451.2 found 451.5.

Example 51. (3S,4S)-8-(8-imidazo[1,2-a]pyridin-7-yl-7-methyl-imidazo[1,2-c]pyrimidin-5-yl)-3-methyl-2-oxa-8-azaspiro[4.5]decan-4-amine

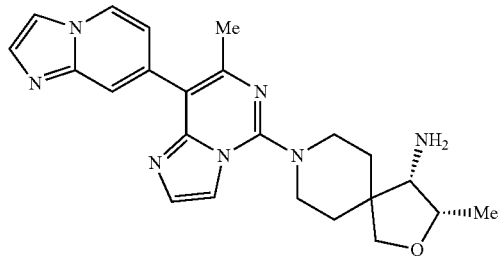 [SMILES: Cc1nc(N2CCC3(CC2)CO[C@@H](C)[C@H]3N)n2ccnc2c1-c1ccn2ccnc2c1]

(3S,4S)-8-(8-imidazo[1,2-a]pyridin-7-yl-7-methyl-imidazo[1,2-c]pyrimidin-5-yl)-3-methyl-2-oxa-8-azaspiro[4.5]decan-4-amine except 1H-indazol-6-ylboronic acid was substituted with 7-(4,4,5,5-tetramethyl-1,3,2-dioxaborolan-2-yl)imidazo[1,2-a]pyridine. $^1$H NMR (400 MHz, Mehtanol-d$_4$) δ 8.53 (d, J=7.06 Hz, 1H) 7.92 (s, 1H) 7.71 (s, 1H) 7.63 (d, J=1.10 Hz, 1H) 7.60 (s, 1H) 7.48 (d, J=1.32 Hz, 1H) 7.02-6.96 (m, 1H) 4.32-4.21 (m, 1H) 3.90 (d, J=8.82 Hz, 1H) 3.77 (br d, J=8.82 Hz, 3H) 3.22 (br t, J=10.91 Hz, 1H) 3.11 (d, J=4.63 Hz, 1H) 2.39 (s, 3H) 2.13-1.96 (m, 2H) 1.82 (br t, J=15.88 Hz, 2H) 1.24 (d, J=6.39 Hz, 3H). LCMS (ESI): m/z: [M+H] calculated for C$_{23}$H$_{28}$N$_7$O: 418.2; found 418.2.

Example 52. Synthesis of (3S,4S)-8-[8-(5-chloro-1H-indol-7-yl)-7-methylimidazo[1,2-c]pyrimidin-5-yl]-3-methyl-2-oxa-8-azaspiro[4.5]decan-4-amine

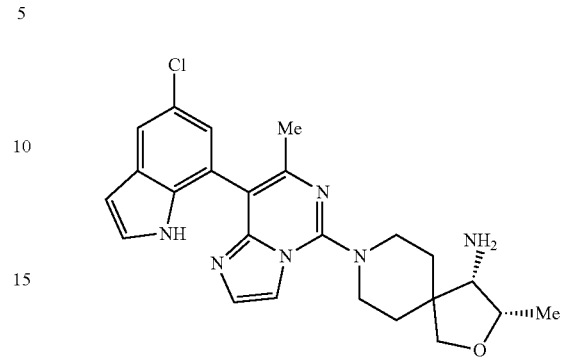

(3S,4S)-8-[8-(5-chloro-1H-indol-7-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with 5-chloro-7-(4,4,5,5-tetramethyl-1,3,2-dioxaborolan-2-yl)-1H-indole. $^1$H NMR (500 MHz, Methanol-d$_4$) δ 8.50 (s, 1H), 7.69 (d, J=1.6 Hz, 1H), 7.61 (d, J=2.0 Hz, 1H), 7.40 (d, J=1.5 Hz, 1H), 7.19 (d, J=3.2 Hz, 1H), 7.05 (d, J=2.0 Hz, 1H), 6.48 (d, J=3.2 Hz, 1H), 4.35-4.23 (m, 1H), 3.95 (d, J=9.0 Hz, 1H), 3.82 (dd, J=20.8, 11.6 Hz, 3H), 3.21 (dd, J=36.2, 12.1 Hz, 2H), 2.20 (s, 3H), 2.04 (d, J=22.7 Hz, 2H), 1.93 (d, J=10.0 Hz, 1H), 1.81 (d, J=13.3 Hz, 1H), 1.29 (d, J=6.5 Hz, 3H). LCMS (ESI): m/z: [M+H] calculated for C$_{24}$H$_{28}$ClN$_6$O 451.2 found 451.4.

Example 53. Synthesis of (3S,4S)-3-methyl-8-(7-methyl-8-{1H-pyrrolo[3,2-b]pyridin-7-yl}imidazo[1,2-c]pyrimidin-5-yl)-2-oxa-8-azaspiro[4.5]decan-4-amine

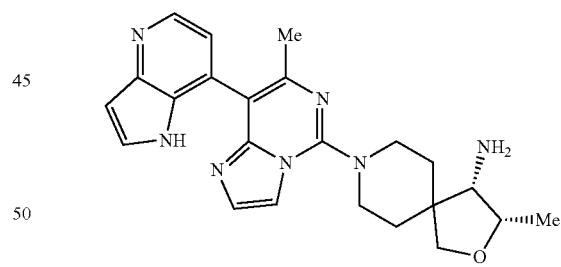

(3S,4S)-3-methyl-8-(7-methyl-8-{1H-pyrrolo[3,2-b]pyridin-7-yl}imidazo[1,2-c]pyrimidin-5-yl)-2-oxa-8-azaspiro[4.5]decan-4-amine was synthesized in a manner similar to Example 15, except 1H-indazol-6-ylboronic acid was substituted with 4-azaindole-7-boronic acid pinacol ester. $^1$H NMR (500 MHz, Methanol-d$_4$) δ 8.41 (d, J=3.0 Hz, 2H), 7.71 (d, J=1.6 Hz, 1H), 7.53 (d, J=3.3 Hz, 1H), 7.42 (d, J=1.6 Hz, 1H), 7.18 (d, J=5.0 Hz, 1H), 6.67 (d, J=3.3 Hz, 1H), 4.37-4.24 (m, 1H), 3.99 (d, J=9.1 Hz, 1H), 3.96-3.81 (m, 3H), 3.46 (d, J=4.1 Hz, 1H), 3.19 (dd, J=27.9, 14.8 Hz, 2H), 2.23 (s, 3H), 2.08 (tt, J=11.1, 5.0 Hz, 2H), 1.98 (t, J=14.7 Hz, 1H), 1.81 (d, J=13.0 Hz, 1H), 1.31 (d, J=6.5 Hz, 3H). LCMS (ESI): m/z: [M+H] calculated for C$_{23}$H$_{28}$N$_7$O 418.5 found 418.5.

Example 54. Synthesis of 4-{5-[(3S,4S)-4-amino-3-methyl-2-oxa-8-azaspiro[4.5]decan-8-yl]-7-methyl-imidazo[1,2-c]pyrimidin-8-yl}-2,3-dichlorophenol

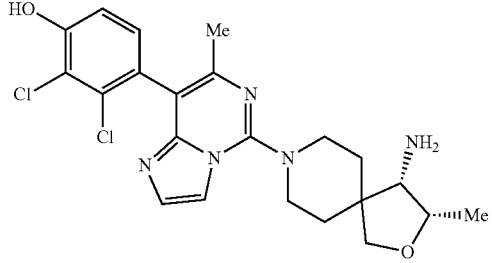 [SMILES: Cc1nc(N2CCC3(CC2)CO[C@@H](C)[C@H]3N)n2ccnc2c1-c1ccc(O)c(Cl)c1Cl]

4-{5-[(3S,4S)-4-amino-3-methyl-2-oxa-8-azaspiro[4.5]decan-8-yl]-7-methylimidazo[1,2-c]pyrimidin-8-yl}-2,3-dichlorophenol was synthesized in a manner similar to Example 15, except 1H-indazol-6-ylboronic acid was substituted with (2,3-dichloro-4-hydroxy-phenyl)boronic acid. $^1$H NMR (400 MHz, Deuterium oxide) δ 7.82 (d, J=1.8 Hz, 1H), 7.70 (d, J=1.6 Hz, 1H), 7.21 (d, J=8.6 Hz, 1H), 7.11 (d, J=8.4 Hz, 1H), 4.43 (m, 1H), 3.88-4.02 (m, 4H), 3.63 (br d, J=3.8 Hz, 1H), 3.25-3.32 (m, 2H), 2.28 (s, 3H), 1.97-2.07 (m, 4H), 1.83-1.86 (m, 1H), 1.31 (d, J=6.4 Hz, 3H). LCMS (ESI): m/z: [M+H] calculated for $C_{22}H_{26}N_5O_2Cl_2$: 462.4; found 462.1.

Example 55. Synthesis of (3S,4S)-8-[8-(3-fluoro-1H-indol-7-yl)-7-methylimidazo[1,2-c]pyrimidin-5-yl]-3-methyl-2-oxa-8-azaspiro[4.5]decan-4-amine

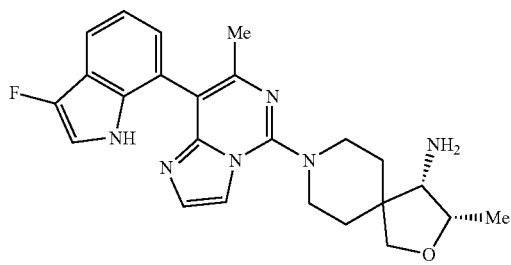 [SMILES: Cc1nc(N2CCC3(CC2)CO[C@@H](C)[C@H]3N)n2ccnc2c1-c1cccc2c(F)c[nH]c12]

(3S,4S)-8-[8-(3-fluoro-1H-indol-7-yl)-7-methylimidazo[1,2-c]pyrimidin-5-yl]-3-methyl-2-oxa-8-azaspiro[4.5]decan-4-amine was synthesized in a manner similar to Example 15, except 1H-indazol-6-ylboronic acid was substituted with [1-(diethylcarbamoyl)-3-fluoro-2-(trimethylsilyl)-1H-indol-7-yl]boronic acid. $^1$H NMR (500 MHz, Methanol-d$_4$) δ 8.45 (s, 3H), 7.67 (d, J=1.6 Hz, 1H), 7.59 (d, J=7.9 Hz, 1H), 7.39 (d, J=1.5 Hz, 1H), 7.17 (t, J=7.6 Hz, 1H), 7.10 (d, J=7.1 Hz, 1H), 6.94 (d, J=2.8 Hz, 1H), 4.60 (s, 1H), 4.36-4.24 (m, 1H), 3.97 (d, J=9.1 Hz, 1H), 3.84 (dd, J=29.1, 12.6 Hz, 3H), 3.61 (s, 1H), 3.41 (d, J=4.7 Hz, 1H), 2.17 (s, 3H), 2.07 (s, 2H), 1.95 (d, J=13.1 Hz, 1H), 1.81 (d, J=13.4 Hz, 1H), 1.30 (d, J=6.5 Hz, 3H). LCMS (ESI): m/z: [M+H] calculated for $C_{24}H_{28}FN_6O$: 435.2; found 435.6.

Synthesis of [1-(diethylcarbamoyl)-3-fluoro-2-(trimethylsilyl)-1H-indol-7-yl]boronic acid

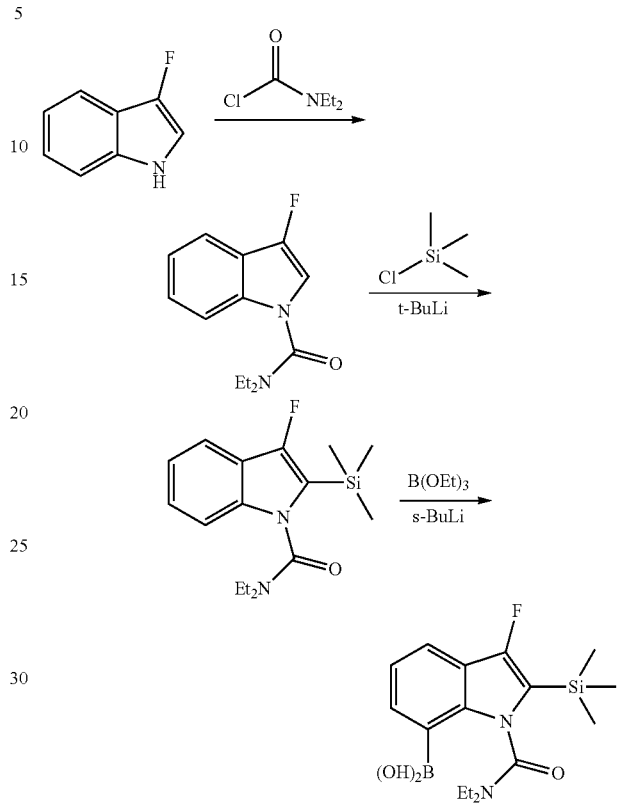

Step 1. Synthesis of N,N-diethyl-3-fluoro-1H-indole-1-carboxamide

A solution of 3-chloro-1H-indole (250 mg, 1.6 mmol) in 2 ml THF was added to a suspension of sodium hydride (49 mg, 2 mmol) in 1 ml THF at 0° C. and the mixture stirred for 1 hr at room temperature. After re-cooling to 0° C., N,N-diethylcarbamoylchloride (5.58 ml, 44 mmol) was added and the reaction mixture was at room temperature for 18 h. The resulting reaction mixture was diluted with aq. NH$_4$Cl (sat.) and EtOAc. The organic layer was separated, dried over MgSO$_4$, filtered, and concentrated under reduced pressure. The resulting residue was carried onto the next step without any further purification. LCMS (ESI): m/z: [M+H] calculated for $C_{13}H_{16}FN_2O$: 235.3; found 235.3.

Step 2. Synthesis of N,N-diethyl-3-fluoro-2-(trimethylsilyl)-1H-indole-1-carboxamide To a solution of N,N-diethyl-3-fluoro-1H-indole-1-carboxamide (200 mg, 853 μmol) in tetrahydrofuran (5.3 mL) was added chlorotrimethylsilane (225 μL, 1.78 mmol). The mixture was cooled to −78° C. before adding in t-butyl (1.04 mL, 1.78 mmol) dropwise. The reaction mixture was stirred in a capped vial at −78° C. for 3 h. The resulting reaction mixture was quenched with sat. NH$_4$Cl (aq.) and then diluted with EtOAc. The organic layer was separated, dried over MgSO$_4$, filtered, and concentrated under reduced pressure. The resulting residue was carried onto the next step without any further purification. LCMS (ESI): m/z: [M+H] calculated for $C_{16}H_{24}FN_2OSi$: 307.5; found 307.4.

Step 3. Synthesis of [1-(diethylcarbamoyl)-3-fluoro-2-(trimethylsilyl)-1H-indol-7-yl]boronic acid To a solution of N,N-diethyl-3-fluoro-2-(trimethylsilyl)-1H-indole-1-carboxamide (440 mg, 1.43 mmol) in tetrahydrofuran (4.29 mL) was added TMEDA (320 μL, 2.14 mmol) and then cooled to −78° C. Then was added sec-butyl group lithium (1.52 mL, 2.14 mmol) dropwise. The mixture was stirred in a capped vial at −78° C. for 3 h. Then triethyl borate (363 μL, 2.14 mmol) was added to the mixture at −78° C. and the reaction mixture was stirred to room temperature gradually and stirred there for 18 h. The resulting reaction mixture was diluted with aq. NH₄Cl (sat.) and EtOAc. The organic layer was separated, dried over MgSO₄, filtered, and concentrated under reduced pressure. The residue was purified by chromatography to afford [1-(diethylcarbamoyl)-3-fluoro-2-(trimethylsilyl)-1H-indol-7-yl]boronic acid (240 mg, 685 μmol, 48.0%). LCMS (ESI): m/z: [M−H] calculated for $C_{16}H_{23}BFN_2O_3Si$: 349.16; found 349.1.

Example 56. Synthesis of (3S,4S)-8-[8-(2,3-dichlorophenyl)imidazo[1,2-c]pyrimidin-5-yl]-3-methyl-2-oxa-8-azaspiro[4.5]decan-4-amine

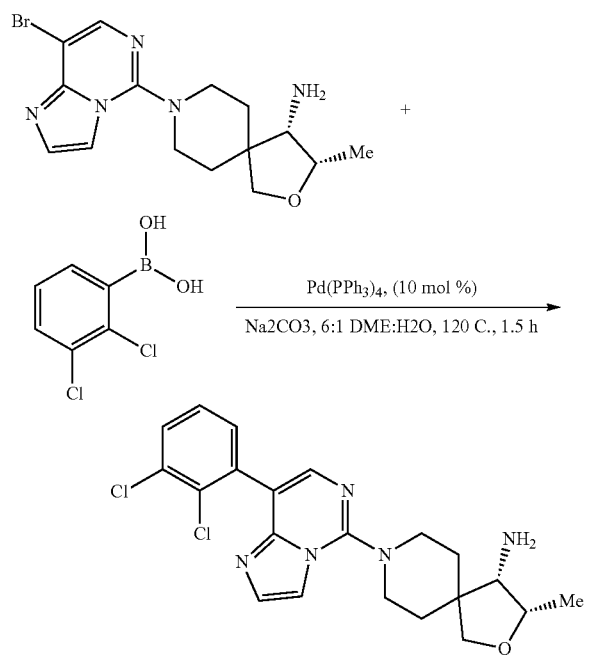

To a microwave vial was added (3S,4S)-8-{8-bromoimidazo[1,2-c]pyrimidin-5-yl}-3-methyl-2-oxa-8-azaspiro[4.5]decan-4-amine (80 mg, 218 μmol), (2,3-dichlorophenyl)boronic acid (62 mg, 327 μmol), tetrakis(triphenylphosphine) palladium (25 mg, 22 μmol), and sodium carbonate (46.2 mg, 436 μmol). The vial was evacuated under house vac for 10 mins before adding in 1,2-dimethoxyethane (0.8 mL) and water (0.13 mL). The reaction vial was evacuated and purged with N₂ three times before stirring under microwave conditions at 120° C. for 1.5 h. The resulting reaction mixture was filtered through a pad of celite, washing with DCM and MeOH. The filtrate was concentrated and the resulting residue was purified by reverse phase HPLC to afford (3S,4S)-8-[8-(2,3-dichlorophenyl)imidazo[1,2-c]pyrimidin-5-yl]-3-methyl-2-oxa-8-azaspiro[4.5]decan-4-amine (21 mg, 49 μmol, 22%) as the formic acid salt. ¹H NMR (500 MHz, Methanol-d₄) δ 7.81 (d, J=1.6 Hz, 1H), 7.75 (s, 1H), 7.69-7.64 (m, 1H), 7.59 (d, J=1.6 Hz, 1H), 7.45-7.40 (m, 2H), 4.31 (qd, J=6.5, 4.6 Hz, 1H), 3.96 (d, J=8.9 Hz, 1H), 3.83 (dd, J=9.5, 5.2 Hz, 3H), 3.54-3.09 (m, 4H), 2.16-2.00 (m, 2H), 1.96-1.77 (m, 1H), 1.30 (d, J=6.5 Hz, 3H). LCMS (ESI): m/z: [M+H] calculated for $C_{21}H_{24}Cl_2N_5O$: 432.1; found 432.3.

Example 57: Synthesis of (3S,4S)-8-[8-(2-chloro-3-methoxyphenyl)imidazo[1,2-c]pyrimidin-5-yl]-3-methyl-2-oxa-8-azaspiro[4.5]decan-4-amine

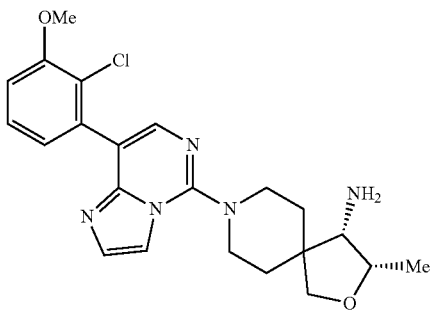 [SMILES: COc1cccc(-c2cnc(N3CCC4(CC3)CO[C@@H](C)[C@H]4N)n3ccnc23)c1Cl]

(3S,4S)-8-[8-(2-chloro-3-methoxyphenyl)imidazo[1,2-c]pyrimidin-5-yl]-3-methyl-2-oxa-8-azaspiro[4.5]decan-4-amine was synthesized in a manner similar to Example 56, except (2,3-dichlorophenyl)boronic was substituted with 2-chloro-3-methoxyphenylboronic acid. ¹H NMR (500 MHz, Methanol-d₄) δ 7.79 (s, 1H), 7.70 (s, 1H), 7.58 (s, 1H), 7.38 (t, J=7.9 Hz, 11H), 7.19 (d, J=8.3 Hz, 11H), 7.04 (d, J=7.6 Hz, 1H), 4.33 (d, J=7.1 Hz, 11H), 3.99 (d, J=9.1 Hz, 1H), 3.94 (s, 3H), 3.86 (dd, J=18.7, 12.2 Hz, 3H), 3.22 (dt, J=27.6, 11.8 Hz, 2H), 2.15-2.03 (m, 2H), 1.95 (d, J=13.6 Hz, 1H), 1.82 (d, J=12.8 Hz, 1H), 1.38-1.28 (m, 3H). LCMS (ESI): m/z: [M+H] calculated for $C_{22}H_{27}ClN_5O_2$ 428.2; found 428.4.

Example 58. Synthesis of (3S,4S)-8-[8-(2-aminopyridin-4-yl)imidazo[1,2-c]pyrimidin-5-yl]-3-methyl-2-oxa-8-azaspiro[4.5]decan-4-amine

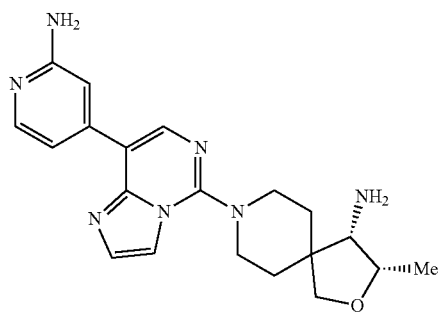 [SMILES: C[C@@H]1OCC2(CCN(c3ncc(-c4ccnc(N)c4)c4nccn34)CC2)[C@@H]1N]

(3S,4S)-8-[8-(2-aminopyridin-4-yl)imidazo[1,2-c]pyrimidin-5-yl]-3-methyl-2-oxa-8-azaspiro[4.5]decan-4- amine was synthesized in a manner similar to Example 56, except (2,3-dichlorophenyl)boronic was substituted with (2-amino-4-pyridyl)boronic acid. $^1$H NMR (400 MHz, Methanol-d$_4$) δ 8.36 (br s, 1H), 8.06 (s, 1H), 7.96 (d, J=6.0 Hz, 1H), 7.79 (d, J=1.5 Hz, 11H), 7.66 (d, J=1.3 Hz, 11H), 7.34 (s, 1H), 7.16 (dd, J=1.5, 6.0 Hz, 11H), 4.35-4.28 (m, 11H), 4.35-4.28 (m, 11H), 4.01-3.85 (m, 4H), 3.47 (d, J=4.2 Hz, 11H), 3.28-3.16 (m, 2H), 2.13-2.01 (m, 2H), 1.99-1.93 (m, 1H), 1.81 (br d, J=12.3 Hz, 1H), 1.33 (d, J=6.4 Hz, 3H). LCMS (ESI): m/z: [M+H] calculated for C$_{20}$H$_{26}$N$_7$O: 380.2; found 380.2.

Example 59. Synthesis of (3S,4S)-3-methyl-8-(8-{1H-pyrrolo[2,3-b]pyridin-4-yl}imidazo[1,2-c]pyrimidin-5-yl)-2-oxa-8-azaspiro[4.5]decan-4-amine

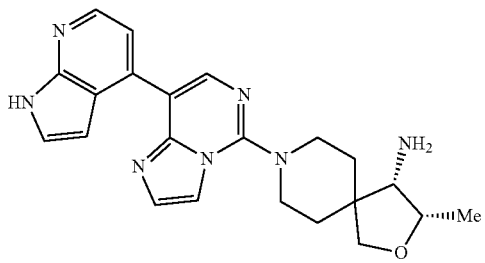 [SMILES: C[C@@H]1OCC2(CCN(c3ncc(-c4ccnc5[nH]ccc45)c4nccn34)CC2)[C@@H]1N]

(3S,4S)-3-methyl-8-(8-{1H-pyrrolo[2,3-b]pyridin-4-yl}imidazo[1,2-c]pyrimidin-5-yl)-2-oxa-8-azaspiro[4.5]decan-4-amine was synthesized in a manner similar to Example 56, except (2,3-dichlorophenyl)boronic was substituted with 4-(4,4,5,5-tetramethyl-1,3,2-dioxaborolan-2-yl)-1H-pyrrolo[2,3-b]pyridine. $^1$H NMR (400 MHz, Methanol-d$_4$) δ 8.30 (d, J=5.07 Hz, 1H) 8.11 (s, 1H) 7.84 (d, J=1.54 Hz, 1H) 7.63 (d, J=1.54 Hz, 1H) 7.54 (d, J=5.07 Hz, 1H) 7.45 (d, J=3.53 Hz, 1H) 6.54 (d, J=3.53 Hz, 1H) 4.24-4.31 (m, 1H) 3.92 (d, J=8.60 Hz, 1H) 3.75-3.85 (m, 3H) 3.38 (br t, J=10.25 Hz, 1H) 3.27 (br s, 1H) 3.10 (d, J=4.85 Hz, 1H) 1.98-2.12 (m, 2H) 1.84 (br t, J=13.45 Hz, 2H) 1.25 (d, J=6.39 Hz, 3H). LCMS (ESI): m/z: [M+H] calculated for C$_{22}$H$_{26}$N$_7$O: 404.2; found 404.1.

Example 60. (3S,4S)-8-[8-(2-amino-3-chloropyridin-4-yl)imidazo[1,2-c]pyrimidin-5-yl]-3-methyl-2-oxa-8-azaspiro[4.5]decan-4-amine

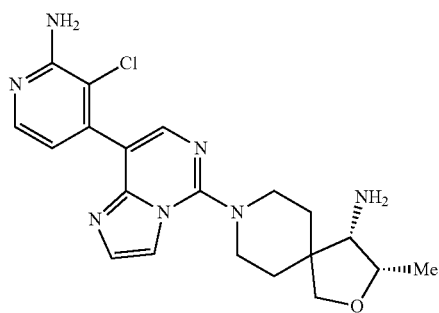 [SMILES: C[C@@H]1OCC2(CCN(c3ncc(-c4ccnc(N)c4Cl)c4nccn34)CC2)[C@@H]1N]

(3S,4S)-8-[8-(2-amino-3-chloropyridin-4-yl)imidazo[1,2-c]pyrimidin-5-yl]-3-methyl-2-oxa-8-azaspiro[4.5]decan-4-amine was synthesized in a manner similar to Example 56, except (2,3-dichlorophenyl)boronic was substituted with (2-amino-3-chloro-4-pyridyl)boronic acid. $^1$H NMR (400 MHz, Methanol-d$_4$) δ 8.47 (br s, 1H), 7.97 (d, J=5.1 Hz, 1H), 7.81-7.79 (m, 2H), 7.60 (d, J=1.3 Hz, 1H), 6.75 (d, J=5.3 Hz, 1H), 4.36-4.29 (m, 1H), 4.03-3.98 (m, 1H), 3.94-3.86 (m, 3H), 3.46 (d, J=4.0 Hz, 1H), 3.29-3.15 (m, 2H), 2.13-2.02 (m, 2H), 2.00-1.93 (m, 1H), 1.82 (br d, J=13.2 Hz, 1H), 1.33 (d, J=6.4 Hz, 3H). LCMS (ESI): m/z: [M+H] calculated for C$_{20}$H$_{25}$ClN$_7$O: 414.2; found 414.1.

Example 61. Synthesis of (3S,4S)-8-{8-[(2-amino-3-chloropyridin-4-yl)sulfanyl]-7-methyl-[1,2,4]triazolo[4,3-c]pyrimidin-5-yl}-3-methyl-2-oxa-8-azaspiro[4.5]decan-4-amine

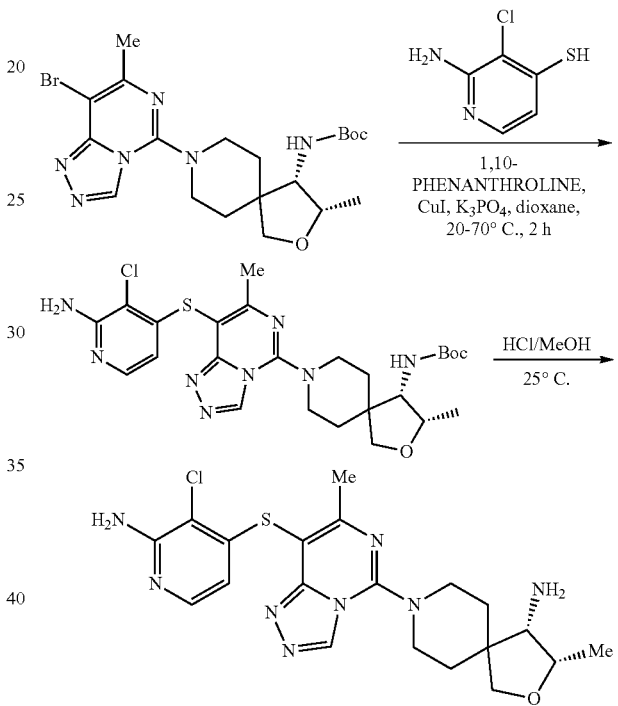

Step 1. Synthesis of tert-butyl N-[(3S,4S)-8-[8-[(2-amino-3-chloro-4-pyridyl)sulfanyl]-7-methyl-[1,2,4]triazolo[4,3-c]pyrimidin-5-yl]-3-methyl-2-oxa-8-azaspiro[4.5]decan-4-yl]carbamate To a solution of tert-butyl N-[(3S,4S)-8-(8-bromo-7-methyl-[1,2,4]triazolo[4,3-c]pyramid in-5-yl)-3-methyl-2-oxa-8-azaspiro[4.5]decan-4-yl]carbamate (100 mg, 208 µmol) in dioxane (0.5 mL) was added 1,10-Phenanthroline (7.49 mg, 41.55 µmol), K$_3$PO$_4$ (88 mg, 415 µmol) and CuI (4 mg, 21 µmol) at 25° C. The mixture was stirred at 120° C. for 2 h. The mixture was diluted with EtOAc (5 mL) and the solvent was removed under reduced pressure. The resulting residue was purified by chromatography to afford tert-butyl N-[(3S,4S)-8-[8-[(2-amino-3-chloro-4-pyridyl)sulfanyl]-7-methyl-[1,2,4]triazolo[4,3-c]pyrimidin-5-yl]-3-methyl-2-oxa-8-azaspiro[4.5]decan-4-yl]carbamate (35 mg, 43 µmol, 21% yield) as a white solid. LCMS (ESI): m/z: [M+H] calculated for C$_{25}$H$_{34}$ClN$_8$O$_3$S: 561.2; found 561.3.

Step 2. Synthesis of (3S,4S)-8-[8-[(2-aino-3-chlor-4-pyridl)sulfanyl]-7-methyl-[1,2,4]triazolo[4,3-c]pyrimidin-5-yl]-3-methyl-2-oxa-8-azaspiro[4.5]decan-4-amine A mixture of tert-butyl N-[(3S,4S)-8-[8-[(2-amino-3-chloro-4-pyridyl)sulfanyl]-7-methyl-[1,2,4]triazolo[4,3-c]pyrimidin-5-yl]-3-methyl-2-oxa-8-azaspiro[4.5]decan-4-yl] carbamate (35 mg, 62 umol) in HCl/MeOH (3 mL) was stirred at 25° C. for 0.5 h. The reaction mixture was diluted with EtOAc (5 mL) and the solvent was removed under reduced pressure. The resulting residue was purified by prep-HPLC to afford (3S,4S)-8-{8-[(2-amino-3-chloropyridin-4-yl)sulfanyl]-7-methyl-[1,2,4]triazolo[4,3-c]pyrimidin-5-yl}-3-methyl-2-oxa-8-azaspiro[4.5]decan-4-amine (5 mg, 11 μmol, 17% yield) as a white solid. $^1$H NMR (400 MHz, Methanol-$d_4$) δ 8.25 (s, 1H), 7.52 (d, J=5.30 Hz, 1H), 5.86 (d, J=5.30 Hz, 1H), 4.84-4.77 (m, 2H), 4.28-4.25 (m, 1H), 3.93 (d, J=8.80 Hz, 1H), 3.84-3.73 (m, 3H), 3.10 (d, J=4.80 Hz, 1H), 2.54 (s, 3H), 2.01-1.91 (m, 2H), 1.83-1.74 (m, 2H), 1.24 (d, J=6.60 Hz, 3H). LCMS (ESI): m/z: [M+H] calculated for $C_{20}H_{26}ClN_8OS$: 461.2; found 461.1.

Example 62. Synthesis of 1-[(4R)-4-amino-8-[8-(2,3-dichlorophenyl)-7-methylimidazo[1,2-c]pyrimidin-5-yl]-8-azaspiro[4.5]decan-2-yl]azetidine-3-carbonitrile

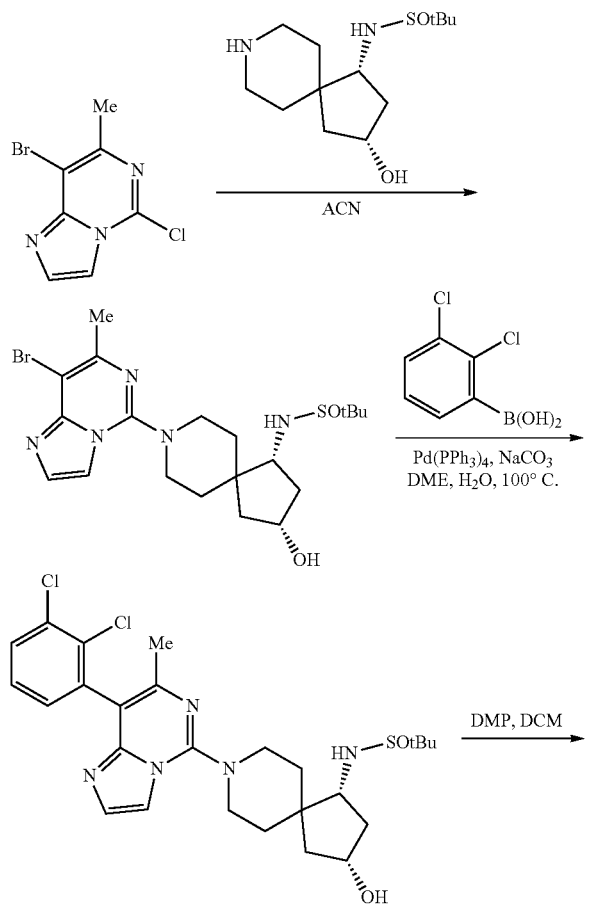

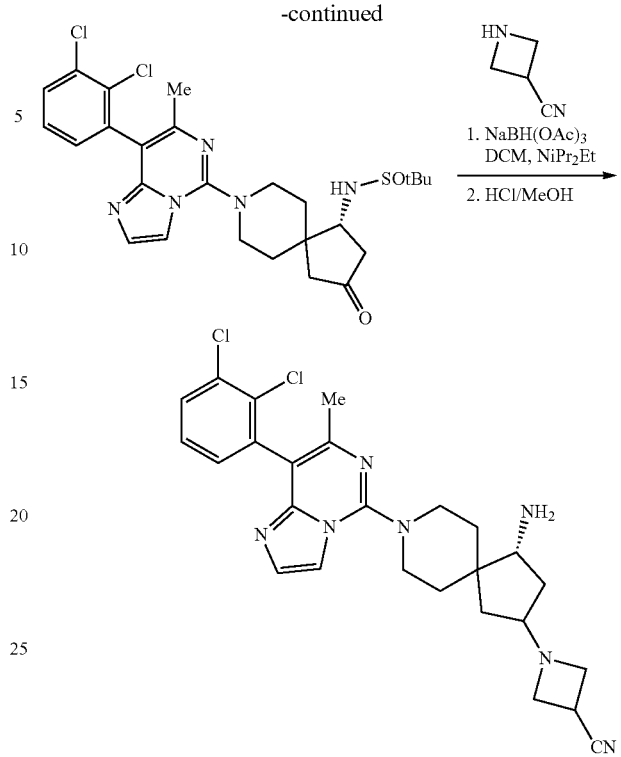

Step 1. Synthesis of N-[(1R,3R)-8-{8-bromo-7-methylimidazo[1,2-c]pyrimidin-5-yl}-3-hydroxy-8-azaspiro[4.5]decan-1-yl]-2-methylpropane-2-sulfinamide A solution of tert-butyl (1R,3R)-3-hydroxy-1-[(2-methylpropane-2-sulfinyl)amino]-8-azaspiro[4.5]decane-8-carboxylate (2 g, 5.3 mmol) was dissolved in TFA:DCM (1:4) (6.6 mL) and stirred at room temperature for 30 minutes. The reaction was quenched with saturated aq. sodium bicarbonate and diluted with EtOAc. The aqueous layer was removed and evaporated under reduced pressure. The remaining residue was dissolved in $CH_3CN$ (5.3 mL) and N,N-diisopropylethylamine (680 mg, 5.3 mmol) and 8-bromo-5-chloro-7-methylimidazo[1,2-c]pyrimidine (655 mg, 3.55 mmol) were subsequently added. The solution was heated at 60° C. for 1 h after which the solution was cooled to room temperature and purified by silica gel chromatography to afford N-[(1R,3R)-8-{8-bromo-7-methylimidazo[1,2-c]pyrimidin-5-yl}-3-hydroxy-8-azaspiro[4.5]decan-1-yl]-2-methylpropane-2-sulfinamide as a white solid (750 mg, 59% yield). LCMS (ESI): m/z: [M+H] calculated for $C_{20}H_{31}BrN_5O_2S$ 486.1; found 486.1

Step 2. Synthesis of N-[(1R,3R)-8-[8-(2,3-dichlorophenyl)-7-methylimidazo[1,2-c]pyrimidin-5-yl]-3-hydroxy-8-azaspiro[4.5]decan-1-yl]-2-methylpropane-2-sulfinamide To a solution of 2,3-dichlorophenylboornic acid (406 mg, 2.13 μmol, 1.5 eq) and N-[(1R,3R)-8-{8-bromo-7-methylimidazo[1,2-c]pyrimidin-5-yl}-3-hydroxy-8-azaspiro[4.5]decan-1-yl]-2-methylpropane-2-sulfinamide (690 mg, 142 μmol) in DME (4.7 mL) and $H_2O$ (1.2 mL) was added $K_2CO_3$ (391 mg, 284 μmol) and Pd(PPh$_3$)$_4$ (164 mg, 142 umol) under $N_2$ at 25° C. The mixture was stirred at 100° C.

for 3 h. The mixture was cooled to 25° C. and the mixture was filtered. The resulting solution was concentrated under reduced pressure and the resulting residue was purified by prep-HPLC to afford N-[(1R,3R)-8-[8-(2,3-dichlorophenyl)-7-methylimidazo[1,2-c]pyrimidin-5-yl]-3-hydroxy-8-azaspiro[4.5]decan-1-yl]-2-methylpropane-2-sulfinamide as a white solid (360 mg, 46% yield). LCMS (ESI): m/z: [M+H] calculated for $C_{26}H_{34}C_2N_5O_2S$ 550.2; found 550.5.

Step 3. Synthesis of N-[(1R)-8-[8-(2,3-dichlorophenyl)-7-methylimidazo[1,2-c]pyrimidin-5-yl]-3-oxo-8-azaspiro[4.5]decan-1-yl]-2-methylpropane-2-sulfinamide To a solution of N-[(1R,3R)-8-[8-(2,3-dichlorophenyl)-7-methylimidazo[1,2-c]pyrimidin-5-yl]-3-hydroxy-8-azaspiro[4.5]decan-1-yl]-2-methylpropane-2-sulfinamide (60 mg, 108 μmol) in DCM (1 mL) was added DMP (50 mg, 118 μmol) The reaction was stirred at room temperature for 2.5 h. The mixture was then directly purified by silica gel chromatography to afford N-[(1R)-8-[8-(2,3-dichlorophenyl)-7-methylimidazo[1,2-c]pyrimidin-5-yl]-3-oxo-8-azaspiro[4.5]decan-1-yl]-2-methylpropane-2-sulfinamide (40 mg, 68% yield). LCMS (ESI): m/z: [M+H] calculated for $C_{26}H_{32}Cl_2N_5O_2S$ 548.2; found 548.4.

Step 4. Synthesis of 1-[(4R)-4-amino-8-[8-(2,3-dichlorophenyl)-7-methylimidazo[1,2-c]pyrimidin-5-yl]-8-azaspiro[4.5]decan-2-yl]azetidine-3-carbonitrile To a solution of N-[(1R)-8-[8-(2,3-dichlorophenyl)-7-methylimidazo[1,2-c]pyrimidin-5-yl]-3-oxo-8-azaspiro[4.5]decan-1-yl]-2-methylpropane-2-sulfinamide (20 mg, 36 μmol, 1 eq.), N,N-diisopropylethylamine (7 mg), and azetidine-3-carbonitrile hydrochloride (6 mg, 47 umol, 1.3 eq.) in DMC (0.3 mL) was added sodium triacetoxyborohydride (12 mg, 55 μmol) at room temperature. The reaction was stirred at room temperature for 2 h and then filtered. The filtrate was concentrated under reduced pressure and the remaining residue was purified by column chromatography to afford crude N-[(1R)-3-(3-cyanoazetidin-1-yl)-8-[8-(2,3-dichlorophenyl)-7-methylimidazo[1,2-c]pyrimidin-5-yl]-8-azaspiro[4.5]decan-1-yl]-2-methylpropane-2-sulfinamide. To a solution of this material in MeOH (0.3 mL) was added HCL (4M solution in dioxane, 0.1 mL) dropwise at room temperature. The mixture was let stirred at room temperature for 2 h. The solution was concentrated under reduced pressure and purified by reverse phase HPLC to afford 1-[(4R)-4-amino-8-[8-(2,3-dichlorophenyl)-7-methylimidazo[1,2-c]pyrimidin-5-yl]-8-azaspiro[4.5]decan-2-yl]azetidine-3-carbonitrile (3 mg) as a white solid. $^1$H NMR (500 MHz, Methanol-$d_4$) δ 8.36 (s, 3H), 7.74-7.70 (m, 1H), 7.68 (dd, J=8.1, 1.5 Hz, 11H), 7.48 (d, J=1.5 Hz, 1H), 7.45 (t, J=7.9 Hz, 1H), 7.33 (dd, J=7.7, 1.6 Hz, 1H), 3.95 (d, J=10.3 Hz, 1H), 3.88 (d, J=9.0 Hz, 1H), 3.62 (dd, J=19.9, 6.5 Hz, 2H), 3.49-3.38 (m, 3H), 3.24 (t, J=12.6 Hz, 3H), 3.12 (dq, J=6.7, 3.3 Hz, 1H), 2.26 (dd, J=14.0, 6.5 Hz, 1H), 2.21 (s, 3H), 1.99 (dtd, J=36.6, 13.2, 12.5, 5.7 Hz, 3H), 1.83 (d, J=12.8 Hz, 1H), 1.76 (d, J=13.8 Hz, 1H), 1.70 (d, J=14.0 Hz, 2H). LC-MS (ESI): m/z [M+H]$^+$ calculated for $C_{26}H_{30}Cl_2N_7$ 510.2; found 510.5.

Example 63. Synthesis of (2R,4R)-4-amino-8-[8-(2,3-dichlorophenyl)-7-methylimidazo[1,2-c]pyrimidin-5-yl]-8-azaspiro[4.5]decan-2-yl N-methylcarbamate

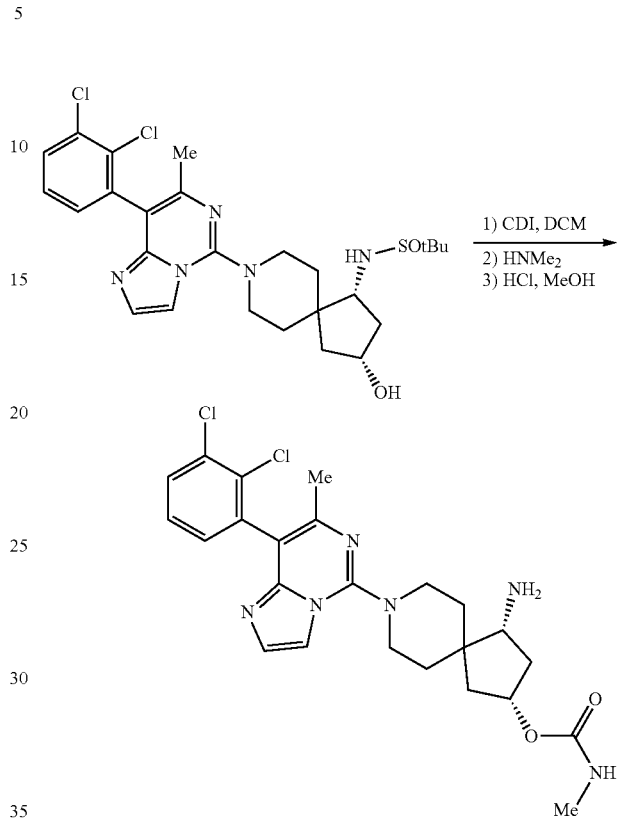

Carbonyldiimidazole (7 mg) was added to a solution of N-[(1R,3R)-8-[8-(2,3-dichlorophenyl)-7-methylimidazo[1,2-c]pyrimidin-5-yl]-3-hydroxy-8-azaspiro[4.5]decan-1-yl]-2-methylpropane-2-sulfinamide (Example 62) in DCM (0.15 mL) and the reaction mixture was stirred at room temperature for 1 h. After 1 h the reaction was passed through a short plug of silica and the filtrate was concentrated under reduced pressure. The resulting crude residue was dissolved in DCM and a solution of methyl amine (2M in THF, 0.15 mL) was added. The reaction mixture was stirred at room temperature for 2 h. The reaction mixture was concentrated under reduced pressure and the resulting crude residue was dissolved in MeOH (0.2 mL) and a solution of HCL in dioxane (4M) (0.1 mL) was then added. The reaction was stirred for 30 mins. The solution was then concentrated under reduced pressure and the reaming residue was purified by reverse phase HPLC to afford (2R,4R)-4-amino-8-[8-(2,3-dichlorophenyl)-7-methylimidazo[1,2-c]pyrimidin-5-yl]-8-azaspiro[4.5]decan-2-yl N-methylcarbamate as a white solid (1.2 mg, 16% yield over 3 steps). $^1$H NMR (500 MHz, Methanol-$d_4$) δ 8.56 (s, 1H), 7.73-7.59 (m, 2H), 7.50-7.39 (m, 2H), 7.32 (dt, J=7.7, 1.5 Hz, 1H), 5.15 (s, 1H), 3.93 (d, J=19.8 Hz, 2H), 3.31-3.11 (m, 3H), 2.73 (s, 3H), 2.67 (q, J=7.2 Hz, 1H), 2.21 (s, 3H), 2.16 (td, J=15.1, 14.5, 5.3 Hz, 1H), 2.10-1.75 (m, 4H), 1.59 (d, J=13.4 Hz, 1H). LC-MS (ESI): m/z [M+H]+ calculated for $C_{24}H_{29}Cl_2N_6O_2$ 503.2; found 503.4.

Example 64. Synthesis of (2R,4R)-8-[8-(2-chloro-3-methoxy-phenyl)-7-methyl-imidazo[1,2-c]pyrimidin-5-yl]-2-(oxetan-3-yloxy)-8-azaspiro[4.5]decan-4-amine
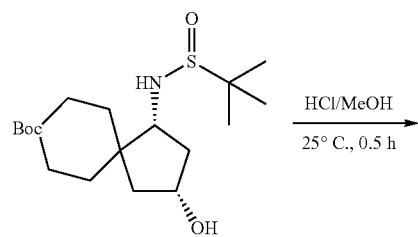
HCl/MeOH
25° C., 0.5 h
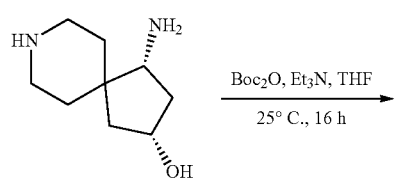
Boc₂O, Et₃N, THF
25° C., 16 h
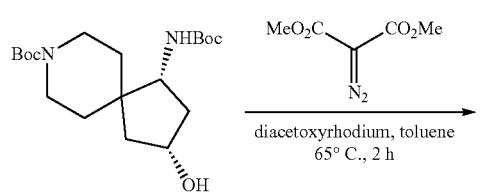
MeO₂C⧸⧹CO₂Me
N₂
diacetoxyrhodium, toluene
65° C., 2 h
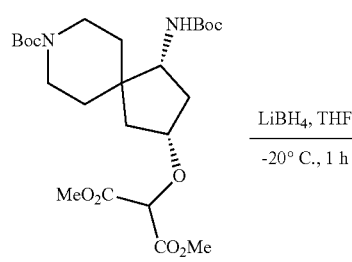
LiBH₄, THF
−20° C., 1 h
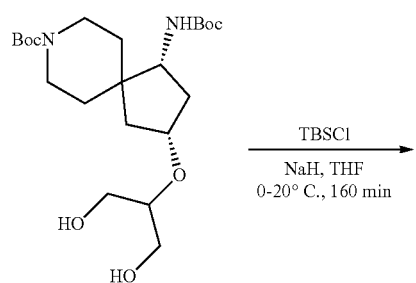
TBSCl
NaH, THF
0-20° C., 160 min
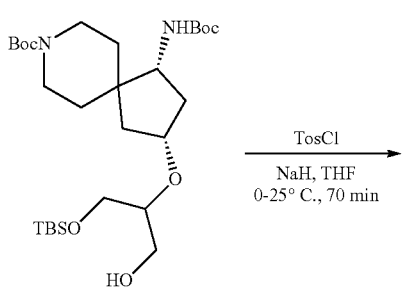
TosCl
NaH, THF
0-25° C., 70 min
-continued
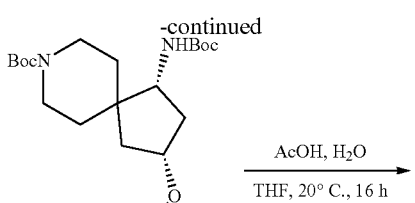
AcOH, H₂O
THF, 20° C., 16 h
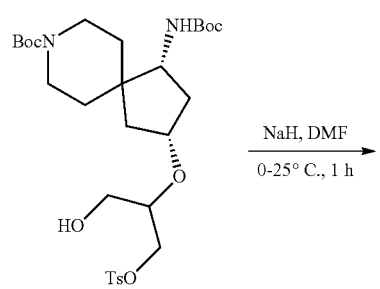
NaH, DMF
0-25° C., 1 h
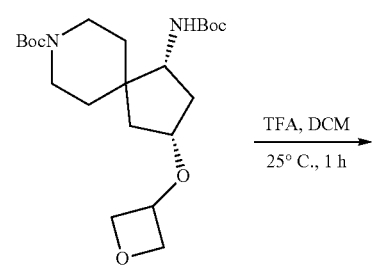
TFA, DCM
25° C., 1 h
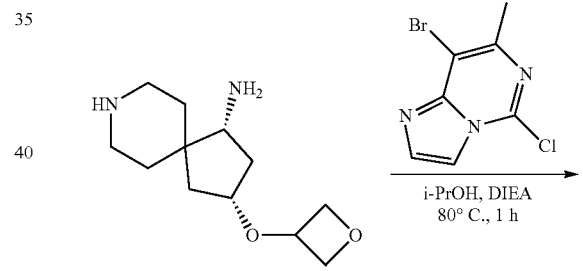
i-PrOH, DIEA
80° C., 1 h
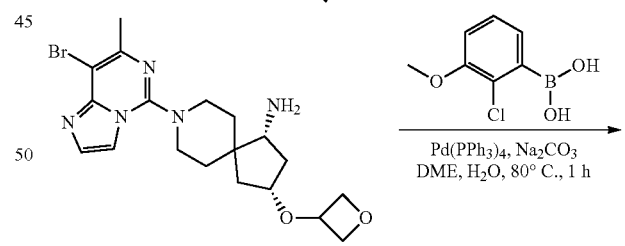
Pd(PPh₃)₄, Na₂CO₃
DME, H₂O, 80° C., 1 h
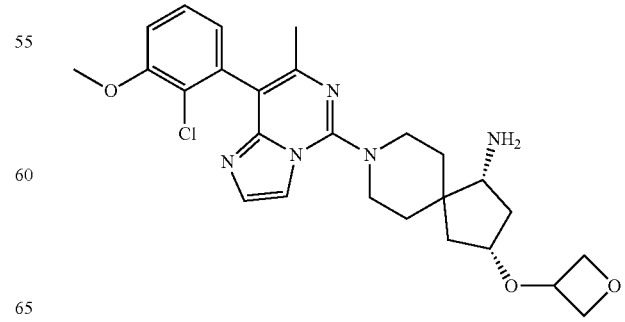

Step 1. Synthesis of (2R,4R)-4-amino-8-azaspiro [4.5]decan-2-ol

A mixture of tert-butyl (2R,4R)-4-(tert-butylsulfinylamino)-2-hydroxy-8-azaspiro[4.5]decane-8-carboxylate (1 g, 2.7 mmol) in HCl/MeOH (20 mL) was stirred at 25° C. for 0.5 h. The mixture was concentrated under reduced pressure to afford (2R,4R)-4-amino-8-azaspiro[4.5]decan-2-ol (660 mg, crude) as a white solid.

Step 2. Synthesis of tert-butyl (2R,4R)-4-(tert-butoxycarbonylamino)-2-hydroxy-8-azaspiro[4.5]decane-8-carboxylate To a solution of (2R,4R)-4-amino-8-azaspiro[4.5]decan-2-ol (650 mg, 3.8 mmol) in THF (10 mL) was added TEA (1.4 g, 13.3 mmol, 1.9 mL) and Boc$_2$O (2.1 g, 9.5 mmol, 2.2 mL). The reaction mixture was stirred at 25° C. for 16 h. The reaction mixture was concentrated under reduced pressure and the resulting residue was purified by silica gel chromatography to afford tert-butyl (2R,4R)-4-(tert-butoxycarbonylamino)-2-hydroxy-8-azaspiro[4.5]decane-8-carboxylate (0.6 g, 1.62 mmol, 42% yield) as a white solid. $^1$H NMR (400 MHz, Chloroform-d) 85.18 (s, 1H) 4.48-4.35 (m, 1H) 3.92-3.64 (m, 4H) 3.00 (t, J=10.69 Hz, 2H) 2.24-2.15 (m, 1H) 1.87 (d, J=7.72 Hz, 1H) 1.75 (s, 1H) 1.69-1.48 (m, 7H) 1.47-1.42 (m, 18H) 1.32-1.26 (m, 1H).

Step 3. Synthesis of dimethyl-2-[[(2R,4R)-8-tert-butoxycarbonyl-4-(tert-butoxycarbonylamino)-8-azaspiro[4.5]decan-2-yl]oxy]propanedioate To a solution of dimethyl 2-diazopropanedioate (281 mg, 1.8 mmol) in toluene (30 mL) was added tert-butyl (2R,4R)-4-(tert-butoxycarbonylamino)-2-hydroxy-8-azaspiro [4.5]decane-8-carboxylate (0.6 g, 1.6 mmol), and diacetoxyrhodium (7.2 mg, 32 µmol). The reaction mixture was stirred at 65° C. for 2 h. The reaction was quenched by the slow addition of H$_2$O (40 mL) and then extracted with EtOAc (20 mL×3). The combined organic phase was washed with brine (20 mL), dried over anhydrous Na$_2$SO$_4$, filtered and concentrated under reduced pressure. The resulting residue was purified by column chromatography to afford dimethyl 2-[[(2R,4R)-8-tert-butoxycarbonyl-4-(tert-butoxycarbonylamino)-8-azaspiro[4.5]decan-2-yl]oxy]propanedioate (600 mg, 1.2 mmol, 74% yield) as a colorless oil. $^1$H NMR (400 MHz, Chloroform-d) δ 5.34 (d, J=9.92 Hz, 1H) 4.17-4.05 (m, 1H) 3.90 (td, J=6.56, 3.42 Hz, 1H) 3.82 (d, J=1.54 Hz, 6H) 3.81-3.71 (m, 2H) 3.06-2.90 (m, 2H) 2.22-2.11 (m, 1H) 1.96-1.70 (m, 2H) 1.68-1.49 (m, 4H) 1.44 (d, J=1.98 Hz, 18H) 1.32-1.21 (m, 1H). LCMS (ELSD): m/z: [M+Na] calculated for C$_{24}$H$_{40}$N$_2$O$_9$Na: 523.3; found 523.1.

Step 4. Synthesis of tert-butyl (2R,4R)-4-(tert-butoxycarbonylamino)-2-[2-hydroxy-1-(hydroxymethyl)ethoxy]-8-azaspiro[4.5]decane-8-carboxylate To a solution of dimethyl 2-[[(2R,4R)-8-tert-butoxycarbonyl-4-(tert-butoxycarbonylamino)-8-azaspiro[4.5]decan-2-yl]oxy]propanedioate (400 mg, 799 µmol) in THF (6 mL) was added LiBH$_4$ (61 mg, 2.8 mmol) at −20° C. The reaction mixture was stirred at −20° C. for 1 h. The reaction was quenched by the slow addition of H$_2$O (0.1 mL), extracted with EtOAc (15 mL), dried over Na$_2$SO$_4$, filtered and concentrated under reduced pressure. The remaining residue was purified by column chromatography to afford tert-butyl (2R,4R)-4-(tert-butoxycarbonylamino)-2-[2-hydroxy-1-(hydroxymethyl)ethoxy]-8-azaspiro[4.5]decane-8-carboxylate (350 mg, 787 µmol, 98% yield) as colorless oil. $^1$H NMR (400 MHz, Methanol-d$_4$) δ 6.70 (d, J=9.70 Hz, 1H) 4.21 (s, 1H) 3.88-3.74 (m, 2H) 3.72-3.36 (m, 5H) 2.99 (s, 2H) 2.25 (dt, J=13.89, 6.95 Hz, 1H) 1.92-1.65 (m, 3H) 1.63-1.47 (m, 2H) 1.44 (d, J=5.29 Hz, 13H).

Step 5. Synthesis of tert-butyl (2R,4R)-4-(tert-butoxycarbonylamino)-2-[1-[[tert-butyl(dimethyl)-sulfanyl] oxymethyl]-2-hydroxy-ethoxy]-8-azaspiro [4.5]decane-8-carboxylate To a stirred solution of tert-butyl (2R,4R)-4-(tert-butoxycarbonylamino)-2-[2-hydroxy-1-(hydroxymethyl)ethoxy]-8-azaspiro[4.5]decane-8-carboxylate (0.28 g, 629 µmol) in THF (1.5 mL) at 0° C. was added NaH (25.1 mg, 629 µmol, 60% purity). After the solution was stirred at 20° C. for 40 min, TBSCl (95 mg, 629 µmol, 77 uL) was added, and the reaction mixture was stirred at 20° C. for 2 h. The reaction was quenched by the slow addition of H$_2$O (20 mL), extracted with EtOAc (15 mL×3), washed with brine (20 mL), dried over anhydrous Na$_2$SO$_4$, filtered and concentrated under reduced pressure. The remaining residue was purified by silica gel chromatography to afford tert-butyl (2R,4R)-4-(tert-butoxycarbonylamino)-2-[1-[[tert-butyl(dimethyl)-sulfanyl] oxymethyl]-2-hydroxy-ethoxy]-8-azaspiro[4.5]decane-8-carboxylate (210 mg, 373 µmol, 59% yield) as a colorless oil. $^1$H NMR (400 MHz, Methanol-d$_4$) δ 6.57-6.33 (m, 2H) 4.13 (s, 2H) 3.70 (dd, J=8.82, 4.41 Hz, 3H) 3.64-3.49 (m, 5H) 3.45-3.29 (m, 3H) 3.21-3.10 (m, 1H) 2.90 (s, 4H) 2.25-2.07 (m, 2H) 1.84-1.55 (m, 51H) 1.50-1.39 (m, 3H) 1.37-1.11 (m, 24H) 0.90-0.72 (m, 12H) 0.00 (d, J=1.54 Hz, 6H). LCMS (ESI): m/z: [M+Na] calculated for C$_{28}$H$_{54}$N$_2$O$_7$SiNa: 581.4; found 581.1

Step 6. Synthesis of tert-butyl (2R,4R)-4-(tert-butoxycarbonylamino)-2-[1-[[tert-butyl(dimethyl)-sulfanyl]oxymethyl]-2-hydroxy-ethoxy]-8-azaspiro [4.5]decane-8-carboxylate To a solution of tert-butyl (2R,4R)-4-(tert-butoxycarbonylamino)-2-[1-[[tert-butyl(dimethyl)-sulfanyl]oxymethyl]-2-hydroxy-ethoxy]-8-azaspiro[4.5]decane-8-carboxylate (200 mg, 355 µmol) in THF (5 mL) was added NaH (21.32 mg, 533 µmol, 60% purity) at 0° C. The mixture was stirred at 0° C. for 10 min, after which TosCl (101 mg, 533 µmol) was added. The reaction mixture was stirred at 25° C. for 1 h. The reaction was quenched by the slow addition of H$_2$O (20 mL) and then extracted with EtOAc (15 mL×3). The combined organic phase was washed with brine (20 mL), dried over anhydrous Na$_2$SO$_4$, filtered and concentrated under reduced pressure. The remaining residue was purified by silica gel chromatography to afford tert-butyl (2R,4R)-4-(tert-butoxycarbonylamino)-2-[1-[[tert-butyl(dimethyl)-sulfanyl]oxymethyl]-2-(p-tolylsulfonyloxy)ethoxy]-8-azaspiro[4.5]decane-8-carboxylate (150 mg, 209 µmol, 58% yield) as a colorless oil. LCMS (ESI): m/z: [M+Na] calculated for C$_{35}$H$_{60}$N$_2$O$_9$SSiNa: 735.4; found 735.2.

Step 7. Synthesis of tert-butyl (2R,4R)-4-(tert-butoxycarbonylamino)-2-[1-(hydroxymethyl)-2-(p-tolylsulfonyloxy)ethoxy]-8-azaspiro[4.5]decane-8-carboxylate To a solution of tert-butyl (2R,4R)-4-(tert-butoxycarbonylamino)-2-[1-[[tert-butyl(dimethyl)-sulfanyl]oxymethyl]-2-(p-tolylsulfonyloxy)ethoxy]-8-azaspiro[4.5]decane-8-carboxylate (150 mg, 209 umol) in HOAc (2.6 mL) was added H$_2$O (1.4 mL) and THF (0.6 mL). The reaction mixture was stirred at 20° C. for 16 h. The reaction was quenched by H$_2$O (20 mL) and extracted with EtOAc (15 mL×3). The combined organic phases were washed with brine (20 mL), dried over anhydrous Na$_2$SO$_4$, filtered and concentrated under reduced pressure. The remaining residue was purified by silica gel chromatography to afford tert-butyl (2R,4R)-4-(tert-butoxycarbonylamino)-2-[1-(hydroxymethyl)-2-(p-tolylsulfonyloxy)ethoxy]-8-azaspiro[4.5]decane-8-carboxylate (120 mg, 200 μmol, 95% yield) as a colorless oil. $^1$H NMR (400 MHz, Methanol-d$_4$) δ 7.77-7.65 (m, 2H) 7.36 (d, J=8.31 Hz, 2H) 6.49-6.30 (m, 1H) 4.08-3.86 (m, 3H) 3.77-3.64 (m, 2H) 3.57-3.39 (m, 4H) 2.82 (s, 2H) 2.37 (s, 3H) 2.15-2.00 (m, 1H) 1.74-1.60 (m, 2H) 1.48-1.32 (m, 23H). LCMS (ESI): m/z: [M+Na] calculated for C$_{29}$H$_{46}$N$_2$O$_9$SNa: 621.3; found 621.1.

Step 8. Synthesis of tert-butyl (2R,4R)-4-(tert-butoxycarbonylamino)-2-(oxetan-3-yloxy)-8-azaspiro[4.5]decane-8-carboxylate To a solution of tert-butyl (2R,4R)-4-(tert-butoxycarbonylamino)-2-[1-(hydroxymethyl)-2-(p-tolylsulfonyloxy)ethoxy]-8-azaspiro[4.5]decane-8-carboxylate (100 mg, 167 μmol) in DMF (5 mL) was added NaH (8 mg, 200 μmol, 60% purity) at 0° C. The reaction mixture was stirred at 25° C. for 1 h. The reaction was quenched by H$_2$O (20 mL) and extracted with EtOAc (15 mL×3). The combined organic phases were washed with brine (20 mL), dried over anhydrous Na$_2$SO$_4$, filtered and concentrated under reduced pressure to afford tert-butyl (2R,4R)-4-(tert-butoxycarbonylamino)-2-(oxetan-3-yloxy)-8-azaspiro[4.5]decane-8-carboxylate (70 mg, 164 umol, 98% yield) as a colorless oil. $^1$H NMR (400 MHz, Methanol-d$_4$) δ 4.70-4.65 (m, 2H) 4.56-4.50 (m, 1H) 4.48-4.41 (m, 2H) 3.88-3.68 (m, 4H) 3.62-3.35 (m, 4H) 2.84 (s, 2H) 2.15 (dt, J=13.39, 6.88 Hz, 2H) 1.70 (d, J=5.87 Hz, 3H) 1.35 (s, 18H) 1.20 (s, 2H) 0.79 (s, 3H); LCMS (ESI): m/z: [M+Na] calculated for C$_{22}$H$_{38}$N$_2$O$_6$Na: 449.3; found 449.1.

Step 9. Synthesis of (2R,4R)-2-(oxetan-3-yloxy)-8-azaspiro[4.5]decan-4-amine

To a solution of tert-butyl (2R,4R)-4-(tert-butoxycarbonylamino)-2-(oxetan-3-yloxy)-8-azaspiro[4.5]decane-8-carboxylate (35 mg, 82 μmol, 1 eq) in DCM (0.5 mL) was added TFA (0.5 mL). The reaction mixture was stirred at 25° C. for 1 h. The reaction mixture was concentrated under reduced pressure to afford (2R,4R)-2-(oxetan-3-yloxy)-8-azaspiro[4.5]decan-4-amine (77 mg, crude) as a white solid. LCMS (ESI): m/z: [M+H] calculated for C$_{12}$H$_{23}$N$_2$O$_2$ 227.2; found 227.2.

Step 10. Synthesis of (2R,4R)-8-(8-bromo-7-methyl-imidazo[1,2-c] pyrimidin-5-yl)-2-(oxetan-3-yloxy)-8-azaspiro[4.5]decan-4-amine To a solution of 8-bromo-5-chloro-7-methyl-imidazo[1,2-c]pyrimidine (19 mg, 77 μmol) in i-PrOH (1 mL) was added (2R,4R)-2-(oxetan-3-yloxy)-8-azaspiro[4.5]decan-4-amine (38 mg, 84 μmol, 2TFA), and DIEA (49.8 mg, 385 μmol, 67 μL). The reaction mixture was stirred at 80° C. for 1 h, concentrated under reduced pressure and the resulting residue was purified by column chromatography to afford give (2R,4R)-8-(8-bromo-7-methyl-imidazo[1,2-c]pyrimidin-5-yl)-2-(oxetan-3-yloxy)-8-azaspiro[4.5]decan-4-amine (30 mg, 68 μmol, 44% yield) as a white solid. LCMS (ESI): m/z: [M+H] calculated for C$_{19}$H$_{27}$BrN$_5$O$_2$:436.1; found 436.3. $^1$H NMR (400 MHz, Methanol-d$_4$) δ 7.61 (d, J=1.59 Hz, 1H) 7.46 (d, J=1.47 Hz, 1H) 4.70 (q, J=6.07 Hz, 2H) 4.59 (dt, J=11.28, 5.55 Hz, 1H) 4.53-4.45 (m, 2H) 4.00 (dt, J=6.72, 3.12 Hz, 1H) 3.83-3.66 (m, 2H) 3.15-3.00 (m, 3H) 2.46 (s, 3H) 2.39 (dt, J=14.21, 6.89 Hz, 1H) 2.05-1.67 (m, 7H) 1.46 (d, J=12.35 Hz, 1H)

Step 11. Synthesis of (2R,4R)-8-[8-(2-chloro-3-methoxy-phenyl)-7-methyl-imidazo[1,2-c]pyrimidin-5-yl]-2-(oxetan-3-yloxy)-8-azaspiro[4.5]decan-4-amine To a solution of (2R,4R)-8-(8-bromo-7-methyl-imidazo[1,2-c]pyrimidin-5-yl)-2-(oxetan-3-yloxy)-8-azaspiro[4.5]decan-4-amine (25 mg, 57 μmol) in DME (1 mL) and H$_2$O (0.2 mL) was added (2-chloro-3-methoxy-phenyl)boronic acid (21 mg, 114 μmol), Na$_2$CO$_3$ (12 mg, 114 umol), and Pd(PPh$_3$)$_4$ (6.6 mg, 5.73 μmol). The mixture was stirred at 80° C. for 1 h. The reaction was filtered and concentrated under reduced pressure. The resulting residue was purified by prep-HPLC to afford (2R,4R)-8-[8-(2-chloro-3-methoxy-phenyl)-7-methyl-imidazo[1,2-c]pyrimidin-5-yl]-2-(oxetan-3-yloxy)-8-azaspiro[4.5]decan-4-amine (2 mg, 3.9 μmol, 7% yield) as a white solid. LCMS (ESI): m/z: [M+H] calculated for C$_{26}$H$_{33}$ClN$_5$O$_3$ 498.2; found 498.0. 1H NMR (500 MHz, Methanol-d$_4$) δ 8.52 (s, 1H) 7.65 (s, 1H) 7.43 (d, J=1.54 Hz, 1H) 7.39 (t, J=8.05 Hz, 1H) 7.18 (d, J=7.06 Hz, 1H) 6.91 (dd, J=7.50, 1.32 Hz, 1H) 4.82-4.76 (m, 3H) 4.69 (dt, J=11.30, 5.71 Hz, 1H) 4.60 (dd, J=6.06, 3.20 Hz, 3H) 4.14-4.05 (m, 1H) 3.94 (s, 3H) 3.85 (d, J=9.70 Hz, 1H) 3.24-3.09 (m, 2H) 2.49 (dt, J=14.22, 7.00 Hz, 1H) 2.17 (s, 3H) 2.13-1.79 (m, 6H) 1.58 (d, J=14.11 Hz, 1H).

Example 65. Synthesis of (3S,4S)-8-{8-[(2-amino-3-chloropyridin-4-yl)sulfanyl]imidazo[1,2-a]pyrazin-5-yl}-3-methyl-2-oxa-8-azaspiro[4.5]decan-4-amine

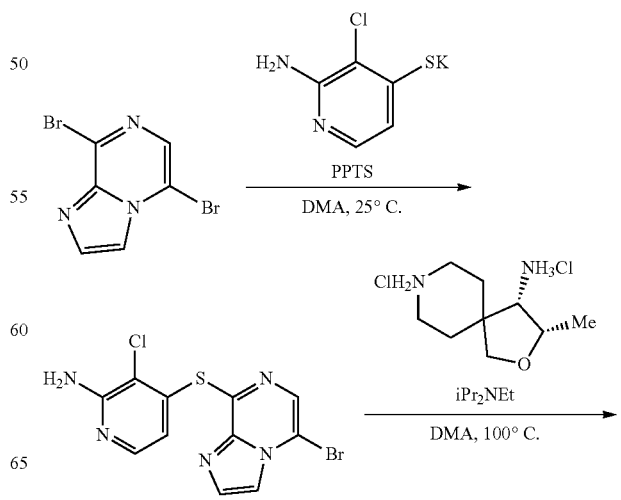

-continued

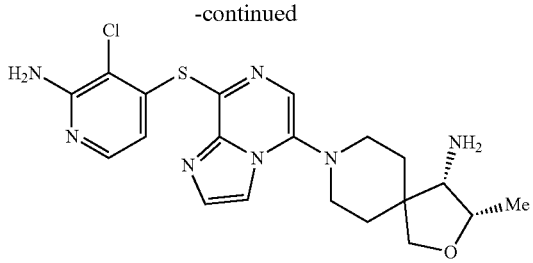

Step 1. Synthesis of 4-({5-bromoimidazo[1,2-a]pyrazin-8-yl}sulfanyl)-3-chloropyridin-2-amine 3-chloro-4-(potassiosulfanyl)pyridin-2-amine (78.8 mg, 397 µmol) and pyridinium p-toluenesulfonate (108 mg, 433 µmol) were dissolved in DMA (1.8 mL). The resulting solution was stirred was stirred at room temperature for 5 minutes, then 5,8-dibromoimidazo[1,2-a]pyrazine (100 mg, 361 µmol) was added. The reaction was stirred for 5.5 h, then purified directly via column chromatography to afford 4-({5-bromoimidazo[1,2-a]pyrazin-8-yl}sulfanyl)-3-chloropyridin-2-amine (112 mg, 317 µmol, 88% yield). LCMS (ESI): m/z: [M+H] calculated for $C_{11}H_8BrClN_5S$: 355.94; found 356.1.

Step 2. Synthesis of (3S,4S)-8-{8-[(2-amino-3-chloropyridin-4-yl)sulfanyl]imidazo[1,2-a]pyrazin-5-yl}-3-methyl-2-oxa-8-azaspiro[4.5]decan-4-amine To a mixture of 4-({5-bromoimidazo[1,2-a]pyrazin-8-yl}sulfanyl)-3-chloropyridin-2-amine (112.1 mg, 314 µmol) and N-[(3S,4S)-8-chloro-3-methyl-2-oxa-8-azaspiro[4.5]decan-4-yl]chloranamine (89.9 mg, 376 µmol) in DMA (1.56 mL) was added N,N-diisopropylethylamine (545 µL, 3.14 mmol). The reaction was sparged with $N_2$ for 5 minutes, sealed, and heated to 100° C. After 14 h, the resulting mixture was purified by prep HPLC to afford (3S,4S)-8-{8-[(2-amino-3-chloropyridin-4-yl)sulfanyl]imidazo[1,2-a]pyrazin-5-yl}-3-methyl-2-oxa-8-azaspiro[4.5]decan-4-amine as the formic acid salt (15 mg, 31 µmol, 10% yield). $^1$H NMR (500 MHz, Methanol-$d_4$) δ 8.55 (s, 1H), 7.99 (d, J=1.3 Hz, 1H), 7.83 (d, J=1.2 Hz, 1H), 7.72 (d, J=5.5 Hz, 1H), 7.55 (s, 1H), 6.49 (d, J=5.5 Hz, 1H), 4.36-4.27 (m, 1H), 3.96 (d, J=8.9 Hz, 1H), 3.84 (d, J=8.9 Hz, 1H), 3.53-3.42 (m, 3H), 3.31 (d, J=4.6 Hz, 1H), 3.16-3.01 (m, 2H), 2.14-2.03 (m, 2H), 1.99-1.91 (m, 1H), 1.89-1.81 (m, 1H), 1.31 (d, J=6.5 Hz, 3H). LC-MS (ESI): m/z: [M+H] calculated for $C_{20}H_{25}ClN_7OS$: 446.15; found 446.2.

Example 66. 2-({8-[(2-amino-3-chloropyridin-4-yl)sulfanyl]imidazo[1,2-c]pyrimidin-5-yl}amino)acetamide

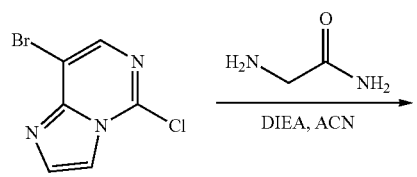

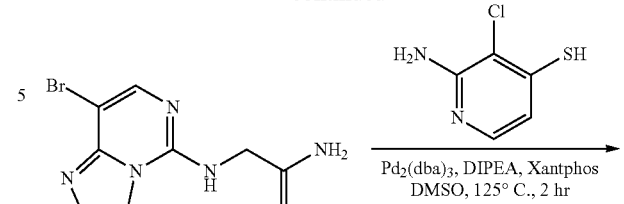

Step 1. Synthesis of 2-[(8-bromoimidazo[1,2-c]pyrimidin-5-yl)amino]acetamide To a solution of 8-bromo-5-chloro-imidazo[1,2-c]pyrimidine (200 mg, 860 µmol) and 2-aminoacetamide (95.6 mg, 1.29 mmol) in $CH_3CN$ (3 mL) was added DIEA (556 mg, 4.3 mmol, 749 L). The mixture was stirred at 50° C. for 0.5 h. The reaction mixture was filtered affording 2-[(8-bromoimidazo[1,2-c]pyrimidin-5-yl)amino]acetamide (210 mg, 778 µmol, 90% yield) as a white solid. LCMS (ESI): m/z: [M+H] calculated for $C_8H_9BrN_5O$: 268.99, 271.99; found 270.1, 272.1.

Step 2. Synthesis of 2-({8-[(2-amino-3-chloropyridin-4-yl)sulfanyl]imidazo[1,2-c]pyrimidin-5-yl}amino)acetamide To a solution of 2-amino-3-chloro-pyridine-4-thiol (187 mg, 1.2 mmol) and 2-[(8-bromoimidazo[1,2-c]pyrimidin-5-yl)amino]acetamide (210 mg, 777.53 µmol) in DMSO (2 mL) was added Xantphos (269.94 mg, 466.52 µmol), DIEA (301.46 mg, 2.33 mmol, 406.29 L), and $Pd_2(dba)_3$ (142 mg, 156 umol). The mixture was stirred at 125° C. for 0.5 h. The reaction mixture was filtered; the filtrate was concentrated under reduced pressure. The remaining residue was purified by prep-HPLC to afford 2-({8-[(2-amino-3-chloropyridin-4-yl)sulfanyl]imidazo[1,2-c]pyrimidin-5-yl}amino)acetamide (9.6 mg, 27 µmol, 4% yield) as a white solid. $^1$H NMR (500 MHz, DMSO-$d_6$) δ 8.62 (s, 1H), 8.10 (d, J=1.5 Hz, 1H), 7.90 (s, 1H), 7.60 (s, 1H), 7.55 (d, J=5.4 Hz, 1H), 7.51 (d, J=1.5 Hz, 1H), 7.13 (s, 1H), 6.29 (s, 2H), 5.76 (d, J=5.4 Hz, 1H), 4.10 (d, J=5.9 Hz, 2H). LCMS (ESI): m/z: [M+H] calculated for $C_{13}H_{13}ClN_7OS$: 350.1; found 350.0.

Examples 67-80 were prepared in the same manner as Example 66.

| Example | | M + 1 Found |
|---|---|---|
| 67 | (structure) | 377.0 |
| 68 | (structure) | 363.0 |
| 69 | (structure) | 377.0 |
| 70 | (structure) | 367.0 |
| 71 | (structure) | 375.0 |
| 72 | (structure) | 377.0 |
| 73 | (structure) | 337.3 |

-continued

| Example | | M + 1 Found |
|---|---|---|
| 74 | [structure] | 351.3 |
| 75 | [structure] | 349.1 |
| 76 | [structure] | 363.3 |
| 77 | [structure] | 363.5 |
| 78 | [structure] | 427.4 |
| 79 | [structure] | 391.4 |
| 80 | [structure] | 376.86 |

Example 81. 4-[(5-{[(1S,3R)-3-aminocyclopentyl]oxy}imidazo[1,2-c]pyrimidin-8-yl)sulfanyl]-3-chloropyridin-2-amine

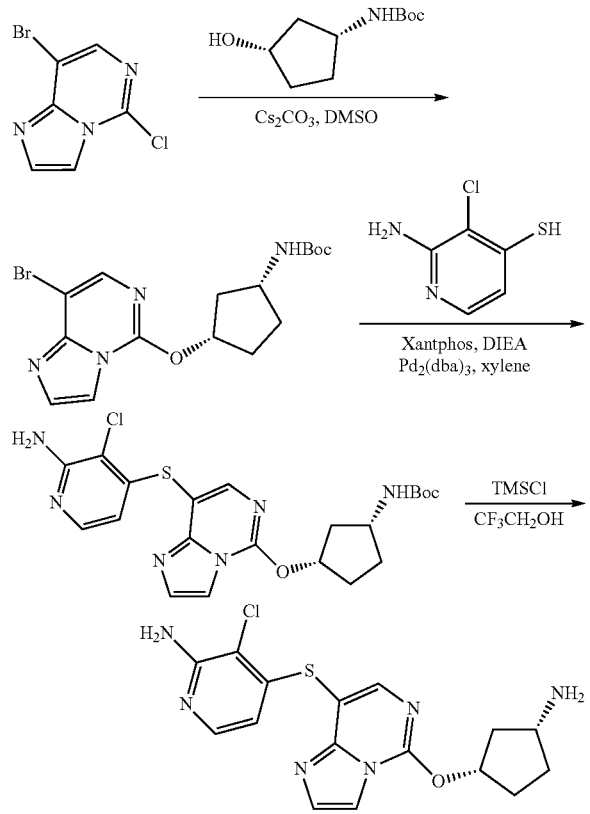

Step 1. Synthesis of tert-butyl N-[(1R,3S)-3-(8-bromoimidazo[1,2-c]pyrimidin-5-yl)oxycyclopentyl]carbamate To a mixture of 8-bromo-5-chloro-imidazo[1,2-c]pyrimidine (200 mg, 860 μmol) and tert-butyl N-[(1R,3S)-3-hydroxycyclopentyl]carbamate (190 mg, 946 μmol) in DMSO (2 mL) was added $Cs_2CO_3$ (561 mg, 1.7 mmol) in one portion at 25° C. under $N_2$. The mixture was stirred at 25° C. for 4 h. $H_2O$ (10 mL) was added dropwise into the reaction mixture and the aqueous phase was extracted with EtOAc. The combined organic phase was washed with brine (5 mL×2), dried with anhydrous $Na_2SO_4$, concentrated under reduced pressure. The residue was purified by column chromatography to afford tert-butyl N-[(1R,3S)-3-(8-bromoimidazo[1,2-c]pyrimidin-5-yl)oxycyclopentyl]carbamate (187 mg, 471 μmol, 55% yield) as a white solid. $^1$H NMR (500 MHz, Chloroform-d) δ 7.79 (s, 1H) 7.63 (dd, J=9.48, 1.10 Hz, 2H) 5.63 (br s, 1H) 4.69 (br s, 1H) 2.49-2.60 (m, 1H) 2.09-2.19 (m, 3H) 1.85-1.94 (m, 1H) 1.73-1.80 (m, 1H) 1.45 (d, J=2.21 Hz, 8H) 1.42-1.48 (m, 1H).

Step 2. Synthesis of tert-butyl N-[(1R,3S)-3-[8-[(2-amino-3-chloro-4-pyridyl)sulfanyl]imidazo[1,2-c]pyrimidin-5-yl]oxycyclopentyl]carbamate To a mixture of tert-butyl N-[(1R,3S)-3-(8-bromoimidazo[1,2-c]pyrimidin-5-yl)oxycyclopentyl]-carbamate (187 mg, 470 umol) and 2-amino-3-chloro-pyridine-4-thiol (151 mg, 941 μmol) in m-xylene (5 mL) was added Xantphos (109 mg, 188 μmol) DIEA (304 mg, 2.4 mmol, 410 μL) and $Pd_2(dba)_3$ (86.21 mg, 94.14 μmol) in one portion at 25° C. under $N_2$. The mixture was stirred at 140° C. for 3 h. The reaction was filtered and purified by HPLC to afford tert-butyl N-[(1R,3S)-3-[8-[(2-amino-3-chloro-4-pyridyl)sulfanyl]imidazo[1,2-c]pyrimidin-5-yl]oxycyclopentyl]carbamate (60 mg, 124 μmol, 26% yield) as a white solid. LCMS (ESI): m/z: [M+H] calculated for $C_{21}H_{26}ClN_6O_3S$: 477.1; found 477.2.

Step 3. 4-[(5-{[(1R,3S)-3-aminocyclopentyl]oxy}imidazo[1,2-c]pyrimidin-8-yl)sulfanyl]-3-chloropyridin-2-amine To a solution of TMSCl (26 mg, 236 μmol, 30 μL) in $CF_3CH_2OH$ (0.1 mL) that had been pre-stirred at 25° C. under $N_2$ for 30 min was added a solution of tert-butyl N-[(1R,3S)-3-[8-[(2-amino-3-chloro-4-pyridyl)sulfanyl]imidazo[1,2-c]pyrimidin-5-yl]oxycyclopentyl]carbamate (30.00 mg, 62.9 μmol) in $CF_3CH_2OH$ (0.3 mL) dropwise. The mixture was stirred at 25° C. for 2 h. The mixture was purified by HPLC to afford 4-[(5-{[(1R,3S)-3-aminocyclopentyl]oxy}imidazo[1,2-c]pyrimidin-8-yl)sulfanyl]-3-chloropyridin-2-amine (6.8 mg, 18.04 μmol, 29% yield) as a white solid. $^1$H NMR (500 MHz, Methanol-$d_4$) δ 8.04 (s, 1H) 7.93 (s, 1H) 7.54 (s, 1H) 7.50 (d, J=5.62 Hz, 1H) 5.89 (d, J=5.62 Hz, 1H) 5.74 (dt, J=6.17, 3.03 Hz, 1H) 3.45 (quin, J=6.97 Hz, 1H) 2.61 (dt, J=14.58, 7.20 Hz, 1H) 2.01-2.30 (m, 3H) 1.69-1.91 (m, 2H). LCMS (ESI): m/z: [M+H] calculated for $C_{16}H_{18}ClN_6OS$: 376.1; found 377.0.

Example 82. (3S,4S)-8-{8-[(2-amino-3-chloropyridin-4-yl)sulfanyl]imidazo[1,2-a]pyrazin-5-yl}-3-methyl-2-oxa-8-azaspiro[4.5]decan-4-amine

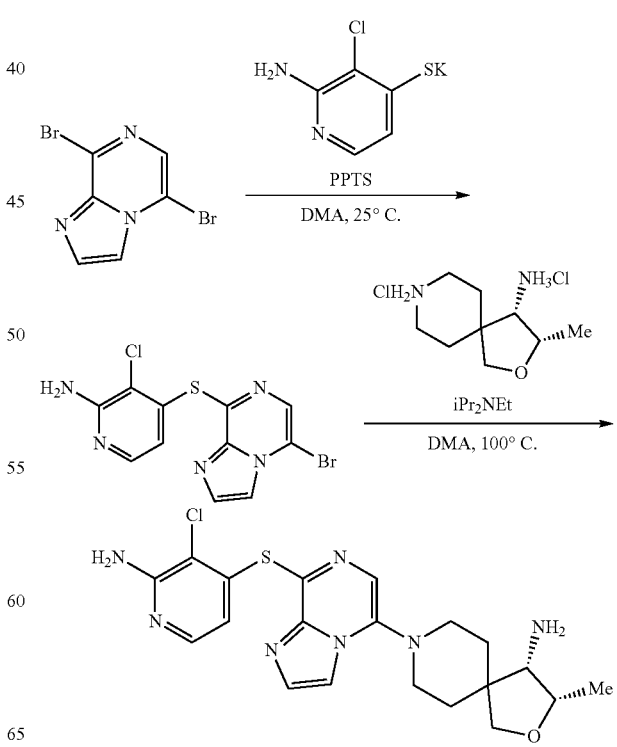

Step 1. Synthesis of 4-({5-bromoimidazo[1,2-a]pyrazin-8-yl}sulfanyl)-3-chloropyridin-2-amine 3-chloro-4-(potassiosulfanyl)pyridin-2-amine (78.8 mg, 397 μmol) and pyridinium p-toluenesulfonate (108 mg, 433 μmol) were dissolved in DMA (1.8 mL). The resulting solution was stirred was stirred at room temperature for 5 minutes, then 5,8-dibromoimidazo[1,2-a]pyrazine (100 mg, 361 μmol) was added. The reaction was stirred for 5.5 h then purified directly via column chromatography to afford 4-({5-bromoimidazo[1,2-a]pyrazin-8-yl}sulfanyl)-3-chloropyridin-2-amine (112 mg, 317 μmol, 88% yield). LC-MS (ESI): m/z: [M+H] calculated for $C_{11}H_8BrClN_5S$: 355.9; found 356.1.

Step 2. (3S,4S)-8-{8-[(2-amino-3-chloropyridin-4-yl)sulfanyl]imidazo[1,2-a]pyrazin-5-yl}-3-methyl-2-oxa-8-azaspiro[4.5]decan-4-amine To a mixture of 4-({5-bromoimidazo[1,2-a]pyrazin-8-yl}sulfanyl)-3-chloropyridin-2-amine (112.1 mg, 314 μmol) and N-[(3S,4S)-8-chloro-3-methyl-2-oxa-8-azaspiro[4.5]decan-4-yl]chloranamine (89.9 mg, 376 μmol) in DMA (1.56 mL) was added N,N-diisopropylethylamine (545 μL, 3.14 mmol). The reaction was sparged with $N_2$ for 5 minutes, sealed, and heated to 100° C. After 14 h, the resulting mixture was purified by prep HPLC to afford (3S,4S)-8-{8-[(2-amino-3-chloropyridin-4-yl)sulfanyl]imidazo[1,2-a]pyrazin-5-yl}-3-methyl-2-oxa-8-azaspiro[4.5]decan-4-amine as the formic acid salt (15 mg, 31 μmol, 10% yield). $^1$H NMR (500 MHz, Methanol-$d_4$) δ 8.55 (s, 1H), 7.99 (d, J=1.3 Hz, 1H), 7.83 (d, J=1.2 Hz, 1H), 7.72 (d, J=5.5 Hz, 1H), 7.55 (s, 1H), 6.49 (d, J=5.5 Hz, 1H), 4.36-4.27 (m, 1H), 3.96 (d, J=8.9 Hz, 1H), 3.84 (d, J=8.9 Hz, 1H), 3.53-3.42 (m, 3H), 3.31 (d, J=4.6 Hz, 1H), 3.16-3.01 (m, 2H), 2.14-2.03 (m, 2H), 1.99-1.91 (m, 1H), 1.89-1.81 (m, 1H), 1.31 (d, J=6.5 Hz, 3H). LC-MS (ESI): m/z: [M+H] calculated for $C_{20}H_{25}ClN_7OS$: 446.2; found 446.2.

Example 83. Synthesis of (3S,4S)-8-[12-(2,3-dichlorophenyl)-3,6,8,10,11-pentaazatricyclo[7.3.0.0$^{2,6}$]dodeca-1(12),2,4,7,9-pentaen-7-yl]-3-methyl-2-oxa-8-azaspiro[4.5]decan-4-amine

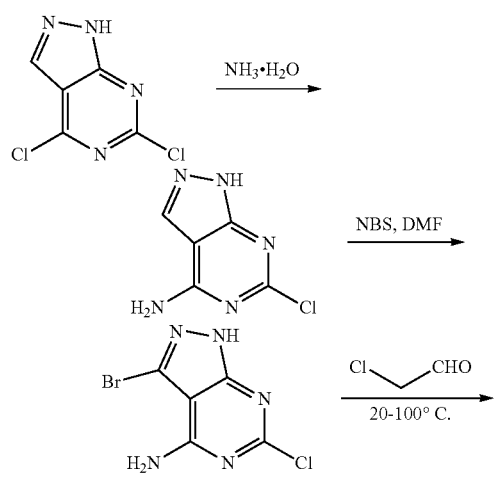

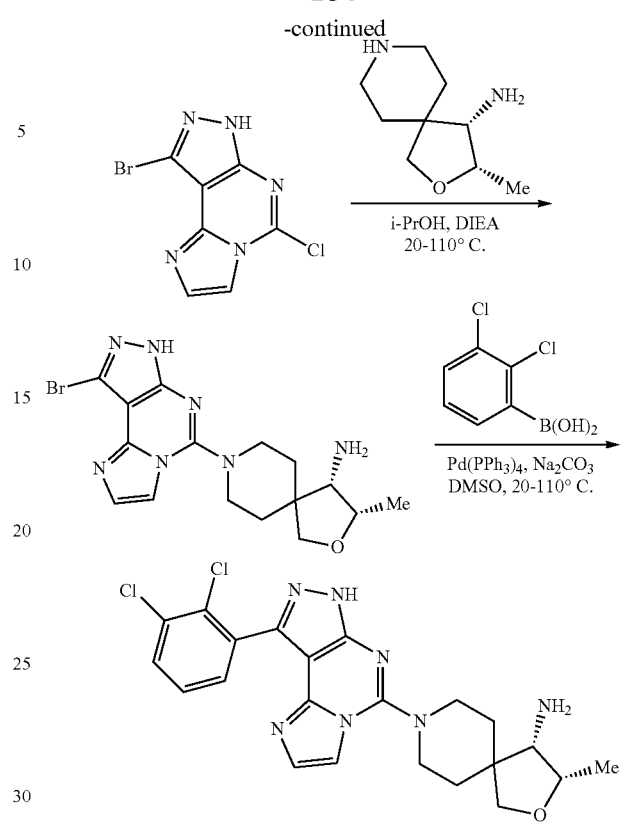

Step 1. Synthesis of 6-chloro-1H-pyrazolo[3,4-d]pyrimidin-4-amine

A mixture of 4,6-dichloro-1H-pyrazolo[3,4-d]pyrimidine (5 g, 26.4 mmol) in aqueous ammonia (100 mL, 25%) was stirred at room temperature for 12 h. The reaction mixture was then filtered and the filter cake was purified by prep-HPLC to afford 6-chloro-1H-pyrazolo[3,4-d]pyrimidin-4-amine (3.4 g, 75% yield) as a white solid. LCMS (ELSD): m/z: [M+H] calculated for $C_5H_5ClN_5$: 170.0; found 170.1; $^1$H NMR (400 MHz, DMSO-$d_6$) δ 13.4 (s, 1H) 8.19 (s, 1H) 8.08 (s, 1H) 8.04 (s, 1H).

Step 2. Synthesis of 3-bromo-6-chloro-1H-pyrazolo[3,4-d]pyrimidin-4-amine

To a solution of 6-chloro-1H-pyrazolo[3,4-d]pyrimidin-4-amine (1 g, 5.9 mmol) in DMF (40 mL) was added NBS (2.1 g, 11.8 mmol). The reaction was stirred at room temperature for 16 h, after which sat.$Na_2S_2O_3$ (20 mL) and water (20 mL) were added. A white precipitate formed and filtered to afford 3-bromo-6-chloro-1H-pyrazolo[3,4-d]pyrimidin-4-amine (1.2 g, 82% yield).

Step 3. Synthesis of 9-bromo-5-chloro-7H-imidazo[1,2-c]pyrazolo[4,3-e] pyrimidine A mixture of 3-bromo-6-chloro-1H-pyrazolo[3,4-d]pyrimidin-4-amine (1.2 g, 4.83 mmol) and 2-chloroacetaldehyde (12 mL) was stirred at 100° C. for 2 h. After cooling to room temperature and removal of excess reagent under reduced pressure the crude residue was purified by reversed phase column chromatography to afford 9-bromo-5-chloro-7H-imidazo[1,2-c]pyrazolo[4,3-e] pyrimidine (0.7 g, 5 3% yield). ¹H NMR (500 MHz, DMSO-d₆) δ 14.51 (s, 1H) 8.06 (d, J=1.6 Hz, 1H) 7.60 (d, J=1.6 Hz, 1H).

Step 4. Synthesis of (3S,4S)-8-(9-bromo-7H-imidazo[1,2-c]pyrazolo[4,3-e]pyrimidin-5-yl)-3-methyl-2-oxa-8-azaspiro[4.5]decan-4-amine To a solution of 9-bromo-5-chloro-7H-imidazo[1,2-c]pyrazolo[4,3-e] pyrimidine (0.7 g, 2.6 mmol) in i-PrOH (28 mL) was added (3S,4S)-3-methyl-2-oxa-8-azaspiro[4.5]decan-4-amine bis-hydrochloride (749 mg, 3.1 mmol) and DIEA (4.5 ml, 25.6 mmol). The reaction was stirred at 110° C. for 3 h, cooled to room temperature and concentrated under reduced pressure. The crude product was purified by prep-HPLC to afford (3S,4S)-8-(9-bromo-7H-imidazo[1,2-c]pyrazolo[4,3-e]pyrimidin-5-yl)-3-methyl-2-oxa-8-azaspiro[4.5]decan-4-amine (0.42 g, 40% yield). ¹H NMR (500 MHz, Methanol-d₄) δ 8.46 (s, 1H) 7.71 (d, J=2.0 Hz, 1H) 7.48 (d, J=1.6 Hz, 1H) 4.32-4.29 (m, 1H) 3.98 (d, J=8.8 Hz, 1H) 3.87-3.85 (m, 3H) 3.46 (d, J=4.0 Hz, 1H) 3.24-3.16 (m, 2H) 2.09-2.04 (m, 3H) 1.96-1.93 (m, 1H) 1.82-1.79 (m, 1H) 1.32 (d, J=6.4 Hz, 13H).

Step 5. Synthesis of (3S,4S)-8-[12-(2,3-dichlorophenyl)-3,6,8,10,11-pentaazatricyclo[7.3.0.0²,⁶]dodeca-1(12),2,4,7,9-pentaen-7-yl]-3-methyl-2-oxa-8-azaspiro[4.5]decan-4-amine To a solution of (3S,4S)-8-(9-bromo-7H-imidazo[1,2-c]pyrazolo[4,3-e]pyrimidin-5-yl)-3-methyl-2-oxa-8-azaspiro[4.5]decan-4-amine (0.25 g, 0.62 mmol) in DMSO (7.5 mL) was added (2,3-dichlorophenyl)boronic acid (1.53 g, 8.0 mmol), Na₂CO₃ (652 mg, 6.2 mmol) and Pd(PPh₃)₄ (142 mg, 120 µmol). The reaction was heated at 110° C. for 5 h, cooled to room temperature, and filtered. The solvent was removed under reduced pressure and the crude residue was purified by prep-HPLC to afford (3S,4S)-8-[12-(2,3-dichlorophenyl)-3,6,8,10,11-pentaazatricyclo[7.3.0.0²,⁶]dodeca-1(12),2,4,7,9-pentaen-7-yl]-3-methyl-2-oxa-8-azaspiro[4.5]decan-4-amine (6 mg, 2% yield). ¹H NMR (500 MHz, Methanol-d₄) δ 8.50 (s, 1H) 7.71-7.67 (m, 2H) 7.55 (d, J=6.4 Hz, 1H) 7.44-7.42 (m, 1H) 7.35 (d, J=1.6 Hz, 1H) 4.33-4.28 (m, 1H) 3.97-3.95 (m, 1H) 3.86-3.79 (m, 3H) 3.36-3.34 (m, 1H) 3.30-3.22 (m, 1H) 2.10-2.04 (m, 2H) 1.95-1.91 (m, 1H) 1.83-1.80 (m, 1H) 1.29 (d, J=6.8 Hz, 3H). LCMS (ESI): m/z: [M+H] calculated for $C_{22}H_{24}Cl_2N_7O$: 472.1; found 472.1.

Biological Examples—SHP2 Allosteric Inhibition Assay

Without wishing to be bound by theory, SHP2 is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

The phosphatase reactions were performed at room temperature in 96-well black polystyrene plate, flat bottom, non-binding surface (Corning, Cat #3650) using a final reaction volume of 100 µL and the following assay buffer conditions: 50 mM HEPES, pH 7.2, 100 mM NaCl, 0.5 mM EDTA, 0.05% P-20, 1 mM DTT.

The inhibition of SHP2 by compounds of the invention (concentrations varying from 0.00005-10 µM) was monitored using an assay in which 0.2 nM of SHP2 was incubated with 0.5 µM of Activating Peptide 1 (sequence: H₂N-LN(pY)IDLDLV(dPEG8)LST(pY)ASINFQK-amide) or Activating Peptide 2 (sequence: H₂N-LN(pY)AQLWHA(dPEG8)LTI(pY)ATIRRF-amide). After 30-60-minutes incubation at 25° C., the surrogate substrate DiFMUP (Invitrogen, Cat #D6567) was added to the reaction and activity was determined by a kinetic read using a microplate reader (Envision, Perkin-Elmer or Spectramax M5, Molecular Devices). The excitation and emission wavelengths were 340 nm and 450 nm, respectively. Initial rates were determined from a linear fit of the data, and the inhibitor dose response curves were analyzed using normalized IC₅₀ regression curve fitting with control based normalization.

Using the above-protocol, SHP2 inhibition measured as set forth in Table 1.

TABLE 1

SHP2 Inhibition of Tested Compounds

| Compound | SHP2 IC50, nM |
|---|---|
| Compound 1 (Example 1) | 1 |
| Compound 6 (Example 6) | 10 |
| Compound 4 (Example 4) | 29 |
| Compound 2 (Example 2) | 120 |

Using the above-protocol, SHP2 inhibition measured as set forth in Table 2. In the table below: "+++" refers to <=50 nM; "++" refers to >50 nM to <=500 nM; and "+" refers to >500 nM.

TABLE 2

SHP2 Inhibition of Tested Compounds

| Compound | | SHP2 IC₅₀, nM |
|---|---|---|
| 1 | 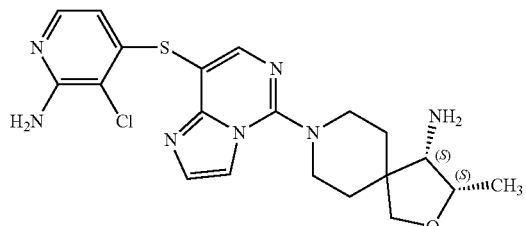 | +++ |

TABLE 2-continued

SHP2 Inhibition of Tested Compounds

| Compound | Structure | SHP2 IC$_{50}$, nM |
|---|---|---|
| 2 | | ++ |
| 3 | | + |
| 4 | | +++ |
| 5 | | + |
| 6 | | +++ |

TABLE 2-continued

SHP2 Inhibition of Tested Compounds

| Compound | SHP2 IC$_{50}$, nM |
|---|---|
| 7 | ++ |
| 8 | +++ |
| 9 | +++ |
| 10 | +++ |
| 11 | +++ |

TABLE 2-continued

SHP2 Inhibition of Tested Compounds

| Compound | | SHP2 IC$_{50}$, nM |
|---|---|---|
| 12 | [structure] | +++ |
| 13 | [structure] | +++ |
| 14 | [structure] | ++ |
| 15 | [structure] | +++ |
| 16 | [structure] | ++ |
| 17 | [structure] | +++ |

TABLE 2-continued

SHP2 Inhibition of Tested Compounds

| Compound | | SHP2 IC$_{50}$, nM |
|---|---|---|
| 18 | [structure] | ++ |
| 19 | [structure] | + |
| 20 | [structure] | ++ |
| 21 | [structure] | + |
| 22 | [structure] | + |
| 23 | [structure] | + |

TABLE 2-continued

SHP2 Inhibition of Tested Compounds

| Compound | | SHP2 IC$_{50}$, nM |
|---|---|---|
| 24 | (structure) | ++ |
| 25 | (structure) | ++ |
| 26 | (structure) | + |
| 27 | (structure) | + |
| 28 | (structure) | + |
| 29 | (structure) | +++ |

TABLE 2-continued

SHP2 Inhibition of Tested Compounds

| Compound | | SHP2 IC$_{50}$, nM |
|---|---|---|
| 30 | (structure) | +++ |
| 31 | (structure) | +++ |
| 32 | (structure) | +++ |
| 33 | (structure) | +++ |
| 34 | (structure) | +++ |

TABLE 2-continued

SHP2 Inhibition of Tested Compounds

| Compound | | SHP2 IC$_{50}$, nM |
|---|---|---|
| 35 | | +++ |
| 36 | | +++ |
| 37 | | +++ |
| 38 | | +++ |
| 39 | | +++ |

TABLE 2-continued

SHP2 Inhibition of Tested Compounds

| Compound | | SHP2 IC$_{50}$, nM |
|---|---|---|
| 40 | | +++ |
| 41 | | +++ |
| 42 | | +++ |
| 43 | | +++ |
| 44 | | +++ |

TABLE 2-continued

SHP2 Inhibition of Tested Compounds

| Compound | | SHP2 IC$_{50}$, nM |
|---|---|---|
| 45 | (structure) | +++ |
| 46 | (structure) | +++ |
| 47 | (structure) | +++ |
| 48 | (structure) | +++ |
| 49 | (structure) | +++ |

TABLE 2-continued

SHP2 Inhibition of Tested Compounds

| Compound | | SHP2 IC$_{50}$, nM |
|---|---|---|
| 50 | [structure] | +++ |
| 51 | [structure] | ++ |
| 52 | [structure] | +++ |
| 53 | [structure] | +++ |
| 54 | [structure] | +++ |

TABLE 2-continued
SHP2 Inhibition of Tested Compounds
| Compound | | SHP2 IC$_{50}$, nM |
|---|---|---|
| 55 | 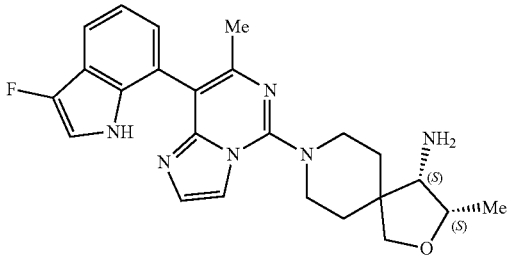 | +++ |
| 56 | 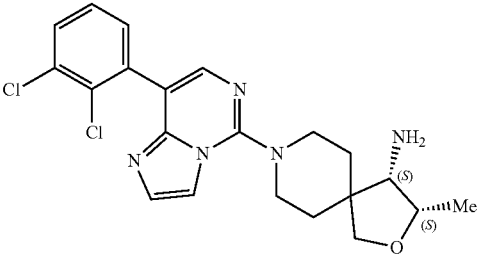 | +++ |
| 57 | 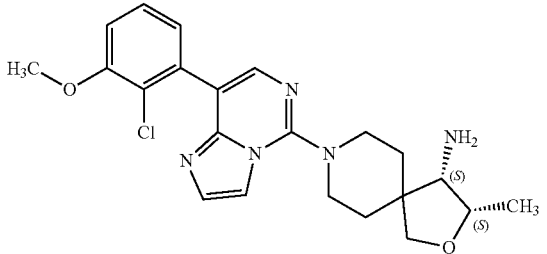 | ++ |
| 58 | 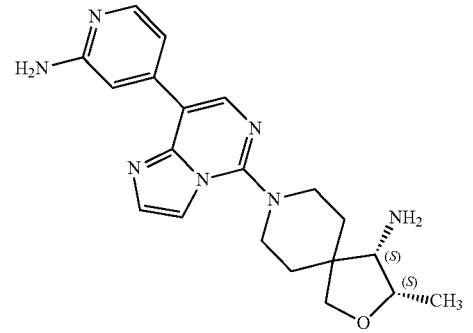 | + |
| 59 | 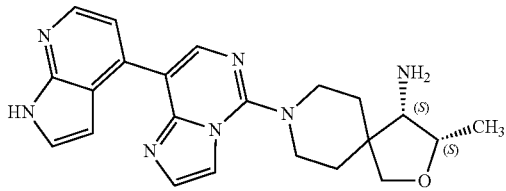 | + |

TABLE 2-continued

SHP2 Inhibition of Tested Compounds

| Compound | | SHP2 IC$_{50}$, nM |
|---|---|---|
| 60 | | + |
| 61 | | +++ |
| 62 | | +++ |
| 63 | | +++ |

TABLE 2-continued

SHP2 Inhibition of Tested Compounds

| Compound | | SHP2 IC$_{50}$, nM |
|---|---|---|
| 64 | [structure] | +++ |
| 65 | [structure] | + |
| 66 | [structure] | + |
| 67 | [structure] | + |
| 68 | [structure] | + |
| 69 | [structure] | + |

TABLE 2-continued

SHP2 Inhibition of Tested Compounds

| Compound | | SHP2 IC$_{50}$, nM |
|---|---|---|
| 70 | | + |
| 71 | | + |
| 72 | | + |
| 73 | | + |
| 74 | | + |
| 75 | | + |
| 76 | | + |

TABLE 2-continued

SHP2 Inhibition of Tested Compounds

| Compound | | SHP2 IC$_{50}$, nM |
|---|---|---|
| 77 | [Structure] | + |
| 78 | [Structure] | + |
| 79 | [Structure] | + |
| 80 | [Structure] | + |
| 81 | [Structure] | + |
| 82 | [Structure] | + |

TABLE 2-continued

SHP2 Inhibition of Tested Compounds

| Compound | | SHP2 IC$_{50}$, nM |
|---|---|---|
| 83 | 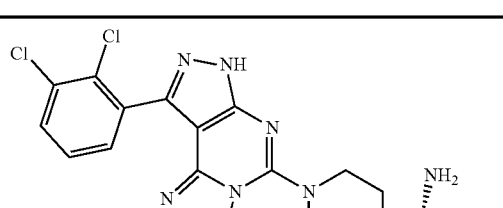 | +++ |

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

The invention claimed is:

1. A compound of the Formula II':

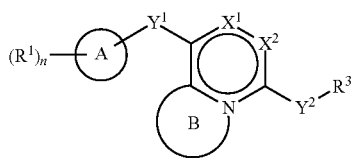

or a pharmaceutically acceptable salt, tautomer, or stereoisomer thereof, wherein:

A is cycloalkyl, heterocyclyl, aryl, or heteroaryl, wherein cycloalkyl, heterocyclyl, aryl, and heteroaryl are 5- to 12-membered monocyclic or 5- to 12-membered polycyclic;

$R^1$ is independently, at each occurrence, —H, —C$_1$-C$_6$alkyl, —C$_2$-C$_6$alkenyl, —C$_4$-C$_8$cycloalkenyl, —C$_2$-C$_6$alkynyl, —OH, —OR$^6$, halogen, —NO$_2$, —CN, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)R$^5$, —CO$_2$R$^5$, —C(O)NR$^5$R$^6$, —NR$^5$C(O)R$^6$, monocyclic or polycyclic heterocyclyl, spiroheterocyclyl, or oxo, wherein each alkyl, alkenyl, cycloalkenyl, alkynyl, heterocyclyl, or spiroheterocyclyl is optionally substituted with one or more —OH, halogen, —NO$_2$, oxo, =O, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

$Y^1$ is —S—, a direct bond, —NH—, —S(O)$_2$—, —S(O)$_2$—NH—, —C(=CH$_2$)—, —CH$_2$—, or —S(O)—;

$X^1$ is N or CR$^2$;

$X^2$ is N or CH;

B, including the atoms at the points of attachment, is

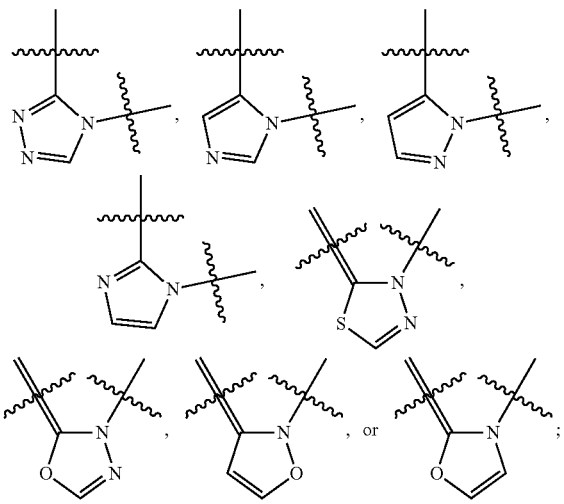

$Y^2$ is —NR$^a$—; wherein the bond on the left side of $Y^2$, as drawn, is bound to the ring and the bond on the right side of the $Y^2$ moiety, as drawn, is bound to $R^3$;

$R^b$ is independently, at each occurrence, —H, —OH, —C$_1$-C$_6$alkyl, —C$_3$-C$_8$cycloalkyl, —C$_2$-C$_6$alkenyl, —(CH$_2$)$_n$-aryl, heterocyclyl containing 1-5 heteroatoms selected from the group consisting of N, S, P, and O, or heteroaryl containing 1-5 heteroatoms selected from the group consisting of N, S, P, and O; wherein each alkyl, cycloalkyl, alkenyl, heterocycle, heteroaryl, or —(CH$_2$)$_n$-aryl is optionally substituted with one or more —OH, halogen, —NO$_2$, oxo, —CN, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, —C(O)NR$^5$R$^6$, —NR$^5$C(O)R$^6$, heterocycle, aryl, heteroaryl, —(CH$_2$)$_n$OH, —C$_1$-C$_6$alkyl, —CF$_3$, —CHF$_2$, or —CH$_2$F;

$R^2$ is independently —H, —NH$_2$, —OR$^b$, —CN, —C$_1$-C$_6$alkyl, —C$_2$-C$_6$alkenyl, —C$_4$-C$_8$cycloalkenyl, —C$_2$-C$_6$alkynyl, halogen, —C(O)OR$^b$, —C$_3$-C$_8$cycloalkyl, or heterocyclyl containing 1-5 heteroatoms selected from the group consisting of N, S, P, and O; wherein each alkyl, alkenyl, cycloalkenyl, alkynyl, cycloalkyl, or heterocyclyl is optionally substituted with one or more —OH, halogen, —NO$_2$, oxo, —R$^5$, —OR$^5$, —NR$^5$R$^6$, —SR$^5$, —S(O)$_2$NR$^5$R$^6$, —S(O)$_2$R$^5$, —NR$^5$S(O)$_2$NR$^5$R$^6$, —NR$^5$S(O)$_2$R$^6$, —S(O)NR$^5$R$^6$, —S(O)R$^5$, —NR$^5$S(O)NR$^5$R$^6$, —NR$^5$S(O)R$^6$, heterocycle, aryl, or heteroaryl;

R$^3$ combines with R$^a$ to form a 3- to 12-membered monocyclic or polycyclic heterocycle or a 5- to 12-membered spiroheterocycle, wherein each heterocycle or spiroheterocycle is optionally substituted with one or more —C$_1$-C$_6$alkyl, halogen, —OH, —OR$^b$, —NH$_2$, —NHR$^b$, optionally substituted heteroaryl, optionally substituted heterocyclyl, —(CH$_2$)$_n$NH$_2$, —(CH$_2$)$_n$OH, —COOR$^b$, —CONHR$^b$, —CONH(CH$_2$)$_n$COOR$^b$, —NHCOOR$^b$, —CF$_3$, —CHF$_2$, —CH$_2$F, or =O; wherein the heteroaryl and heterocyclyl are optionally substituted with —CN;

R$^5$ and R$^6$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, a monocyclic or polycyclic 3- to 12-membered heterocycle, —OR$^7$, —SR$^7$, halogen, —NR$^7$R$^8$, —NO$_2$, —CF$_3$, or —CN;

R$^7$ and R$^8$ are independently, at each occurrence, —H, —C$_1$-C$_6$alkyl, —C$_2$-C$_6$alkenyl, —C$_4$-C$_8$cycloalkenyl, —C$_2$-C$_6$alkynyl, —C$_3$-C$_8$cycloalkyl, —OR$^b$, or a monocyclic or polycyclic 3- to 12-membered heterocycle, wherein each alkyl, alkenyl, cycloalkenyl, alkynyl, cycloalkyl, or heterocycle is optionally substituted with one or more —OH, —SH, —NH$_2$, —NO$_2$, or —CN;

m is independently 1, 2, 3, 4, 5 or 6; and n is independently 0, 1, 2, 3, 4, 5, 6, 7, 8, 9, or 10.

2. The compound of claim 1, or a pharmaceutically acceptable salt, tautomer, or stereoisomer thereof, wherein Y$^1$ is —S— or a direct bond.

3. The compound of claim 1, or a pharmaceutically acceptable salt, tautomer, or stereoisomer thereof, wherein X$^1$ is N.

4. The compound of claim 1, or a pharmaceutically acceptable salt, tautomer, or stereoisomer thereof, wherein X$^1$ is CR$^2$.

5. The compound of claim 1, or a pharmaceutically acceptable salt, tautomer, or stereoisomer thereof, wherein X$^2$ is N.

6. The compound of claim 1, or a pharmaceutically acceptable salt, tautomer, or stereoisomer thereof, wherein X$^2$ is CH.

7. The compound of claim 1, or a pharmaceutically acceptable salt, tautomer, or stereoisomer thereof, wherein A is heterocyclyl.

8. The compound of claim 1, or a pharmaceutically acceptable salt, tautomer, or stereoisomer thereof, wherein wherein A is aryl or heteroaryl.

9. The compound of claim 1, or a pharmaceutically acceptable salt, tautomer, or stereoisomer thereof, wherein A is phenyl or pyridyl.

10. The compound of claim 1, or a pharmaceutically acceptable salt, tautomer, or stereoisomer thereof, wherein R$^1$ is independently —OH, —NO$_2$, —CN, halogen, or —NR$^5$R$^6$.

11. The compound of claim 1, or a pharmaceutically acceptable salt, tautomer, or stereoisomer thereof, wherein R$^3$ and R$^a$ together with the atom to which they are attached combine to form a 5- to 12-membered spiroheterocycle.

12. The compound of claim 11, or a pharmaceutically acceptable salt, tautomer, or stereoisomer thereof, wherein the spirocycle formed by R$^3$ and R$^a$ is substituted with one or more substituents selected from the group consisting of C$_1$-C$_6$alkyl, —OH, halogen, —NH$_2$, —NHR$^b$, —CF$_3$, —CHF$_2$, or —CH$_2$F.

13. A compound, or a pharmaceutically acceptable salt, tautomer, or stereoisomer thereof, selected from the group consisting of:

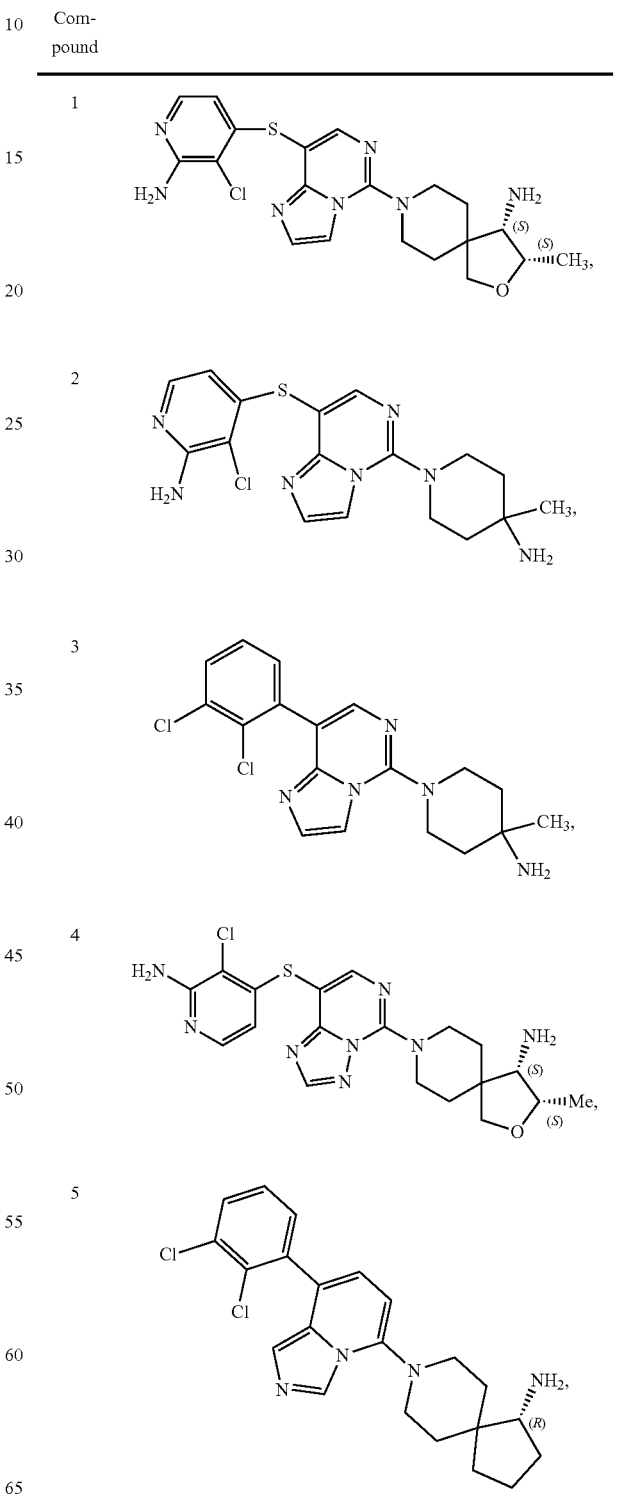

-continued

| Compound | |
|---|---|
| 6 | [structure: 2,3-dichlorophenyl-methyl-triazolo-pyrimidine linked to piperidine-spiro-tetrahydrofuran with (S),(S) NH2 and CH3] |
| 7 | [structure: 2-amino-3-chloropyridin-4-yl-thio-triazolo-pyrimidine linked to 4-methyl-4-amino-piperidine] |
| 8 | [structure: 2,3-dichlorophenyl-methyl-imidazo-pyrimidine linked to piperidine-spiro-tetrahydrofuran with NH2 and Me, and] |
| 9 | [structure: 3-methoxy-2-chlorophenyl-methyl-imidazo-pyrimidine linked to piperidine-spiro-tetrahydrofuran with NH2 and Me] |

14. A compound, or a pharmaceutically acceptable salt, tautomer, or stereoisomer thereof, selected from the group consisting of:

(1) [structure of compound 1]

-continued (2) [structure of compound 2]

(3) [structure of compound 3]

(4) [structure of compound 4]

(5) [structure of compound 5]

(6) [structure of compound 6]

(7) [structure of compound 7]

(8)
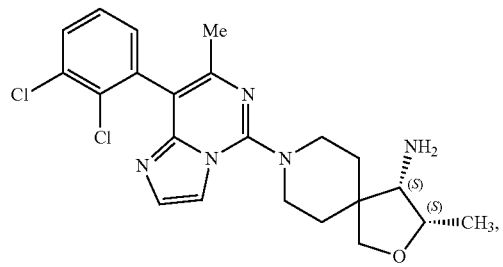
(14)
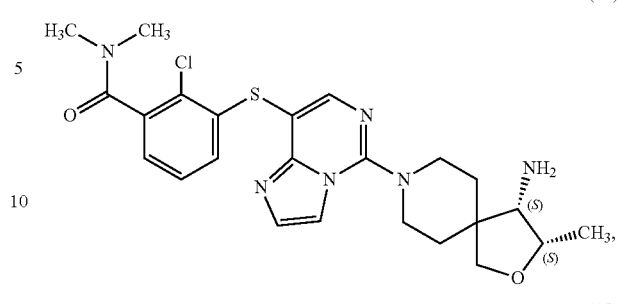
(9)
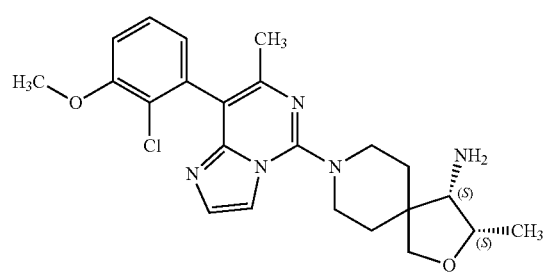
(15)
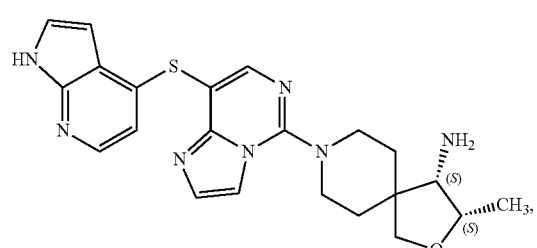
(10)
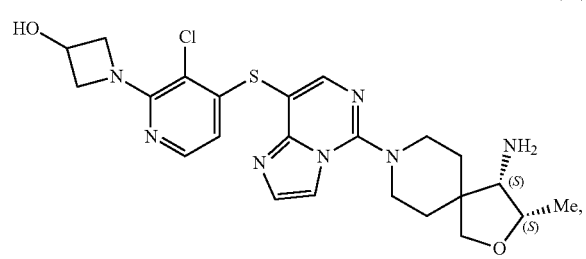
(16)
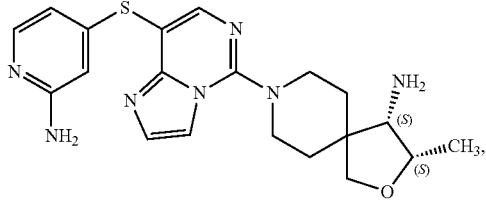
(12)
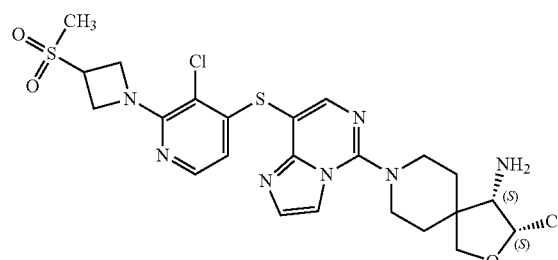
(17)
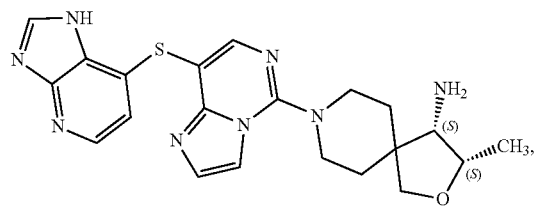
(18)
(13)
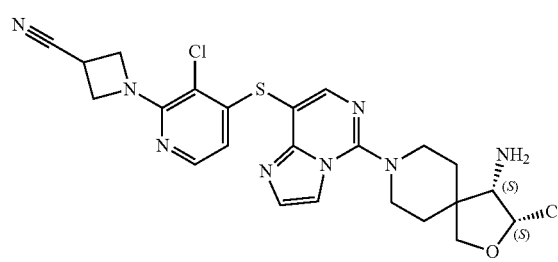
(19)
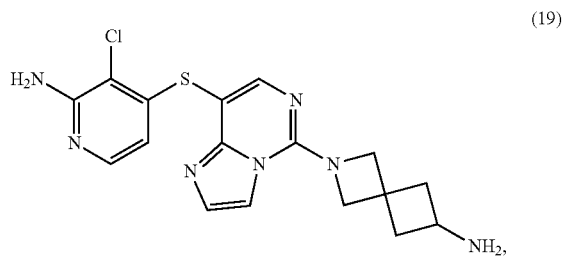

-continued
(20)
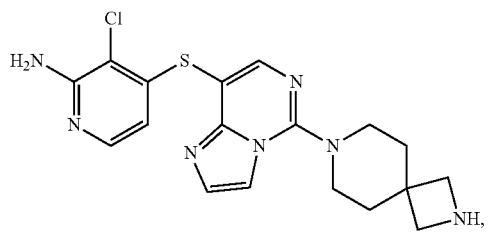
(21)
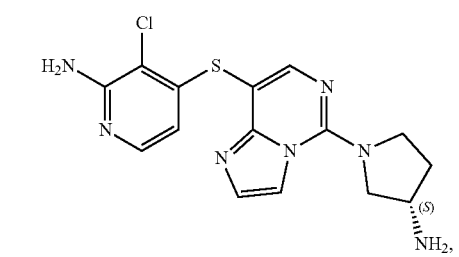
(22)
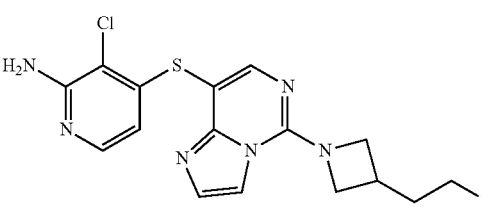
(23)
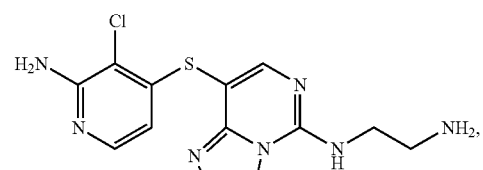
(24)
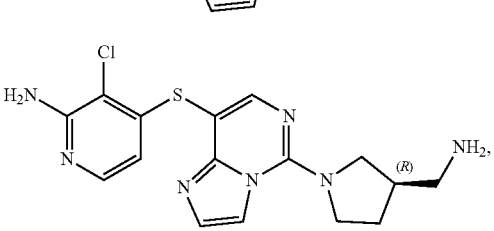
(25)
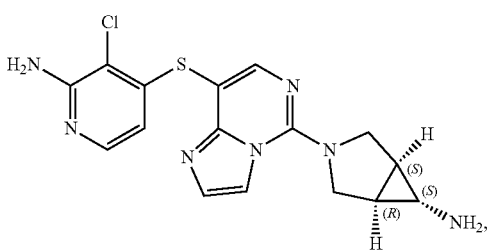
(26)
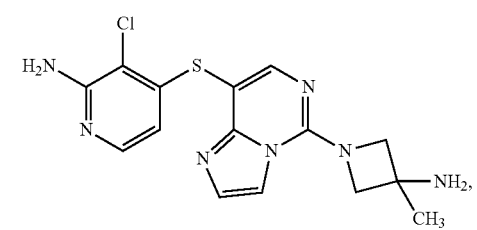
-continued
(27)
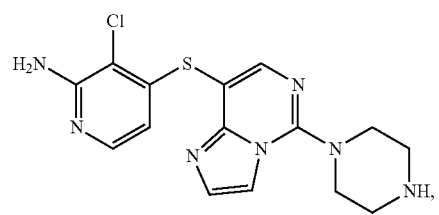
(28)
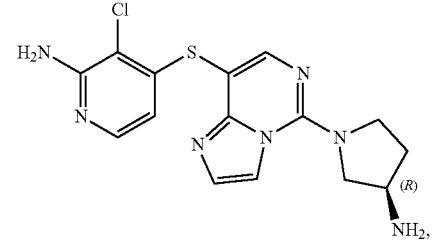
(29)
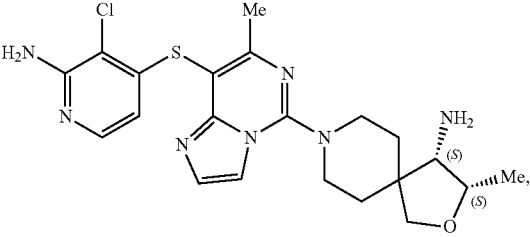
(30)
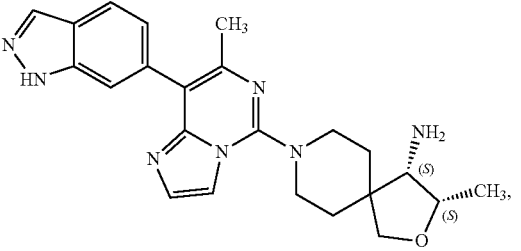
(31)
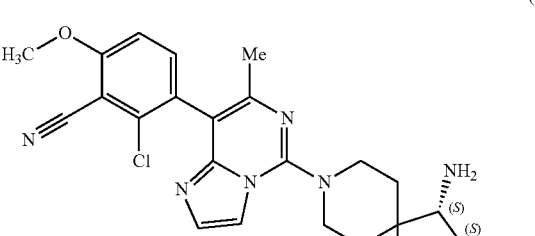
(32)
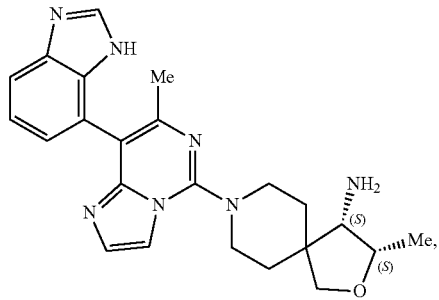

227
-continued
(33)
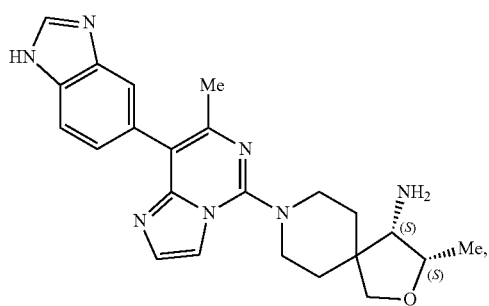
(34)
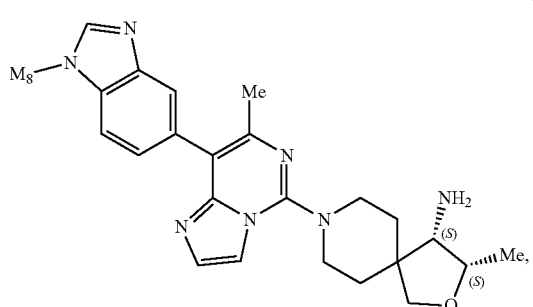
(35)
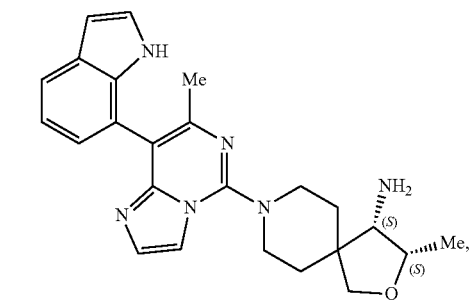
(36)
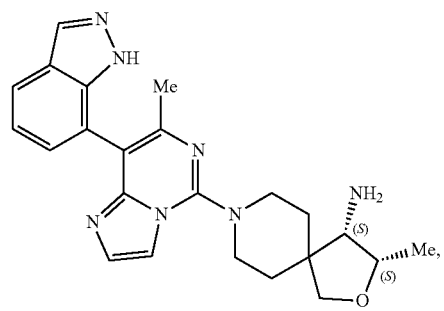
(37)
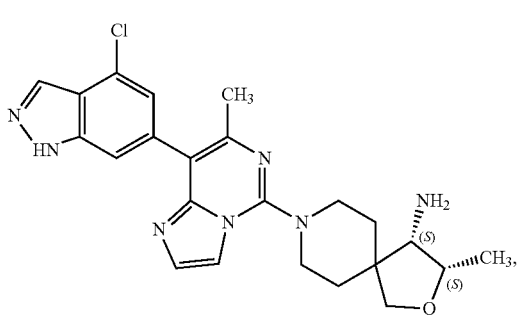
228
-continued
(38)
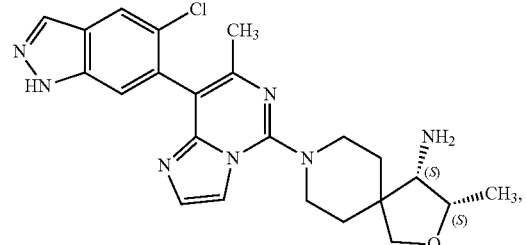
(39)
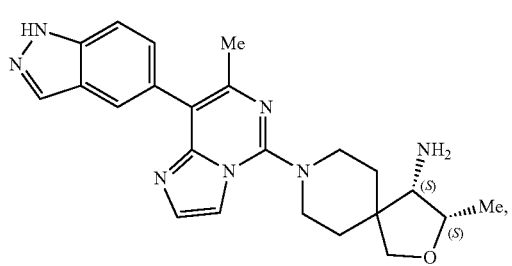
(40)
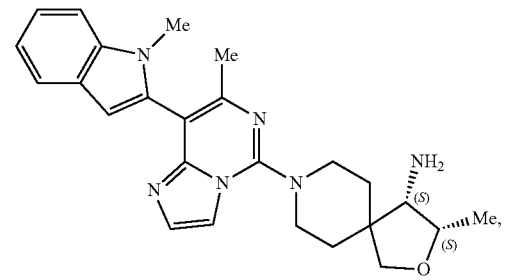
(41)
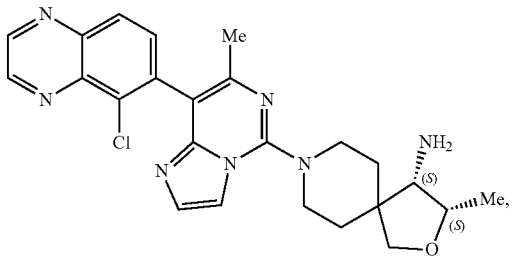
(42)
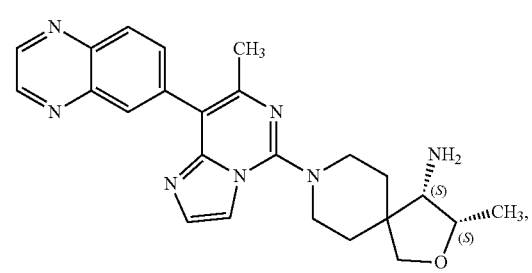

(43)
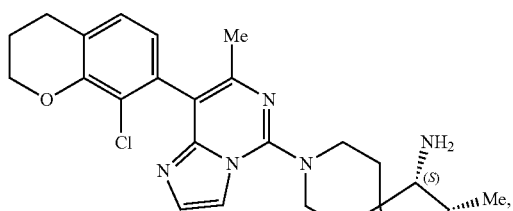
(44)
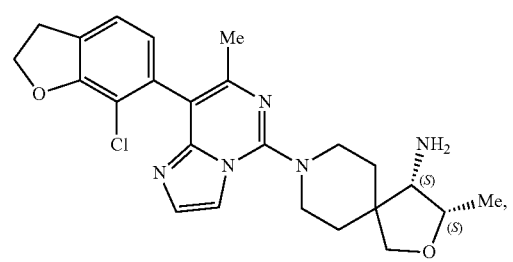
(45)
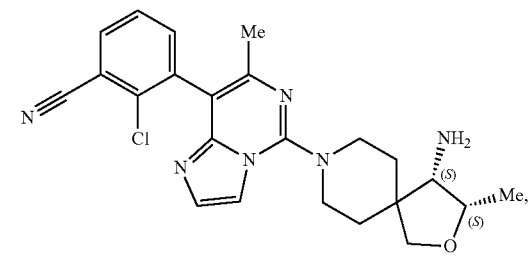
(46)
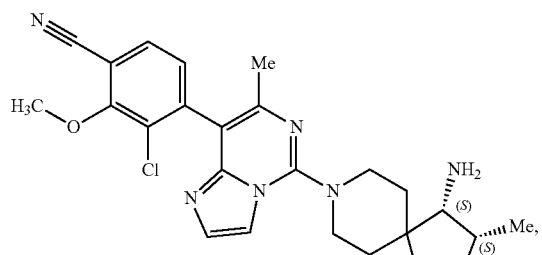
(47)
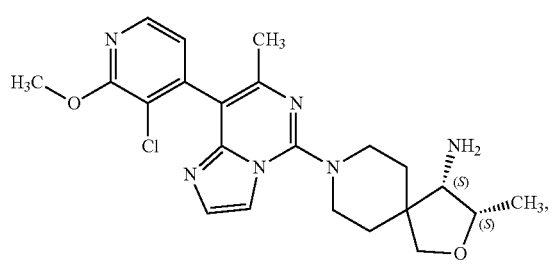
(48)
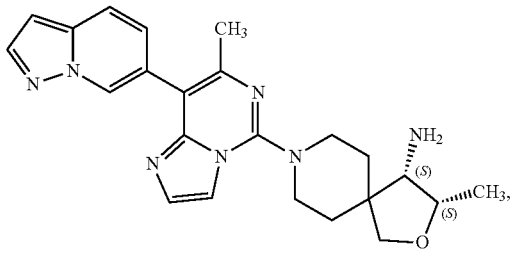
(49)
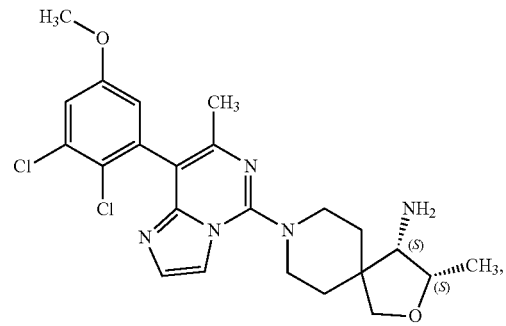
(50)
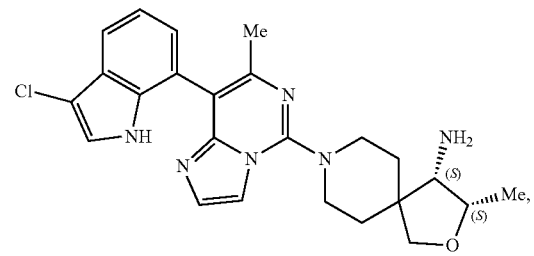
(51)
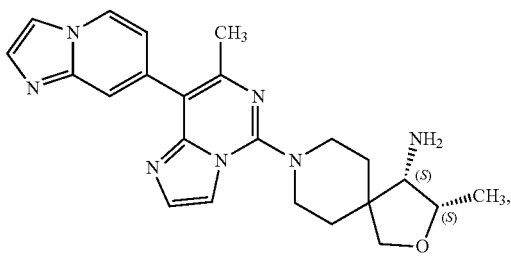
(52)
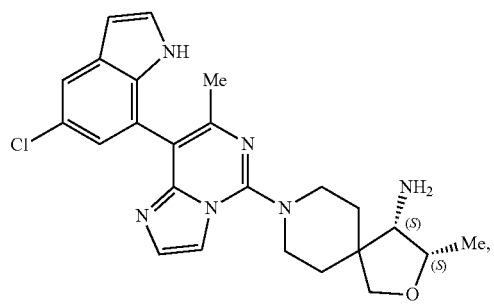

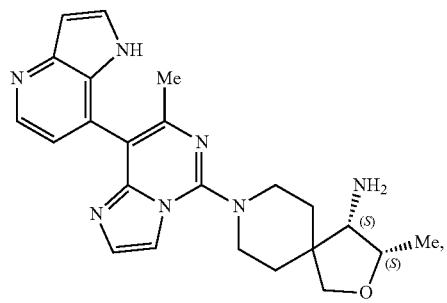
(53)
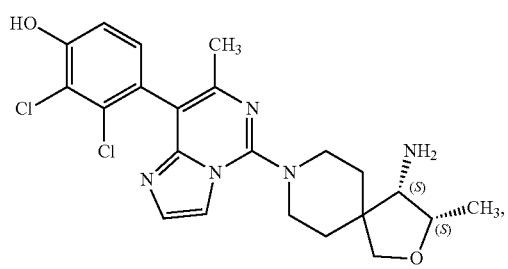
(54)
(55)
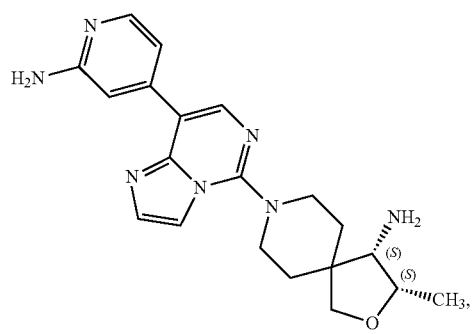
(58)
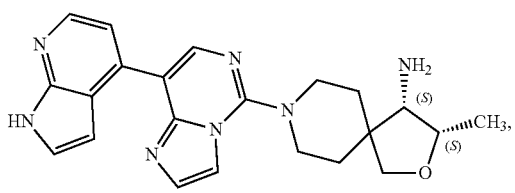
(59)
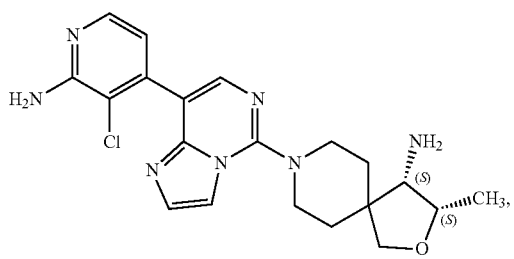
(60)
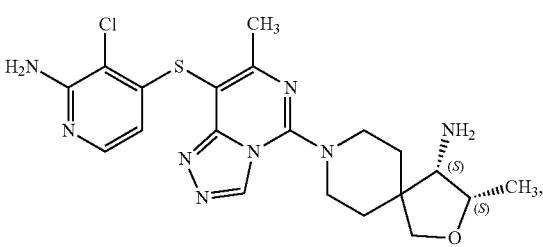
(61)
(56)
(57)
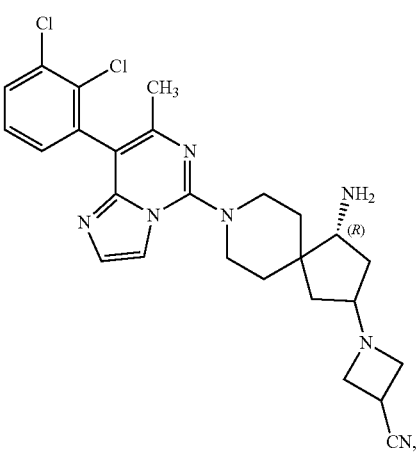
(62)

(63)
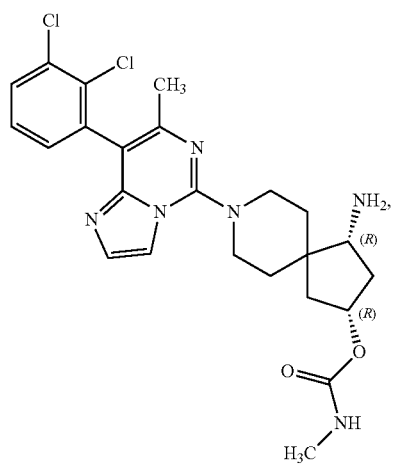
(64)
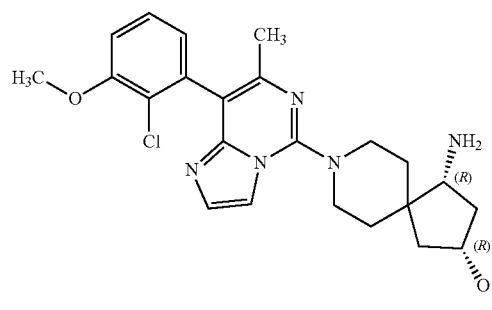
(65)
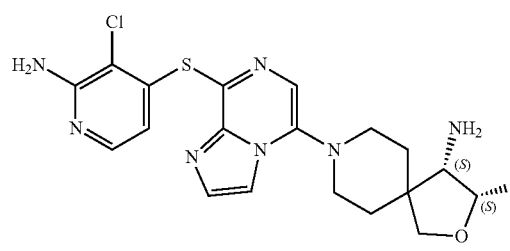
(66)
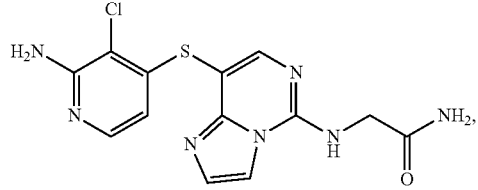
(67)
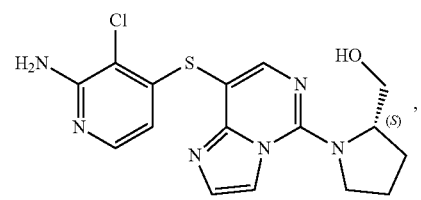
(68)
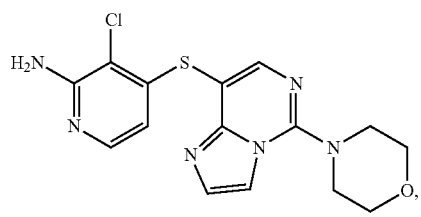
(69)
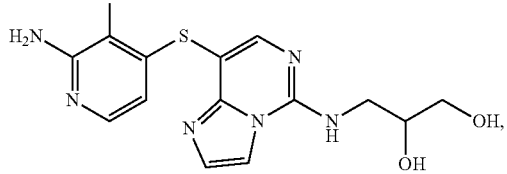
(70)
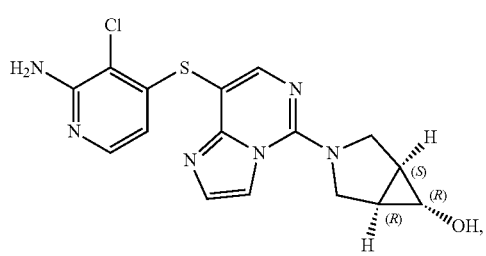
(71)
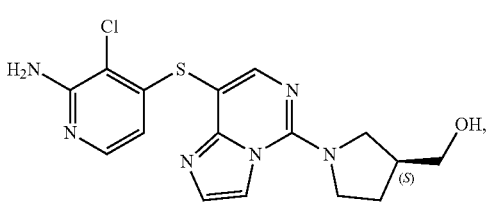
(72)
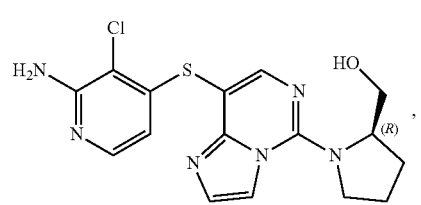
(73)
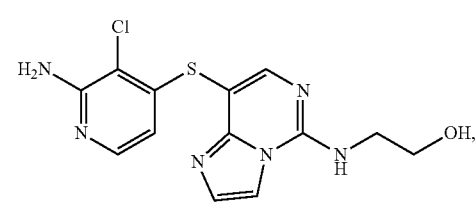
(74)
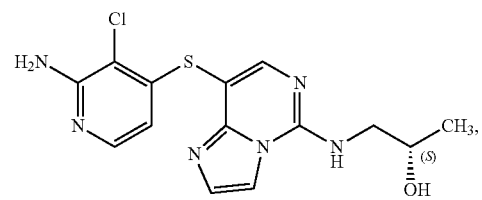

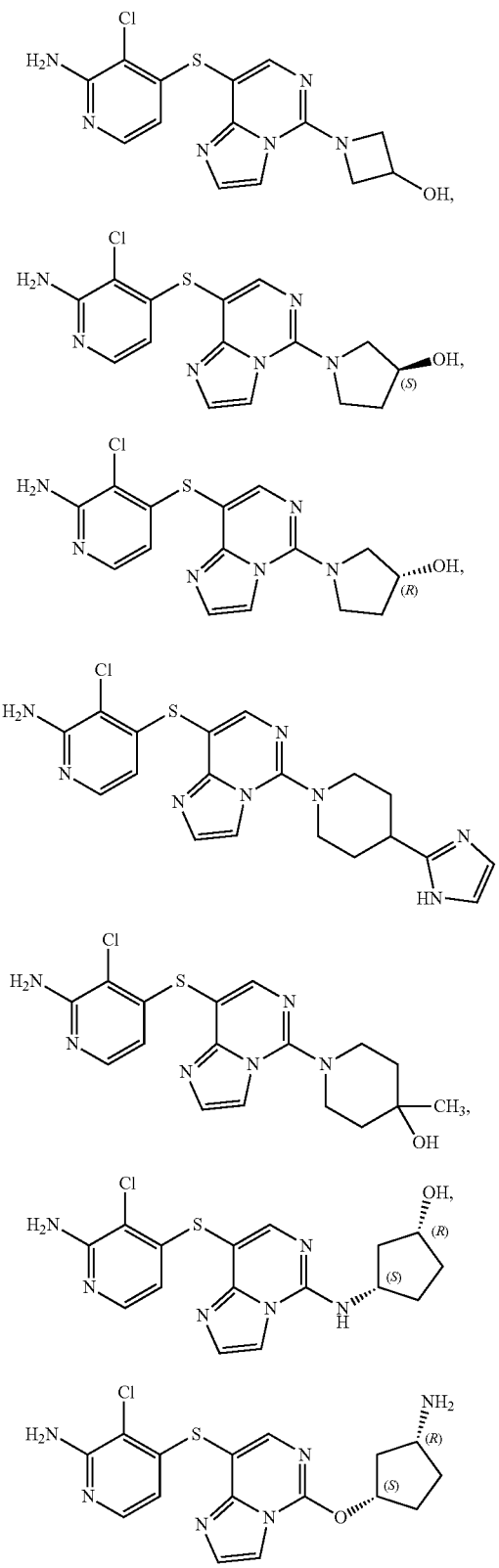

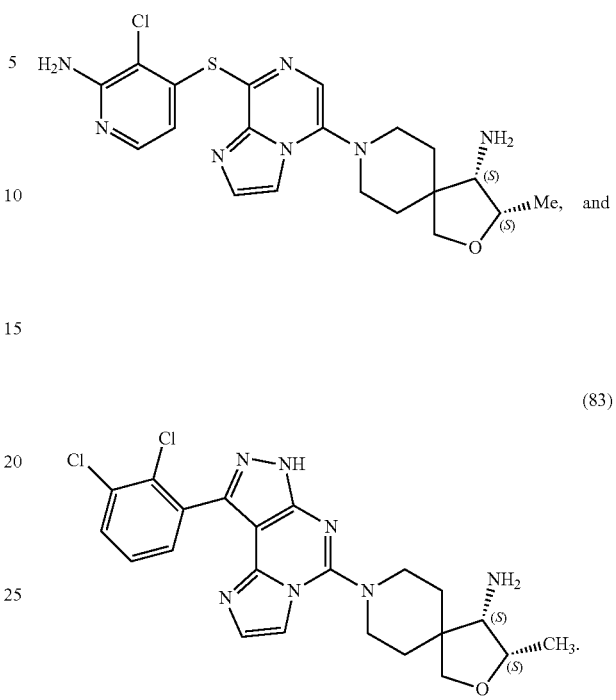

15. A pharmaceutical composition comprising a compound of claim 1, or a pharmaceutically acceptable salt, tautomer, or stereoisomer thereof, and a pharmaceutically acceptable carrier.

16. A method of treating a disease selected from the group consisting of Noonan Syndrome, Leopard Syndrome, juvenile myelomonocytic leukemias, neuroblastoma, melanoma, acute myeloid leukemia and cancers of the breast, lung and colon in a subject in need thereof, comprising administering to the subject an effective amount of a compound of claim 1, or a pharmaceutically acceptable salt, tautomer, or stereoisomer thereof.

17. A method of treating a disease selected from the group consisting of Noonan Syndrome, Leopard Syndrome, juvenile myelomonocytic leukemias, neuroblastoma, melanoma, acute myeloid leukemia and cancers of the breast, lung and colon in a subject in need thereof, comprising administering to the subject an effective amount of a pharmaceutical composition of claim 15.

18. The compound of claim 1, or a pharmaceutically acceptable salt, tautomer, or stereoisomer thereof, wherein $R^3$ and $R^a$ together with the atom to which they are attached combine to form a 3- to 12-membered monocyclic heterocycle.

19. The compound of claim 1, or a pharmaceutically acceptable salt, tautomer, or stereoisomer thereof, wherein $R^3$ and $R^a$ together with the atom to which they are attached combine to form a 3- to 12-membered polycyclic heterocycle.

* * * * *